US010280419B2

(12) United States Patent
Tremblay et al.

(10) Patent No.: US 10,280,419 B2
(45) Date of Patent: May 7, 2019

(54) REDUCTION OF AMYLOID BETA PEPTIDE PRODUCTION VIA MODIFICATION OF THE APP GENE USING THE CRISPR/CAS SYSTEM

(71) Applicant: UNIVERSITÉ LAVAL, Québec (CA)

(72) Inventors: Jacques P. Tremblay, Stoneham et Tewkesbury (CA); Joël Rousseau, Québec (CA); Pierre Chapdelaine, Lévis (CA)

(73) Assignee: UNIVERSITÉ LAVAL, Québec (CA)

( * ) Notice: Subject to any disclaimer, the term of this patent is extended or adjusted under 35 U.S.C. 154(b) by 0 days.

(21) Appl. No.: 15/309,693

(22) PCT Filed: May 8, 2015

(86) PCT No.: PCT/CA2015/050411
§ 371 (c)(1),
(2) Date: Nov. 8, 2016

(87) PCT Pub. No.: WO2015/168800
PCT Pub. Date: Nov. 12, 2015

(65) Prior Publication Data
US 2017/0240888 A1 Aug. 24, 2017

Related U.S. Application Data

(60) Provisional application No. 61/991,054, filed on May 9, 2014.

(51) Int. Cl.
*C12N 15/10* (2006.01)
*C12N 15/113* (2010.01)
*C07K 14/47* (2006.01)
*C12N 9/22* (2006.01)
C12N 15/63 (2006.01)
A61K 38/00 (2006.01)
A61K 48/00 (2006.01)

(52) U.S. Cl.
CPC ........ *C12N 15/113* (2013.01); *C07K 14/4711* (2013.01); *C12N 9/22* (2013.01); *C12N 15/102* (2013.01); *A61K 38/00* (2013.01); *A61K 48/00* (2013.01); *C12N 15/63* (2013.01); *C12N 2310/10* (2013.01); *C12N 2310/20* (2017.05)

(58) Field of Classification Search
None
See application file for complete search history.

(56) References Cited

U.S. PATENT DOCUMENTS 8,889,356 B2 11/2014 Zhang
2014/0357530 A1* 12/2014 Zhang ............... C12N 15/63 506/16
2015/0005351 A1 1/2015 Soriano et al.
2015/0166980 A1 6/2015 Liu et al.
2015/0232883 A1 8/2015 Dahlman et al.
2017/0152528 A1* 6/2017 Zhang .................. C12N 15/907

FOREIGN PATENT DOCUMENTS

WO   WO-2008106981 A1 * 9/2008 ........... A01K 7/0271
WO   2014/071219   5/2014
WO   2014/093595   6/2014
WO   2014/093701   6/2014

OTHER PUBLICATIONS

Jonsson et al "A mutation in APP protects against Alzheimer's disease and age-related cognitive decline" (Nature, vol. 488, No. 7409, Jul. 11, 2012, pp. 96-99). (Year: 2012).*
Jorgensen et al Score result 4 database rag pdf downloaded May 2018 (Year: 2018).*
Ran et al., In vivo genome editing using *Staphylococcus aureus* Cas9, Nature, 2015, 520:186-202.
Ran et al., Double nicking by RNA-guided CRISPR Cas9 for enhanced genome editing specificity. Cell, 2013, 154 (6):1380-1389.
Rossi et al., A family with Alzheimer disease and strokes associated with A713T mutation of the APP gene. Neurology, 2004, 63(5):910-912.
Salomone et al., A novel chimeric cell-penetrating peptide with membrane-disruptive properties for efficient endosomal escape. J Control Release, 2012,163(3):293-303.
Sapranauskas et al., The *Streptococcus thermophilus* CRISPR/Cas system provides immunity in *Escherichia coli*. Nucleic Acids Res, 2011, 39(21):9275-9282.
Schmitt, Protein ubiquitination, degradation and the proteasome in neuro-degenerative disorders: no clear evidence for a significant pathogenetic role of proteasome failure in Alzheimer disease and related disorders. Med Hypotheses, 2006, 67(2):311-317.
Shah et al., Protospacer recognition motifs, RNA Biology, 2013, 10:5, 891-899.
Sinha et al., Purification and cloning of amyloid precursor protein beta-secretase from human brain. Nature, 1999, 402(6761):537-540.
St-George-Hyslop, Molecular genetics of Alzheimer's disease. Biological psychiatry, 2000, 47(3):183-199.
Theuns et al., Alzheimer dementia caused by a novel mutation located in the APP C-terminal intracytosolic fragment. Hum Mutat, 2006, 27(9):888-896.

(Continued)

*Primary Examiner* — Catherine S Hibbert
(74) *Attorney, Agent, or Firm* — S. Serge Shahinian

(57) ABSTRACT

Methods and products are described related to use of the CRISPR/Cas9 system to introduce a modification into an APP gene, such as guide RNAs and recombinant proteins, for decreasing amyloid beta peptide produced by a cell. Also described are uses of such methods and products for the treatment of Alzheimer's disease and/or age-related cognitive decline in a cell from a subject in need thereof.

4 Claims, 39 Drawing Sheets
Specification includes a Sequence Listing.

(56) References Cited

OTHER PUBLICATIONS

Ting et al., Absence of A673T amyloid-B precursor protein variant in Alzheimer's disease and other neurological diseases, Neurobiology of aging, 2013, 34; 2441.e7-2441.e8.
Tomiyama et al., A new amyloid beta variant favoring oligomerization in Alzheimer's-type dementia. Ann Neurol, 2008, 63(3):377-387.
Trehin et al., Cellular uptake but low permeation of human calcitonin-derived cell penetrating peptides and Tat (47-57) through well-differentiated epithelial models. Pharm Res, 2004, 21(7):1248-1256.
Tsai et al., Dimeric CRISPR RNA-guided FokI nucleases for highly specific genome editing. Nat Biotechnol, 2014, 32:6, 569-577.
Wakutani et al., Novel amyloid precursor protein gene missense mutation (D678N) in probable familial Alzheimer's disease. J Neurol Neurosurg Psychiatry, 2004, 75(7):1039-1042.
Woodruff et al., The Presenilin-1 E9 Mutation Results in Reduced y-Secretase Activity, but Not Total Loss of PS1 Function, in Isogenic Human Stem Cells, Cell Reports 5, 2013, 974-985.
Zender et al., VP22-mediated intercellular transport of p53 in hepatoma cells in vitro and in vivo. Cancer Gene Ther, 2002, 9(6):489-496.
Zhang et al., APP processing in Alzheimer's disease. Molecular brain, 2011, 4:3, 1-13.
International Search Report and Written Opinion of corresponding International Application No. PCT/CA2015/050411.
International Preliminary Report on Patentability (IPRP) of corresponding International Application No. PCT/CA2015/050411.
Extended European Search Report dated Nov. 16, 2017, of corresponding European Application No. 15789631.7.
Altschul et al., Basic local alignment search tool. J Mol Biol, 1990, 215(3):403-410.
Ancolio et al., Unusual phenotypic alteration of beta amyloid precursor protein (betaAPP) maturation by a new Val-715 → Met betaAPP-770 mutation responsible for probable early-onset Alzheimer's disease. Proc Natl Acad Sci U S A, 1999, 96(7):4119-4124.
Arnould et al., The I-CreI meganuclease and its engineered derivatives: applications from cell modification to gene therapy. Protein engineering, design & selection : PEDS, 2011, 24(1-2):27-31.
Brouwers et al., Molecular genetics of Alzheimer's disease: An update. Ann Med. 2008, 40(8):562-583.
Carter et al., More missense in amyloid gene. Nat Genet, 1992, 2(4):255-256.
Chartier-Harlin et al., Early-onset Alzheimer's disease caused by mutations at codon 717 of the beta-amyloid precursor protein gene. Nature, 1991, 353(6347):844-846.
Deltcheva et al., CRISPR RNA maturation by trans-encoded small RNA and host factor RNase III. Nature, 2011, 471(7340):602-607.
Eckman et al., A new pathogenic mutation in the APP gene (I716V) increases the relative proportion of A beta 42 (43). Hum Mol Genet, 1997, 6(12):2087-2089.
El-Sayed et al., Delivery of macromolecules using arginine-rich cell-penetrating peptides: ways to overcome endosomal entrapment. The AAPS journal, 2009, 11(1):13-22.
Ferri et al., Global prevalence of dementia: a Delphi consensus study. Lancet, 2005, 366(9503):2112-2117.
Fominaya et al., A chimeric fusion protein containing transforming growth factor-alpha mediates gene transfer via binding to the EGF receptor Gene Ther, 1998, 5(4):521-530.
Gaj et al., ZFN, TALEN, and CRISPR/Cas-based methods for genome engineering. Trends Biotechnol, 2013, 31 (7):397-405.
Goate et al., Segregation of a missense mutation in the amyloid precursor protein gene with familial Alzheimer's lisease. Nature, 1991, 349(6311):704-706.
Grabowski et al., Novel amyloid precursor protein mutation in an Iowa family with dementia and severe cerebral amyloid angiopathy. Ann Neurol, 2001, 49(6):697-705.

Guardia-Laguarta et al., Clinical, neuropathologic, and biochemical profile of the amyloid precursor protein I716F mutation. J Neuropathol Exp Neurol, 2010, 69(1):53-59.
Guerreiro et al., Genetic screening of Alzheimer's disease genes in Iberian and African samples yields novel mutations in presenilins and APP. Neurobiology of aging, 2010, 31(5):725-731.
Hendriks et al., Presenile dementia and cerebral haemorrhage linked to a mutation at codon 692 of the beta-amyloid precursor protein gene. Nat Genet, 1992, 1(3):218-221.
Hou et al., Efficient genome engineering in human pluripotent stem cells using Cas9 from Neisseria meningitidis. Proc Natl Acad Sci U S A, 2013, 110(39):15644-15649.
Hussain et al., Identification of a novel aspartic protease (Asp 2) as beta-secretase. Mol Cell Neurosci, 1999, 14 (6):419-427.
Janssen et al., Early onset familial Alzheimer's disease: Mutation frequency in 31 families. Neurology, 2003, 60 (2):235-239.
Jinek et al., A programmable dual-RNA-guided DNA endonuclease in adaptive bacterial immunity. Science, 2012, 337(6096):816-821.
Jones et al., Mutation in codon 713 of the beta amyloid precursor protein gene presenting with schizophrenia. Nat Genet, 1992, 1(4):306-309.
Jonsson et al., A mutation in APP protects against Alzheimer's disease and age-related cognitive decline. Nature, 2012, 488(7409):96-99.
Kakimoto et al., The conjugation of diphtheria toxin T domain to poly(ethylenimine) based vectors for enhanced endosomal escape during gene transfection. Biomaterials, 2009, 30(3):402-408.
Kakudo et al., Transferrin-modified liposomes equipped with a pH-sensitive fusogenic peptide: an artificial viral-like delivery system. Biochemistry, 2004, 43(19):5618-5628.
Kamino et al., Linkage and mutational analysis of familial Alzheimer disease kindreds for the APP gene region. Am J Hum Genet, 1992, 51(5):998-1014.
Kero et al., Amyloid precursor protein (APP) A673T mutation in the elderly Finnish population. Neurobiology of aging, 2013, 34(5):1518 e1511-1513.
Kichler et al., Histidine-rich amphipathic peptide antibiotics promote efficient delivery of DNA into mammalian cells. Proc Natl Acad Sci U S A, 2003, 100(4):1564-1568.
Kumar-Singh et al., Nonfibrillar diffuse amyloid deposition due to a gamma(42)-secretase site mutation points to an essential role for N-truncated A beta(42) in Alzheimer's disease. Hum Mol Genet, 2000, 9(18):2589-2598.
Kwok et al., Novel Leu723Pro amyloid precursor protein mutation increases amyloid beta42(43) peptide levels and induces apoptosis. Ann Neurol, 2000, 47(2):249-253.
Kwon et al., Application of an HIV gp41-derived peptide for enhanced intracellular trafficking of synthetic gene and siRNA delivery vehicles. Bioconjug Chem, 2008, 19(4):920-927.
Lan et al., A novel APP mutation (D678H) in a Taiwanese patient exhibiting dementia and cerebral microvasculopathy. Journal of clinical neuroscience : official journal of the Neurosurgical Society of Australasia, 2014, 21(3):513-515.
Levy et al., Mutation of the Alzheimer's disease amyloid gene in hereditary cerebral hemorrhage, Dutch type. Science, 1990, 248(4959):1124-1126.
Lorieau et al., The complete influenza hemagglutinin fusion domain adopts a tight helical hairpin arrangement at the lipid:water interface. Proc Natl Acad Sci U S A, 2010, 107(25):11341-11346.
Lundberg et al., Delivery of short interfering RNA using endosomolytic cell-penetrating peptides. FASEB J, 2007, 21 (11):2664-2671.
Mali et al., RNA-guided human genome engineering via Cas9. Science, 2013, 339(6121):823-826.
Masters et al., Neuronal origin of a cerebral amyloid: neurofibrillary tangles of Alzheimer's disease contain the same protein as the amyloid of plaque cores and blood vessels. EMBO J, 1985, 4(11):2757-2763.
Menke, Engineering subtle targeted mutations into the mouse genome, Genesis, 2013, 51(9):605-618.
Midoux et al., Membrane permeabilization and efficient gene transfer by a peptide containing several histidines. Bioconjug Chem,1998, 9(2):260-267.

(56) References Cited

OTHER PUBLICATIONS

Moro et al., APP mutations in the Abeta coding region are associated with abundant cerebral deposition of Abeta38. Acta Neuropathol, 2012, 124(6):809-821.

Mullan et al., A pathogenic mutation for probable Alzheimer's disease in the APP gene at the N-terminus of beta-amyloid. Nat Genet, 1992, 1(5):345-347.

Murrell et al., A mutation in the amyloid precursor protein associated with hereditary Alzheimer's disease. Science, 1991, 254(5028):97-99.

Murrell et al., Early-onset Alzheimer disease caused by a new mutation (V717L) in the amyloid precursor protein gene. Arch Neurol, 2000, 57(6):885-887.

Noguchi et al., PDX-1 protein containing its own antennapedia-like protein transduction domain can transduce pancreatic duct and islet cells. Diabetes, 2003, 52(7):1732-1737.

Obici et al., A novel AbetaPP mutation exclusively associated with cerebral amyloid angiopathy. Ann Neurol, 2005, 58 (4):639-644.

Pasalar et al., An Iranian family with Alzheimer's disease caused by a novel APP mutation (Thr714Ala). Neurology, 2002, 58(10):1574-1575.

Pearson et al., Improved tools for biological sequence comparison. Proc Natl Acad Sci U S A, 1988, 85 (8):2444-2448.

Plassman et al., Prevalence of dementia in the United States: the aging, demographics, and memory study, Neuroepidemiology, 2007, 29:125-132.

Prat et al., Heterogeneity of T-Lymphocyte Function in Primary Progressive Multiple Sclerosis: Relation to Magnetic Resonance Imaging Lesion Volume, Ann Neurol, 2000, 47:234-237.

Qiu et al., Epidemiology of Alzheimer's disease:occurence, determinants, and strategies toward intervention, Dialogues in clinical neuroscience, 2009, 11(2):111-128.

Yao-Wen, Liu et al., Absence of A673T variant in APP gene indicates an alternative protective mechanism contributing to longevity in Chinese individuals, Neurobiology & Aging (2014) 35 : 935.e11-935.e12.

\* cited by examiner

```
MLPGLALLLLAAWTARALEVPTDGNAGLLAEPQIAMFCGRLNMHMNVQNGKWDSDPSGTKTCIDTKEGILQYCQEVYP
ELQITNVVEANQPVTIQNWCKRGRKQCKTHPHFVIPYRCLVGEFVSDALLVPDKCKFLHQERMDVCETHLHWHTVAKE
TCSEKSTNLHDYGMLLPCGIDKFRGVEFVCCPLAEESDNVDSADAEEDDSDVWWGGADTDYADGSEDKVVEVAEEEEV
AEVEEEEADDDEDDEDGDEVEEEAEEPYEEATERTTSIATTTTTTESVEEVVREVCSEQAETGPCRAMISRWYFDVT
EGKCAPFFYGGCGGNRNNFDTEEYCMAVCGSAMSQSLLKTTQEPLARDPVKLPTTAASTPDAVDKYLETPGDENEHAH
FQKAKERLEAKHRERMSQVMREWEEAERQAKNLPKADKKAVIQHFQEKVESLEQEAANERQQLVETHMARVEAMLNDR
RRLALENYITALQAVPPRPRHVFNMLKKYVRAEQKDRQHTLKHFEHVRMVDPKKAAQIRSQVMTHLRVIYERMNQSLS
LLYNVPAVAEEIQDEVDELLQKEQNYSDDVLANMISEPRISYGNDALMPSLTETKTTVELLPVNGEFSLDDLQPWHSF
GADSVPANTENEVEPVDARPAADRGLTTRPGSGLTNIKTEEISEVKMDAEFRHDSGYEVHHQKLVFFAEDVGSNKGAI
IGLMVGGVVIATVIVITLVMLKKKQYTSIHHGVVEVDAAVTPEERHLSKMQQNGYENPTYKFFEQMQN
```

```
Gt tct ggg ttg aca aat atc aag acg gag gag atc tct gaa gtg aag
   S   G   L   T   N   I   K   T   E   E   I   S   E   V   K
                       target of gRNA#8
atg gat gca gaa ttc cga cat gac tca gga tat gaa gtt cat cat caa
 M   D   A   E   F   R   H   D   S   G   Y   E   V   H   H   Q
aaa ttg
 K   L
```

B

```
Gt tct ggg ttg aca aat atc aag acg gag gag atc tct gaa gtg aag
   S   G   L   T   N   I   K   T   E   E   I   S   E   V   K atg gat AcG gaG ttT AgG caC gaT tca gga tat gaa gtt cat cat caa
 M   D   T   E   F   R   H   D   S   G   Y   E   V   H   H   Q
aaa ttg
 K   L
```

Figure 4

A pMiniT-Patch plasmid

```
CCGGTTCAGACAGGATAAAGAGGAAAGAATGTTAGACAACACCCGCTTACGCATAGCTATTCAGAAATCAGGCCGTTTAAGC
GATGATTCACGAGAATTGCTGGCCCGCTGCGGCATAAAAATTAATTTACACACTCAGCGCTGATGAATCCCCTAATGATTTT
GGTAAAAATCATTAAGTTAAGGTGGACACACATCTTGTCATATGATTAAATGGTTTCGCGAAAAATCAATAATCAGACAACA
AGATGTGCGAACTCGATATTTTACACGACTCTCTTTACCAATTCTGCCCCGAATTACACTTAA

AACGACTCAACAGCTTAACGTTGGCTTGCCACGCATTACTTGACTGTAAAACTCTCACTCTTACCGAACTTGGCCGTA
        MiniTfw
ACCTGCCAACCAAAGCGAGAACAAAACATAACATCAAACGAATCGACCGATTGTTAGGTAATCGTCACCTCCACAAAG
                                                          gRNA#8target
AGCGACTCGCTGTATCGCTCGAGGGATCCGAATTCAGGAGGTAAAAACCATGATATAGCAGAATTCCGACATGACTCA
              Bfw
GGTTCAGCAGACGAACCAATTACAATCTGTGTAACTAGAACACTTGACTAAAATTATATAATTTTTACAACGCTTCACTGCA
TAGATACATGAACATAATTTATTTGTAATTGGAACAAAGCCCCAAAGTAGCAGTTTTGTTCTACCAGGTAATTAATGCTCAT
TTTTAAAGCCTTTTATTATTATTTCTGAAGTAATGAGTGCACATGAAAAAGACACATAATAGGCTAAACAATAAGCCCGTA
AGCCAAGCCAACATATTCCAGGAACAAATCCTTGCCAACCTCTCAACCAGGATTTAACTTCTGCTTTTCCCCCATTTTCAAA
AATTATAGCATGTATTTAAAGGCAGCAGAAGCCTTACTTTCAGGTTTCCCTTACCCTTTCATTTCTTTTTGTTCAAAATAGG
TAGTAATTGAAGTTTTAAATATAGGGTATCATTTTTCTTTAAGAGTCATTTATCAATTTTCTTCTAACTTCAGGCCTAGAAA
GAAGTTTTGGGTAGGCTTTGTCTTACAGTGTTATTATTTATGAGTAAAACTAATTGGTTGTCCTGCATACTTTAATTATGAT
GTAATACAGGTTCTGGGTTGACAAATATCAAGACGGAGGAGATCTCTGAA
                IRMUfw
GTGAAGATGGATaCgGAgTTtaGgCAcGAtTCAGGATATGAAGTTCATCATCAAAAATTGGTACGTAAAATAATTTAC
                    ILMUrev New SpeI
CTCTTTCCACTAGTGTTTGTCTTGCCAAATGACCTATTAACTCTGGTTCATCCTGTGCTAGAAATCAAATTAAGGAAAAGAT
AAAAATACAATGCTTGCCTATAGGATTACCATGAAAACATGAAGAAAATAAATAGGCTAGGCTGAGCGCAGTGGCTCAAGCC
TGTAATCCCAGCACTTTGGGAGGCCAAGGCGGGTGGATCACGAGGTCAGAAATTCGAGACCAGCCTGGCCAATATGGTGAAA
CCCCATCTNTACTAAAAATACAAAAAAGATTAGCTGGGTGTGGTGGCAAACNCCTGTAGTCCCAGCTGCTGGGGAGGCTGAC
GCAGGAGACTTGCTTGAACCCAGGAGGTGGAGGTTGCAGTGAGCTGAGATCGTGCCTAGGCGACAGAGCGAGACTCCATCCC
AAAAAAAAAAAAAGAAAAGAAAGAGGCTGTATGTATAGTTCTTTCAGACTACAAGGCA
              gRNA#8target
GCAAAGTTCGTGCAGAATTCCGACATGACTCAGGACTGATAATAATGACGTCAGAATTCTCGAGTCGGGGAAATGTGC MiniTRev
GCGGAACCCCTATTTGTTTATTTTTCTAAATACATTCAAATATGTATCCGCTCATGAGACAATAACCCTGATAAATGCTTCA
ATAATATTGAAAAAGGAAGAGTATGAGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACAATTAATAGACTGGATGGAGGCGG
ATAAAGTTGCAGGACCACTTCTGCGCTCGGCCCTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAAGATCCTTTTGATAATCTCATGAC
CAAAATCCCTTAACGTGAGTTTTCGTTCCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTGGTTTGTTGCCGGATCAAGAGCTACCAA
CTCTTTTTCCGAAGGTAACTGGCTTCAGCAGAGCGCAGATACCAAATACTGTTCTTCTAGTGTAGCCGTAGTTAGGCCACCA
CTTCAAGAACTCTGTAGCACCGCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGGGGGCGGAGCCTATGGA
AAAACGCCAGCAATGCGGCCTTTTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCGCGCGTTGGCCGATTCATTAATGCAG
```

Figure 7B

```
277141 aagttacagg gaagctgatt ctggcttcat gtaaaaaaag gacagtttgg gcaggcaaat
277201 ctatcaaaaa atggagggaa attgatacat tcctctatgt tcaaacagga actgacaatc Cfw
277261 tgccctggg tgggaacacg gtagagaaga tgacttcaaa agccctttc atcctaaaat
277321 tctgatgttt gataattaaa tgttatagca tggacactga catttacatt ttttacttat
277381 gttttggtt tttaaatgac tctgcatttt gttttaagct tcaaattatt atttgaataa
277441 tgaaattcat cagaacaatt agtgttaaga atcatatagc aatttataga aaagaaagag
277501 ttcgtaggtt ataaattctg ttagttgcta agaagcattt ttaaaattat gtactatagc Afw /Bfw
277561 tctttattca gcagacgaac caattacaat ctgtgtaact agaacacttg actaaaatta
277621 tataattttt acaacgcttc actgcataga tacatgaaca taatttattt gtaattggaa
277681 caaagcccca aagtagcagt tttgttctac caggtaatta atgctcattt ttaaagcctt
277741 ttattattat ttctgaagta atgagtgcac atggaaaaag acacataata ggctaaacaa
277801 taagcccgta agccaagcca acatattcca ggaacaaatc cttgccaacc tctcaaccag
277861 gatttaactt ctgcttttcc cccatttca aaaattatag catgtattta aaggcagcag
277921 aagccttact ttcaggtttc ccttacccctt tcatttcttt ttgttcaaaa taggtagtaa
277981 ttgaagtttt aaatataggg tatcattttt ctttaagagt catttatcaa ttttcttcta
278041 acttcaggcc tagaaagaag ttttgggtag gctttgtctt acagtgttat tatttatgag
278101 taaaactaat tggttgtcct gcatacttta attatgatgt aatacaggtt ctgggttgac IRMUfw
278161 aaatatcaag acggaggaga tctctgaagt gaagatggat acggagttta ggcacgattc SpeI site
278221 aggatatgaa gttcatcatc aaaaattggt acgtaaaata atttacctct ttccactagt
278281 gtttgtcttg ccaaatgacc tattaactct ggttcatcct gtgctagaaa tcaaattaag
278341 gaaaagataa aaatacaatg cttgcctata ggattaccat gaaaacatga agaaaataaa
278401 taggctaggc tgacgcagt ggctcaagcc tgtaatccca gcacttttggg aggccaaggc
278461 gggtggatca cgaggtcaga aattcgagac cagcctggcc aatatggtga aaccccatct
278521 ctactaaaaa tacaaaaaag attagctggg tgtggtggca acacctgta gtcccagctg
278581 ctggggaggc tgacgcagga gacttgcttg aacccaggag gtggaggttg cagtgagctg
278641 agatcgtgcc taggcgacag agcgagactc catcccaaaa aaaaaaaaga aagaaagag Brev
278701 gctgtatgta tagttctttc agactacaag gcagcaaagt tcgtgcatga ctcgggactt Arev
278761 aaagtggaat taatttcaat atagcagcca ctttgacttc cactgtgttt tctgggaaaa
278821 taggtttaca ataggtttat ttgaaggatc aaacacatgc atacactgct tggtttaca
278881 gaacacttta tgtggcttaa attcacatcc ggaactgtct tcctttaccc attcatttct
278941 cccccagctc tttcttttca ttccctcccc tacctcccat gatttaactt ctcttgcaag
279001 agtaagatca tggagtgagc aggaccccat gatgttcccg atagtgttat tcatcaaaag
279061 gtttgtgcaa agaagacagc agcttccttt tcagatgaaa tcacttttcc cccctaatgt
279121 tagaattgga gtaaatcaaa aagccacatc tcctttgtgg tcagctctag tagttatata
279181 aaatccttta ccaaaagctt agaaatggag ataaatcaaa tcgtggatta tgttagggtt Crev
279241 ccatcttatc agtaggtgca gtaagagggt taaattaatg aagacgacaa ttttatcaca
279301 ttcagtggtg gacagaaaaa tggtaagaaa atttccatag caataatact taaagttatc
279361 tcaggcactt cttttgtttt gttttgtgtg tgtgtgtgtg tgagtgttac ttttttccaa
279421 gcagaaaatg tcttttcaat attcataaag ttgataaatc ctagtattaa tctctaaaag
279481 aaacacctcc aaattattat ttatgcctta cttgactcca ataattgta gcaaataaaa
```

Figure 8C

A
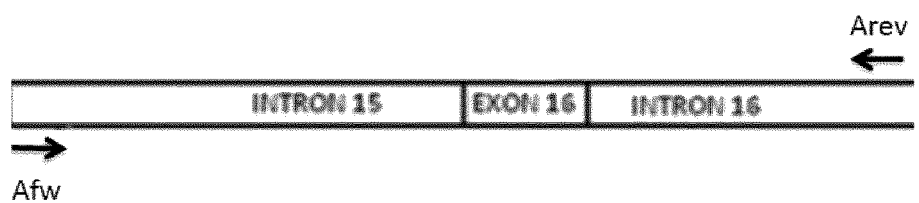
B
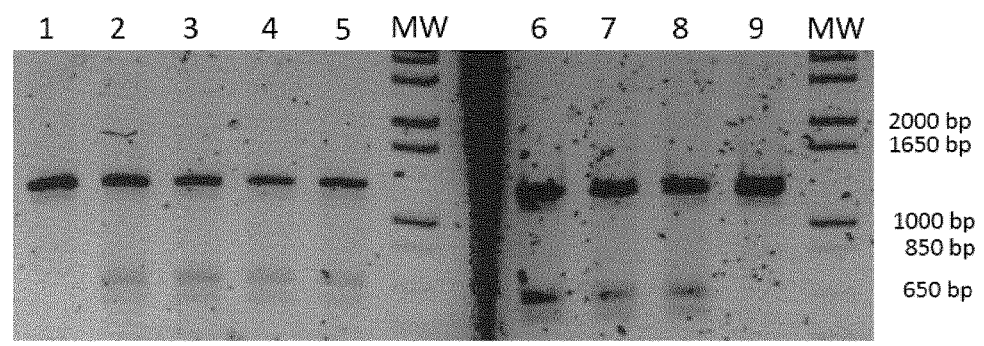
Figure 9

A
pMiniT-Patch plasmid
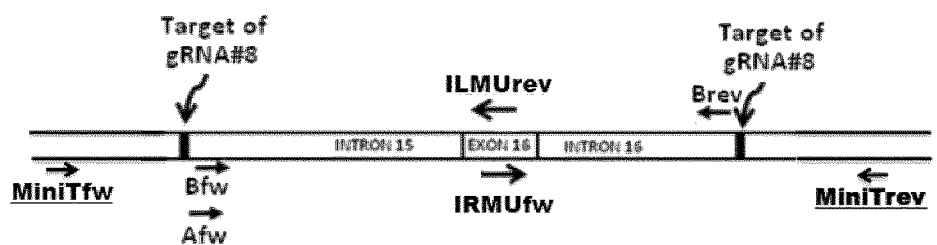
B
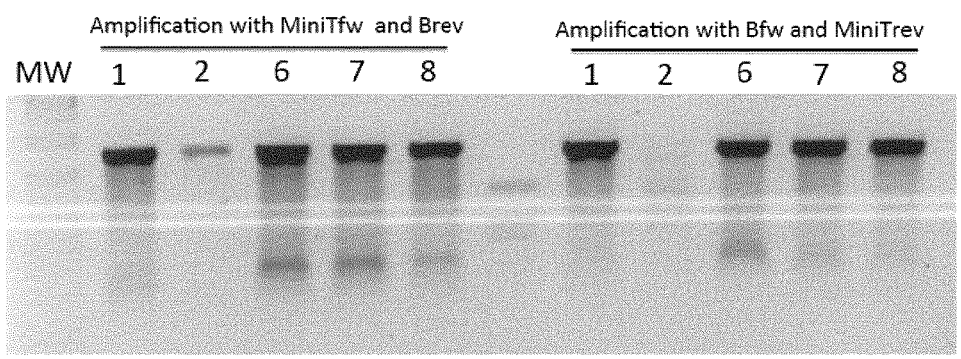
Figure 10

A
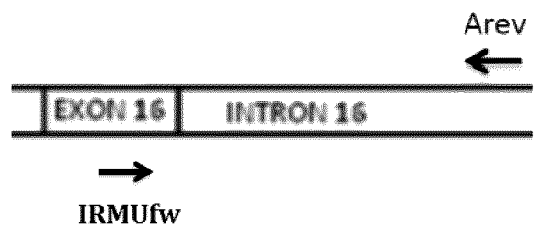
B
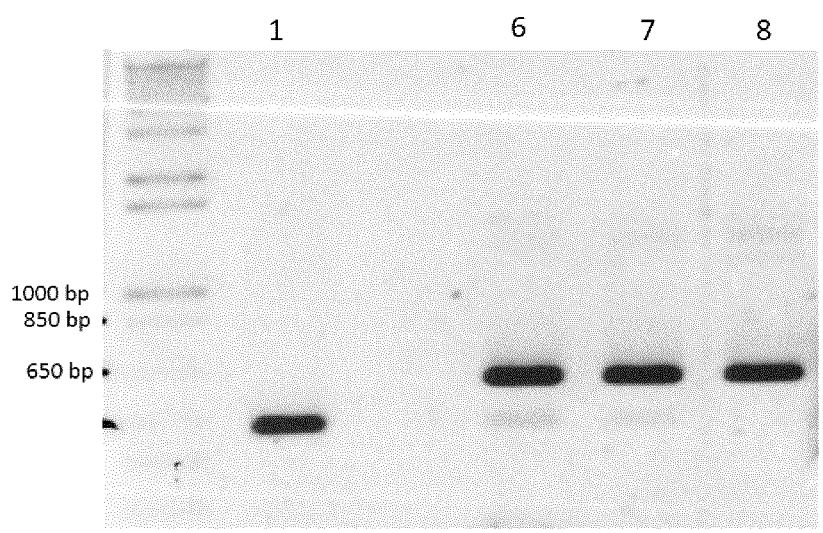
Figure 11

```
IRMUfw/Arev (PCR 608pb)
                 10        20        30        40
WT 608           TGGATGCAGAATTCCGACATGACTCAGGATATGAAGTTCATCAT
                 ::::: : :: ::   : :: :: :::::::::::::::::::
L8               TGGATACGGAGTTTAGGCACGATTCAGGATATGAAGTTCATCAT
          70        80        90       100       110       120

50        60        70        80        90       100
WT 608 CAAAAATTGGTACGTAAAATAATTTACCTCTTTCCACTACTGTTTGTCTTGCCAAATGAC
       :::::::::::::::::::::::::::::::::::::: :::::::::::::::::::
L8     CAAAAATTGGTACGTAAAATAATTTACCTCTTTCCACTAGTGTTTGTCTTGCCAAATGAC
         130       140       150       160       170       180
                                       SpeI
       110       120       130       140       150       160
WT 608 CTATTAACTCTGGTTCATCCTGTGCTAGAAATCAAATTAAGGAAAAGATAAAAATACAAT
       ::::::::::::::::::::::::::::::::::::::::::::::::::::::::::::
L8     CTATTAACTCTGGTTCATCCTGTGCTAGAAATCAAATTAAGGAAAAGATAAAAATACAAT
         190       200       210       220       230       240

170       180       190       200       210       220
WT 608 GCTTGCCTATAGGATTACCATGAAAACATGAAGAAAATAAATAGGCTAGGCTGAGCGCAG
       ::::::::::::::::::::::::::::::::::::::::::::::::::::::::::::
L8     GCTTGCCTATAGGATTACCATGAAAACATGAAGAAAATAAATAGGCTAGGCTGAGCGCAG
         250       260       270       280       290       300

230       240       250       260       270       280
WT 608 TGGCTCAAGCCTGTAATCCCAGCACTTTGGGAGGCCAAGGCGGGTGGATCACGAGGTCAG
       ::::::::::::::::::::::::::::::::::::::::::::::::::::::::::::
L8     TGGCTCAAGCCTGTAATCCCAGCACTTTGGGAGGCCAAGGCGGGTGGATCACGAGGTCAG
         310       320       330       340       350       360

290       300       310       320       330       340
WT 608 AAATTCGAGACCAGCCTGGCCAATATGGTGAAACCCCATCTCTACTAAAAATACAAAAAA
       ::::::::::::::::::::::::::::::::::::::::::::::::::::::::::::
L8     AAATTCGAGACCAGCCTGGCCAATATGGTGAAACCCCATCTCTACTAAAAATACAAAAAA
         370       380       390       400       410       420

350       360       370       380       390       400
WT 608 GATTAGCTGGGTGTGGTGGCAAACACCTGTAGTCCCAGCTGCTGGGGAGGCTGACGCAGG
       ::::::::::::::::::::::::::::::::::::::::::::::::::::::::::::
L8     GATTAGCTGGGTGTGGTGGCAAACACCTGTAGTCCCAGCTGCTGGGGAGGCTGACGCAGG
         430       440       450       460       470       480

410       420       430       440       450       460
WT 608 AGACTTGCTTGAACCCAGGAGGTGGAGGTTGCAGTGAGCTGAGATCGTGCCTAGGCGACA
       ::::::::::::::::::::::::::::::::::::::::::::::::::::::::::::
L8     AGACTTGCTTGAACCCAGGAGGTGGAGGTTGCAGTGAGCTGAGATCGTGCCTAGGCGACA
         490       500       510       520       530       540

470       480       490       500       510       520
WT 608 GAGCGAGACTCCATCCCAAAAAAAAAAAAAGAAAAGAAAGAGGCTGTATGTATAGTTCTT
       ::::::::::::::::::::::::::::::::::::::::::::::::::::::::::::
B)     GAGCGAGACTCCATCCCAAAAAAAAAAAAAGAAAAGAAAGAGGCTGTATGTATAGTTCTT
         550       560       570       580       590       600

530       540       550       560       570       580
WT 608 TCAGACTACAAGGCAGCAAAGTTCGTGCATGACTCGGGACTTAAAGTGGAATTAATTTCA
       ::::::::::::::::::::::::::::::::::::::::::::::::::::::::::::
L8     TCAGACTACAAGGCAGCAAAGTTCGTGCATGACTCGGGACTTAAAGTGGAATTAATTTCA
         610       620       630       640       650       660

590       600
WT 608 ATATAGCAGCCACTTTGACTTCCAC
       :::::::::::::::::::::::::
L8     ATATAGCAGCCACTTTGACTTCCAC
         670       680
```

Figure 14

```
WT  947 CACGGTAGAGAAGATGACTTCAAAAGCCCTTTTCATCCTAAAATTCTGATGTTTGATAAT
        ::::::::::::::::::::::::::::::::::::::::::::::::::::::::::::
C       CACGGTAGAGAAGATGACTTCAAAAGCCCTTTTCATCCTAAAATTCTGATGTTTGATAAT
                 10        20        30        40        50        60

70        80        90       100       110       120
WT  947 TAAATGTTATAGCATGGACACTGACATTTACATTTTTTACTTATGTTTTGGTTTTTAAA
        ::::::::::::::::::::::::::::::::::::::::::::::::::::::::::::
C       TAAATGTTATAGCATGGACACTGACATTTACATTTTTTACTTATGTTTTGGTTTTTAAA
                 70        80        90       100       110       120

130       140       150       160       170       180
WT  947 TGACTCTGCATTTTGTTTTAAGCTTCAAATTATTATTTGAATAATGAAATTCATCAGAAC
        ::::::::::::::::::::::::::::::::::::::::::::::::::::::::::::
C       TGACTCTGCATTTTGTTTTAAGCTTCAAATTATTATTTGAATAATGAAATTCATCAGAAC
                130       140       150       160       170       180

190       200       210       220       230       240
WT  947 AATTAGTGTTAAGAATCATATAGCAATTTATAGAAAAGGAAGAGTTCGTAGGTTATAAAT
        ::::::::::::::::::::::::::::::::::::::::::::::::::::::::::::
C       AATTAGTGTTAAGAATCATATAGCAATTTATAGAAAAGGAAGAGTTCGTAGGTTATAAAT
                190       200       210       220       230       240

250       260       270       280       290       300
WT  947 TCTGTTAGTTGCTAAGAAGCATTTTTAAAATTATGTACTATAGCTCTTTATTCAGCAGAC
        ::::::::::::::::::::::::::::::::::::::::::::::::::::::::::::
C)      TCTGTTAGTTGCTAAGAAGCATTTTTAAAATTATGTACTATAGCTCTTTATTCAGCAGAC
                250       260       270       280       290       300

310       320       330       340       350       360
WT  947 GAACCAATTACAATCTGTGTAACTAGAACACTTGACTAAAATTATATAATTTTTACAACG
        ::::::::::::::::::::::::::::::::::::::::::::::::::::::::::::
C       GAACCAATTACAATCTGTGTAACTAGAACACTTGACTAAAATTATATAATTTTTACAACG
                310       320       330       340       350       360

370       380       390       400       410       420
WT  947 CTTCACTGCATAGATACATGAACATAATTTATTTGTAATTGGAACAAAGCCCCAAAGTAG
        ::::::::::::::::::::::::::::::::::::::::::::::::::::::::::::
C       CTTCACTGCATAGATACATGAACATAATTTATTTGTAATTGGAACAAAGCCCCAAAGTAG
                370       380       390       400       410       420

430       440       450       460       470       480
WT  947 CAGTTTTGTTCTACCAGGTAATTAATGCTCATTTTTAAAGCCTTTTATTATTATTTCTGA
        ::::::::::::::::::::::::::::::::::::::::::::::::::::::::::::
C)      CAGTTTTGTTCTACCAGGTAATTAATGCTCATTTTTAAAGCCTTTTATTATTATTTCTGA
                430       440       450       460       470       480

490       500       510       520       530       540
WT  947 AGTAATGAGTGCACATGGAAAAAGACACATAATAGGCTAAACAATAAGCCCGTAAGCCAA
        ::::::::::::::::::::::::::::::::::::::::::::::::::::::::::::
C       AGTAATGAGTGCACATGGAAAAAGACACATAATAGGCTAAACAATAAGCCCGTAAGCCAA
                490       500       510       520       530       540

550       560       570       580       590       600
WT  947 GCCAACATATTCCAGGAACAAATCCTTGCCAACCTCTCAACCAGGATTTAACTTCTGCTT
        ::::::::::::::::::::::::::::::::::::::::::::::::::::::::::::
C       GCCAACATATTCCAGGAACAAATCCTTGCCAACCTCTCAACCAGGATTTAACTTCTGCTT
                550       560       570       580       590       600

610       620       630       640       650       660
WT  947 TTCCCCCATTTTCAAAAATTATAGCATGTATTTAAAGGCAGCAGAAGCCTTACTTTCAGG
        ::::::::::::::::::::::::::::::::::::::::::::::::::::::::::::
C       TTCCCCCATTTTCAAAAATTATAGCATGTATTTAAAGGCAGCAGAAGCCTTACTTTCAGG
                610       620       630       640       650       660

670       680       690       700       710       720
WT  947 TTTCCCTTACCCTTTCATTTCTTTTTGTTCAAAATAGGTAGTAATTGAAGTTTTAAATAT
        ::::::::::::::::::::::::::::::::::::::::::::::::::::::::::::
C       TTTCCCTTACCCTTTCATTTCTTTTTGTTCAAAATAGGTAGTAATTGAAGTTTTAAATAT
                670       680       690       700       710       720
```

Figure 15A

```
         730       740       750       760       770       780
WT 947 AGGGTATCATTTTTCTTTAAGAGTCATTTATCAATTTTCTTCTAACTTCAGGCCTAGAAA
       ::::::::::::::::::::::::::::::::::::::::::::::::::::::::::::
C      AGGGTATCATTTTTCTTTAAGAGTCATTTATCAATTTTCTTCTAACTTCAGGCCTAGAAA
         730       740       750       760       770       780

790       800       810       820       830       840
WT 947 GAAGTTTTGGGTAGGCTTTGTCTTACAGTGTTATTATTTATGAGTAAAACTAATTGGTTG
       ::::::::::::::::::::::::::::::::::::::::::::::::::::::::::::
C      GAAGTTTTGGGTAGGCTTTGTCTTACAGTGTTATTATTTATGAGTAAAACTAATTGGTTG
         790       800       810       820       830       840

850       860       870       880       890       900
WT 947 TCCTGCATACTTTAATTATGATGTAATACAGGTTCTGGGTTGACAAATATCAAGACGGAG
       ::::::::::::::::::::::::::::::::::::::::::::::::::::::::::::
C      TCCTGCATACTTTAATTATGATGTAATACAGGTTCTGGGTTGACAAATATCAAGACGGAG
         850       860       870       880       890       900

910       920       930       940
WT 947 GAGATCTCTGAAGTGAAGATGGATGCAGAATTCCGACATGACTCAGG
       :::::::::::::::::::::::: : :: ::  : :: :: :::::
C      GAGATCTCTGAAGTGAAGATGGATACGGAGTTTAGGCACGATTCAGG
```

Figure 15B

IRMUfw/Crev (PCR 1073 pb)

```
              10         20         30         40         50         60
WT 107 TGGATGCAGAATTCCGACATGACTCAGGATATGAAGTTCATCATCAAAAATTGGTACGTA
       ::::: : :: :: : :: :: :::::::::::::::::::::::::::::::::::::
D      TGGATACGGAGTTTAGGCACGATTCAGGATATGAAGTTCATCATCAAAAATTGGTACGTA
              10         20         30         40         50         60

70         80         90        100        110        120
WT 107 AAATAATTTACCTCTTTCCACTACTGTTTGTCTTGCCAAATGACCTATTAACTCTGGTTC
       :::::::::::::::::::::::      ::::::::::::::::::::::::::::::::
D      AAATAATTTACCTCTTTCCACTAGTGTTTGTCTTGCCAAATGACCTATTAACTCTGGTTC
              70         80         90        100        110        120
                         SpeI
             130        140        150        160        170        180
WT 107 ATCCTGTGCTAGAAATCAAATTAAGGAAAAGATAAAAATACAATGCTTGCCTATAGGATT
       ::::::::::::::::::::::::::::::::::::::::::::::::::::::::::::
D      ATCCTGTGCTAGAAATCAAATTAAGGAAAAGATAAAAATACAATGCTTGCCTATAGGATT
             130        140        150        160        170        180

190        200        210        220        230        240
WT 107 ACCATGAAAACATGAAGAAAATAAATAGGCTAGGCTGAGCGCAGTGGCTCAAGCCTGTAA
       ::::::::::::::::::::::::::::::::::::::::::::::::::::::::::::
D      ACCATGAAAACATGAAGAAAATAAATAGGCTAGGCTGAGCGCAGTGGCTCAAGCCTGTAA
             190        200        210        220        230        240

250        260        270        280        290        300
WT 107 TCCCAGCACTTTGGGAGGCCAAGGCGGGTGGATCACGAGGTCAGAAATTCGAGACCAGCC
       ::::::::::::::::::::::::::::::::::::::::::::::::::::::::::::
D      TCCCAGCACTTTGGGAGGCCAAGGCGGGTGGATCACGAGGTCAGAAATTCGAGACCAGCC
             250        260        270        280        290        300

310        320        330        340        350        360
WT 107 TGGCCAATATGGTGAAACCCCATCTCTACTAAAAATACAAAAAAGATTAGCTGGGTGTGG
       ::::::::::::::::::::::::::::::::::::::::::::::::::::::::::::
D      TGGCCAATATGGTGAAACCCCATCTCTACTAAAAATACAAAAAAGATTAGCTGGGTGTGG
             310        320        330        340        350        360

370        380        390        400        410        420
WT 107 TGGCAAACACCTGTAGTCCCAGCTGCTGGGGAGGCTGACGCAGGAGACTTGCTTGAACCC
       ::::::::::::::::::::::::::::::::::::::::::::::::::::::::::::
D      TGGCAAACACCTGTAGTCCCAGCTGCTGGGGAGGCTGACGCAGGAGACTTGCTTGAACCC
             370        380        390        400        410        420

430        440        450        460        470        480
WT 107 AGGAGGTGGAGGTTGCAGTGAGCTGAGATCGTGCCTAGGCGACAGAGCGAGACTCCATCC
       ::::::::::::::::::::::::::::::::::::::::::::::::::::::::::::
D      AGGAGGTGGAGGTTGCAGTGAGCTGAGATCGTGCCTAGGCGACAGAGCGAGACTCCATCC
             430        440        450        460        470        480

490        500        510        520        530        540
WT 107 CAAAAAAAAAAAGAAAAGAAAGAGGCTGTATGTATAGTTCTTTCAGACTACAAGGCAGC
       ::::::::::::::::::::::::::::::::::::::::::::::::::::::::::::
D      CAAAAAAAAAAAGAAAAGAAAGAGGCTGTATGTATAGTTCTTTCAGACTACAAGGCAGC
             490        500        510        520        530        540

550        560        570        580        590        600
WT 107 AAAGTTCGTGCATGACTCGGGACTTAAAGTGGAATTAATTTCAATATAGCAGCCACTTTG
       ::::::::::::::::::::::::::::::::::::::::::::::::::::::::::::
D      AAAGTTCGTGCATGACTCGGGACTTAAAGTGGAATTAATTTCAATATAGCAGCCACTTTG
             550        560        570        580        590        600

610        620        630        640        650        660
WT 107 ACTTCCACTGTGTTTTCTGGGAAAATAGGTTTACAATAGGTTTATTTGAAGGATCAAACA
       ::::::::::::::::::::::::::::::::::::::::::::::::::::::::::::
D      ACTTCCACTGTGTTTTCTGGGAAAATAGGTTTACAATAGGTTTATTTGAAGGATCAAACA
             610        620        630        640        650        660
```

Figure 16A

```
            670        680        690        700        710        720
WT  107 CATGCATACACTGCTTGGTTTTACAGAACACTTTATGTGGCTTAAATTCACATCCGGAAC
        ::::::::::::::::::::::::::::::::::::::::::::::::::::::::::::
D       CATGCATACACTGCTTGGTTTTACAGAACACTTTATGTGGCTTAAATTCACATCCGGAAC
            670        680        690        700        710        720

730        740        750        760        770        780
WT  107 TGTCTTCCTTTACCCATTCATTTCTCCCCCAGCTCTTTCTTTTCATTCCCTCCCCTACCT
        ::::::::::::::::::::::::::::::::::::::::::::::::::::::::::::
D       TGTCTTCCTTTACCCATTCATTTCTCCCCCAGCTCTTTCTTTTCATTCCCTCCCCTACCT
            730        740        750        760        770        780

790        800        810        820        830        840
WT  107 CCCATGATTTAACTTCTCTTGCAAGAGTAAGATCATGGAGTGAGCAGGACCCCATGATGT
        ::::::::::::::::::::::::::::::::::::::::::::::::::::::::::::
D       CCCATGATTTAACTTCTCTTGCAAGAGTAAGATCATGGAGTGAGCAGGACCCCATGATGT
            790        800        810        820        830        840

850        860        870        880        890        900
WT  107 TCCCGATAGTGTTATTCATCAAAAGGTTTGTGCAAAGAAGACAGCAGCTTCCTTTTCAGA
        ::::::::::::::::::::::::::::::::::::::::::::::::::::::::::::
D       TCCCGATAGTGTTATTCATCAAAAGGTTTGTGCAAAGAAGACAGCAGCTTCCTTTTCAGA
            850        860        870        880        890        900

910        920        930        940        950        960
WT  107 TGAAATCACTTTTCCCCCCTAATGTTAGAATTGGAGTAAATCAAAAAGCCACATCTCCTT
        ::::::::::::::::::::::::::::::::::::::::::::::::::::::::::::
D       TGAAATCACTTTTCCCCCCTAATGTTAGAATTGGAGTAAATCAAAAAGCCACATCTCCTT
            910        920        930        940        950        960

970        980        990       1000       1010       1020
WT  107 TGTGGTCAGCTCTAGTAGTTATATAAAATCCTTTACCAAAAGCTTAGAAATGGAGATAAA
        ::::::::::::::::::::::::::::::::::::::::::::::::::::::::::::
D       TGTGGTCAGCTCTAGTAGTTATATAAAATCCTTTACCAAAAGCTTAGAAATGGAGATAAA
            970        980        990       1000       1010       1020

1030       1040       1050       1060       1070
WT  107 TCAAATCGTGGATTATGTTAGGGTTCCATCTTATCAGTAGGTGCAGTAAGAGG
        ::::::::::::::::::::::::::::::::::::::::::::::::::::
D       TCAAATCGTGGATTATGTTAGGGTTCCATCTTATCAGTAGGTGCAGTAAGAGG
           1030       1040       1050       1060       1070
```

AATTGGTTGTCCTGCATACTTTAATTATGATGTAATACAGgttctgggttgacaaatatc
aagacggaggagatctctgaagtgaagatggatacggagtttaggcacgattcaggatat
gaagttcatcatcaaaaattgGTACGTAAAATAATTTACCTCTTTCCACTAGTGTTTGTC
TTGCCAAATGACCTATTAA

B

```
CNCTTGGGCANGNNNNNNNNNCNCTNTCACGAATCGACCGATTGTTAGGTAATCGTCACC
TCCACAAAGAGCGACTCGCTGTATCGCTCGAGGGATCCGAATTCAGGAGGTAAAAACCAT
GATATAGCAGAATTCCGACATGACTCAGGTTCAGCAGACGAACCAATTACAATCTGTGTA
ACTAGAACACTTGACTAAAATTATATAATTTTTACAACGCTTCACTGCATAGATACATGA
ACATAATTTATTTGTAATTGGAACAAAGCCCCAAAGTAGCAGTTTTGTTCTACCAGGTAA
TTAATGCTCATTTTTAAAGCCTTTTATTATTATTTCTGAAGTAATGAGTGCACATGGAAA
AAGACACATAATAGGCTAAACAATAAGCCCGTAAGCCAAGCCAACATATTCCAGGAACAA
ATCCTTGCCAACCTCTCAACCAGGATTTAACTTCTGCTTTTCCCCCATTTTCAAAAATTA
TAGCATGTATTTAAAGGCAGCAGAAGCCTTACTTTCAGGTTTCCTTACCCTTTCATTTCT
TTTGTTCAAATAGGTAGTAATTGAAGTTTAAATATAGGGTATCATTTTCTTTAAGAGTCA
TTTATCAATTTTCTTCTAACTTCAGGCCTAGAAAGAAGTTTTGGGTAGGCTTTGTCTTAC
AGTGTTATTATTTATGAGTAAAACTAATTGGTTGTCCTGCATACTTTAATTATGATGTAA
TACAGgttctgggttgacaaatatcaagacggaggagatctctgaagtgaagatggatac
ggagtttaggcacgattcaggatatgaagttcatcatcaaaaattggactacaaagacca
tgacggtgattataaagatcatgacatcgactacaaggatgacgatgncaagtgataaGT
ACGTAAAATAATTTACCTCTTTCCACTAGTGTTTGTCTTGCCAAATGACCTATTAANTCT
GGTTCATCCTGTGCTAGAAATCAAATTAAGGAAAAGATAAAAATACAATGCTTGCCTATA
GGATTACCATGAAAACATGAAGAAAATAAATAGGCTAGGCTGAGCGCAGTGGCTCAAGCC
TGTAATCCCAGCACTTTGGGAGGCCAAGGCGGGTGGATCACGAGGTCAGAAATTCGAGAC
CAGCCTGGCCAATATGGTGAAACCCCATCTNTACTAAAAATACAAAAAAGATTAGCTGGG
TGTGGTGGCAAACACCTGTAGTCCCAGCTGCTGGGGAGGCTGACGCAGGAGACTTGCTTG
AACCCAGGAGGTGGAGGTTGCAGTGAGCTGAGATCGTGCCTAGGNGACAGAGCGAGACTC
CATCCCAAAAAAAAAAAAGAAAAGAAAGAGGCTGTATGTATAGTTCTTTCAGACTACAA
GGCAGCAAAGTTCGTGCAGAATTCCGACATGACTCAGGACTGATAATAATGACGTCAGAA
TTCTCGAGTCGGGGAAATGTGCGCGGAACCCCTATTTGTTTATTTTCTAAANCATCAANN
GNANNTNNNNTNCCCCTCNNATG
```

Figure 18

```
CNCTTGGGCANGNNNNNNNNNNCNCTNTCACGAATCGACCGATTGTTAGGTAATCGTCACC
TCCACAAAGAGCGACTCGCTGTATCGCTCGAGGGATCCGAATTCAGGAGGTAAAAACCAT
GATATAGCAGAATTCCGACATGACTCAGGTTCAGCAGACGAACCAATTACAATCTGTGTA
ACTAGAACACTTGACTAAAATTATATAATTTTTACAACGCTTCACTGCATAGATACATGA
ACATAATTTATTTGTAATTGGAACAAAGCCCCAAAGTAGCAGTTTTGTTCTACCAGGTAA
TTAATGCTCATTTTTAAAGCCTTTTATTATTATTTCTGAAGTAATGAGTGCACATGGAAA
AAGACACATAATAGGCTAAACAATAAGCCCGTAAGCCAAGCCAACATATTCCAGGAACAA
ATCCTTGCCAACCTCTCAACCAGGATTTAACTTCTGCTTTTCCCCATTTTCAAAAATTA
TAGCATGTATTTAAAGGCAGCAGAAGCCTTACTTTCAGGTTTCCTTACCCTTTCATTTCT
TTTGTTCAAATAGGTAGTAATTGAAGTTTAAATATAGGGTATCATTTTCTTTAAGAGTCA
TTTATCAATTTTCTTCTAACTTCAGGCCTAGAAAGAAGTTTTGGGTAGGCTTTGTCTTAC
AGTGTTATTATTTATGAGTAAAACTAATTGGTTGTCCTGCATACTTTAATTATGATGTAA
TACAGgttctgggttgacaaatatcaagacggaggagatctctgaagtgaagatggatac
ggagtttaggcacgattcaggatatgaagttcatcatcaaaaattgGACTACAAAGACCA
TGACGGTGATTATAAAGATCATGACATCGACTACAAGGATGACGATGNCAAGGTACGTAA
AATAATTTACCTCTTTCCACTAGTGTTTGTCTTGCCAAATGACCTATTAANTCTGGTTCA
TCCTGTGCTAGAAATCAAATTAAGGAAAAGATAAAAATACAATGCTTGCCTATAGGATTA
CCATGAAAACATGAAGAAAATAAATAGGCTAGGCTGAGCGCAGTGGCTCAAGCCTGTAAT
CCCAGCACTTTGGGAGGCCAAGGCGGGTGGATCACGAGGTCAGAAATTCGAGACCAGCCT
GGCCAATATGGTGAAACCCCATCTNTACTAAAAATACAAAAAAGATTAGCTGGGTGTGGT
GGCAAACACCTGTAGTCCCAGCTGCTGGGGAGGCTGACGCAGGAGACTTGCTTGAACCCA
GGAGGTGGAGGTTGCAGTGAGCTGAGATCGTGCCTAGGNGACAGAGCGAGACTCCATCCC
AAAAAAAAAAAAGAAAAGAAAGAGGCTGTATGTATAGTTCTTTCAGACTACAAGGCAGC
AAAGTTCGTGCAGAATTCCGACATGACTCAGGACTGATAATAATGACGTCAGAATTCTCG
AGTCGGGGAAATGTGCGCGGAACCCCTATTTGTTTATTTTCTAAANCATCAANNGNANNT
NNNNTNCCCCTCNNATG
```

TTCAGCAGACGAACCAATTACAATCTGTGTAACTAGAACACTTGACTAAAATTATATAAT
      Bfw

TTTTACAACGCTTCACTGCATAGATACATGAACATAATTTATTTGTAATTGGAACAAAGC
CCCAAAGTAGCAGTTTTGTTCTACCAGGTAATTAATGCTCATTTTTAAAGCCTTTTATTA
TTATTTCTGAAGTAATGAGTGCACATGGAAAAAGACACATAATAGGCTAAACAATAAGCC
CGTAAGCCAAGCCAACATATTCCAGGAACAAATCCTTGCCAACCTCTCAACCAGGATTTA
ACTTCTGCTTTTCCCCCATTTTCAAAAATTATAGCATGTATTTAAAGGCAGCAGAAGCCT
TACTTTCAGGTTTCCCTTACCCTTTCATTTCTTTTTGTTCAAAATAGGTAGTAATTGAAG
TTTTAAATATAGGGTATCATTTTTCTTTAAGAGTCATTTATCAATTTTCTTCTAACTTCa
                                                                     gBlockfw ggcttAGAAAGAAGTTTTGGGTAGGCTTTGTCTTACAGTGTTATTATTTATGAGTAAAAC
TAATTGGTTGTCCTGCATACTTTAATTATGATGTAATACAGGTTCTGGGTTGACAAATAT
CAAGACGGAGGAGATCTCTGAAGTGAAGATGGATgCaGAaTTccGaCAtGAcTCAGGATA TGAAGTTCATCATCAAAAATTGGTACGTAAAATAATTTACCTCTTTCCACTAcTGTTTGT
CTTGCCAAATGACCTATTAACTCTGGTTCATCCTGTGCTAGAAATCAAATTAAGGAAAAG
ATAAAAATACAATGCTTGCCTATAGGATTACCATGAAAACATGAAGAAAATAAATAGGCT
AGGCTGAGCGCAGTGGCTCAAGCCTGTAATCccagcactttgggaggcCAAGGCGGGTGG
                                                                    GBlockrev ATCACGAGGTCAGAAATTCGAGACCAGCCTGGCCAATATGGTGAAACCCCATCTCTACTA
AAAATACAAAAAAGATTAGCTGGGTGTGGTGGCAAACACCTGTAGTCCCAGCTGCTGGGG
AGGCTGACGCAGGAGACTTGCTTGAACCCAGGAGGTGGAGGTTGCAGTGAGCTGAGATCG
TGCCTAGGCGACAGAGCGAGACTCCATCCCAAAAAAAAAAAAAGAAAAGAAAGAGGCTGT
ATGTATAGTTCTTTCAGACTACAAGGCAGCAAAGTTCGTG
                             Brev

B

ATCAATTTTCTTCTAACTTCAGGCCTAGAAAGAAGTTTTGGGTAGGCTTTGTCTTACAGT
GTTATTATTTATGAGTAAAACTAATTGGTTGTCCTGCATACTTTAATTATGATGTAATAC
AGgttctgggttgacaaatatcaagacggaggagatctctgaagtgaagatggatacgga
gtttaggcacgattcaggatatgaagttcatcatcaaaaattgGTACGTAAAATAATTTA
CCTCTTTCCACTAgTGTTTGTCTTGCCAAATGACCTATTAACTCTGGTTCATCCTGTGCT
AGAAATCAAATTAAGGAAAAGATAAAAATACAATGCTTGCCTATAGGATTACCATGAAAA
CATGAAGAAAATAAATAGGCTAGGCTGAGCGCAGTGGCTCAAGCCTGTAATCCCAGCACT
TTGGGAGGCCAAGGCGGGTGG

*CAGAATTCCGACATGACTCAGG*TTCAGCAGACGAACCAATTACAATCTGTGTAACTAGAA
　*gRNA#8 target site*　　　　Bfw CACTTGACTAAAATTATATAATTTTTACAACGCTTCACTGCATAGATACATGAACATAAT
TTATTTGTAATTGGAACAAAGCCCCAAAGTAGCAGTTTTGTTCTACCAGGTAATTAATGC
TCATTTTTAAAGCCTTTTATTATTATTTCTGAAGTAATGAGTGCACATGGAAAAAGACAC
ATAATAGGCTAAACAATAAGCCCGTAAGCCAAGCCAACATATTCCAGGAACAAATCCTTG
CCAACCTCTCAACCAGGATTTAACTTCTGCTTTTCCCCCATTTTCAAAAATTATAGCATG
TATTTAAAGGCAGCAGAAGCCTTACTTTCAGGTTTCCCTTACCCTTTCATTTCTTTTTGT
TCAAAATAGGTAGTAATTGAAGTTTTAAATATAGGGTATCATTTTTCTTTAAGAGTCATT
TATCAATTTTCTTCTAACTTCAGGCCTAGAAAGAAGTTTTGGGTAGGCTTTGTCTTACAG
TGTTATTATTTATGAGTAAAACTAATTGGTTGTCCTGCATACTTTAATTATGATGTAATA
CAGgttctgggttgacaaatatcaagacggaggagatctctgaagtgaagatggatacgg
agtttaggcacgattcaggatatgaagttcatcatcaaaaattgGTACGTAAAATAATTT
ACCTCTTTCCACTAgTGTTTGTCTTGCCAAATGACCTATTAACTCTGGTTCATCCTGTGC
TAGAAATCAAATTAAGGAAAAGATAAAAATACAATGCTTGCCTATAGGATTACCATGAAA
ACATGAAGAAAATAAATAGGCTAGGCTGAGCGCAGTGGCTCAAGCCTGTAATCCCAGCAC
TTTGGGAGGCCAAGGCGGGTGGATCACGAGGTCAGAAATTCGAGACCAGCCTGGCCAATA
TGGTGAAACCCCATCTCTACTAAAAATACAAAAAAGATTAGCTGGGTGTGGTGGCAAACA
CCTGTAGTCCCAGCTGCTGGGGAGGCTGACGCAGGAGACTTGCTTGAACCCAGGAGGTGG
AGGTTGCAGTGAGCTGAGATCGTGCCTAGGCGACAGAGCGAGACTCCATCCCAAAAAAAA
AAAAAGAAAAGAAAGAGGCTGTATGTATAGTTCTTTCAGACTACAAGGCAGCAAAGTTCG
　　　　　　　　　　　　　　　　　　　　　　　　　　　　Brev TG*CAGAATTCCGACATGACTCAGG*
　　*gRNA#8 target site*

ATCAATTTTCTTCTAACTTCAGGCCTAGAAAGAAGTTTTGGGTAGGCTTTGTCTTACAGT
GTTATTATTTATGAGTAAAACTAATTGGTTGTCCTGCATACTTTAATTATGATGTAATAC
AGgttctggttgacaaatatcaagacggaggagatctctgaagtgaagatggatacgga
gtttaggcacgattcaggatatgaagttcatcatcaaaaattg<u>gactacaaagaccatga
cggtgattataaagatcatgacatcgactacaaggatgacgatgacaag</u>GTACGTAAAAT
AATTTACCTCTTTCCACTAgTGTTTGTCTTGCCAAATGACCTATTAACTCTGGTTCATCC
TGTGCTAGAAATCAAATTAAGGAAAAGATAAAAATACAATGCTTGCCTATAGGATTACCA
TGAAAACATGAAGAAAATAAATAGGCTAGGCTGAGCGCAGTGGCTCAAGCCTGTAATCCC
AGCACTTTGGGAGGCCAAGGCGGGTGG

B

ATCAATTTTCTTCTAACTTCAGGCCTAGAAAGAAGTTTTGGGTAGGCTTTGTCTTACAGT
GTTATTATTTATGAGTAAAACTAATTGGTTGTCCTGCATACTTTAATTATGATGTAATAC
AGgttctggttgacaaatatcaagacggaggagatctctgaagtgaagatggatacgga
gtttaggcacgattcaggatatgaagttcatcatcaaaaattggactacaaagaccatga
cggtgattataaagatcatgacatcgactacaaggatgacgatgacaagtgataaGTACG
TAAAATAATTTACCTCTTTCCACTAGTGTTTGTCTTGCCAAATGACCTATTAACTCTGGT
TCATCCTGTGCTAGAAATCAAATTAAGGAAAAGATAAAAATACAATGCTTGCCTATAGGA
TTACCATGAAAACATGAAGAAAATAAATAGGCTAGGCTGAGCGCAGTGGCTCAAGCCTGT
AATCCCAGCACTTTGGGAGGCCAAGGCGGGTGG

C

GGGTNGGCCCCGAACNNNCNNTAATAACGATCGACCGATTGTTAGGTAATCGTCACCTCC
ACAAAGAGCGACTCGCTGTATCGCTCGAGGGATCCGAATTCAGGAGGTAAAAACCATGAT
ATAGCAGAATTCCGACATGACTCAGGTTCAGCAGACGAACCAATTACAATCTGTGTAACT
AGAACACTTGACTAAAATTATATAATTTTTACAACGCTTCACTGCATAGATACATGAACA
TAATTTATTTGTAATTGGAACAAAGCCCCAAAGTAGCAGTTTTGTTCTACCAGGTAATTA
ATGCTCATTTTTAAAGCCTTTTATTATTATTTCTGAAGTAATGAGTGCACATGGAAAAAG
ACACATAATAGGCTAAACAATAAGCCCGTAAGCCAAGCCAACATATTCCAGGAACAAATC
CTTGCCAACCTCTCAACCAGGATTTAACTTCTGCTTTTCCCCCATTTTCAAAAATTATAG
CATGTATTTAAAGGCAGCAGAAGCCTTACTTTCAGGTTTCCCTTACCCTTTCATTTCTTT
TGTTCAAAATAGGTAGTAATTGAAGTTTTAAATATAGGGTATCATTTTCTTTAAGAGTCA
TTTATCAATTTTCTTCTAACTTCAGGCCTAGAAAGAAGTTTTGGGTAGGCTTTGTCTTAC
AGTGTTATTATTTATGAGTAAAACTAATTGGTTGTCCTGCATACTTTAATTATGATGTAA
TACAGGTTCTGGGTTGACAAATATCAAGACGGAGGAGATCTCTGAAGTGAAGATGGATAC
GGAGTTTAGGCACGATTCAGGATATGAAGTTCATCATCAAAAATTGGACTACAAAGACCA
TGACTGTGATTATAAAGATCATGACATCGACTNCAAGGATGACGATGACAAGTGATAAGT
ACGTAAAATAATTTACCTCTTTCCACTAGTGTTTGTCTTGCCAAATGACCTATTAACTCT
GGTTCATCCTGTGCTAGAAATCAAATTAAGGAAAAGATAAAAATACAATGCTTGCCTATA
GGATTACCATGAAAACATGAAGAAAATAAATAGGCTAGGCTGAGCGCAGTGGCTCAAGCC
TGTAATCCCAGCACTTTGGGAGGCCAAGGCGGGTGGATCACGAGGTCAGAAATTCGAGAC
CAGCCTGGCCAATATGGTGAAACCCCATCTCTACTAAAAATACAAAAAAGATTAGCTGGG
TGTGGTGGCAAACACCTGTAGTCCCAGCTGCTGGGAGGCTGACGCAGGAGACTTGCTTG
AACCCAGGAGGTGGAGGTTGCAGTGAGCTGAGATCGTGCCTAGGCGACAGAGCGAGACTC
CATCCCAAAAAAAAAAAAGAAAAGAAAGAGGCTGTATGTATAGTTCTTTCAGAC<u>TACAA
GGCAGCAAAGTTCGTG</u>CAGAATTCCGACATGACTCAGGACTGATAATAATGACGTCAGAA
TTCTCGAGTCGGGGAATGTGCGCGGAACCCCTATTTGTTTATTTCTAAANCATCAANGG

GGGTNGGCCCCGAACNNNCNNTAATAACGATCGACCGATTGTTAGGTAATCGTCACCTCCA
CAAAGAGCGACTCGCTGTATCGCTCGAGGGATCCGAATTCAGGAGGTAAAAACCATGATAT
AGCAGAATTCCGACATGACTCAGG<u>TTCAGCAGACGAACCAATTACA</u>ATCTGTGTAACTAGA
ACACTTGACTAAAATTATATAATTTTTACAACGCTTCACTGCATAGATACATGAACATAATTTA
TTTGTAATTGGAACAAAGCCCCAAAGTAGCAGTTTTGTTCTACCAGGTAATTAATGCTCATTT
TTAAAGCCTTTTATTATTATTTCTGAAGTAATGAGTGCACATGGAAAAAGACACATAATAGGC
TAAACAATAAGCCCGTAAGCCAAGCCAACATATTCCAGGAACAAATCCTTGCCAACCTCTCA
ACCAGGATTTAACTTCTGCTTTTCCCCCATTTTCAAAAATTATAGCATGTATTTAAAGGCAGC
AGAAGCCTTACTTTCAGGTTTCCCTTACCCTTTCATTTCTTTTGTTCAAAATAGGTAGTAATT
GAAGTTTTAAATATAGGGTATCATTTTCTTTAAGAGTCATTTATCAATTTTCTTCTAACTTCAG
GCCTAGAAAGAAGTTTTGGGTAGGCTTTGTCTTACAGTGTTATTATTTATGAGTAAAACTAAT
TGGTTGTCCTGCATACTTTAATTATGATGTAATACAGGTTCTGGGTTGACAAATATCAAGAC
GGAGGAGATCTCTGAAGTGAAGATGGATACGGAGTTTAGGCACGATTCAGGATATGAAGTT
CATCATCAAAAATTGGACTACAAAGACCATGACTGTGATTATAAAGATCATGACATCGACTN
CAAGGATGACGATGACAAGTGATAAGTACGTAAAATAATTTACCTCTTTCCACTAGTGTTTG
TCTTGCCAAATGACCTATTAACTCTGGTTCATCCTGTGCTAGAAATCAAATTAAGGAAAAGAT
AAAAATACAATGCTTGCCTATAGGATTACCATGAAAACATGAAGAAAATAAATAGGCTAGGC
TGAGCGCAGTGGCTCAAGCCTGTAATCCCAGCACTTTGGGAGGCCAAGGCGGGTGGATCA
CGAGGTCAGAAATTCGAGACCAGCCTGGCCAATATGGTGAAACCCCATCTCTACTAAAAAT
ACAAAAAAGATTAGCTGGGTGTGGTGGCAAACACCTGTAGTCCCAGCTGCTGGGGAGGCT
GACGCAGGAGACTTGCTTGAACCCAGGAGGTGGAGGTTGCAGTGAGCTGAGATCGTGCCT
AGGCGACAGAGCGAGACTCCATCCCAAAAAAAAAAAAAGAAAAGAAAGAGGCTGTATGTAA
GTTCTTTCAGA<u>CTACAACAAAGTTCGTG</u>CAGAATTCCGACATGACTCAGGACTGATAATAAT
GACGTCAGAATTCTCGAGTCGGGGAAATGTGCGCGGAACCCCTATTTGTTTATTTCTAAAN
CATCAANGGGTTAANANNNANNNNNNNNNG

A
gagggcctatttcccatgattccttcatatttgcatatacgatacaaggctgttagagagataat
tggaattaatttgactgtaaacacaaagatattagtacaaaatacgtgacgtagaaagtaataat
ttcttgggtagtttgcagttttaaaattatgttttaaaatggactatcatatgcttaccgtaact
tgaaagtatttcgatttcttggctttatatatcttGTGGAAAGGACGAAACACCggGTCTTCgaG
AAGACctgttttagagctaGAAAtagcaagttaaaataaggctagtccgttatcaacttgaaaaa
gtggcaccgagtcggtgcTTTTTTgttttagagctagaaatagcaagttaaaataaggctagtcc
gtTTTTagcgcgtgcgccaattctgcagacaaatggctctagaggtacccgttacataacttacg
gtaaatggcccgcctggctgaccgcccaacgaccccccgcccattgacgtcaatagtaacgccaat
agggactttccattgacgtcaatgggtggagtatttacggtaaactgcccacttggcagtacatc
aagtgtatcatatgccaagtacgccccctattgacgtcaatgacggtaaatggcccgcctggcat
tGtgcccagtacatgaccttatgggactttcctacttggcagtacatctacgtattagtcatcgc
tattaccatggtcgaggtgagccccacgttctgcttcactctcccatctccccccctccccac
ccccaattttgtatttatttattttttaattattttgtgcagcgatggggcggggggggggggg
gggcgcgcgccaggcggggcggggcggggcgaggggcggggcggggcgaggcggagaggtgcggc
ggcagccaatcagagcggcgcgctccgaaagtttccttttatggcgaggcggcggcggcggcggc
cctataaaaagcgaagcgcgcggcgggcgggagtcgctgcgacgctgccttcgcccgtgccccg
ctccgccgccgcctcgcgccgcccgccccggctctgactgaccgcgttactcccacaggtgagcg
ggcgggacggcccttctcctccgggctgtaattagctgagcaagaggtaagggtttaagggatgg
ttggttggtggggtattaatgtttaattacctggagcacctgcctgaaatcacttttttttcaggt
tGGaccggtgccacc**ATGGACTATAAGGACCACGACGGAGACTACAAGGATCATGATATTGATTA
CAAAGACGATGACGATAAGATGGCCCCAAAGAAGAAGCGGAAGGTC**GGTATCCACGGAGTCCCAG
CAGCCGACAAGAAGTACAGCATCGGCCTGGACATCGGCACCAACTCTGTGGGCTGGGCCGTGATC
ACCGACGAGTACAAGGTGCCCAGCAAGAAATTCAAGGTGCTGGGCAACACCGACCGGCACAGCAT
CAAGAAGAACCTGATCGGAGCCCTGCTGTTCGACAGCGGCGAAACAGCCGAGGCCACCCGGCTGA
AGAGAACCGCCAGAAGAAGATACACCAGACGGAAGAACCGGATCTGCTATCTGCAAGAGATCTTC
AGCAACGAGATGGCCAAGGTGGACGACAGCTTCTTCCACAGACTGGAAGAGTCCTTCCTGGTGGA
AGAGGATAAGAAGCACGAGCGGCACCCCATCTTCGGCAACATCGTGGACGAGGTGGCCTACCACG
AGAAGTACCCCACCATCTACCACCTGAGAAAGAAACTGGTGGACAGCACCGACAAGGCCGACCTG
CGGCTGATCTATCTGGCCCTGGCCCACATGATCAAGTTCCGGGGCCACTTCCTGATCGAGGGCGA
CCTGAACCCCGACAACAGCGACGTGGACAAGCTGTTCATCCAGCTGGTGCAGACCTACAACCAGC
TGTTCGAGGAAAACCCCATCAACGCCAGCGGCGTGGACGCCAAGGCCATCCTGTCTGCCAGACTG
AGCAAGAGCAGACGGCTGGAAAATCTGATCGCCCAGCTGCCCGGCGAGAAGAAGAATGGCCTGTT
CGGAAACCTGATTGCCCTGAGCCTGGGCCTGACCCCCAACTTCAAGAGCAACTTCGACCTGGCCG
AGGATGCCAAACTGCAGCTGAGCAAGGACACCTACGACGACGACCTGGACAACCTGCTGGCCCAG
ATCGGCGACCAGTACGCCGACCTGTTTCTGGCCGCCAAGAACCTGTCCGACGCCATCCTGCTGAG
CGACATCCTGAGAGTGAACACCGAGATCACCAAGGCCCCCCTGAGCGCCTCTATGATCAAGAGAT
ACGACGAGCACCACCAGGACCTGACCCTGCTGAAAGCTCTCGTGCGGCAGCAGCTGCCTGAGAAG
TACAAAGAGATTTTCTTCGACCAGAGCAAGAACGGCTACGCCGGCTACATTGACGGCGGAGCCAG
CCAGGAAGAGTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGGCAGCATCCCC
CACCAGATCCACCTGGGAGAGCTGCACGCCATTCTGCGGCGGCAGGAAGATTTTTACCCATTCCT

Figure 23A - 1

```
GAAGGACAACCGGGAAAAGATCGAGAAGATCCTGACCTTCCGCATCCCCTACTACGTGGGCCCTC
TGGCCAGGGGAAACAGCAGATTCGCCTGGATGACCAGAAAGAGCGAGGAAACCATCACCCCTGG
AACTTCGAGGAAGTGGTGGACAAGGGCGCTTCCGCCCAGAGCTTCATCGAGCGGATGACCAACTT
CGATAAGAACCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGCCTTCCTGAGC
GGCGAGCAGAAAAAGGCCATCGTGGACCTGCTGTTCAAGACCAACCGGAAAGTGACCGTGAAGCA
GCTGAAAGAGGACTACTTCAAGAAAATCGAGTGCTTCGACTCCGTGGAAATCTCCGGCGTGGAAG
ATCGGTTCAACGCCTCCCTGGGCACATACCACGATCTGCTGAAAATTATCAAGGACAAGGACTTC
CTGGACAATGAGGAAAACGAGGACATTCTGGAAGATATCGTGCTGACCCTGACACTGTTTGAGGA
CAGAGAGATGATCGAGGAACGGCTGAAAACCTATGCCCACCTGTTCGACGACAAAGTGATGAAGC
AGCTGAAGCGGCGGAGATACACCGGCTGGGGCAGGCTGAGCCGGAAGCTGATCAACGGCATCCGG
GACAAGCAGTCCGGCAAGACAATCCTGGATTTCCTGAAGTCCGACGGCTTCGCCAACAGAAACTT
CATGCAGCTGATCCACGACGACAGCCTGACCTTTAAAGAGGACATCCAGAAAGCCCAGGTGTCCG
GCCAGGGCGATAGCCTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGGCACAAGCCCGAGAA
CATCGTGATCGAAATGGCCAGAGAGAACCAGACCACCCAGAAGGGACAGAAGAACAGCCGCGAGA
GAATGAAGCGGATCGAAGAGGGCATCAAAGAGCTGGGCAGCCAGATCCTGAAAGAACACCCCGTG
GAAAACACCCAGCTGCAGAACGAGAAGCTGTACCTGTACTACCTGCAGAATGGGCGGGATATGTA
CGTGGACCAGGAACTGGACATCAACCGGCTGTCCGACTACGATGTGGACCATATCGTGCCTCAGA
GCTTTCTGAAGGACGACTCCATCGACAACAAGGTGCTGACCAGAAGCGACAAGAACCGGGGCAAG
AGCGACAACGTGCCCTCCGAAGAGGTCGTGAAGAAGATGAAGAACTACTGGCGGCAGCTGCTGAA
CGCCAAGCTGATTACCCAGAGAAAGTTCGACAATCTGACCAAGGCCGAGAGAGGCGGCCTGAGCG
AACTGGATAAGGCCGGCTTCATCAAGAGACAGCTGGTGGAAACCCGGCAGATCACAAAGCACGTG
GCACAGATCCTGGACTCCCGGATGAACACTAAGTACGACGAGAATGACAAGCTGATCCGGGAAGT
GAAAGTGATCACCCTGAAGTCCAAGCTGGTGTCCGATTTCCGGAAGGATTTCCAGTTTTACAAAG
TGCGCGAGATCAACAACTACCACCACGCCCACGACGCCTACCTGAACGCCGTCGTGGGAACCGCC
CTGATCAAAAAGTACCCTAAGCTGGAAAGCGAGTTCGTGTACGGCGACTACAAGGTGTACGACGT
GCGGAAGATGATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGGAAGCGGCCT
CTGATCGAGACAAACGGCGAAACCGGGGAGATCGTGTGGGATAAGGGCCGGGATTTTGCCACCGT
GCGGAAAGTGCTGAGCATGCCCCAAGTGAATATCGTGAAAAAGACCGAGGTGCAGACAGGCGGCT
TCAGCAAAGAGTCTATCCTGCCCAAGAGGAACAGCGATAAGCTGATCGCCAGAAAGAAGGACTGG
GACCCTAAGAAGTACGGCGGCTTCGACAGCCCCACCGTGGCCTATTCTGTGCTGGTGGTGGCCAA
AGTGGAAAAGGGCAAGTCCAAGAAACTGAAGAGTGTGAAAGAGCTGCTGGGGATCACCATCATGG
AAAGAAGCAGCTTCGAGAAGAATCCCATCGACTTTCTGGAAGCCAAGGGCTACAAAGAAGTGAAA
AAGGACCTGATCATCAAGCTGCCTAAGTACTCCCTGTTCGAGCTGGAAAACGGCCGGAAGAGAAT
GCTGGCCTCTGCCGGCGAACTGCAGAAGGGAAACGAACTGGCCCTGCCCTCCAAATATGTGAACT
TCCTGTACCTGGCCAGCCACTATGAGAAGCTGAAGGGCTCCCCCGAGGATAATGAGCAGAAACAG
CTGTTTGTGGAACAGCACAAGCACTACCTGGACGAGATCATCGAGCAGATCAGCGAGTTCTCCAA
GAGAGTGATCCTGGCCGACGCTAATCTGGACAAAGTGCTGTCCGCCTACAACAAGCACCGGGATA
```

Figure 23A-2

AGCCCATCAGAGAGCAGGCCGAGAATATCATCCACCTGTTTACCCTGACCAATCTGGGAGCCCCT
GCCGCCTTCAAGTACTTTGACACCACCATCGACCGGAAGAGGTACACCAGCACCAAAGAGGTGCT
GGACGCCACCCTGATCCACCAGAGCATCACCGGCCTGTACGAGACACGGATCGACCTGTCTCAGC
TGGGAGGCGACAAAAGGCCGGCGGCCACGAAAAAGGCCGGCCAGGCAAAAAGAAAAAGtaagaa
ttcCTAGAGCTCGCTGATCAGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGACAGCA
AGGGGGAGGATTGGGAAGAgAATAGCAGGCATGCTGGGGAgcggccgcaggaacccctagtgatg
gagttggccactccctctctgcgcgctcgctcgctcactgaggccgggcgaccaaaggtcgcccg
acgcccgggctttgcccgggcggcctcagtgagcgagcgagcgcgcagctgcctgcaggggcgcc
tgatgcggtattttctccttacgcatctgtgcggtatttcacaccgcatacgtcaaagcaaccat
agtacgcgccctgtagcggcgcattaagcgcggcgggtgtggtggttacgcgcagcgtgaccgct
acacttgccagcgccctagcgcccgctcctttcgcttccttccttcctttctcgccacgttcgc
cggctttccccgtcaagctctaaatcggggctcccttttagggttccgatttagtgctttacggc
acctcgaccccaaaaaacttgatttgggtgatggttcacgtagtgggccatcgccctgatagacg
gtttttcgccctttgacgttggagtccacgttctttaatagtggactcttgttccaaactggaac
aacactcaaccctatctcgggctattcttttgatttataagggattttgccgatttcggcctatt
ggttaaaaaatgagctgatttaacaaaaatttaacgcgaattttaacaaaatattaacgtttaca
attttatggtgcactctcagtacaatctgctctgatgccgcatagttaagccagccccgacaccc
gccaacacccgctgacgcgccctgacgggcttgtctgctcccggcatccgcttacagacaagctg
tgaccgtctccgggagctgcatgtgtcagaggttttcaccgtcatccgaaacgcgcgagacga
aagggcctcgtgatacgcctattttataggttaatgtcatgataataatggtttcttagacgtc
aggtggcacttttcggggaaatgtgcgcggaaccccatttgtttattttctaaatacattcaa
atatgtatccgctcatgagacaataaccctgataaatgcttcaataatattgaaaaaggaagagt
atgagtattcaacatttccgtgtcgcccttattccctttttgcggcattttgccttcctgtttt
tgctcacccagaaacgctggtgaaagtaaaagatgctgaagatcagttgggtgcacgagtgggtt
acatcgaactggatctcaacagcggtaagatccttgagagttttcgccccgaagaacgttttcca
atgatgagcacttttaaagttctgctatgtggcgcggtattatcccgtattgacgccgggcaaga
gcaactcggtcgccgcatacactattctcagaatgacttggttgagtactcaccagtcacagaaa
agcatcttacggatggcatgacagtaagagaattatgcagtgctgccataaccatgagtgataac
actgcggccaacttacttctgacaacgatcggaggaccgaaggagctaaccgcttttttgcacaa
catggggatcatgtaactcgccttgatcgttgggaaccggagctgaatgaagccataccaaacg
acgagcgtgacaccacgatgcctgtagcaatggcaacaacgttgcgcaaactattaactggcgaa
ctacttactctagcttcccggcaacaattaatagactggatggaggcggataaagttgcaggacc
acttctgcgctcggcccttccggctggctggtttattgctgataaatctggagccggtgagcgtg
ggaagccgcggtatcattgcagcactggggccagatggtaagccctcccgtatcgtagttatctac
acgacggggagtcaggcaactatggatgaacgaaatagacagatcgctgagataggtgcctcact
gattaagcattggtaactgtcagaccaagtttactcatatatactttagattgatttaaaacttc
atttttaatttaaaaggatctaggtgaagatcctttttgataatctcatgaccaaaatcccttaa
cgtgagttttcgttccactgagcgtcagaccccgtagaaaagatcaaaggatcttcttgagatcc
ttttttctgcgcgtaatctgctgcttgcaaacaaaaaaaccaccgctaccagcggtggtttgtt
tgccggatcaagagctaccaactctttttccgaaggtaactggcttcagcagagcgcagatacca
aatactgtccttctagtgtagccgtagttaggccaccacttcaagaactctgtagcaccgcctac

Figure 23A-3

```
Atacctcgctctgctaatcctgttaccagtggctgctgccagtggcgataagtcgtgtcttaccg
ggttggactcaagacgatagttaccggataaggcgcagcggtcgggctgaacgggggttcgtgc
acacagcccagcttggagcgaacgacctacaccgaactgagatacctacagcgtgagctatgaga
aagcgccacgcttcccgaagggagaaaggcggacaggtatccggtaagcggcagggtcggaacag
gagagcgcacgagggagcttccaggggggaaacgcctggtatctttatagtcctgtcgggtttcgc
cacctctgacttgagcgtcgattttgtgatgctcgtcaggggggcggagcctatggaaaaacgc
cagcaacgcggcctttttacggttcctggcctttttgctggccttttgctcacatgt
```

B

MDYKDHDGDYKDHDIDYKDDDDKMAPKKRKVGIHGVPAADKKYSIGLDIGTNSVGWAVITDE
YKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLA
LAHMIKFRGHFLIEGDLNPDNSDVDKLFIQLVQTYNQLFEENPINASGVDAKAILSARLSKSRRLEN
LIAQLPGEKKNGLFGNLIALSLGLTPNFKSNFDLAEDAKLQLSKDTYDDDLDNLLAQIGDQYADLFL
AAKNLSDAILLSDILRVNTEITKAPLSASMIKRYDEHHQDLTLLKALVRQQLPEKYKEIFFDQSKNG
YAGYIDGGASQEEFYKFIKPILEKMDGTEELLVKLNREDLLRKQRTFDNGSIPHQIHLGELHAILRR
QEDFYPFLKDNREKIEKILTFRIPYYVGPLARGNSRFAWMTRKSEETITPWNFEEVVDKGASAQSF
IERMTNFDKNLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIKDKDFLDNEENEDILEDIVLTLTL
FEDREMIEERLKTYAHLFDDKVMKQLKRRRYTGWGRLSRKLINGIRDKQSGKTILDFLKSDGFAN
RNFMQLIHDDSLTFKEDIQKAQVSGQGDSLHEHIANLAGSPAIKKGILQTVKVVDELVKVMGRHKP
ENIVIEMARENQTTQKGQKNSRERMKRIEEGIKELGSQILKEHPVENTQLQNEKLYLYYLQNGRD
MYVDQELDINRLSDYDVDHIVPQSFLKDDSIDNKVLTRSDKNRGKSDNVPSEEVVKKMKNYWRQ
LLNAKLITQRKFDNLTKAERGGLSELDKAGFIKRQLVETRQITKHVAQILDSRMNTKYDENDKLIR
EVKVITLKSKLVSDFRKDFQFYKVREINNYHHAHDAYLNAVVGTALIKKYPKLESEFVYGDYKVYD
VRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPKYSLFELENGRKRMLASAG
ELQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDKRPAATKKAGQAKKKK

Figures 23A-4 and 23B

```
gagggcctatttcccatgattccttcatatttgcatatacgatacaaggctgttagagagataattggaattaatttg
actgtaaacacaaagatattagtacaaaatacgtgacgtagaaagtaataatttcttgggtagtttgcagttttaaaa
ttatgttttaaaatggactatcatatgcttaccgtaacttgaaagtatttcgatttcttggctttatatatcttGTGG
AAAGGACGAAACACCggGTCTTCgaGAAGACctgttttagagctaGAAAtagcaagttaaaataaggctagtccgtta
tcaacttgaaaaagtggcaccgagtcggtgcTTTTTTgttttagagctagaaatagcaagttaaaataaggctagtcc
gtTTTTagcgcgtgcgccaattctgcagacaaatggctctagaggtacccgttacataacttacggtaaatggcccgc
ctggctgaccgcccaacgaccccgcccattgacgtcaatagtaacgccaatagggactttccattgacgtcaatggg
tggagtatttacggtaaactgcccacttggcagtacatcaagtgtatcatatgccaagtacgccccctattgacgtca
atgacggtaaatggcccgcctggcattGtgcccagtacatgaccttatgggactttcctacttggcagtacatctacg
tattagtcatcgctattaccatggtcgaggtgagccccacgttctgcttcactctccccatctcccccccctcccac
ccccaatttttgtatttatttattttttaattattttgtgcagcgatggggcgggggggggggggggcgcgcgccag
gcggggcggggcggggcgaggggcggggcggggcgaggcggagaggtgcggcggcagccaatcagagcggcgcgctcc
gaaagtttcctttatggcgaggcggcggcggcggccctataaaaagcgaagcgcgcggcgggcgggagtcgctg
cgacgctgccttcgccccgtgcccgctccgcccgcctcgcgcgcccgccccggctctgactgaccgcgttactc
ccacaggtgagcgggcgggacggcccttctcctccgggctgtaattagctgagcaagaggtaagggtttaagggatgg
ttggttggtggggtattaatgtttaattacctggagcacctgcctgaaatcacttttttttcaggttGGaccggtgcca
ccATGGACTATAAGGACCACGACGGAGACTACAAGGATCATGATATTGATTACAAAGACGATGACGATAAGATGGCCC
CAAAGAAGAAGCGGAAGGTCGGTATCCACGGAGTCCCAGCAGCCGACAAGAAGTACAGCATCGGCCTGGACATCGGCA
CCAACTCTGTGGGCTGGGCCGTGATCACCGACGAGTACAAGGTGCCCAGCAAGAAATTCAAGGTGCTGGGCAACACCG
ACCGGCACAGCATCAAGAAGAACCTGATCGGAGCCCTGCTGTTCGACAGCGGCGAAACAGCCGAGGCCACCCGGCTGA
AGAGAACCGCCAGAAGAAGATACACCAGACGGAAGAACCGGATCTGCTATCTGCAAGAGATCTTCAGCAACGAGATGG
CCAAGGTGGACGACAGCTTCTTCCACAGACTGGAAGAGTCCTTCCTGGTGGAAGAGGATAAGAAGCACGAGCGGCACC
CCATCTTCGGCAACATCGTGGACGAGGTGGCCTACCACGAGAAGTACCCCACCATCTACCACCTGAGAAGAAACTGG
TGGACAGCACCGACAAGGCCGACCTGCGGCTGATCTATCTGGCCCTGGCCCACATGATCAAGTTCCGGGGCCACTTCC
TGATCGAGGGCGACCTGAACCCCGACAACAGCGACGTGGACAAGCTGTTCATCCAGCTGGTGCAGACCTACAACCAGC
TGTTCGAGGAAAACCCCATCAACGCCAGCGGCGTGGACGCCAAGGCCATCCTGTCTGCCAGACTGAGCAAGAGCAGAC
GGCTGGAAAATCTGATCGCCCAGCTGCCCGGCGAGAAGAAGAATGGCCTGTTCGGAAACCTGATTGCCCTGAGCCTGG
GCCTGACCCCCAACTTCAAGAGCAACTTCGACCTGGCCGAGGATGCCAAACTGCAGCTGAGCAAGGACACCTACGACG
ACGACCTGGACAACCTGCTGGCCCAGATCGGCGACCAGTACGCCGACCTGTTTCTGGCCGCCAAGAACCTGTCCGACG
CCATCCTGCTGAGCGACATCCTGAGAGTGAACACCGAGATCACCAAGGCCCCCCTGAGCGCCTCTATGATCAAGAGAT
ACGACGAGCACCACCAGGACCTGACCCTGCTGAAAGCTCTCGTGCGGCAGCAGCTGCCTGAGAAGTACAAAGAGATTT
TCTTCGACCAGAGCAAGAACGGCTACGCCGGCTACATTGACGGCGGAGCCAGCCAGGAAGAGTTCTACAAGTTCATCA
AGCCCATCCTGGAAAAGATGGACGGCACCGAGGAACTGCTCGTGAAGCTGAACAGAGAGGACCTGCTGCGGAAGCAGC
GGACCTTCGACAACGGCAGCATCCCCCACCAGATCCACCTGGGAGAGCTGCACGCCATTCTGCGGCGGCAGGAAGATT
TTTACCCATTCCTGAAGGACAACCGGGAAAAGATCGAGAAGATCCTGACCTTCCGCATCCCCTACTACGTGGGCCCTC
TGGCCAGGGGAAACAGCAGATTCGCCTGGATGACCAGAAAGAGCGAGGAAACCATCACCCCCTGGAACTTCGAGGAAG
TGGTGGACAAGGGCGCTTCCGCCCAGAGCTTCATCGAGCGGATGACCAACTTCGATAAGAACCTGCCCAACGAGAAGG
TGCTGCCCAAGCACAGCCTGCTGTACGAGTACTTCACCGTGTATAACGAGCTGACCAAAGTGAAATACGTGACCGAGG
GAATGAGAAAGCCCGCCTTCCTGAGCGGCGAGCAGAAAAAGGCCATCGTGGACCTGCTGTTCAAGACCAACCGGAAAG
TGACCGTGAAGCAGCTGAAAGAGGACTACTTCAAGAAAATCGAGTGCTTCGACTCCGTGGAAATCTCCGGCGTGGAAG
ATCGGTTCAACGCCTCCCTGGGCACATACCACGATCTGCTGAAATTATCAAGGACAAGGACTTCCTGGACAATGAGG
AAAACGAGGACATTCTGGAAGATATCGTGCTGACCCTGACACTGTTTGAGGACAGAGAGATGATCGAGGAACGGCTGA
AAACCTATGCCCACCTGTTCGACGACAAAGTGATGAAGCAGCTGAAGCGGCGGAGATACACCGGCTGGGGCAGGCTGA
GCCGGAAGCTGATCAACGGCATCCGGGACAAGCAGTCCGGCAAGACAATCCTGGATTTCCTGAAGTCCGACGGCTTCG
CCAACAGAAACTTCATGCAGCTGATCCACGACGACAGCCTGACCTTTAAAGAGGACATCCAGAAAGCCCAGGTGTCCG
GCCAGGGCGATAGCCTGCACGAGCACATTGCCAATCTGGCCGGCAGCCCCGCCATTAAGAAGGGCATCCTGCAGACAG
TGAAGGTGGTGGACGAGCTCGTGAAAGTGATGGGCCGGCACAAGCCCGAGAACATCGTGATCGAAATGGCCAGAGAGA
ACCAGACCACCCAGAAGGGACAGAAGAACAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAGAAGCTGTACCTGTACTACCTGCAGAATG
GGCGGGATATGTACGTGGACCAGGAACTGGACATCAACCGGCTGTCCGACTACGATGTGGACCATATCGTGCCTCAGA
GCTTTCTGAAGGACGACTCCATCGACAACAAGGTGCTGACCAGAAGCGACAAGAACCGGGGCAAGAGCGACAACGTGC
CCTCCGAAGAGGTCGTGAAGAAGATGAAGAACTACTGGCGGCAGCTGCTGAACGCCAAGCTGATTACCCAGAGAAAGT
TCGACAATCTGACCAAGGCCGAGAGAGGCGGCCTGAGCGAACTGGATAAGGCCGGCTTCATCAAGAGACAGCTGGTGG
AAACCCGGCAGATCACAAAGCACGTGGCACAGATCCTGGACTCCCGGATGAACACTAAGTACGACGAGAATGACAAGC
TGATCCGGGAAGTGAAAGTGATCACCCTGAAGTCCAAGCTGGTGTCCGATTTCCGGAAGGATTTCCAGTTTTACAAAG
TGCGCGAGATCAACAACTACCACCACGCCCACGACGCCTACCTGAACGCCGTCGTGGGAACCGCCCTGATCAAAAAGT
ACCCTAAGCTGGAAAGCGAGTTCGTGTACGGCGACTACAAGGTGTACGACGTGCGGAAGATGATCGCCAAGAGCGAGC
AGGAAATCGGCAAGGCTACCGCCAAGTACTTCTTCTACAGCAACATCATGAACTTTTTCAAGACCGAGATTACCCTGG
CCAACGGCGAGATCCGGAAGCGGCCTCTGATCGAGACAAACGGCGAAACCGGGGAGATCGTGTGGGATAAGGGCCGGG
```

Figure 24A

```
ATTTTGCCACCGTGCGGAAAGTGCTGAGCATGCCCCAAGTGAATATCGTGAAAAAGACCGAGGTGCAGACAGGCGGCT
TCAGCAAAGAGTCTATCCTGCCCAAGAGGAACAGCGATAAGCTGATCGCCAGAAAGAAGGACTGGGACCCTAAGAAGT
ACGGCGGCTTCGACAGCCCCACCGTGGCCTATTCTGTGCTGGTGGTGGCCAAAGTGGAAAAGGGCAAGTCCAAGAAAC
TGAAGAGTGTGAAAGAGCTGCTGGGGATCACCATCATGGAAAGAAGCAGCTTCGAGAAGAATCCCATCGACTTTCTGG
AAGCCAAGGGCTACAAAGAAGTGAAAAAGGACCTGATCATCAAGCTGCCTAAGTACTCCCTGTTCGAGCTGGAAAACG
GCCGGAAGAGAATGCTGGCCTCTGCCGGCGAACTGCAGAAGGGAAACGAACTGGCCCTGCCCTCCAAATATGTGAACT
TCCTGTACCTGGCCAGCCACTATGAGAAGCTGAAGGGCTCCCCCGAGGATAATGAGCAGAAACAGCTGTTTGTGGAAC
AGCACAAGCACTACCTGGACGAGATCATCGAGCAGATCAGCGAGTTCTCCAAGAGAGTGATCCTGGCCGACGCTAATC
TGGACAAAGTGCTGTCCGCCTACAACAAGCACCGGGATAAGCCCATCAGAGAGCAGGCCGAGAATATCATCCACCTGT
TTACCCTGACCAATCTGGGAGCCCCTGCCGCCTTCAAGTACTTTGACACCACCATCGACCGGAAGAGGTACACCAGCA
CCAAAGAGGTGCTGGACGCCACCCTGATCCACCAGAGCATCACCGGCCTGTACGAGACACGGATCGACCTGTCTCAGC
TGGGAGGCGACAAAAGGCCGGCGGCCACGAAAAAGGCCGGCCAGGCAAAAAAGAAAAAGgaattcGGCAGTGGAGAGG
GCAGAGGAAGTCTGCTAACATGCGGTGACGTCGAGGAGAATCCTGGCCCAGTGAGCAAGGGCGAGGAGCTGTTCACCG
GGGTGGTGCCCATCCTGGTCGAGCTGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCCCGTGCCCTGGCCCACCCTCGTGA
CCACCCTGACCTACGGCGTGCAGTGCTTCAGCCGCTACCCCGACCACATGAAGCAGCACGACTTCTTCAAGTCCGCCA
TGCCCGAAGGCTACGTCCAGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGACGGCAACATCCTGGGGCACA
AGCTGGAGTACAACTACAACAGCCACAACGTCTATATCATGGCCGACAAGCAGAAGAACGGCATCAAGGTGAACTTCA
AGATCCGCCACAACATCGAGGACGGCAGCGTGCAGCTCGCCGACCACTACCAGCAGAACACCCCCATCGGCGACGGCC
CCGTGCTGCTGCCCGACAACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACAAGgaattctaaCTAGAGC
TCGCTGATCAGCCTCGACTGTGCCTTCTAGTTGCCAGCCATCTGTTGTTTGCCCCTCCCCCGTGCCTTCCTTGACCCT
GGAAGGTGCCACTCCCACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGAgAATAGCAGGCATGCTGGGGAgcggccgca
ggaacccctagtgatggagttggccactccctctgcgcgctcgctcgctcactgaggccgggcgaccaaaggtcgc
ccgacgcccgggctttgcccgggcggcctcagtgagcgagcgagcgcgcagctgcctgcaggggcgcctgatgcggta
ttttctccttacgcatctgtgcggtatttcacaccgcatacgtcaaagcaaccatagtacgcgccctgtagcggcgca
ttaagcgcggcgggtgtggtggttacgcgcagcgtgaccgctacacttgccagcgccctagcgcccgctcctttcgct
ttcttcccttcctttctcgccacgttcgccggctttccccgtcaagctctaaatcgggggctcccctttagggttccga
tttagtgctttacggcacctcgaccccaaaaaacttgatttgggtgatggttcacgtagtgggccatcgccctgatag
acggttttcgccctttgacgttggagtccacgttctttaatagtggactcttgttccaaactggaacaacactcaac
cctatctcgggctattcttttgatttataagggattttgccgatttcggcctattggttaaaaaatgagctgatttaa
caaaaatttaacgcgaattttaacaaaatattaacgtttacaattttatggtgcactctcagtacaatctgctctgat
gccgcatagttaagccagccccgacacccgccaacacccgctgacgcgccctgacgggcttgtctgctcccggcatcc
gcttacagacaagctgtgaccgtctccgggagctgcatgtgtcagaggttttcaccgtcatcaccgaaacgcgcgaga
cgaaagggcctcgtgatacgcctatttttataggttaatgtcatgataataatggtttcttagacgtcaggtggcact
tttcggggaaatgtgcgcggaacccctatttgtttatttttctaaatacattcaaatatgtatccgctcatgagacaa
taaccctgataaatgcttcaataatattgaaaaaggaagagtatgagtattcaacatttccgtgtcgcccttattccc
ttttttgcggcattttgccttcctgtttttgctcacccagaaacgctggtgaaagtaaaagatgctgaagatcagttg
ggtgcacgagtgggttacatcgaactggatctcaacagcggtaagatccttgagagttttcgccccgaagaacgtttt
ccaatgatgagcacttttaaagttctgctatgtggcgcggtattatcccgtattgacgccgggcaagagcaactcggt
cgccgcatacactattctcagaatgacttggttgagtactcaccagtcacagaaaagcatcttacggatggcatgaca
gtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaat
gaagccataccaaacgacgagcgtgacaccacgatgcctgtagcaatggcaacaacgttgcgcaaactattaactggc
gaactacttactctagcttcccggcaacaattaatagactggatggaggcggataaagttgcaggaccacttctgcgc
tcggcccttccggctggctggtttattgctgataaatctggagccggtgagcgtggaagccgcggtatcattgcagca
ctggggccagatggtaagccctcccgtatcgtagttatctacacgacggggagtcaggcaactatggatgaacgaaat
agacagatcgctgagataggtgcctcactgattaagcattggtaactgtcagaccaagtttactcatatatacttta
attgatttaaaacttcattttaatttaaaaggatctaggtgaagatcctttttgataatctcatgaccaaaatccct
taacgtgagttttcgttccactgagcgtcagaccccgtagaaaagatcaaaggatcttcttgagatccttttttctg
cgcgtaatctgctgcttgcaaacaaaaaaaccaccgctaccagcggtggtttgtttgccggatcaagagctaccaact
cttttccgaaggtaactggcttcagcagagcgcagataccaaatactgtccttctagtgtagccgtagttaggccac
cacttcaagaactctgtagcaccgcctacatacctcgctctgctaatcctgttaccagtggctgctgccagtggcgat
aagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacg
```

Figure 24B

```
cttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgattttttgtgatgctcg
tcagggggcggagcctatggaaaaacgccagcaacgcggccttttttacggttcctggccttttgctggccttttgct
cacatgt
```

Figure 24C

```
WT     792   TAGGCTTTGTCTTACAGTGTTATTATTTATGAGTAAAACTAATTGGTTGTCCTGCATACT   851
             | ||||||||||||||||||||||||||||||||||||||||||||||||||||||||||
clone  761   TAGGCTTTGTCTTACAGTGTTATTATTTATGAGTAAAACTAATTGGTTGTCCTGCATACT   702

WT     852   TTAATTATGATGTAATACAGGTTCTGGGTTGACAAATATCAAGACGGAGGAGATCTCTGA   911
             | ||||||||||||||||||||||||||||||||||||||||||||||||||||||||||
clone  701   TTAATTATGATGTAATACAGGTTCTGGGTTGACAAATATCAAGACGGAGGAGATCTCTGA   642

WT     912   AGTGAAGATGGATGCAGAATTCCGACATGACTCAGGATATGAAGTTCATCATCAAAAATT   971
             | |||||||||||| |  || || ||| || |||||||||||||||||||||||||||||
clone  641   AGTGAAGATGGATACGGAGTTTAGGCACGATTCAGGATATGAAGTTCATCATCAAAAATT   582

WT     972   GGTACGTAAAATAATTTACCTCTTTCCACTACTGTTTGTCTTGCCAAATGACCTATTAAC
1031
             | ||||||||||||||||||||||||||||| ||||||||||||||||||||||||||||
Clone  581   GGTACGTAAAATAATTTACCTCTTTCCACTAGTGTTTGTCTTGCCAAATGACCTATTAAC   522

WT     1032  TCTGGTTCATCCTGTGCTAGAAATCAAATTAAGGAAAAGATAAAAATACAATGCTTGCCT
1091
             | |||||||||||||||||||||||||||||||||||||||||||||||||||||||||||
Clone  521   TCTGGTTCATCCTGTGCTAGAAATCAAATTAAGGAAAAGATAAAAATACAATGCTTGCCT   462

WT     1092  ATAGGATTACCATGAAAACATGAAGAAAATAAATAGGCTAGGCTGAGCGCAGTGGCTCAA
1151
             | |||||||||||||||||||||||||||||||||||||||||||||||||||||||||||
Clone  461   ATAGGATTACCATGAAAACATGAAGAAAATAAATAGGCTAGGCTGAGCGCAGTGGCTCAA   402
```

Figure 25

REDUCTION OF AMYLOID BETA PEPTIDE PRODUCTION VIA MODIFICATION OF THE APP GENE USING THE CRISPR/CAS SYSTEM

CROSS REFERENCE TO RELATED APPLICATIONS

The present application is a National Stage Application of PCT Application No. PCT/CA2015/050411 filed on May 8, 2015 and published in English under PCT Article 21(2), which claims the benefit of U.S. Provisional Application Ser. No. 61/991,054 filed on May 9, 2014. All documents above are incorporated herein by reference in their entirety.

SEQUENCE LISTING

Pursuant to 37 C.F.R. 1.821(c), a sequence listing is submitted herewith as an ASCII compliant text file named "11229_365_SeqList.txt", created Sep. 18, 2018 and having a size of about 132 KB, which is incorporated herein by reference.

FIELD OF THE INVENTION

The present invention relates to the introduction of modifications in the Amyloid β Precursor Protein (APP) gene and uses thereof to reduce the production of toxic Aβ peptides. Such reduction may be used for example to prevent or treat Alzheimer's disease and/or age-related cognitive decline.

BACKGROUND OF THE INVENTION

More than 5% of the population of the Western world above the age of 60 is affected by dementia. Two thirds of these cases are due to Alzheimer's disease (AD) (1-3). The prevalence of AD doubles every 5 years after age 65. Thus in persons older than 90 years of age there is a prevalence of more than 25% (3). The diagnosis of AD is confirmed by 2 major histopathologic hallmarks: senile plaques, which are extracellular deposits of amyloid β (Aβ) peptide, and neurofibrillary tangles, which are somatic inclusions of the microtubule-associated protein tau.

The Amyloid Cascade Hypothesis: Structure and Metabolic Processing of the Amyloid β Precursor Protein (APP)

A role of Amyloid β (Aβ) peptide aggregation and deposition in AD pathogenesis is widely accepted. Toxic peptides are produced by the metabolic processing of Amyloid β Precursor Protein (APP). APP is an integral membrane protein expressed in many tissues and concentrated in the synapses of neurons. APP proteolysis generates beta amyloid (Aβ), a 37 to 49 amino acid peptide whose amyloid fibrillar form is the primary component of amyloid plaques found in the brains of Alzheimer's disease patients.

Genetic alterations in APP suffice to cause early-onset Familial Alzheimer's disease. Abnormalities induced by aggregated Aβ have been linked to synaptic and neuronal degeneration. This is consistent with the "dying-back" pattern of degeneration that characterizes neurons affected in AD.

Amyloid plaque formation is a central pathological feature of AD. These plaques largely consist of Aβ peptides (4). The Aβ peptides are formed through sequential proteolytic processing of APP made by the β- and γ-secretases (5) (FIG. 1). The γ-secretase is part of the presenilin complex. The aspartyl protease β-site APP cleaving enzyme 1 (BACE1) was originally identified over a decade ago (6, 7). It cleaves APP mostly at a unique site. However, the γ-secretase complex cleaves the resulting carboxy-terminal fragment at several places, especially at positions 40 and 42. The cleavage by this enzyme leads to the formation of amyloid-β1-40 (Aβ1-40) and Aβ1-42 peptides (5). Alternative processing of APP at the α-site prevents the formation of amyloid-β, because the α-site is located within amyloid-β. The neurotoxic potential of the Aβ peptides results from their biochemical properties that favor aggregation into insoluble oligomers and protofibrils. These oligomers and protofibrils accumulate into senile and neuritic plaques. These plaques, along with a reduction of Aβ clearance from the brain, leads to the extracellular accumulation of Aβ. This leads to activation of neurotoxic cascades and ultimately to cytoskeletal changes, neuronal dysfunction and cellular death.

The amyloid cascade hypothesis is based mostly on findings from in vitro and in vivo studies, and is further strengthened by the discovery of genetic mutations associated with early-onset, familial AD. Familial AD is a severe form of the disease, in which massive intra-cerebral amyloidogenesis occurs prematurely as a consequence of mutations all affecting APP metabolism (i.e., mutations in the APP gene in chromosome 21, and in presenilin 1 and 2 (PS-1 and PS-2) genes in chromosomes 14 and 1 respectively). Currently, two proteins are deemed as intimately involved in the clearance of Aβ peptides from the brain: apolipoprotein E (APOE) and the insulin-degrading enzyme (IDE). Disadvantageous genetic polymorphisms (such as the ε4 allele of APOE) and pathological conditions related to abnormal IDE homeostasis (e.g., diabetes mellitus) also favor the amyloidogenic cleavage of APP and/or decrease the Aβ clearance from the brain. This facilitates the accumulation of Aβ in the neural tissues and promote downstream effects of the amyloid cascade (8).

Mutations in APP that are Responsible for Early Onset Familial Alzheimer's Disease Over thirty coding mutations in the APP gene have been identified (6). Twenty five of these mutations are pathogenic, usually resulting in early onset autosomal dominant Alzheimer's disease (FIG. 2A). Substitutions at or near the β- and γ-proteolytic sites result in over-production of either total amyloid-β or a shift in the $A\beta_{1-40}:A\beta_{1-42}$ ratio towards formation of the more toxic $A\beta_{1-42}$ peptide. On the other hand, substitutions within the amyloid-β peptide result in formation of Aβ, which aggregates more easily (9). Mutations in APP are also responsible for the common, late-onset form of Alzheimer's disease.

Mutation that Prevents Alzheimer's Disease

Jonsson et al. (10) searched for low-frequency variants in the APP gene, which significantly reduces the risk of Alzheimer's disease. They studied coding variants in APP in whole-genome sequence data obtained from 1,795 Icelanders. They reported a coding mutation, i.e., an alanine to threonine substitution at position 673 in the APP gene (A673T), which protects against Alzheimer's disease. This mutation is adjacent to the aspartyl protease β-site in APP and is located at position 2 in the amyloid-β peptide. The proximity of A673T mutation to the proteolytic site of BACE1 suggests that this variant might result in impaired BACE1 cleavage of APP.

The A673T mutation reduces by about 40% the formation of amyloidogenic peptides in vitro (10). The strong protective effect of the A673T mutation against Alzheimer's disease provided a proof of principle that reducing the β-cleavage of APP may protect against the disease. Moreover, the A673T mutation also protects against cognitive decline in the elderly without Alzheimer's disease. The carriers of this A673T mutation have a 1.47 times greater chance of reaching the age of 85 without developing AD than non-carriers. Jonsson et al. (10) concluded that the A673T mutation confers a strong protection against Alzheimer's disease. Kero et al. (11) found the A673T variant in one person who died at the age of 104.8 years with little beta-amyloid pathology. This observation supports the concept that this variant protects the brain against β-amyloid pathology and Alzheimer disease.

The present description refers to a number of documents and sequence database entries, the content of which is herein incorporated by reference in their entirety.

SUMMARY OF THE INVENTION

The present invention relates to introducing one or more modifications into a target gene involved in Aβ peptide production by gene editing using one or more site-specific endonucleases and one or more donor or patch nucleic acids. The modifications introduced are specifically designed to decrease the production of Aβ peptide (e.g., by reducing APP expression and/or APP processing). In an aspect, a guide RNA (gRNA) is designed and used in combination with a Cas9 nuclease or nickase to specifically introduce a cut in the targeted gene DNA. This cut, allows to specifically modify the target gene by introducing in the target gene (e.g., by homologous recombination) a donor (patch) nucleic acid comprising one or more modifications of interest. The target gene thus modified, will ultimately reduce the level of Aβ peptide produced by the cell. The present invention further relates to uses of such gRNAs, site-specific endonucleases and donor/patch nucleic acids for decreasing Aβ-peptide expression/levels in a cell. The present invention also concerns uses of such gRNAs, site-specific endonucleases and donor/patch nucleic acid for the prevention or treatment of Alzheimer's disease and/or age related cognitive decline.

Accordingly, in an aspect, the present invention provides a method for decreasing Amyloid Precursor Protein (APP) processing into Aβ peptide by a cell comprising introducing at least one modification within an endogenous polynucleotide target gene sequence of the cell, wherein the modification decreases the amount of Aβ peptide produced by the cell and wherein the endogenous polynucleotide target gene encodes a protein that regulates Aβ-peptide production.

In an embodiment, the target gene encodes an α-secretase, a β-secretase or a γ-secretase. In an embodiment, the target gene encodes APP.

In an embodiment, the above-mentioned methods comprise providing the cell with:
i) a site-specific endonuclease specifically targeting a nucleic acid sequence in the endogenous APP polynucleotide gene sequence of the cell; and
ii) a donor nucleic acid comprising an APP polynucleotide gene sequence or fragment thereof, which comprises at least one modification with respect to the endogenous APP polynucleotide gene sequence present in the cell.

In an embodiment, the site-specific endonuclease is a meganuclease, a zinc finger nuclease, a transcription activator-like effector nuclease (TALEN), a Cas9 nuclease (including a dCas-FokI nuclease), or a Cas9 nickase.

In an embodiment, the donor nucleic acid further comprises on each side of the APP polynucleotide gene sequence or fragment thereof, a target sequence recognized by a gRNA for cutting the donor nucleic acid in the presence of the gRNA and a Cas9 nuclease, or a Cas9 nickase or a dCas9-FokI.

In an embodiment, the donor nucleic acid comprises a modification, which introduces an additional endonuclease restriction site when the donor nucleic acid is integrated in the endogenous APP polynucleotide gene sequence in the cell.

In an embodiment, the donor nucleic acid comprises a modified APP polynucleotide gene fragment encoding exon 16 or exon 17.

In an embodiment, the at least one modification in the donor nucleic acid results in an APP polynucleotide gene sequence encoding an APP protein in which the alanine at position 673 has been substituted with another amino acid when the donor nucleic acid is integrated in the endogenous APP polynucleotide gene sequence of the cell. In an embodiment, the at least one modification changes the alanine at position 673 of the APP protein into a threonine. In another embodiment, the at least one modification in the donor nucleic acid results in a modification of one or more amino acids recognized by an α, β, or γ secretase in the APP protein encoded by the APP polynucleotide gene sequence. In an embodiment, the at least one modification corrects a mutation associated with an increased risk of developing Alzheimer's disease present in the endogenous APP polynucleotide gene sequence of the cell.

In an embodiment, the above-mentioned methods comprise providing the cell with:
(i) at least one guide RNA (gRNA) comprising:
    (a) a gRNA guide sequence comprising a seed region of at least 10 consecutive nucleotides of a target sequence in an endogenous APP gene polynucleotide sequence present in said cell;
    (b) a Cas9 recognition sequence,
    wherein the target sequence of the gRNA guide sequence is contiguous to a protospacer adjacent motif (PAM) in the endogenous APP gene polynucleotide sequence and wherein said PAM is recognized by a ribonucleoprotein complex comprising a Cas9 nuclease or nickase;
(ii) a Cas9 nuclease or nickase or a nucleic acid encoding a Cas9 nuclease or nickase; and
(iii) a donor nucleic acid comprising an APP polynucleotide gene sequence or fragment thereof, which comprises at least one modification with respect to the endogenous APP polynucleotide gene sequence present in said cell,
wherein the donor nucleic acid is integrated in said APP gene polynucleotide sequence of said cell and wherein said modification decreases the amount of Aβ produced by said cell.

In an embodiment, the site-specific endonuclease is a Cas9 nuclease or nickase; and the method further comprises providing the cell with at least on one guide RNA (gRNA) comprising a nucleotide seed region perfectly complementary to a target sequence (minus (−) strand) in the endogenous APP polynucleotide gene sequence of the cell.

In an embodiment, the Cas9 nuclease or nickase is a hSpCas9 nuclease, a hSaCas9, a hSpCas9 nickase, a hSaCas9 nickase or a dCas9-FokI nuclease.

In an embodiment, the guide RNA (gRNA) comprises a nucleotide seed region of at least 8 nucleotides perfectly complementary to the target nucleic acid sequence (minus (−) strand) in the endogenous APP polynucleotide gene, wherein the target nucleic acid sequence is immediately adjacent to a protospacer adjacent motif (PAM) recognized by a Cas ribonucleoprotein complex comprising the Cas9 nuclease or nickase.

In an embodiment, the PAM comprises a NGG trinucleotide-sequence or an NNGRR nucleotide sequence.

In an embodiment, the donor nucleic acid is a single stranded oligodeoxynucleotide (ssODN) or a PCR amplicon. In an embodiment, the donor nucleic acid is comprised in a vector. In an embodiment, the donor nucleic acid further comprises on each side of the APP polynucleotide gene sequence or fragment thereof, a target sequence recognized by a gRNA for cutting said donor nucleic acid in the presence of said gRNA and said Cas9 nuclease or nickase. In an embodiment, the donor nucleic acid comprises a modification which introduces an additional endonuclease restriction site when the donor nucleic acid is integrated in the endogenous APP polynucleotide gene sequence in said cell. In an embodiment, the donor nucleic acid comprises a modified APP polynucleotide gene fragment encoding exon 16, or a fragment thereof. In an embodiment, the donor nucleic acid comprises a modified APP polynucleotide gene fragment comprising at least part of intron 15, exon 16, and at least part of intron 16 of the endogenous APP polynucleotide sequence.

In an embodiment, the least one modification is located in Exon 16 of the APP polynucleotide gene sequence. In an embodiment, the at least one modification in the donor nucleic acid results in an APP polynucleotide gene sequence encoding an APP protein comprising at least one amino acid substitution between amino acid positions 656 and 688, wherein said amino acid positions are with respect to the APP protein sequence as set forth in SEQ ID NO: 30 (FIG. 3). In an embodiment, the at least one amino acid substitution corresponds to at least one substitution at amino acid position 670, 671, 673, 678, 682, 692, 603, 694, 704, 711, 712, 713, 714, and/or 715 of the APP protein. In an embodiment, the at least one amino acid substitution introduces a threonine at position 673. In an embodiment, the at least one modification in said donor nucleic acid results in a modification of one or more amino acids recognized by an α, β, or γ secretase in the APP protein encoded by said APP polynucleotide gene sequence present in said cell. In an embodiment, the at least one modification corrects a mutation associated with an increased risk of developing Alzheimer's disease present in said endogenous APP polynucleotide gene sequence present in said cell.

In an embodiment of the above-mentioned method, the cell is from a subject having at least one family member which has been diagnosed with Alzheimer's disease. In a related embodiment, the cell is from a subject having at least one mutation associated with early onset Alzheimer's disease.

In a preferred embodiment of the above methods, the guide RNA (gRNA) sequence of the present invention consists of at least 19 or 20 contiguous nucleotides of the target sequence in the endogenous APP polynucleotide gene.

In an embodiment, the target nucleic acid sequence of the above-mentioned gRNA is located in an exon of the APP polynucleotide gene sequence encoding the APP protein. In an embodiment, the target sequence of said gRNA is located in intron 15, exon 16 or intron 16 of the endogenous APP polynucleotide gene sequence present in said cell.

In an embodiment, the above-mentioned target sequence is located between (i) nucleotide 277141 and nucleotide 279540; (ii) nucleotide 277567 and nucleotide 278754; (iii) nucleotide 277141 and nucleotide 278147; (iv) nucleotide 278149 and nucleotide 278250; (v) nucleotide 278251 and nucleotide 279540; (vi) nucleotide 277277 and nucleotide 278147; (vii) nucleotide 277559 and nucleotide 278147; (viii) nucleotide 277567 and nucleotide 278147; (ix) nucleotide 278149 and nucleotide 278220; (x) nucleotide 278202 and nucleotide 278250; (xi) nucleotide 278721 and nucleotide 279540; (xii) nucleotide 278781 and nucleotide 279540; (xiii) nucleotide 279245 and nucleotide 279540; (xiv) nucleotide 278049 and nucleotide 278312; or (xv) nucleotide 278127 and nucleotide 278230 of the APP polynucleotide gene sequence set forth in FIG. 5, or the complement thereof, or in a corresponding location in the endogenous APP polynucleotide gene sequence present in said cell.

In an embodiment, the above-mentioned target sequence of said gRNA comprises the following nucleic acid sequence:

```
                                            (SEQ ID NO: 1)
(i)        5'-ATTTATGAGTAAAACTAAT-3';

(SEQ ID NO: 3)
(ii)       5'-TTTAATTATGATGTAATAC-3';

(SEQ ID NO: 5)
(iii)      5'-TATGATGTAATACAGGTTC-3';

(SEQ ID NO: 7)
(iv)       5'-ATGATGTAATACAGGTTCT-3';

(SEQ ID NO: 9)
(v)        5'-GGGTTGACAAATATCAAGA-3';

(SEQ ID NO: 11)
(vi)       5'-TTGACAAATATCAAGACGG-3';

(SEQ ID NO: 13)
(vii)      5'-GAGATCTCTGAAGTGAAGA-3';

(SEQ ID NO: 15)
(viii)     5'-CAGAATTCCGACATGACTCA-3';

(SEQ ID NO: 17)
(ix)       5'-GAAGTTCATCATCAAAAAT-3';

(SEQ ID NO: 19)
(x)        5'-CCAAATGACCTATTAACTC-3'
``` of the human APP polynucleotide gene sequence having reference number NCBI NG_007376.1.

In an embodiment, the above-mentioned target sequence of the gRNA of the present invention comprises the following nucleic acid sequence:

```
                                            (SEQ ID NO: 21)
(i)        5'-CTACCCAAAACTTCTTTCT-3';

(SEQ ID NO: 23)
(ii)       5'-CATCATAATTAAAGTATGC-3';

(SEQ ID NO: 25)
(iii)      5'-TTCATATCCTGAGTCATGT-3';
or
                                            (SEQ ID NO: 27)
(iv)       5'-GACAAACAGTAGTGGAAAG-3'
``` of the complementary strand (minus strand) of human APP polynucleotide gene sequence having reference number NCBI NG_007376.1.

In an embodiment, the above-mentioned methods comprise providing the cell with a gRNA targeting the nucleic acid sequence CAGAATTCCGACATGACTC (SEQ ID NO: 15) corresponding to nucleotide positions 278202 to 278220 of the human APP polynucleotide gene sequence having reference number NCBI NG_007376.1.

In an embodiment, of the above-mentioned methods the at least one modification within said endogenous APP polynucleotide gene sequence of said cell is introduced by Non-Homologous End Joining. In an embodiment, the at least one modification within said endogenous APP polynucleotide gene sequence of said cell is introduced by homologous recombination between said donor nucleic acid and said endogenous APP polynucleotide gene sequence.

In a specific embodiment, the method comprises providing the cell with a gRNA targeting the nucleic acid sequence CAGAATTCCGACATGACTC (SEQ ID NO:16) corresponding to nucleotide positions 278202 to 278220 of the human APP polynucleotide gene sequence having reference number NCBI NG_007376.1. In another aspect, the present invention provides a gRNA and a donor nucleic acid as defined in the above-mentioned methods. The present invention also provides a vector comprising the above-mentioned gRNAs and/or donor nucleic acids and host cells expressing such gRNA, site-specific nucleases (e.g., Cas9 nucleases or nickases) and donor nucleic acids. In an embodiment, the vector is a viral vector. In an embodiment, the viral vector is a lentiviral vector, Adeno-Associated viral vector, adenovirus viral vector or herpes virus viral vector.

In a particular embodiment, the above-mentioned vectors further comprise a nucleic acid encoding a site-specific endonuclease or nickase. In an embodiment, the vector further comprises a nucleic acid encoding a Cas9 nuclease (e.g., hSpCas9, hSaCas 9, dCas9-Fokl) or a Cas 9 nickase (e.g., hSpCas9, hSaCas 9). In an embodiment, the Cas9 nuclease is a dCas9-Fokl nuclease.

In a further aspect, the present invention concerns a composition comprising: i) one or more of the above-mentioned gRNAs, ii) one or more of the above-mentioned donor nucleic acids; and/or iii) one or more of the above-mentioned vectors, and a pharmaceutically acceptable carrier. The present invention also concerns a kit comprising: i) one or more of the above-mentioned gRNAs, ii) one or more of the above-mentioned donor nucleic acids; and/or iii) one or more of the above-mentioned vectors, and instructions to use the kit in accordance with the present invention.

In an embodiment, the composition or kit further comprises a site-specific nuclease. In an embodiment, the site-specific nuclease is a Cas9 nuclease (e.g., hSpCas9, hSaCas 9, dCas9-Fokl) or a Cas9 nickase (e.g., hSpCas9, hSaCas 9, dCas9-Fokl).

In an embodiment, the present invention concerns the above-mentioned gRNAs, donor nucleic acids, vectors, host cells, compositions and/or kits for use in decreasing Amyloid Precursor Protein (APP) processing into Aβ peptide by a cell.

In another embodiment, the present invention concerns the above-mentioned gRNAs, donor nucleic acids, vectors, host cells, compositions and/or kits for use in treating or preventing Alzheimer's disease or age-related cognitive decline in a subject in need thereof.

In a related aspect, the present invention concerns the above-mentioned gRNAs, donor nucleic acids, vectors, host cells, compositions and/or kits for the preparation of a medicament for decreasing Amyloid Precursor Protein (APP) processing into Aβ peptide by a cell.

The present invention also concerns the above-mentioned gRNAs, donor nucleic acids, vectors, host cells, compositions and/or kits for the preparation of a medicament for treating or preventing Alzheimer's disease or age-related cognitive decline in a subject in need thereof.

The present invention further concerns the use of the above-mentioned gRNAs, donor nucleic acids, vectors, host cells, compositions and/or kits for decreasing Amyloid Precursor Protein (APP) processing into Aβ peptide by a cell.

In another embodiment, the present invention relates to the use of the above-mentioned gRNAs, donor nucleic acids, vectors, host cells, compositions and/or kits for preventing or treating Alzheimer's disease or age-related cognitive decline in a subject in need thereof.

In another embodiment, the present invention relates to a method of preventing or treating Alzheimer's disease or age-related cognitive decline in a subject in need thereof, comprising introducing into or contacting a cell of the subject with the above-mentioned gRNAs, donor nucleic acids, vectors, host cells and/or compositions.

In an embodiment of the above-mentioned methods, the cell is from subject in need thereof. In a particular embodiment, the subject in need thereof is a subject at risk of developing Alzheimer's disease. In another embodiment, the subject in need thereof is a subject diagnosed with Alzheimer's disease or age-related cognitive decline.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

FIG. 3 shows the complete amino acid sequence of the human Amyloid β Precursor Protein (APP) gene (NCBI Reference Sequence: NG_007376.1, (SEQ ID NO: 30), wild-type sequence). The position of mutation A673T is located in exon 16 of the human APP gene and is shown in bold and is underlined;

FIG. 4 (A) shows the nucleotide (SEQ ID NO: 31) and amino acid (SEQ ID NO: 32) sequences of exon 16 from APP (NCBI Reference sequence NG_007376.1). (B) shows the nucleotide (SEQ ID NO: 33) and amino acid (SEQ ID NO: 34) sequences of mutated APP exon 16 after Homology Directed Repair with pMiniT-Patch. The amino acid alanine (A) at position 673 (in bold) in Panel A is modified to a threonine (T) to protect against Alzheimer's disease (see panel B). The highlighted sequence (CAGAATTCCGA-CATGACTC, SEQ ID NO: 15) in panel A is the sequence targeted by the gRNA#8 (Tables 3 and 4). The sequence in italic (AGG) located after the highlighted sequence in panels A and B is the PAM recognized by the Cas9 complex;

FIG. 9 shows that the pMiniT-Patch plasmid when expressed with the gRNA#8 and Cas9 nuclease can produce either micro-insertions or micro-deletions (INDELs) or Homologous Directed Repair (HDR) in the APP gene. (A) Schematic representation of PCR amplification used to verify insertion of the pMiniT-Patch sequence. (B) Surveyor™ enzyme test of the PCR product obtained by amplification of the APP gene with primers Afw and Arev in human cells (293T) transfected with the following plasmids. Lane 1: 5 µg of pMiniT-patch plasmid alone in cells grown in a 6 well plate. There is no additional band in this negative control because no Cas9 nuclease was introduced in the cells and thus no mutations in the APP gene were present. In lanes 2-5, cells were transfected with decreasing amounts of pX330™ (coding for gRNA#8 and Cas9). Lane 2: 5 µg of pX330™, Lane 3: 4 µg of pX330™ and 1 µg of mock/carrier DNA (pEGFP), Lane 4: 2.5 µg of pX330™ and 2.5 µg of carrier/mock DNA and Lane 5: 1 µg of pX330 and 4 µg of carrier/mock DNA. As seen in lanes 2-5, the Surveyor™ enzyme produced additional bands because the gRNA#8 and the Cas9 induced cuts in the APP gene that were repaired by Non Homologous End Joining (NHEJ). In lanes 6, 7, 8 various amount of pMiniT-Patch and pX330™ plasmids were transfected in human cells. Lane 6: Four (4) µg of pMiniT-Patch and 1 µg of pX330™. Lane 7: 2.5 µg pMiniT-Patch and 2.5 µg of pX330™. Lane 8: 1 µg of pMiniT-Patch and 4 µg of pX330™. The presence of additional bands on the gel is due to the cut introduced in the APP gene by the expressed gRNA#8 and Cas9 nuclease. This cut is repaired endogenously either by NHEJ or by Homologous Directed Repair (HDR) with the pMiniT-patch. Lane 9: negative control corresponding to untransfected cells;

FIG. 10 shows that the pMiniT-Patch sequence is cut by the gRNA#8 and Cas9. (A) Schematic representation of the pMiniT-Patch plasmid showing the position of the primers along the pMiniT-Patch nucleic acid sequence. (B) Human cells (HEK 293T) were transfected with various amounts of pX330™ alone or in combination with the pMiniT-Patch plasmid. Lane 1: Lane 1: 5 μg of pMiniT-patch plasmid alone. Lane 2: 5 μg of pX330™. Lane 6: 4 μg of pMiniT-Patch and 1 μg of pX330™. Lane 7: 2.5 μg pMiniT-Patch and 2.5 μg of pX330™. Lane 8: 1 μg of pMiniT-Patch and 4 μg of pX330™. The left side of panel B corresponds to Surveyor™ enzyme test following amplification of the pMiniT-Patch plasmid present in the transfected cells using one primer (MiniTfw) hybridizing with a backbone of the pMiniT-Patch plasmid and one primer (Brev) hybridizing with a sequence in the APP sequence present in the pMiniT-Patch plasmid. The right side of panel B shows the Surveyor™ enzyme test following amplification of the pMiniT-Patch plasmid present in the transfected cells using one primer (MiniTrev) hybridizing with a backbone of the pMiniT-Patch plasmid and one primer (Bfw) hybridizing with a sequence in the APP patch present in the pMiniT-Patch plasmid. The cuts induced by the Surveyor™ enzyme are due to double stranded breaks produced by the presence of gRNA#8 and Cas9 in the gRNA#8 target sequences, which is present at each end of the APP patch in the pMini-Patch plasmid. These cuts were repaired by NHEJ resulting in a mutated plasmid and thus the amplicons contained mutations, which were cut by the Surveyor™ enzyme. These results confirm that the pMiniT-Patch plasmid was cut by the CRISPR system (gRNA and Cas9) inside the cells and thus that the APP patch was linearized and liberated from the pMiniT plasmid backbone;

FIG. 11 shows the PCR amplification with primers IRMUfw (SEQ ID NO: 49) and Arev (SEQ ID NO: 41) of the mutated APP gene in human cells. The mutation was introduced by Homologous Recombination between the pMiniT-Patch plasmid and the endogenous APP gene following cell transfection with the pMiniT-Patch and pX330™ plasmids (encoding gRNA#8 and Cas9 nuclease) as described in Example 3. (A) Schematic representation of the primer positions on the targeted mutated APP gene. Primer IRMUfw (SEQ ID NO: 49) binds specifically to the mutated sequence of APP exon 16 present in the donor plasmid (pMiniT-Patch) and in the mutated genomic DNA. Primer Arev (SEQ ID NO: 41) hybridizes with a sequence in the APP gene in 5' of the sequence that is present in the pMiniT-Patch. Amplification is possible only if the APP gene has been modified by Homology Directed Repair with the patch present in the pMiniT-Patch plasmid. (B) RedSafe™ agarose gel showing amplified product (608 bp). Lane 1: negative control: cells in a 6 well plate transfected only with the pMiniT-patch plasmid. Lane 6: cells transfected with 4 μg of pMiniT-Patch and 1 μg of pX330™. Lane 7: cells transfected with 2.5 μg pMiniT-Patch and 2.5 μg of pX330™. Lane 8: cells transfected with 1 μg of pMiniT-Patch and 4 μg of pX330™;

FIG. 14 shows a nucleic acid sequence comparison between the amplicon in lane #8 (L8, (SEQ ID NO: 53)) of FIG. 11 and the wild type (WT) APP gene sequence (SEQ ID NO: 54). The IRMUfw (5' forward, (SEQ ID NO: 49)) and the Arev (3' reverse, (SEQ ID NO: 41)) primer sequences are underlined. The additional Spe1 site introduced in the APP gene with the pMiniT-Patch plasmid is in bold and underlined and is indicated at position 161 of the amplicon;

FIG. 15 shows a nucleic acid sequence comparison between a portion of WT APP (SEQ ID NO: 55) and an amplicon containing the mutated APP gene following the modification with gRNA#8 and the MiniT-Patch nucleic acid (SEQ ID NO: 56). The sequences of the Cfw (5' forward, (SEQ ID NO: 42)) and ILMUrev (3' reverse, (SEQ ID NO: 50)) primers are underlined. Since the Cfw primer hybridizes with a sequence, which is present in the genome but not in the pMiniT-Patch, and the ILMUrev primer hybridizes with a sequence, which is present in the pMiniT-Patch but not in the wild type genome, DNA amplification with these primers demonstrates that the genomic DNA has been modified by Homology Directed Repair with the pMiniT-Patch;

FIG. 16 shows a nucleic acid sequence comparison between the wild type (WT) APP nucleic acid sequence (SEQ ID NO: 57) and that of a bacterial clone (D, (SEQ ID NO: 58)) containing the mutated APP gene following modification with gRNA#8/Cas9 and the MiniT-Patch sequence. The sequences of the IRMUfw (5' forward, (SEQ ID NO: 49)) and Crev (3' reverse, (SEQ ID NO: 42)) primers are underlined. Since the Crev primer anneals with a sequence, which is present in the genome but not in the pMiniT-Patch, and the ILMUfw anneals with a sequence, which is in the pMiniT-Patch but not in the wild type genome, these primers can be used to demonstrate that the genomic DNA has been modified by Homology Directed Repair with the pMiniT-Patch sequence. Homologous recombination between the APP gene and the pMiniT-Patch introduces an additional Spe1 endonuclease restriction site (ACTAGT, in bold and underlined) at position 85 of the amplicon obtained with clone D. This site is used to confirm the presence of the mutation and proper integration;

FIG. 18 shows the nucleic acid sequence of the pMiniT-Patch-FLAG-STOP donor sequence (SEQ ID NO: 61). The portion of the nucleic acid sequence coding for exon 16 of the APP gene is shown in lower case and the portion of the nucleic acid sequence coding for the FLAG tag (SEQ ID NO: 62) (DYKDHDGDYKDHDIDYKDDDDK, SEQ ID NO: 63) is shown in bold. There are two stop codons after the FLAG (sequence underlined) in this version of the patch sequence;

FIG. 19 shows the nucleic acid sequence of the pMiniT-Patch-FLAG donor sequence (SEQ ID NO: 64). The portion of the nucleic acid sequence coding for exon 16 of the APP gene is shown in lower case and the portion of the nucleic acid sequence coding for the FLAG tag (SEQ ID NO: 62) (DYKDHDGDYKDHDIDYKDDDDK, SEQ ID NO: 63) is shown in bold;

FIG. 21 shows the nucleic acid sequence of pMiniT-Patch plasmid with wild type APP gene insert and gBlock with APP gene mutations. (A) Wild-type APP insert (SEQ ID NO: 65, 1180 bp APP intron 15/exon 16/intron 16) in the pMiniT plasmid. The mutations to be introduced are shown in lowercases. Primer sequences are also identified (underlined: gBlockfw (SEQ ID NO 69); gBlockrev (SEQ ID NO: 70), Bfw, and Brev are also shown) (B) gBlock of 441 bp (SEQ ID NO: 66) including 9 mutations in APP gene. The mutations are in lowercase, bold and underlined. The sequence shown in lowercase corresponds to the sequence coding for exon 16 of the APP gene (C) Patch repair final sequence of 1224 bp in the pMiniT plasmid (SEQ ID NO: 67) including two gRNAs target sites (in italics). The sequence of Exon 16, as corrected, (SEQ ID NO: 68) is shown in lower case. Primer sequences are underlined;

FIG. 22 shows the nucleic acid sequence of the gBlock for 3×FLAG and 3×FLAG-STOP donor/patch sequence. (A) gBlock 3×FLAG: 507 pb (SEQ ID NO: 71). (B) gBlock 3×FLAG-STOP: 513 pb (SEQ ID NO: 72). (C) Sequencing result of insert of plasmid pMiniT-Patch-3×FLAG (SEQ ID NO: 73), gRNAs sequences are in bold and primer targeting sequences (Bfw and Brev) are underlined; and (D) Sequencing result of insert of plasmid pMiniT-Patch-3×FLAG-STOP (SEQ ID NO: 74), gRNAs sequences are in bold and primer targeting sequences are underlined;

FIG. 23 shows the nucleic acid sequence of the pX330-U6-Chimeric_BB-CBh-hSpCas9 vector sequence used in accordance with an embodiment of the present invention (gift from Feng Zhang, plasmid #42230 from Addgene). (A) Vector sequence of pX330™ (SEQ ID NO: 75). The BbsI cloning sites for cloning the gRNA target sequence are shown (GTCTTCgaGAAGAC, SEQ ID NO: 76). Expression of the gRNA is under the control of the U6 promoter, therefore a "G" is preferably present in 5' of the target sequence (or it can be added to the insert) for optimal expression of the gRNA. The humanized Cas9 (hSpCas9) nuclease expressed by this vector comprises a 3× Flag tag (in N-terminal, for purification or for verifying expression by western blot) and a nuclear localization signal (SV40 NLS) for proper nuclear targeting of the nuclease. The humanized Cas9 is derived from S. pyogenes and is under the control of the CBh promoter. The sequence coding for the 3×FLAG TAG is shaded and in bold (SEQ ID NO: 77). The NLS (CCAAAGAAGAAGCGGAAGGTC, SEQ ID NO: 78) is shaded and underlined and the portion coding for the hSpCas9 is underlined (SEQ ID NO: 79). (B) Amino acid sequence of the hSpCas9 nuclease expressed by the pX330™ vector (SEQ ID NO: 80; SEQ ID NO:114 (haspCas9 without NLS and TAG), the NLS is in bold and the TAG is underlined and bold;

FIG. 24 shows sequences from the pX458™ plasmid (SEQ ID NO: 81) used in an embodiment of the present invention. The pX458™ plasmid (gift from Feng Zhang, Addgene plasmid #48138) expresses a humanized form of S pyogenes Cas9 nuclease (SEQ ID NOs: 79 and 80) fused to GFP (SpCas9-2A-GFP) under the Cbh promoter. The hSpCas9 is fused to a 3×FLAG (SEQ ID NO: 77) at its N-terminal end and comprises a nuclear localization signal (SV40 NLS, SEQ ID NO: 78) for proper nuclear targeting of the nuclease. The vector includes a cloning backbone for gRNA expression under the U6 promoter (https://www.addgene.org/48138/) as in the pX330™ plasmid described in FIG. 23;

FIG. 25 shows a sequence Comparison between the wild type APP (SEQ ID NO: 82) sequence and the sequence of the mutated clone (SEQ ID NO:83) described in Example 7;

DESCRIPTION OF ILLUSTRATIVE EMBODIMENTS

Figure 1:
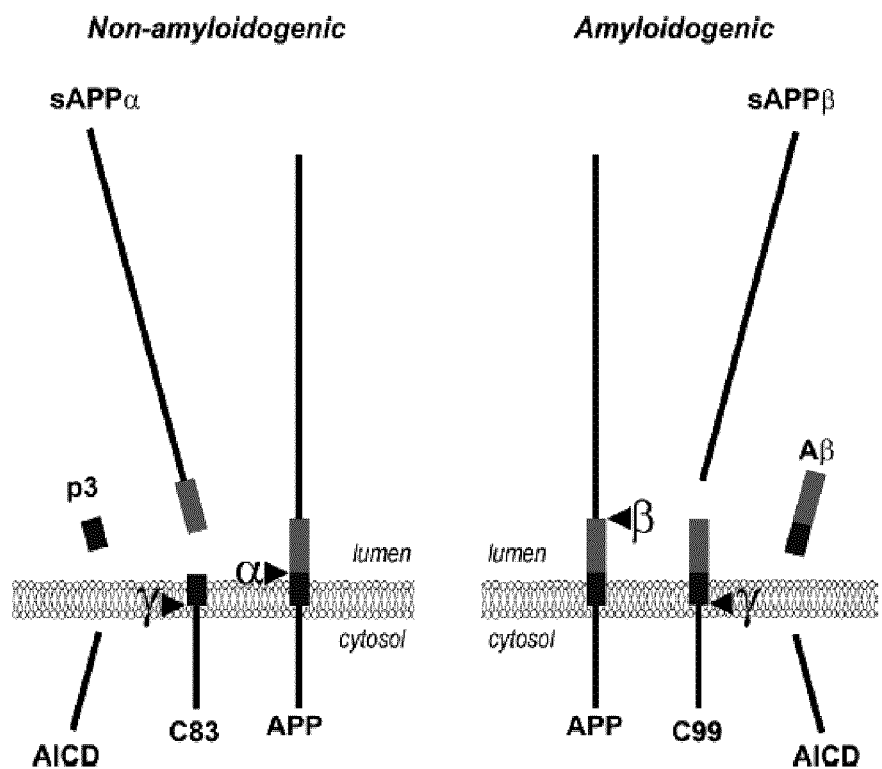
FIG. 1 shows pathways for metabolic processing of Amyloid β Precursor Protein (APP). The figure illustrates the two most prominent metabolic routes and the APP proteolytic derivatives. APP is the substrate for either α- or β-secretases. Thus, the two pathways (nonamyloidogenic and the amyloidogenic) are mutually exclusive. β-site APP-cleaving enzyme 1 (BACE1) is the only known aspartyl-protease with β-secretase activity. The fragments C83 and C99 (also known as α- and β-carboxy-terminal fragments) are substrates for the γ-secretase, a protein complex that includes at least 4 different proteins: anterior pharynx defective 1, nicastrin, presenilin 1 (PS-1) or presenilin 2 (PS-2), and presenilin enhancer-2. AICD is the intracytoplasmic domain of APP. The figure was adapted from E. A. Bignante et al. Neurobiology of Aging 34 (2013) 2525-2537.
Figure 2:
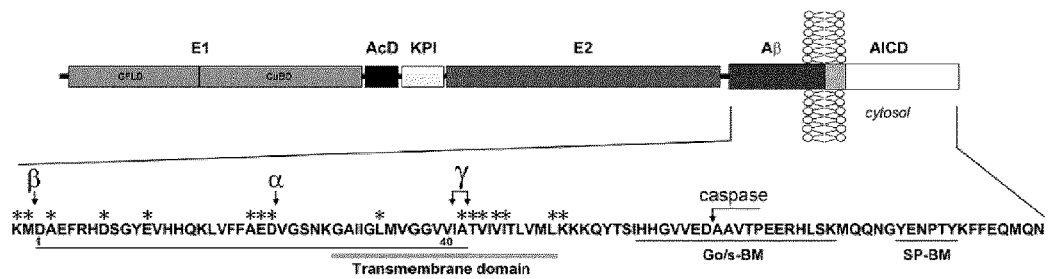
FIG. 2 is a schematic representation of the domain structure of amyloid β precursor protein (APP). The E1 domain consisting of the Growth Factor Like Domain (GFLD) and the Copper-Binding Domain (CuBD). The acidic domain (AcD) and the Kunitz-type inhibitory domain (Kunitz protease inhibitor [KPI], not present in neurons) bridge the E1 and E2 domains. The E2 domain consists of 2 coiled-coil substructures connected through a continuous helix. The amino acid sequence of amyloid β(Aβ)/transmembrane/intracellular (intracytoplasmic domain of APP [AICD]) domains is shown in the lower part of the figure (SEQ ID NO: 29). Asterisks denote amino acids substituted in familiar forms of AD and APP variants. Arrows indicate cleavage sites for both secretases and caspases. Binding motifs for heterotrimeric Go/s proteins (Go/s-BM) and scaffolding proteins (SP-BM; e.g., Fe65, Mint/X11-family proteins, Dab1, c-Jun N-terminal kinase) are underlined. The Aβ sequence is also underlined. Figure is from E. A. Bignante et al. Supra.

The present invention shows that it is possible to introduce one or more modifications into a target gene involved in Aβ peptide production by gene editing using one or more site-specific endonucleases and one or more donor or patch nucleic acids. The modifications introduced are specifically designed to decrease the production of Aβ peptide (e.g., by reducing APP expression and/or APP processing).

Applicants show herein that the endogenous APP polynucleotide gene sequence within a cell may be efficiently genetically modified to introduce one or more modifications designed to decrease Aβ-peptide production. The modifications are introduced by providing the cell with a donor nucleic acid (patch sequence) and a site-specific endonuclease (e.g., Cas 9) specifically targeting and cutting the endogenous APP polynucleotide gene sequence. The donor nucleic acid has a nucleic acid sequence, which is highly similar to the endogenous APP polynucleotide gene sequence but which comprises one or more modifications, which, once introduced into the endogenous APP polynucleotide gene sequence in the cell will reduce Aβ peptide production.

Following the cut(s) (e.g., a double stranded break (DSB) or two single strand breaks (SSB)) introduced by the site-specific endonuclease/nickase into the APP DNA, the donor or patch sequence is integrated (e.g., it replaces the corresponding endogenous APP polynucleotide sequence by homologous recombination) in the endogenous APP polynucleotide gene sequence, thereby modifying it.

Using such methods, modifications into the target gene can be made to correct an endogenous mutation associated with increased risk of Aβ-peptide production or accumulation or to introduce one or more modifications, which decrease APP expression or processing into Aβ-peptide.

For example, mutations in the APP gene associated with familial forms of Alzheimer's disease may be corrected in accordance with the present invention by targeting the endogenous APP gene with a donor or patch sequence encoding the wild-type APP sequence or a portion thereof. In another aspect of the present invention, the APP gene may be modified to introduce a protective mutation in the APP gene associated with decreased levels of Aβ-peptide production or accumulation (a A673T substitution in the APP protein sequence).

As used herein, the terms "APP gene", "APP nucleic acid" and "APP polynucleotide sequence" are used interchangeably and refer to the nucleic acid sequence encoding the Amyloid Precursor Protein (Entrez 351; Ensembl ENSG00000142192; UniProt P05067; RefSeq mRNA NM_000484; RefSeq (protein) NP_000475). A wild-type APP nucleic acid is a nucleic acid, which has the nucleotide sequence of the APP gene naturally found in subjects and which does not comprise mutations (in the coding region of the APP protein or elsewhere in the APP gene), which are associated with an increased risk of developing Alzheimer's disease. A wild type APP nucleic acid thus includes allelic variants not associated with familial forms of Alzheimer's disease and encodes the wild type APP protein (e.g., NM_000484.3; Uniprot P05067, and FIG. 3 (SEQ ID NO: 30)). In a particular embodiment, the wild type APP nucleic acid sequence has the sequence of NCBI Reference Sequence: NG_007376.1. An endogenous APP polynucleotide gene sequence in a cell refers to the unmodified APP nucleic acid sequence found in such cell.

Many mutations causing Alzheimer's disease have been reported in the APP gene and these may be corrected in accordance with the present invention. In a particular aspect of the present invention, the correction involves the replacement of the mutated nucleotide(s) with nucleotide(s) normally found in the APP gene. In another aspect, the correction involves the replacement of the mutated nucleotides with nucleotides encoding the wild type amino acids of the APP protein. In such a case, the replacement nucleotides may be the same as those found in the wild type APP nucleic acid sequence or may be different (e.g., due to codon degeneracy), as long as the corrected sequence encodes the wild type APP protein. Mutations in the exons encoding the APP protein, in the promoter or in any other regulatory sequence in the APP gene modulating the expression of the APP protein may be targeted in accordance with the present invention. For example mutations in any of the 18 exons of the APP gene may be targeted and corrected in accordance with the present invention (i.e., mutations in exon 1, exon 2, exon 3, exon 4, exon 5, exon 6, exon 7, exon 8, exon 9, exon 10, exon 11, exon 12, exon 13, exon 14, exon 15, exon 16, exon 17 and exon 18). Modifications introduced in the portion of the polynucleotide gene sequence encoding the APP protein (e.g., exon sequences) will be reflected in the APP protein expressed by the cell (i.e., the cell will normally express a modified/corrected APP protein).

Non-limiting examples of mutations in the APP protein that may be corrected include: KM670/671NL (12), Ala673Val (13), His677Arg (14), Asp678Asn (15), Asp678His (16), Glu682Lys (17), Ala692Gly (18), Glu693Gln (19), Glu693Gly (20), Glu693del (21), Asp694Asn (22), Leu705Val (23), Ala713Thr (24), Ala713Thr (25), Ala713Val (26), Thr714Ala (27), Thr714Ile (28), Val715Met (29), Ile716Val (30), Ile716Phe (31), Val717Ile (32), Val717Leu (33), Val717Phe (34), Val717Gly (35), Leu723Pro (36), Lys724Asn (37) and His733Pro (38). Thus, possible modifications include amino acid at position 670, 671, 673, 677, 678, 682, 692, 693, 694, 705, 713, 714, 715, 716, 717, 723, 724, and/or 733. The amino acid numbering is with respect to the APP amino acid sequence shown in FIG. 3 (SEQ ID NO: 30). Other modifications also exist. All mutations located between amino acids 656 and 688 are located in exon 16 (SEQ ID NOs: 31 and 34) of the APP gene. In an embodiment, mutations at amino acid positions 670 (lysine in WT APP), 671 (methionine in WT APP), 673 (alanine in WT APP), 677 (histidine in WT APP), 678 (aspartic acid in WT APP) and/or 682 (glutamic acid in WT APP) may be corrected in accordance with the present invention by replacing exon 16 or a part thereof in the endogenous APP polynucleotide gene sequence. Exon 16 has been shown to be efficiently targeted and replaced using an embodiment of the method of the present invention.

Other mutations associated with Alzheimer's disease, such as those found in the Presenilin 1 (PS1) and Presenilin 2 (PS2) genes may also be corrected using the method of the present invention.

In addition to correcting mutations associated with increased risk of developing Alzheimer's disease (e.g., mutations associated with familial forms of AD), it is also possible to introduce modifications in the APP gene, which are known to protect against Alzheimer's disease. One such modification is the replacement of the alanine at position 673 of the APP protein sequence with a threonine (A673T substitution in exon 16). The presence of the A673T variant in subjects has been found to reduce the risk of developing Alzheimer's disease and to protect against age-related cognitive decline. The A673T substitution is adjacent to the beta secretase cleavage site in APP and results in a 40% reduction in the formation of toxic amyloid beta peptides.

Introduction of the A673T substitution in accordance with the present invention may be made alone in the APP gene, or in combination with one or more other modifications aiming, for example, at correcting endogenous mutations associated with an increased risk of developing AD or age-related cognitive decline. For example, mutations associated with increased risk of developing AD present in exon 16 may advantageously be corrected at the same time as the A673T protective substitution is introduced in the APP gene since all targeted modifications are present in the same region of the APP gene. Of course mutations located elsewhere (i.e., in exons other than exon 16) may also be concurrently corrected but the correction will involve the replacement of longer stretch of sequences or of multiple smaller targeted regions in the APP gene.

Modifications in the APP gene or other genes associated with AD may be made in cells (neurons or glial cells) of a subject in need thereof. As used herein, "a subject in need thereof" is a subject, which may benefit from a decreased production of Aβ peptides. Non-limiting examples of a subject in need thereof include a subject having cells showing an increased level of Aβ peptide production (APP expression and/or APP maturation) or activity as compared to cells from a normal subject. In an embodiment, the subject in need thereof is a healthy subject (e.g., a subject at risk of developing AD or age-related cognitive decline) or a subject already diagnosed with AD or age-related cognitive decline. As used herein, a subject at risk of developing AD or age-related cognitive decline, is a subject that has not yet been diagnosed with the disease or condition but which, due to certain factors (age, familial history, heredity) is likely to develop de disease or condition later on in his/her life. In an embodiment, the subject at risk is a subject having a mutation in the APP, PS-1 and/or PS-2 gene(s). In another embodiment, the subject at risk is a subject having a mutation in the APOE-e4 gene. In another embodiment, the subject at risk is a subject having at least one family member (e.g., a mother, father, brother, sister or child) diagnosed with Alzheimer's disease or age-related cognitive decline. In an embodiment, the subject at risk is a subject having a mutation associated with early onset Alzheimer's disease or familial Alzheimer's disease (FAD). In an embodiment, the subject is a mammal, preferably, a human.

The correction or modification may be made in a single allele of a targeted gene within a cell but is preferably made in both alleles of the gene, when necessary.

Modifications in genes associated with AD (e.g., APP, PS-1 and PS-2) in accordance with the present invention can be used to prevent or treat Alzheimer's disease or age-related cognitive decline. As used herein, the term "prevention/preventing/prevent" means that the modification(s) avoid(s) or delay(s) the onset of the disease. As used herein, the term "treat/treating/treatment" includes instances where the genetic modification(s) reduce(s) partially or completely the progression of the disease and instances where symptoms associated with the disease are reduced partially or completely (i.e., one or more symptoms associated with Aβ peptide neurotoxicity).

Preferably, the one or more modifications in a targeted gene (e.g., APP) in cells (e.g., neurons) of a subject are introduced as early as possible after the identification of a risk of developing AD or soon after AD diagnosis. In a particular embodiment, the one or more genetic modifications in cells are made after the detection by Magnetic Resonance Imaging (MRI) of plaques comprising extracellular deposits of amyloid β(Aβ) peptides in the subject's brain.

Methods of introducing one or more genetic modifications in a targeted gene in accordance with the present invention preferably involve Homologous Recombination (HR). The proposed treatment requires the introduction of a double strand break (DSB) in the targeted gene (e.g., APP) using specifically designed endonucleases or nickases. The introduction of a DSB is then used together with a donor (patch) sequence to modify the targeted gene to, for example, reduce the formation of toxic Aβ peptides (e.g., by correcting one or more endogenous mutations in a targeted gene, which is/are associated with increased risk to develop AD and/or by introducing a protective modification in the targeted gene, which reduces Aβ plaque formation on neurons).

As used herein, "donor" or "patch" nucleic acid are used interchangeably and refers to a nucleic acid that corresponds to a fragment of the endogenous targeted gene of a cell (in some embodiments the entire targeted gene), but which includes the desired modifications at specific nucleotides (e.g., the wild type sequence of the targeted gene (e.g., wild type APP gene) in the case of the correction of an endogenous mutation associated with AD or a modified sequence including a protective mutation to be introduced in the targeted gene). The donor (patch) nucleic acid must be of sufficient size and similarity to permit homologous recombination with the targeted gene. Preferably, the donor/patch nucleic acid is at least 90%, 91%, 92%, 93%, 94%, 95%, 96%, 97%, 98% and 99% identical to the endogenous targeted polynucleotide gene sequence. The patch nucleic acid may be provided for example as a ssODN, as a PCR product (amplicon) or within a vector. Preferably, the patch/donor nucleic acid will include modifications with respect to the endogenous gene which i) precludes it from being cut by a gRNA once integrated in the genome of a cell and/or which facilitate the detection of the introduction of the patch nucleic acid by homologous recombination.

As used herein, a "targeted gene" or "targeted polynucleotide gene sequence" corresponds to the polynucleotide within a cell that will be modified by the introduction of the patch nucleic acid. It corresponds to an endogenous gene naturally present within a cell. The targeted gene may comprise one or more mutations associated with a risk of developing AD or age-related cognitive decline which will be corrected by the introduction of the patch nucleic acid (i.e., will be modified to correspond to the WT gene or to a form which is no longer associated with increased risk of developing AD or age-related cognitive decline). One or both alleles of a targeted gene may be corrected within a cell in accordance with the present invention.

Although genetic modifications in a targeted gene are preferably introduced by HR, DSBs in cell DNA may also be spontaneously repaired by Non Homologous End Joining (NHEJ) leading to the presence micro-insertions or micro-deletions (INDELs) in the targeted gene. Although these forms of genetic modifications are not preferred they can nevertheless be useful to prevent the formation of the Aβ peptide (e.g., by for example reducing completely or partially the level of APP synthesized in cells or by preventing a cut of the APP protein by the β-secretase).

Various types of endonucleases or nickases may be used to induce a DSB at selected site(s) in a targeted gene (e.g., APP, PS-1, PS-2, etc.). Non-limiting examples of useful endonucleases and nickases include meganucleases, Zinc Finger Nucleases (ZFNs), Transcription Activator-Like Effector nucleases (TALENs) or the Cas nucleases or Cas nickases used in combination with at least one (e.g., one or two) guide RNA(s) (gRNA) in the Clustered regularly interspaced short palindrome repeat (CRISPR) system (39-41). Each of these technologies can be used to modify a targeted gene in accordance with the present invention.

Preferably, the present invention uses the CRISPR system (i.e., combination of gRNA and Cas nuclease or nickase) together with a donor (patch) sequence to introduce one or more genetic modifications in a targeted gene (e.g., APP). Applicants demonstrate herein that specific gRNAs can be produced and used with a Cas9 nuclease and patch sequence to efficiently modify the endogenous APP gene in human cells.

The CRISPR System

Recent discoveries in the field of bacterial immunity have led to the development of a new system for controlling gene expression in cells. Bacterial and archaea have developed adaptive immune defenses termed clustered regularly interspaced short palindromic repeats (CRISPR) systems, which use crRNAs and Cas proteins to degrade complementary sequences present in invading viral and plasmid DNA (42). Jinek et al. (43) and Mali et al. (42) have engineered a type II bacterial CRISPR system using custom guide RNA (gRNA) to induce double strand break(s) in DNA. Because the original Cas9 nuclease combined with a gRNA may produce off-target mutagenesis, one may alternatively use in accordance with the present invention a pair of specifically designed gRNAs in combination with a Cas9 nickase (44) or in combination with a dCas9-Folkl nuclease (45) to cut both strands of DNA.

Applicant shows herein for the first time that the CRISPR system can be used in combination with a donor (patch) nucleic acid to efficiently modify APP in cells. The introduction of modifications preferably occurs by homologous recombination although Non Homologous End Joining repair may also occur in the presence of a gRNA and Cas9 nuclease or nickase. Various gRNAs targeting the human APP gene were designed and shown to induce Cas9-dependent DSBs in human cell DNA and to enable the efficient targeted modification of the APP gene. Accordingly, a protective modification in the APP gene (i.e., the A673T mutation in Exon 16 of the APP gene) was introduced. This modification has been shown to significantly reduce Aβ peptide formation in cells.

Accordingly, in an aspect, methods of the present invention involve the design of one or more gRNAs for inducing a DSB (or two SSB in the case of a nickase) in a targeted gene involved in toxic Aβ peptide formation and deposition. The gRNA(s), targeting a region of interest in the targeted gene, and a Cas nuclease or nickase (e.g., Cas9) are then used in combination with a donor/patch nucleic acid to introduce the desired modification(s) in the endogenous polynucleotide gene sequence within the cell by homologous recombination. The present invention further relates to uses of such targeted genetic modification(s), such as for reducing Aβ peptide formation in cells from a subject in need thereof, such as for the treatment of Alzheimer's disease and/or age-related cognitive decline.

In order to cut DNA at a specific site, Cas9 proteins require the presence of a gRNA and a protospacer adjacent motif (PAM), which immediately follows the gRNA target sequence in the targeted polynucleotide gene sequence (46). The PAM is located at the 3' end of the gRNA target sequence but is not part of the gRNA. Different Cas proteins require a different PAM. Accordingly, selection of a specific polynucleotide gRNA target sequence (e.g., on the APP nucleic acid sequence) by a gRNA is generally based on the recombinant Cas protein used. The PAM for the *S. pyogenes* Cas9 CRISPR system is 5'-NRG-3', where R is either A or G, and characterizes the specificity of this system in human cells. The PAM of *S. aureus* is NNGRR (65). The *Streptococcus pyogenes* Type II system naturally prefers to use an "NGG" sequence, where "N" can be any nucleotide, but also accepts other PAM sequences, such as "NAG" in engineered systems. Similarly, the Cas9 derived from *Neisseria meningitidis* (NmCas9) normally has a native PAM of NNNNGATT, but has activity across a variety of PAMs, including a highly degenerate NNNNGNNN PAM. In a preferred embodiment, the PAM for a Cas9 protein used in accordance with the present invention is a NGG trinucleotide-sequence.

gRNAs

As used herein, the expression "gRNA" refers to a guide RNA which is a fusion between the gRNA guide sequence (crRNA) and the Cas9 recognition sequence (tracrRNA). It provides both targeting specificity and scaffolding/binding ability for Cas9 nuclease or nickase. gRNAs of the present invention do not exist in nature, i.e., is a non naturally-occurring nucleic acid.

The gRNAs of the present invention generally comprises (or consists of) a "gRNA guide sequence" and a Cas (e.g., Cas9) recognition sequence, which is necessary for Cas (e.g., Cas9) binding to the targeted APP gene.

As used herein, the expression "gRNA guide sequence" refers to the nucleotides that precede the PAM (i.e., in 5' of the PAM) in the genomic DNA. It corresponds to the protospacer on the target polynucleotide gene sequence. It is what gets put into a gRNA expression plasmid, it does not include the PAM sequence. It is the sequence that confers target specificity. It requires a Cas9 recognition sequence (tracrRNA) to bind to Cas9. The "gRNA guide sequence" is between 15-22 nucleotides, preferably between 18-22 nucleotides and even more preferably 19 nucleotides or 20 nucleotides long. The gRNA guide sequence recognizes and binds to the targeted gene of interest. It hybridizes with (i.e., is complementary to) the opposite strand of a target gene sequence, which comprises the PAM (i.e., it hybridizes with the DNA strand opposite to the PAM).

A Cas recognition sequence (e.g., Cas9 recognition sequence) refers to the portion of the gRNA that links the gRNA guide sequence (crRNA) to the Cas nuclease. It acts as a guide for the endonuclease or nickase, which will cleave the nucleic acid. In an embodiment, Cas recognition sequence is a Cas9 recognition sequence having at least 65 nucleotides. In a particular embodiment, the Cas9 recognition sequence comprises the sequence as set forth in SEQ ID NO: 129, 131, 133 or 135 (corresponding DNA sequences for RNA SEQ ID NOs: 131, 133 and 135 SEQ ID NOs are SEQ ID NOs:130, 132 and 134). In an embodiment, Cas recognition sequence is a Cas9 recognition sequence having at least 65 nucleotides In an embodiment, Cas recognition sequence is a Cas9 recognition sequence having at least 85 nucleotides.

A "target region", "target sequence" or "protospacer" in the context of gRNAs and CRISPR system are used herein interchangeably and refers to the region of the target gene, which is targeted by the CRISPR/dCas9-based system, without the PAM. The CRISPR/Cas9-based system may include at least one gRNA, wherein the gRNAs target different DNA sequences on the target gene. The target DNA sequences may be overlapping. The target sequence or protospacer is followed by a PAM sequence at the 3' end of the protospacer. In an embodiment, the target sequence is immediately adjacent to the PAM sequence and is located on the 5' end of the PAM.

The gRNA comprises a "gRNA guide sequence" or "gRNA target sequence" which corresponds to the target sequence on the target polynucleotide gene sequence that is followed by a PAM sequence. The gRNA may comprise a "G" at the 5' end of the polynucleotide sequence. The presence of a "G" in 5' is preferred when the gRNA is expressed under the control of the U6 promoter. The CRISPR/Cas9 system of the present invention may use gRNA of varying lengths. The gRNA may comprise at least a 10 nts, at least 11 nts, at least a 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of the target APP DNA sequence which is followed by a PAM sequence. The "gRNA guide sequence" or "gRNA target sequence" may be least 17 nucleotides (17, 18, 19, 20, 21, 22, 23), preferably between 17 and 30 nts long, more preferably between 18-22 nucleotides long. In an embodiment, gRNA guide sequence is between 10-40, 10-30, 12-30, 15-30, 18-30, or 10-22 nucleotides long. The PAM sequence may be "NGG", where "N" can be any nucleotide. gRNA may target any region of the a target gene (e.g., APP) which is immediately upstream (contiguous, adjoining, in 5') to a PAM (e.g., NGG) sequence. In an embodiment, the gRNA may target any region which is followed by a PAM identified on the APP polynucleotide gene sequence set forth in FIG. 5 or in Entrez 351; Ensembl ENSG00000142192; or NG_007376.1.

Although a perfect match between the gRNA guide sequence and the DNA sequence on the targeted gene is preferred, a mismatch between a gRNA guide sequence and target sequence on the gene sequence of interest is also permitted as along as it still allows hybridization of the gRNA with the complementary strand of the gRNA target polynucleotide sequence on the targeted gene. A seed sequence of between 8-12 consecutive nucleotides in the gRNA, which perfectly matches a corresponding portion of the gRNA target sequence is preferred for proper recognition of the target sequence. The remainder of the guide sequence may comprise one or more mismatches. In general, gRNA activity is inversely correlated with the number of mismatches. Preferably, the gRNA of the present invention comprises 7 mismatches, 6 mismatches, 5 mismatches, 4 mismatches, 3 mismatches, more preferably 2 mismatches, or less, and even more preferably no mismatch, with the corresponding gRNA target gene sequence (less the PAM). Preferably, the gRNA nucleic acid sequence is at least 90%, 91%, 92%, 93%, 94%, 95%, 96%, 97%, 98% and 99% identical to the gRNA target polynucleotide sequence in the gene of interest (e.g., APP). Of course, the smaller the number of nucleotides in the gRNA guide sequence the smaller the number of mismatches tolerated. The binding affinity is thought to depend on the sum of matching gRNA-DNA combinations.

Figure 5:
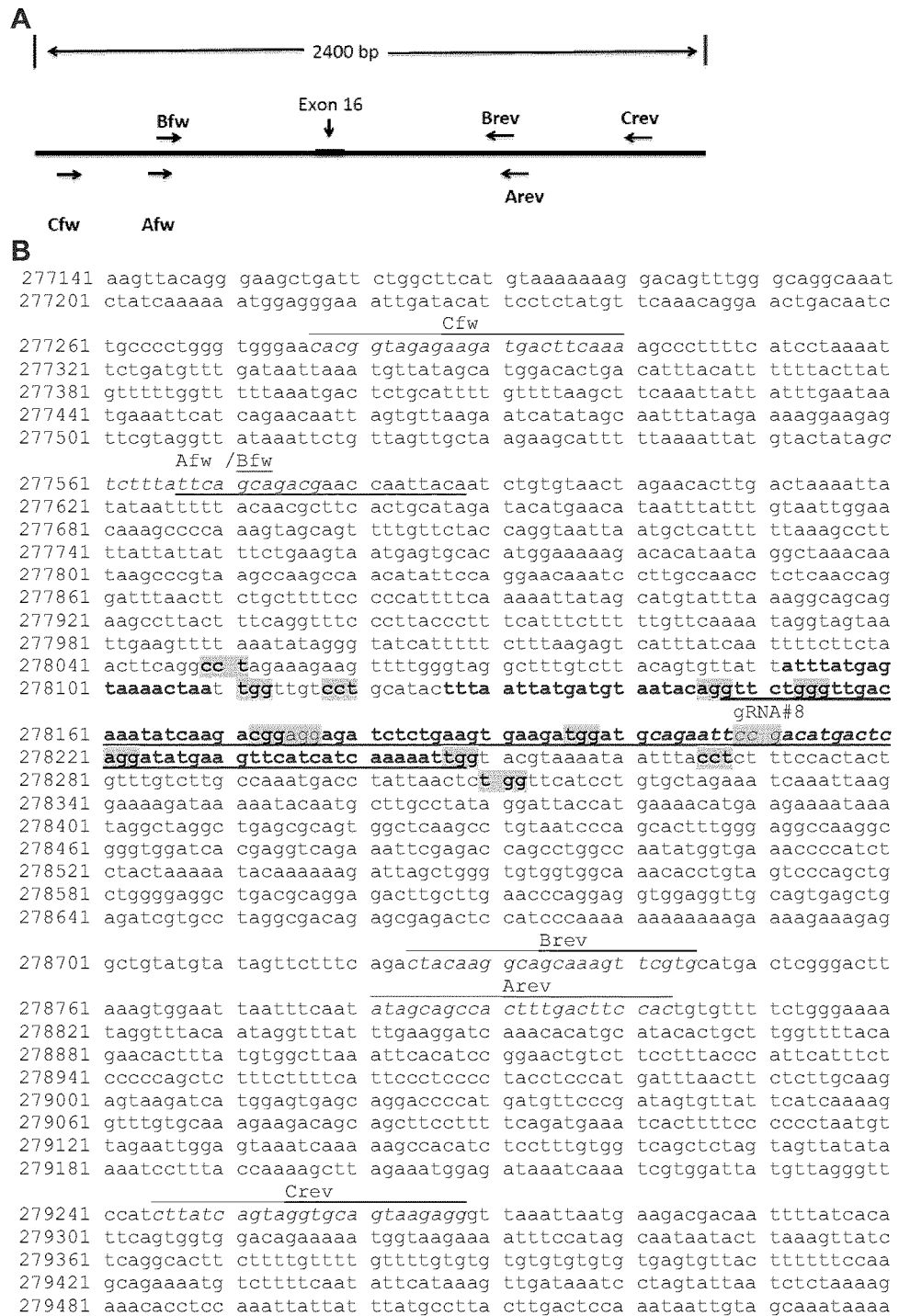
FIG. 5 shows a partial sequence of the wild type APP gene. (A) is a schematic representation of a partial sequence of the wild type APP gene extending before and after exon 16. (B) presents the partial genomic nucleotide sequence of the human APP gene shown in (A) (nucleotides 277141 to 279540 of NCBI NG_007376.1/GI: 166795291, SEQ ID NO: 35) which includes a partial sequence of intron 15 (SEQ ID NO:36), followed by the complete sequence of exon 16 (nucleotides 278148-278248, underlined and bold, (SEQ ID NO: 31)) and a partial sequence of intron 16 (SEQ ID NO: 37). Primer sequences (Cfw (SEQ ID NO: 38), Afw (SEQ ID NO: 39), Brev (SEQ ID NO: 40), Arev (SEQ ID NO: 41) and Crev (SEQ ID NO: 42)) and the gRNA #8 target sequence+PAM (SEQ ID NO: 15, positions 278202 to 278223) are shown in italics. Other PAM sequences used to design alternative gRNAs (gRNAs 1-7 and 9 to 14) are in bold and shaded (see Table 4, in Example 2). The sequence of primer Bfw (SEQ ID NO: 43) is underlined.

Non-limiting examples of gRNAs guide sequences are presented in Table 4 below. Any gRNA guide sequence can be selected in the target gene, as long as it allows introducing at the proper location, the patch/donor sequence of the present invention. Accordingly, the gRNA guide sequence or target sequence of the present invention may be in coding or non-coding regions of the APP gene (i.e., introns or exons). In an embodiment, the gRNA guide sequence is selected in intron 15, exon 16 and/or intron 16 of the APP gene. In an embodiment, the gRNA guide sequence, in combination with the donor/patch sequence allows to replace at least a portion (preferably entirely) exon 16 of an endogenous APP polynucleotide gene sequence within a cell. FIG. 5 presents a fragment of the APP polynucleotide gene sequence comprising part of intron 15, exon 16 and part of intron 16 from which gRNA guide sequence may easily be selected in accordance with the present invention. Of course the complementary strand of the sequence shown in FIG. 5 may alternatively and equally be used to identify proper PAM and gRNA guide sequence. As shown below, gRNA guide sequence may also be selected within a vector nucleotide sequence to allow the removal of the patch sequence, when such patch/donor sequence is provided in a vector.

In an embodiment, the target nucleic acid sequence (gRNA guide sequence) of the gRNA of the present invention is located between (i) nucleotide 277141 and nucleotide 279540; (ii) nucleotide 277567 and nucleotide 27845; (iii) nucleotide 277141 and nucleotide 278147; (iv) nucleotide 278149 and nucleotide 278250; (v) nucleotide 278251 and nucleotide 279540; (vi) nucleotide 277277 and nucleotide 278147; (vii) nucleotide 277559 and nucleotide 278147; (vii) nucleotide 277567 and nucleotide 278147; (viii) nucleotide 278149 and nucleotide 278220; (ix) nucleotide 278202 and nucleotide 278250; (x) nucleotide 278721 and nucleotide 279540; (xi) nucleotide 278781 and nucleotide 279540; (xii) nucleotide 279245 and nucleotide 279540 of the APP polynucleotide gene sequence set forth in FIG. 5, or the complement thereof, or in a corresponding location in the endogenous APP polynucleotide gene sequence present in said cell.

In an embodiment, the gRNA guide sequence on the APP polynucleotide gene sequence is not rich in polyG or polyC. In an embodiment, the gRNA guide sequence on the APP polynucleotide gene sequence does not comprise more than one PAM (e.g., NGG sequence) within its sequence. In an embodiment, the gRNA target sequence on the on the APP polynucleotide gene sequence does not include an NGG (although it is adjacent to a PAM).

The number of gRNAs administered to or expressed in a cell (or subject) or subject in accordance with the methods of the present invention may be at least 1 gRNA, at least 2 gRNAs, at least 3 gRNAs at least 4 gRNAs, at least 5 gRNAs, at least 6 gRNAs, at least 7 gRNAs, at least 8 gRNAs, at least 9 gRNAs, at least 10 gRNAs, at least 11 gRNAs, at least 12 gRNAs, at least 13 gRNAs, at least 14 gRNAs, at least 15 gRNAs, at least 16 gRNAs, at least 17 gRNAs, or at least 18 gRNAs. The number of gRNAs administered to or expressed in a cell may be between at least 1 gRNA and at least 15 gRNAs, at least 1 gRNA to and least 10 gRNAs, at least 1 gRNA and at least 8 gRNAs, at least 1 gRNA and at least 6 gRNAs, at least 1 gRNA and at least 4 gRNAs, at least 1 gRNA to and least 3 gRNAs, at least 2 gRNA and at least 5 gRNAs, at least 2 gRNA and at least 3 gRNAs. Different or identical gRNAs may be used to cut the endogenous target gene of interest and liberate the donor/patch nucleic acid, when provided in a vector.

Nucleases and Nickases

Recently, Q Tsai et al. (45) have designed recombinant dCas9-FokI dimeric nucleases (RFNs) that can recognize extended sequences and edit endogenous genes with high efficiency in human cells. These nucleases comprise a dimerization-dependent wild type FokI nuclease domain fused to a catalytically inactive Cas9 (dCas9) protein. Dimers of the fusion proteins mediate sequence specific DNA cleavage when bound to target sites composed of two half-sites (each bound to a dCas9 (i.e., a Cas9 nuclease devoid of nuclease activity) monomer domain) with a spacer sequence between them. The dCas9-FokI dimeric nucleases require dimerization for efficient genome editing activity and thus, use two gRNAs for introducing a cut into DNA.

The recombinant Cas protein that may be used in accordance with the present invention is i) derived from a naturally occurring Cas; and ii) has a nuclease (or nickase) activity to introduce a DSB (or two SSBs in the case of a nickase) in cellular DNA when in the presence of appropriate gRNA(s). Thus, as used herein, the term "Cas9 nuclease" refers to a recombinant protein which is derived from a naturally occurring Cas9 which has nuclease activity and which function with the gRNAs of the present invention to introduce DSBs in the targeted DNA. In an embodiment, the Cas9 nuclease is a dCas9 protein (i.e., a mutated Cas9 protein devoid of nuclease activity) fused with a dimerization-dependent FokI nuclease domain [45]. In another embodiment, the Cas protein is a Cas9 protein having a nickase activity [39]. As used herein, the term "Cas9 nickase" refers to a recombinant protein which is derived from a naturally occurring Cas9 and which has one of the two nuclease domains inactivated such that it introduces single stranded breaks (SSB) into the DNA. It can be either the RuvC or HNH domain. In a further embodiment, the Cas protein is a Cas9 nuclease. In accordance with the present invention, the Cas9 protein can be derived from any naturally occurring source.

For example, Cas9 proteins are natural effector proteins produced by numerous species of bacteria including *Streptococcus pyogene* (47), *Streptococcus thermophiles* (48), *Staphylococcus aureus* (65), and *Neisseria meningitides* (46). Accordingly, in an embodiment, the Cas protein of the present invention is a Cas9 nuclease/nickase derived from *Streptococcus pyogene, Streptococcus thermophiles, Staphylococcus aureus* or *Neisseria meningitides*. In an embodiment, the Cas9 recombinant protein of the present invention is a human-codon optimized Cas9 derived from *S. pyogenes* (hSpCas9). In an embodiment, the Cas9 recombinant protein of the present invention is a human-codon optimized Cas9 derived from *S. aureus* (hSaCas9). In an embodiment, the hSpCas9 consists essentially of the amino acid sequence set forth in FIG. 23B (SEQ ID NO: 80). In an embodiment, the amino acid sequence of the Cas9 nuclease protein of the present invention comprises an amino acid sequence at least 90%, at least 95% (in embodiments at least 96%, 97%, 98% or 99%) identical to the Cas9 sequence set forth in FIG. 23B (SEQ ID NO: 80).

The Cas9 cuts 3-4 bp upstream of the PAM sequence. There can be some off-target DSBs using wildtype Cas9. The degree of off-target effects depends on a number of factors, including: how closely homologous the off-target sites are compared to the on-target site, the specific site sequence, and the concentration of Cas9 and guide RNA (gRNA). These considerations only matter if the PAM sequence is immediately adjacent to the nearly-homologous target sites. The mere presence of additional PAM sequences should not be sufficient to generate off-target DSBs; there needs to be extensive homology of the protospacer followed by PAM.

In addition to Cas9 derived nucleases or nickases, other nucleases may be used in accordance with the present invention to introduce site specific cuts into DNA, thereby allowing modifications to be introduced in the targeted polynucleotide gene sequence by homologous recombination or non-homologous end joining repair. Such nucleases may be used with a donor (patch) sequence of the present invention to introduce specific modifications into the targeted endogenous polynucleotide gene sequence. Such nucleases/nickases include but are not limited to meganucleases, Zinc finger nucleases and transcription activator-like effector nucleases (TALENs).

The Cas or other nuclease/nickase recombinant protein of the present invention preferably comprises at least one Nuclear Localization Signal (NLS) to target the protein into the cell nucleus. Accordingly, as used herein the expression "nuclear localization signal" or "NLS" refers to an amino acid sequence, which 'tags' a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus. Classical NLSs can be further classified as either monopartite or bipartite. The first NLS to be discovered was the sequence PKKKRKV (SEQ ID NO: 84) in the SV40 Large T-antigen (a monopartite NLS). The NLS of nucleoplasmin, KR[PAATKKAGQA]KKKK (SEQ ID NO: 85), is the prototype of the ubiquitous bipartite signal: two clusters of basic amino acids, separated by a spacer of about 10 amino acids. The Cas9 protein exemplified herein is a mutated Cas9 nuclease comprising a NLS sequence.

There are many other types of NLS, which are qualified as "non-classical", such as the acidic M9 domain of hnRNP A1, the sequence KIPIK in yeast transcription repressor Matα2, the complex signals of U snRNPs as well as a recently identified class of NLSs known as PY-NLSs. Thus, any type of NLS (classical or non-classical) may be used in accordance with the present invention as long as it targets the protein of interest into the nucleus of a target cell. In an embodiment, the NLS is derived from the simian virus 40 large T antigen. In an embodiment, the NLS of the recombinant protein of the present invention comprises the following amino acid sequence: SPKKKRKVEAS (SEQ ID NO: 86). In an embodiment the NLS comprises the sequence KKKRKV (SEQ ID NO: 87). In an embodiment, the NLS comprises the sequence SPKKKRKVEASPKKKRKV (SEQ ID NO: 88). In another embodiment, the NLS comprises the sequence KKKRK (SEQ ID NO: 89).

The nuclease/nickase recombinant protein of the present invention may optionally advantageously be coupled to a protein transduction domain to ensure entry of the protein into the target cells. Alternatively the nucleic acid coding for the gRNA and for the nuclease or nickase (e.g., Cas9 nuclease/nickase) and the donor/patch nucleic acid sequence may be delivered in targeted cells using various viral vectors, virus like particles (VLP) or exosomes.

Protein transduction domains (PTD) may be of various origins and allow intracellular delivery of a given therapeutic by facilitating the translocation of the protein/polypeptide into a cell membrane, organelle membrane, or vesicle membrane. PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle including the mitochondria.

In an embodiment, a PTD is covalently linked to the amino terminus of a recombinant protein of the present invention. In another embodiment, a PTD is covalently linked to the carboxyl terminus of a recombinant protein of the present invention. Exemplary protein transduction domains include but are not limited to a minimal undecapeptide protein transduction domain (corresponding to residues 47-57 of HIV-1 TAT comprising YGRKKRRQRRR (SEQ ID NO: 90); a polyarginine sequence comprising a number of arginines sufficient to direct entry into a cell (e.g., 3, 4, 5, 6, 7, 8, 9, 10, or 10-50 arginines); a VP22 domain (49); an *Drosophila* Antennapedia protein transduction domain (50); a truncated human calcitonin peptide (51); RRQRRTSKLMKR (SEQ ID NO: 91); Transportan GWTLNSAGYLLGKINLKALAALAKKIL (SEQ ID NO: 92); KALAWEAKLAKALAKALAKHLAKALAKALKCEA (SEQ ID NO:93); and RQIKIWFQNRRMKWKK (SEQ ID NO:94). Further exemplary PTDs include but are not limited to, KKRRQRRR (SEQ ID NO: 95), RKKRRQRRR (SEQ ID NO: 96); or an arginine homopolymer of from 3 arginine residues to 50 arginine residues.

Other non-limiting examples of PTD include an endosomal escape peptide. Non-limiting examples of such endosomal escape peptides are listed in the Table 1 below.

TABLE 1

Endosomal escape peptides

| Peptide | Primary sequence | Mechanism | References |
|---------|------------------|-----------|------------|
| DT | VGSSLSCINLDWDVIRDKTKTIE SLKEHGPIKNKMSESPNKTVSEE KAKQYLEEFHQTALEHPELSELKT VTGTNPVFAGANYAAWAVNVAQ VIDSETADNLEKTTAALSILPGIGS VMGIADGAVHHNTEEIVAQSIALS SLMVAQAIPLVGELVDIGFAAYNF VESIINLFQVVHNSYNRPAYSPG | Fusion | (52), (SEQ ID NO: 99) |
| GALA | WEAALAEALAEALAEHLAEALAE ALEALAA | Membrane destabilization, pore formation and flip-flop of membrane lipids | (53), (SEQ ID NO: 100) |
| PEA | VLAGNPAKHDLDIKPTVISHRLHF PEGGSLAALTAHQACHLPLETFT RHRQPRGWEQLEQCGYPVQRLV ALYLAARLSWNQVDQVIRNALAS PGSGGDLGEAIREQPEQARLALT | Pore formation | (54), (SEQ ID NO: 101) |
| INF-7 | GLFEAIEGFIENGWEGMIDGWYG C | Membrane fusion and destabilization | (55), (SEQ ID NO: 102) |
| LAH4 | KKALLALALHHLAHLALHLALALK KA | Membrane destabilization | (56), (SEQ ID NO: 103) |
| CM18 | KWKLFKKIGAVLKVLTTG | Membrane destabilization | (57), (SEQ ID NO: 104) |
| HGP | LLGRRGWEVLKYWWNLLQYWS QEL | Pore formation and fusion | (58), (SEQ ID NO: 105) |
| H5WYG | GLFHAIAHFIHGGWH GLIHGWYG | Membrane destabilization | (59), (SEQ ID NO: 106) |
| HA2 | GLFGAIAGFIENGWEGMIDGWYG | Membrane fusion and destabilization | (60), (SEQ ID NO: 107) |
| EBI | LIRLWSHLIHIWFQNRRLKWKKK | Membrane destabilization | (61), (SEQ ID NO: 108) |
| DT | VGSSLSCINLDWDVIRDKTKTIE SLKEHGPIKNKMSESPNKTVSEE KAKQYLEEFHQTALEHPELSELKT VTGTNPVFAGANYAAWAVNVAQ | Fusion | (52), (SEQ ID NO: 109) |

TABLE 1-continued

Endosomal escape peptides

| Peptide | Primary sequence | Mechanism | References |
|---|---|---|---|
| | VIDSETADNLEKTTAALSILPGIGS
VMGIADGAVHHNTEEIVAQSIALS
SLMVAQAIPLVGELVDIGFAAYNF
VESIINLFQVVHNSYNRPAYSPG | | |

In an embodiment, the protein transduction domain is TAT or Pep-1. In an embodiment, the protein transduction domain is TAT and comprises the sequence SGYGRKKRRQRRRC (SEQ ID NO:97). In another embodiment, the protein transduction domain is TAT and comprises the sequence YGRKKRRQRRR (SEQ ID NO: 90). In another embodiment, the protein transduction domain is TAT and comprises the sequence KKRRQRRR (SEQ ID NO: 95). In another embodiment, the protein transduction domain is Pep-1 and comprises the sequence KETWWETWWTEWSQPKKKRKV (SEQ ID NO: 98).

In addition or alternatively to the above-mentioned protein transduction domains, the nuclease/nickase (e.g., Cas9 nuclease) recombinant protein or nucleic acid, patch nucleic acid sequence and gRNA(s) of the present invention may be coupled to liposomes to further facilitate their delivery into the cells.

Genetic constructs encoding a Cas 9 protein (nuclease or nickase) in accordance with the present invention can be made using either conventional gene synthesis or modular assembly. A humanized Cas9 construct is publicly available for example at the repository Addgene (for example Addgene plasmids pX330™, pX335™ (nickase), pX458™, pX459™, pX460™, pX461™, pX462™, pX165™, pX260™, pX334™ (nickase)).

In an aspect, the gRNAs, recombinant nuclease/nickase (e.g., Cas9) protein and donor/patch nucleic acid of the present invention may be used to decrease toxic Aβ peptides production by decreasing APP mRNA and APP protein in cells. In another aspect, the gRNAs, Cas9 recombinant nuclease/nickase protein and donor/patch nucleic acid of the present invention may be used to decrease APP cleavage at the β-secretase site (e.g., between amino acid 671 and 672 of APP) thereby inhibiting completely or partially the production of toxic Aβ peptides. As used herein, the expression "decreasing" in "decreasing the expression of toxic Aβ peptides in a cell" is meant to include circumstances where, in the absence of a gRNA, of a recombinant nuclease/nickase (e.g., Cas9) protein and of a patch nucleic acid sequence of the present invention, the toxic Aβ peptides are expressed at certain amount (baseline amount), which is decreased in their presence. It comprises decreasing/reducing/inhibiting the expression of APP and/or its maturation (cleavage) into toxic Aβ peptides in cells completely or partially. The cell may be a cell expressing a normal level of APP or Aβ peptides or an abnormal/higher level of Aβ peptides (as compared to normal conditions).

In an embodiment, the gRNA and Cas9 recombinant protein and patch nucleic acid of the present invention may be used to decrease transcription of the APP promoter and expression of the APP protein in cells from a subject in need thereof.

In an embodiment, the present invention relates to a method of decreasing Aβ peptide expression, production or accumulation in a subject in need thereof comprising administering to the subject an effective amount of a gRNA, a Cas recombinant nuclease or nickase protein and a donor/patch nucleic acid of the present invention in order to introduce one or more genetic modifications in a target gene (e.g., APP, PS-1 or PS-2). In an embodiment, the recombinant protein, gRNA and/or donor/patch nucleic acid are specifically formulated for crossing the plasma membrane and reaching the nucleus. In an embodiment, the present invention provides a composition comprising a Cas9, based recombinant protein donor/patch nucleic acid and/or gRNA of the present invention together with a pharmaceutically acceptable carrier. In an embodiment, the method of the present invention corrects a mutation present in a target gene, which is associated with increased risk of developing Alzheimer's disease. In an embodiment, the mutation increases the expression or maturation of APP into toxic Aβ peptides. In another embodiment, the method of the present invention introduces a modification in a target gene, which protects against Alzheimer's disease (i.e., reduces the risk of developing Alzheimer's disease). In an embodiment, the modification decreases the production of toxic Aβ peptide by modifying one or more of the beta and gamma secretases cleavage sites in the APP protein, thereby reducing toxic Aβ peptides secretion. In an embodiment the modification is a modification at amino acid 673 or other amino acids close to that position of the APP protein, which reduces maturation by the beta secretase. In an embodiment, the modification replaces an alanine at position 673 with a threonine.

Optimization of Codon Degeneracy

Because several site-specific nuclease proteins, such as Cas9, are normally expressed in bacteria, it may be advantageous to modify their nucleic acid sequences for optimal expression in eukaryotic cells (e.g., mammalian cells). This has been done for the embodiment of the Cas9 nuclease protein of the present invention described herein.

Codon degeneracy may also be used to distinguish two nucleic acids encoding for the same protein. For example, the donor/patch nucleic acid sequence of the present invention may comprise one or more modifications with respect to the wild type targeted gene sequence, which do not translate into modifications at the amino acid level. These one or more modifications allow distinguishing between the wild type endogenous sequence, the patch sequence and the integrated patch sequence into the targeted endogenous gene. In an embodiment of the present invention the wild type, donor/patch nucleic acid and modified targeted gene cane be distinguished using the appropriate combination of oligonucleotide primers and/or probes. In an embodiment, the oligonucleotide primer(s) or probe(s) overlap the integration site. In another embodiment, the modifications introduced at the nucleic acid level add one or more restriction sites normally not present in the wild-type targeted gene sequence and/or in the donor/patch sequence. The one or more restriction sites may allow identifying a properly integrated patch/donor sequence into the targeted endogenous gene sequence in accordance with the method of the present invention.

Accordingly, the following codon chart (Table 2) may be used, in a site-directed mutagenic scheme, to produce nucleic acids encoding the same or slightly different amino acid sequences of a given nucleic acid:

TABLE 2

Codons encoding the same amino acid

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUG AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CM CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Sequence Similarity

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term "homologous" does not infer evolutionary relatedness, but rather refers to substantial sequence identity). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. For the sake of brevity, the units (e.g., 66, 67 . . . 81, 82, . . . 91, 92% . . . ) have not systematically been recited but are considered, nevertheless, within the scope of the present invention.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman (62), and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (63) 1990 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (64). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (64). Hybridization conditions may be modified in accordance with known methods depending on the sequence of interest. Generally, stringent conditions are selected to be about 5° C. lower than the thermal melting point for the specific sequence at a defined ionic strength and pH.

In another aspect, the invention further provides one or more nucleic acids encoding the above-mentioned Cas nuclease/nickase recombinant protein, gRNA and/or patch/donor sequences. The invention also provides one or more vector(s) comprising one or more of the above-mentioned nucleic acids. In an embodiment, the vector further comprises a transcriptional regulatory element operably-linked to the above-mentioned nucleic acid. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, "operably-linked" DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals, which induce or control transcription of protein coding sequences with which they are operably-linked.

As indicated above, gRNAs, patch/donor and Cas recombinant nucleic acids of the present invention may be delivered into cells using various viral vectors. Accordingly, preferably, the above-mentioned vector is a viral vector for introducing the gRNA and/or Cas nucleic acid encoding the Cas9 nuclease/nickase and/or the donor patch sequence of the present invention in a target cell (preferably a neuron). Non-limiting examples of viral vectors include retrovirus, lentivirus, Herpes virus, adenovirus or adeno Associated Virus, as well known in the art. Herpesvirus, adenovirus, Adeno-Associated virus and lentivirus derived viral vectors have been shown to efficiently infect neuronal cells. Preferably, the viral vector is episomal and not cytotoxic to cells. In an embodiment, the viral vector is an AAV or a Herpes virus.

In yet another aspect, the present invention provides a cell (e.g., a host cell) comprising the modified targeted gene. The invention further provides a recombinant expression system, vectors and host cells, such as those described above, for the expression/production of a recombinant protein, using for example culture media, production, isolation and purification methods well known in the art.

In another aspect, the present invention provides a composition (e.g., a pharmaceutical composition) comprising the above-mentioned gRNA, recombinant nuclease/nickase (e.g., Cas9) nucleic acid or protein and a donor/patch nucleic acid. In an embodiment, the composition comprises the above-mentioned viral vector for targeting the gRNA, nuclease/nickase (e.g., Cas9) and donor/patch nucleic acids into a cell. In an embodiment, the cell is a neuronal cell. In an embodiment, the composition further comprises one or more pharmaceutically acceptable carriers, excipients, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The present invention further provides a kit or package comprising one or more (at least one) of the above-mentioned gRNA, recombinant nuclease/nickase protein and/or patch/donor nucleic acids or compositions, together with instructions for decreasing Aβ peptide production levels (expression or maturation) in a cell or for the treatment of Alzheimer's disease or age-related cognitive decline.

Definitions

The articles "a," "an" and "the" are used herein to refer to one or to more than one (i.e., to at least one) of the grammatical object of the article.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

The present invention is illustrated in further details by the following non-limiting examples.

EXAMPLE 1

Reagents and Methods

Preparation of Donor Plasmids and ssODNs for Homologous DNA Recombination (HDR) to Mutate Exon 16 of APP Gene.

All oligonucleotides and gBlocks gene fragments used to construct the donor plasmids were synthesized by IDT (Integrated DNA technologies, Iowa, USA). The pMiniT™ plasmid was obtained from the NEB PCR cloning kit (Catalog #E1202S, New England Biolabs, MA USA). Phusion™ High-Fidelity Polymerase (Thermo Fisher Scientific). Qiaquick™ gel extraction Kit and Qiaquick™ PCR purification kit were from Qiagen.

A) Construction of the pMiniT-Patch Plasmid

Step 1: A portion of the APP gene containing exon 16 and parts of introns 15 and 16 was initially amplified by PCR from DNA extracted from of 293T cells. The PCR product was sequenced to confirm that the nucleotide sequence was the same as the reference sequence published in NCBI (accession number NG_007376). The procedure for this PCR amplification was as follows: the PCR mix (50 µL) contained 100 ng of each primer Bfw (TTCAGCAGAC-GAACCAATTACA, in intron 15 (SEQ ID NO: 43)) and Brev (CACGAACTTTGCTGCCTTGTAG, in intron 16, (SEQ ID NO: 40)), 200 mM dNTP, 100 ng genomic DNA (from 293T cells), 1× Phusion™ HF buffer and 0.5 µL Phusion™ DNA Polymerase (2 U/µL). The PCR amplification was done in the Hybaid PCR Express™ apparatus using the following cycling program: 1 cycle of denaturation at 98° C. for 1 min; followed by 30 cycles comprising a denaturation step at 98° C. for 10 sec, an annealing step at 58° C. for 20 sec. and elongation step at 72° C. for 40 sec; followed by 1 cycle of final elongation at 72° C. for 10 min and hold at 4° C. indefinitely.

The analysis of the PCR fragment was done on a 1.4% agarose gel stained with Red Safe staining (Intron Biotechnology). After electrophoresis, a PCR product of 1180 pb was observed and extracted from the agarose gel to be further purified with a gel extraction kit (QIAquick™ Gel Extraction Kit, Qiagen). The purified PCR fragment was then cloned directly in a pMiniT plasmid included in the cloning kit (NEB) as follows: 150 ng purified PCR fragment (4 µL), 25 ng/µL linearized pMiniT plasmid (1 µL), 5 µL Cloning Master Mix making a final volume of 10 µL. The mix was left at room temperature 5 minutes and then placed on ice at least 2 minutes before the transformation in competent DH5α bacteria and plated on agar containing ampicillin. After overnight incubation at 37° C., six colonies were picked up and the plasmids were extracted (mini-prep method) from these colonies to verify the presence of the insert by plasmid digestion with the EcoR1 restriction enzyme. Three plasmids containing the insert with appropriate size were sequenced using primers MiniTfw (5'-ACCTGCCAACCAAAGCGAGAAC-3', (SEQ ID NO: 51)) and MiniTrev (5'-TCAGGGTTATTGTCTCAT-GAGCG-3', (SEQ ID NO: 52)). The sequences of the 3 inserts (1180 pb, FIGS. 15 and 16) in the pMiniT plasmid all showed 100% homology with the NCBI sequence (accession number NG_007376).

Step 2: Design of a gBlock permitting to introduce the A673T mutation in the APP gene and additional mutations to prevent a subsequent cut of the mutated APP gene by gRNA#8.

Step 2A: The plasmid pMiniT including the 1180 pb PCR fragment (obtained in step1) corresponding to a portion of the APP gene (portion of intron 15, exon 16 and portion of intron 16) showed two unique restriction enzyme sites (Stu1 and BstX1) near exon 16 (FIG. 21A). These two restriction sites served to introduce different DNA fragments in the original plasmid donor to insert various mutations or an optional tracker (FLAG) to evaluate the efficiency of the correction by HDR. A gBlock was thus designed containing these two restriction enzyme sites and several mutations within the nucleotide sequence targeted in wild exon 16 by sgRNA#8 and including the critical mutation amino acid Alanine (A) in position 673 (coded by gca) to a Threonine (coded by acg) (FIG. 21B). The gBlock also included a nucleotide mutation C for G creating a Spe1 restriction site localized in intron 16 to detect more easily the HDR repair produced by the gRNA8 with the Cas9 nuclease (FIG. 21B). Thus to make all the desired mutations discussed above, the gBlock gene fragment synthesized by IDT (see FIG. 21B) contained a total of 9 mutations (8 nucleotide mutations inside of exon 16 and another one in intron 16 creating a Spe1 site). The gBlock (FIG. 21B) was amplified to obtain a PCR fragment able to be cloned between the restriction enzymes sites Stu 1 and BstX1 of the pMiniT plasmid containing the wild type exon 16 described in step 1.

Step2B: The amplification of the gBlock was done as follows: the PCR reaction (50 µL) contained 100 ng of each primer gBlockfw (5'-ATCAATTTTCTTCTAACTTCAGG-3', (SEQ ID NO: 69)) and gBlockrev (5'-CCACCCGCCT-TGGCCTCCCAAAG-3', (SEQ ID NO: 70)), 200 mM dNTP, 100 ng genomic DNA (from 293T cells), 1× Phusion™ HF buffer and 0.5 µL Phusion™ DNA Polymerase (2 U/µL). The PCR amplification was done in the PCR apparatus (Hybaid PCR Express™) according to the following cycling program: 1 cycle, denaturation at 98° C. for 1 min; 30 cycles, denaturation at 98° C. for 10 sec, annealing at 60° C. for 10 sec and elongation at 72° C. for 10 sec; 1 cycle, elongation at 72° C. for 10 min and hold at 4° C. indefinitely.

Step 2C: The PCR product was electrophoresed on a 1.4% agarose gel and the PCR product (441 pb) was then purified with the Qiaquick™ gel extraction kit (Qiagen). The purified PCR fragment was then directly cloned in a pMiniT plasmid as described in the step1, transformed in competent DH5α bacteria and spread on ampicillin agar plate. A plasmid containing the expected 441 pb insert was prepared (miniprep preparation) from one the resulting clones. This plasmid was digested during 1 hour with restriction enzymes BstX1 followed by Stu1 in 100 µL digestion medium as follows respectively: 10 µL purified plasmid (~5 µg), 10 µL NEBuffer 3.1 (NEB), 90 µL H₂O and 2.5 µL BstX1 (10 000 U/ml). This mixture was incubated during one hour at 37° C. followed by purification of the digested product through a Qiaquick™ PCR column and elution with 90 µL of water. 10 µL of CutSmart™ buffer (NEB) and 2.5 µL of Stu 1 (10 000 U/ml) were added to 90 µL of the purified BstX1 digested product and incubated for one hour at 37° C. The double digested product was loaded directly on a 1.6% agarose gel and electrophoresed to separate the DNA fragment (BstX1/Stu1) (~400 pb). This fragment was purified using the Qiagen gel extraction kit and eluted in 100 µL. This fragment was treated with phenol/Chloroform (24:1) (75 µL) followed by Chloroform only (60 µL), recuperated in 100 µL of water, purified through a Qiaquick™ PCR column and eluted in 30 µL of water.

Figure 20:
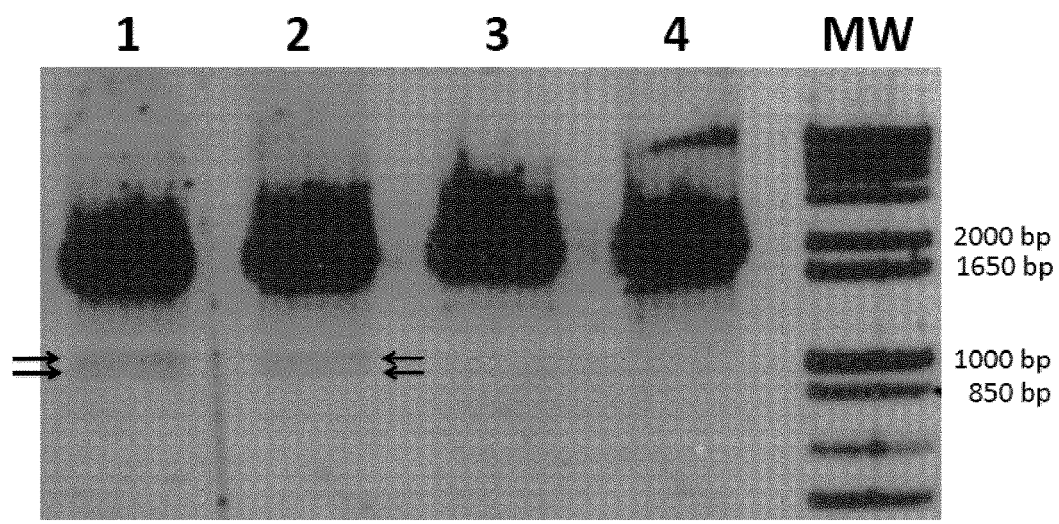
FIG. 20 shows that the APP gene in human cells has been modified to introduce a FLAG or FLAG Stop sequence in exon 16 of the endogenous APP gene. 293T cells were transfected as follows: Lane 1: 400 ng of pX330™ (containing the gRNA#8 and the Cas9 gene) and 400 ng of pMiniT-Patch-FLAG, Lane 2: 400 ng of pX330™ and 400 ng of pMiniT-Patch-FLAG-STOP, Lane 3: only 400 ng of pX330™ and Lane 4: only 400 ng of pMiniT-Patch-FLAG. The genomic DNA was extracted 72 hours post transfection and the APP nucleic acid sequence was amplified with primers Cfw and Crev. The 1993 bp PCR product was digested with Spe1 and migrated on a 2% agarose gel. Two additional bands (1002 and 991 bp) were detected in Lanes 1 and 2 confirming that the APP gene had been mutated by HDR resulting in the insertion of the new Spe1 site, which is present in the donor DNA (pMiniT-Patch-FLAG or pMiniT-Patch-FLAG-STOP) and is thus introduced in intron 16 of the endogenous APP nucleotide sequence following HDR.

Step 2D: The purified PCR fragment (BstX1/Stu1) (~400 pb) described in the step 2C was cloned between the unique sites (Stu1 and BstX1) found in the plasmid pMiniT previously described in Step 1 (FIG. 20A). The same procedure for the digestion and purification of the plasmid was done as described previously in Step 2C for the PCR fragment.

The purified PCR fragment was then cloned in the digested (BstX1/Stu1) plasmid pMiniT containing the wild APP gene sequence (portion of intron 15, exon 16 and portion of intron 16). For the cloning, we proceeded as follows: 100 ng of plasmid vector (1 µL), 300 ng of PCR fragment (BstX1/Stu1) (~400 pb), 5 µL of 2× Quick Ligation Reaction Buffer (NEB) and 0.5 µL of Quick T4 DNA Ligase (provided in the Quick Ligation Kit, NEB) were left at room temperature 5 minutes and then placed on ice before transformation in competent bacteria DH5α as described earlier. The resulting clones were sequenced to confirm that all of the expected 9 nucleotide mutations (FIG. 21B) have been successfully introduced in the original wild type gene (FIG. 21A) by the modified DNA provided by the gBlock.

Step2E: The final step was to add the specific DNA sequence targeted by the gRNA#8 at each 5' and 3' ends of the insert introduced in the pMiniT plasmid containing mutations described in Step 2D. To proceed the plasmid (step 2D) was amplified with the following long primers:

Tgt8bfw:
5'-atagcagaattccgacatgactcaggttcagcagacgaaccaattaca-3' (48 nts, (SEQ ID NO: 112))

Tgt8brev:
5'-cctgagtcatgtcggaattctgcacgaactttgctgccttgtag-3' (49 nts, (SEQ ID NO: 113))

The underlined nucleotides of both primers correspond to the target sequence of gRNA#8 (including in this case a PAM sequence for proper recognition by Cas9), while the rest of the nucleotide sequences correspond to the end of the insert of the plasmid MiniT containing mutations described in step 2D. To produce the final donor/patch, a PCR product (1224 pb) was obtained as follows: the PCR reaction (50 µL) contained 100 ng of each primer Tgt8bfw and Tgt8brev, 200 mM dNTP, 10 ng plasmid DNA (step 2D), 1× Phusion HF buffer and 0.5 μL Phusion DNA Polymerase (2 U/μL). The PCR amplification was done in the Hybaid PCR Express apparatus according to the following cycling program: 1 cycle, denaturation at 98° C. for 1 min; 5 cycles, denaturation at 98° C. for 10 sec, annealing at 55° C. for 20 sec and elongation at 72° C. for 40 sec; 25 cycles, denaturation at 98° C. for 10 sec, annealing at 60° C. for 20 sec and elongation at 72° C. for 40 sec; 1 cycle, elongation at 72° C. for 10 min and hold at 4° C. indefinitely. At the end of the reaction, the PCR product was analyzed on a 1.4% agarose gel and purified with Qiaquick™ gel extraction kit as described earlier. The purified PCR product (1224 pb) was cloned directly in a pMiniT plasmid (NEB PCR cloning kit) as described previously and cloned in competent bacteria DH5α. The clones resulting from the transformation were sequenced to confirm the expected configuration of the pMiniT Patch. The originality of this construct to produce HDR is that the target sites of gRNA#8 (i.e., the same target sequence as in the wild type APP gene) are present at in each side of the plasmid mini-T insert (1224 pb). This feature permits to liberate a linear fragment cassette to facilitate the HDR.

Construction of plasmid pMiniT-Patch containing a 3×FLAG or a 3×FLAG-STOP

To construct the plasmid pMiniT-Patch containing the 3×FLAG or the 3×FLAG-STOP, two gBlocks described in FIGS. 22 A and B were synthesized by IDT. The same procedure described in the above section A steps 2C and 2D for introducing in the plasmid pMiniT-Patch digested with Stu1/BstX1 a DNA fragment obtained by PCR amplification for each gBlock was used. The final cloning result gave a plasmid pMiniT-Patch containing a 3×FLAG and another pMiniT-Patch containing a 3×FLAG-STOP. The inserts in these two plasmids were confirmed by sequencing and the nucleotide sequence insert in the pMiniT-Patch-3×-FLAG (SEQ ID NO:73) and pMiniT-Patch-3×FLAG-STOP (SEQ ID NO: 74) are shown in the FIGS. 22 C and D respectively.

Design and Synthesis of ssODNs 199 nts

Figure 17:
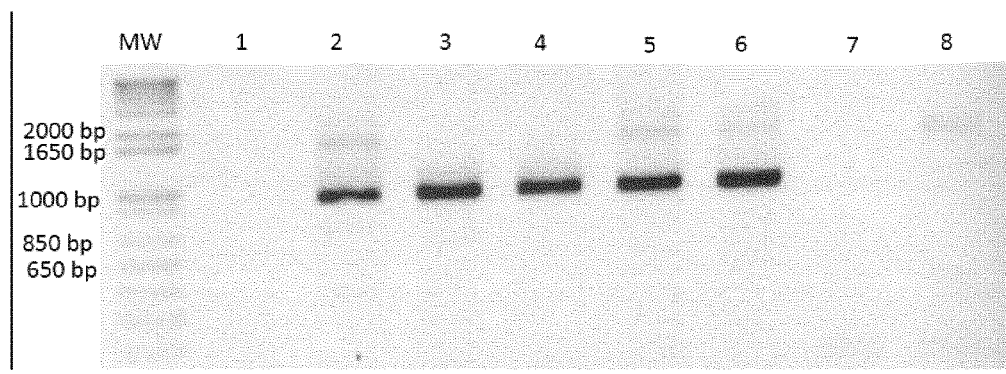
FIG. 17 shows that the endogenous APP gene can be modified by various donor/Patch nucleic acid sequences. (A) Nucleic acid sequence of the single stranded oligodeoxynucleotide (ssODN) used to modify the APP gene as described in Example 5 (SEQ ID NO: 59). Underlined nucleotides correspond to those, which are modified in the wild-type APP gene to introduce the A673T mutation, to prevent the binding of the gRNA#8 to the mutated gene and to insert a new Spe1 site in intron 16. The portion of the sequence in lowercase corresponds to the coding sequence of exon 16 in the APP gene. (B) Correction of the APP gene with the single stranded oligonucleotide described in (A) or with a PCR product (amplicon synthesized with primers Bfw and Brev (SEQ ID NO: 60), see Example 5), with a FLAG or FLAG-STOP patch/donor sequence. The cell DNA was amplified 72 hours post transfection with primers Cfw (SEQ ID NO: 38) and ILMUrev (SEQ ID NO: 42). The presence of a PCR product confirmed that the APP gene had been modified by homologous recombination. The 293T cells in a 24 well plate were transfected with the following plasmids/nucleic acids. Lane 1: 400 ng of pLenti-eGFP and 400 ng of pX330™ (i.e., gRNA#8 and Cas9); Lane 2: APP amplicon (150 ng) of part of pMiniT-Patch and pX330™; Lane 3: 2.5 µg of single stranded oligonucleotide and 400 ng of pX330™; Lane 4: 5 µg of single stranded oligonucleotide and 400 ng of pX330™; Lane 5: 400 ng of pMiniT-Patch-Flag and 400 ng of pX330™; Lane 6: 400 ng of pMiniT-Patch-Flag-Stop and 400 ng of pX330; Lane 7: no transfection (negative control); Lane 8: 400 ng of pMiniT-Patch-Flag (no pX330™)

A long single stranded oligodeoxynucleotides (ssODNs) of 199 nts was designed to correspond to the entire exon 16 of the APP gene extended at each side by 90 nucleotides corresponding respectively to a portion of the 3' end of intron 15 and of the 5' end of intron 16. This ssODN was synthesized by IDT (4 nmoles of Ultramer DNA oligo) and the nucleotide sequence is presented in the FIG. 17A. The ssODN 199 nts contained all the nucleotide mutations described for the plasmid pMiniT-Patch.

Co-Transfection in 293T cells of gRNA#8 with plasmids donors MiniT-Patch, MiniT-Patch-3×FLAG and MiniT-Patch-3×FLAG-STOP, ssODN 199 nts, and PCR fragment of Patch:

Materials: all the transfection reagents (Lipofectamine 2000™ transfection reagent and Opti-MEM-1 ™ culture media) were from Life Technologies.

The day before the transfection, 100,000 293T cells were seeded per well in a 24 well plates in DMEM medium supplemented with 10% FBS and antibiotics (penicillin/streptomycin 1×). The following morning, the culture medium was changed for 500 μl of DMEM medium supplemented with 10% FBS without antibiotics. The plate was incubated at 37° C. in the incubator for the time required to prepare the transfection solution. For the transfection, solutions A and B were first prepared. Solution A contained 48 μl of Opti-MEM™ and 2 μl of Lipofectamine™ 2000 for a final volume of 50 μl. Solution B was prepared as follows: a volume of DNA solution containing 150 ng to 800 ng of DNA was mixed with a volume of Opti-MEM™ to obtain a final volume of 50 μl. For each co-transfection, various amounts of the following plasmids were used: pX330™ (containing gRNA#8 and Cas9, see FIG. 23), pMiniT-Patch, pMiniT-Patch-3×FLAG or pMiniT-Patch-3×FLAG-STOP, ssODN 199 or a PCR fragment of pMiniT-Patch (see FIGS. 17-22 (amplified with Bfw and Brev). Solutions A and B were then mixed by up and down movement and incubated at room temperature for 20 minutes. Then, 100 μl of the mixed solution were added to each well. The plate was let in the $CO_2$ incubator for a period of 4 to 6 hours. The medium was changed by 1 ml of DMEM supplemented with 10% FBS and antibiotics. The plate was incubated for 48-72 hours in the $CO_2$ incubator before extraction of genomic DNA.

DNA Extraction 293T cells were detached from wells by performing up and down movements in 1 ml culture medium with a pipette. These cells were transferred in an Eppendorf tube and centrifuge at 8000 RPM for 10 minutes. The supernatant medium was carefully removed without disturbing the cell pellets. These cell pellets were washed once with 1 ml of HBSS solution and centrifuged at 8000 RPM for 10 minutes. The HBSS was then carefully removed without disturbing the cell pellets. The cells were lysed with 100 μl of lysis buffer containing 1% Sarkosyl and 0.5M EDTA pH 8 supplemented with 10 μl of proteinase K solution (20 mg/ml). These tubes were incubated at 50° C. for 15 minutes. 400 μl of 50 mM Tris pH 8 were then added to each tube. Next, 500 μl of a mixture of phenol: chloroform: isoamyl alcohol (respectively 25:24:1) was added. The tubes were centrifuged at 16 000 RPM for 2 minutes. The aqueous upper phase was transferred to a new tube. 50 μl of NaCl 5 M were added to each tube and mixed thoroughly. One (1) ml of ice cold ethanol 100% was added to each tube and mixed for genomic DNA precipitation. The tubes were centrifuged at 16000 RPM for 7 minutes and ethanol was carefully removed to avoid disturbing the DNA pellets. These DNA pellets were washed once with 400 μl ethanol 70%. The tubes were centrifuged at 16000 RPM for 5 minutes and ethanol was removed to permit to dry the DNA pellet rapidly by lyophilisation. The DNA was solubilized in 50-100 μl of sterile water and stored at −20° C. until quantification was performed. The DNA solutions were dosed at 260 nm with a spectrophotometer.

Genomic DNA PCR Amplification

For PCR amplification of genomic DNA of 293T cells cotransfected with a patch/donor sequence and a gRNA/Cas9 plasmid the following mix was used: genomic DNA (25 ng/μl, 2 μl), 5× HF Phusion™ buffer (10 μl), dNTP 10 mM (1 μl), forward primer (100 ng/μl, 1 μl), reverse primer (100 ng/μl, 1 μl), water (34.75 μl) and Phusion™ enzyme (2 U/μl, 0.25 μl). PCR amplification was as follows: denaturation at 98° C. for 30 sec. followed by (98° C.-10 sec, 60° C.-20 sec. and 72° C. 45 sec. to 1 min) for 35 cycles; and 72° C. for 5 minutes as a final elongation cycle.

Surveyor™ Nuclease Assay for Confirmation of Genome Modification

After transfection, the 293 T cells were incubated at 37° C. for 72 hrs and genomic DNA was extracted as described above. The genomic region flanking the gRNA#8 target site in exon 16 of the APP gene was PCR amplified with different forward primers Bfw or Cfw and different reverse primers Brev or Crev using Phusion™ DNA Polymerase (New England Biolabs) as described in genomic DNA PCR amplification section. After the PCR amplification, 20 μl of unpurified PCR products were heated at 95° C. for 5 minutes and slowly cooled down (5° C. per 30 seconds) to 25° C. using a thermocycler. After the formation of heteroduplexes, 1 µL of Surveyor™ enzyme (Transgenomics inc. Omaha, Nebr., USA) and 1 µL of enhancer in Phusion™ HF Buffer (NEB) were added with to each tube to obtain a 1× final concentration. The mixes were incubated at 42° C. for 25 minutes. 5 µl of loading buffer were added to each tube. All Surveyor™ analysis were done on 2% agarose gels containing RedSafe™ Nucleic Acid staining solution (Froggobio inc., Toronto, ON, Canada) for UV visualization.

were annealed in a thermocycler using the following parameters: 37° C. 30 min, 95° C. 5 min and then ramp down to 25° C. at 5° C./min.

The ligation reaction was done as follows: 50 ng of BbsI digested pX260™, pX330™ or pX458™ from step 2, 1 µl phosphorylated and annealed oligo duplex from step 3 (1:200 dilution), 5 µl 2× Quick Ligation™ Buffer (NEB), 1 µl Quick Ligase (NEB) and ddH$_2$O to obtain a total volume of 11 µl. The mixture was incubated at room temperature for 10 min.

TABLE 3

Primer and gRNA guide sequences targeting the human APP gene

| Location/target | Nucleotide position In genome | Nucleotide sequence of primers/gRNA 5' to 3' | SEQ ID NO: |
|---|---|---|---|
| 3' end of intron 15 | 277141-278147 | | SEQ ID NO: 36 |
| Cfw: in intron 15 | 277277-277300 | CACGGTAGAGAAGATGACTTCAAA | SEQ ID NO: 38 |
| Afw: in intron 15 | 277559-277577 | GCTCTTTATTCAGCAGACG | SEQ ID NO: 39 |
| Bfw: intron 15 | 277567-277588 | TTCAGCAGACGAACCAATTACA | SEQ ID NO: 43 |
| Exon 16 | 278149-278250 | | SEQ ID NOs: 31/32 |
| Target of gRNA#8 | 278202-278220 | CAGAATTCCGACATGACTC | SEQ ID NO: 15 |
| 5' end of intron 16 | 278251-279540 | | SEQ ID NO: 37 |
| Brev: intron 16 (reverse) | 278721-278745 | CACGAACTTTGCTGCCTTGTAG | SEQ ID NO: 40 |
| Arev: intron 16 (reverse) | 278781-278803 | GTGGAAGTCAAAGTGGCTGCTAT | SEQ ID NO: 41 |
| Crev: intron 16 (reverse) | 279245-279278 | CCTCTTACTGCACCTACTGATAAG | SEQ ID NO: 42 |

CRISPR Construction in the pX330™ and pX458™ Plasmids

The pX330™-U6-Chimeric_BB-CBh-hSpCas9 plasmid was purchased from Addgene inc (plasmid #42230 from Addgene). In order to clone the target sequence into the pX330™ (or pX458™ backbone), two oligos having the following sequences were purchased from IDT:

(SEQ ID NO: 110)
Oligo 1: 5' - CACCGNNNNNNNNNNNNNNNNNNNN - 3'

(SEQ ID NO: 111)
Oligo 2: 3' - CNNNNNNNNNNNNNNNNNNNNCAAA - 5'

These oligos are complementary, and their sequences correspond to the gRNA target site and will serve, once cloned into the plasmid to express the desired gRNA. The overhangs serve to clone the annealed oligos into the plasmid using BbsI sites. The following mixture was prepared: 1 µg of pX330™ with 1 µl FastDigest™ BbsI (Fermentas), 1 µl FastAP™ (Fermentas), 2 µl 10× FastDigest™ Buffer. The volume was completed to 20 µl with ddH2O. The mixture was incubated for 30 min at 37° C. The same protocol applies to the use of the p260 and p458 plasmids.

The pX260™, pX330™ or pX458™ plasmids were purified using QIAquick™ Gel Extraction Kit and eluted in the elution buffer.

To phosphorylate and anneal each pair of complementary oligos, the following procedure was used: 1 µl oligo 1 (1 µg), 1 µl oligo 2 (1 µg), 1 µl 10× T4 Ligation Buffer (NEB), 6.5 µl ddH$_2$O, 0.5 µl T4 PNK (NEB) for a total 10 µl. The oligos The nucleotide positions indicated in Table 3 above correspond to the nucleotide positions in the human APP genomic sequence of NCBI reference sequence NG_007376.1.

EXAMPLE 2 gRNAs Efficiently Target the Human App Gene in Cells

In an to attempt to modify the APP gene to reduce the formation of toxic Aβ peptides, fourteen different gRNAs targeting nucleotide sequences near the sequence coding for the alanine at position 673 in the APP gene were first prepared. The mutation A673T is located in exon 16 of the human APP gene. FIG. 4 illustrates the nucleotide and amino acid sequences of exon 16 and FIG. 5 illustrates the nucleotide sequence of part of intron 15, exon 16 and part of intron 16 of the human APP gene. FIG. 4 also indicates the amino acid alanine (A) in position 673 that is to be changed to a threonine (T). Table 4 below, indicates the nucleotide sequences in intron 15, exon 16 and intron 16 in the human APP gene, which were targeted by these gRNAs. Each targeted sequence includes in 3' an NGG sequence, which is the protospacer adjacent motif (PAM), necessary for the formation of a complex between the gRNA, the DNA and the Cas9 nuclease used in the instant examples. The PAM sequence is not part of the gRNA expressed in cells.

TABLE 4 gRNAs target sequences in the human APP gene

| gRNA # | Targeted sequence + PAM sequence (underlined) | Sense/Antisense | Starting position | Ending position | SEQ ID NOs: | Location |
|---|---|---|---|---|---|---|
| 1 | 5'ATTTATGAGTAAAACTAATTGG3' | Sense | 278092 | 278113 | SEQ ID NOs: 1, 2 | Intron 15 |
| 2 | 5'TTTAATTATGATGTAATACAGG3' | Sense | 278127 | 278148 | SEQ ID NOs: 3, 4 | In 15/Ex 16 |
| 3 | 5'TATGATGTAATACAGGTTCTGG3' | Sense | 278133 | 278154 | SEQ ID NOs: 5, 6 | In 15/Ex 16 |
| 4 | 5'ATGATGTAATACAGGTTCTGGG3' | Sense | 278134 | 278155 | SEQ ID NOs: 7, 8 | In 15/Ex 16 |
| 5 | 5'GGGTTGACAAATATCAAGACGG3' | Sense | 278153 | 278174 | SEQ ID NOs: 9, 10 | Exon 16 |
| 6 | 5'TTGACAAATATCAAGACGGAGG3' | Sense | 278156 | 278177 | SEQ ID NOs: 11, 12 | Exon 16 |
| 7 | 5'GAGATCTCTGAAGTGAAGATGG3' | Sense | 278177 | 278198 | SEQ ID NOs: 13, 14 | Exon 16 |
| 8 | 5'CAGAATTCCGACATGACTCAGG3' | Sense | 278202 | 278223 | SEQ ID NOs: 15, 16 | Exon 16 |
| 9 | 5'GAAGTTCATCATCAAAAATTGG3' | Sense | 278228 | 278249 | SEQ ID NOs: 17, 18 | Exon 16 |
| 10 | 5'CCAAATGACCTATTAACTCTGG3' | Sense | 278291 | 278312 | SEQ ID NOs: 19, 20 | Intron 16 |
| 11 | 3'GGATCTTTCTTCAAAACCCATC5' | Antisense | 278049 | 278070 | SEQ ID NOs: 21, 22 | Intron 15 |
| 12 | 3'GGACGTATGAAATTAATACTAC5' | Antisense | 278117 | 278138 | SEQ ID NOs: 23, 24 | Intron 15 |
| 13 | 3'GGCTGTACTGAGTCCTATACTT5' | Antisense | 278209 | 278230 | SEQ ID NOs: 25, 26 | Exon 16 |
| 14 | 3'GGAGAAAGGTGATGACAAACAG5' | Antisense | 278266 | 278287 | SEQ ID NOs: 27, 28 | Intron 16 |

TABLE 5 gRNA sequences corresponding to gRNA target sequences set forth in Table 4.

| gRNA # | gRNA sequence | SEQ ID NO: |
|---|---|---|
| 1 | 5' AUUUAUGAGUAAAACUAAU 3' | SEQ ID NO: 115 |
| 2 | 5' UUUAAUUAUGAUGUAAUAC 3' | SEQ ID NO: 116 |
| 3 | 5' UAUGAUGUAAUACAGGUUC 3' | SEQ ID NO: 117 |
| 4 | 5' AUGAUGUAAUACAGGUUCU 3' | SEQ ID NO: 118 |
| 5 | 5' GGGUUGACAAAUAUCAAGA 3' | SEQ ID NO: 119 |
| 6 | 5' UUGACAAAUAUCAAGACGG 3' | SEQ ID NO: 120 |
| 7 | 5' GAGAUCUCUGAAGUGAAGA 3' | SEQ ID NO: 121 |
| 8 | 5' CAGAAUUCCGACAUGACUCA 3' | SEQ ID NO: 122 |
| 9 | 5' GAAGUUCAUCAUCAAAAAU 3' | SEQ ID NO: 123 |
| 10 | 5' CCAAAUGACCUAUUAACUC 3' | SEQ ID NO: 124 |
| 11 | 5' CUACCCAAAACUUCUUUCU 3' | SEQ ID NO: 125 |
| 12 | 5' CAUCAUAAUUAAAGUAUGC 3' | SEQ ID NO: 126 |
| 13 | 5' UUCAUAUCCUGAGUCAUGU 3' | SEQ ID NO: 127 |
| 14 | 5' GACAAACAGUAGUGGAAAG 3' | SEQ ID NO: 128 |

Figure 6A:
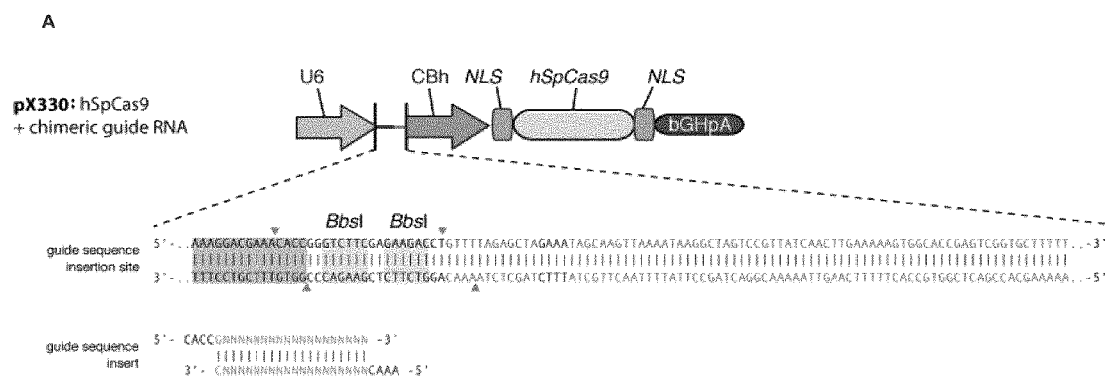
FIG. 6A is from the information pamphlet regarding the pX330™ plasmid. It can be viewed at the Addgene website. The guide sequence insertion site of plasmid pX330™ is shown (SEQ ID NO: 44). For proper sequence insertion into the pX330™ plasmid at the BbsI sites, the guide sequences should have CACC and CAAA overhangs (in 5'). The CACC overhang should preferably be followed by a G for increased expression under the U6 promoter (it can either be present in the gRNA target sequence or be added before the target sequence in the gRNA insert). The Cas9 recognition sequence is also shown (SEQ ID NO:134 (DNA) and SEQ ID NO: 135 (RNA)) (B) Schematic representation of the APP gene fragment of HEK 293T cells amplified by PCR and used in the Surveyor™ Enzyme Test to detect micro-insertions or micro-deletion (INDELs) induced by the expression of gRNAs and Cas9 enzyme. Primers Bfw (SEQ ID NO: 43) and Brev (SEQ ID NO: 40) (see Table 3 for specific sequence) were used. (C) Results of Surveyor™ Enzyme Test for fourteen (14) different gRNAs (see Table 4 for specific sequences). Cells were either not-transfected (C) or transfected with a eGFP plasmid, or with the pX330™ plasmid coding for a humanized Cas9 derived from *S. pyogenes* and one of the fourteen 14 different gRNAs (1 to 14). The DNA was collected from the cells 72 hours post transfection and part of the APP gene (including exon 16) was amplified by PCR with primers Bfw and Brev. The PCR amplicon was then digested with the Surveyor™ enzyme, which cuts miss-matched DNA strands indicating that mutations were introduced in the APP gene.

Each gRNA targeting the APP gene was inserted into plasmid pX330™ (Plasmid 42230: pX330-U6-Chimeric_BB-CBh-hSpCas9 from Addgene) under the control of the U6 promoter and transfected in HEK 293T cells. This plasmid also codes for the humanized Cas9 nuclease (hSpCas9, FIG. 6A and FIG. 23), which cuts double stranded DNA at a specific site when a gRNA efficiently hybridizes with its target sequence. The insert coding for the gRNA in the plasmid corresponds to the gRNA target sequence on the genomic DNA without the PAM. The expressed gRNA includes the target sequence and a tracrRNA sequence (+85 nts) for efficient targeting efficiency/Cas9 recruitment. Once cut, the double stranded breaks in the DNA introduced by Cas9 are then spontaneously repaired by Non Homologous End Joining (NHEJ) resulting in micro-insertions or micro-deletions (INDELs) in the APP gene.

To detect INDELs resulting from Cas9/gRNA expression, cellular DNA was extracted and the APP gene amplified by PCR using primers Bfw and Brev (see Table 3). The amplicons were then heated at 95° C. to separate the two DNA strands and slowly cooled at room temperature to permit the formation of mismatched DNA strands if INDELs were present. These miss-matched DNA were then cut with the Surveyor™ enzyme, resulting in additional bands in an agarose gel.

Figures 6B, 6C:
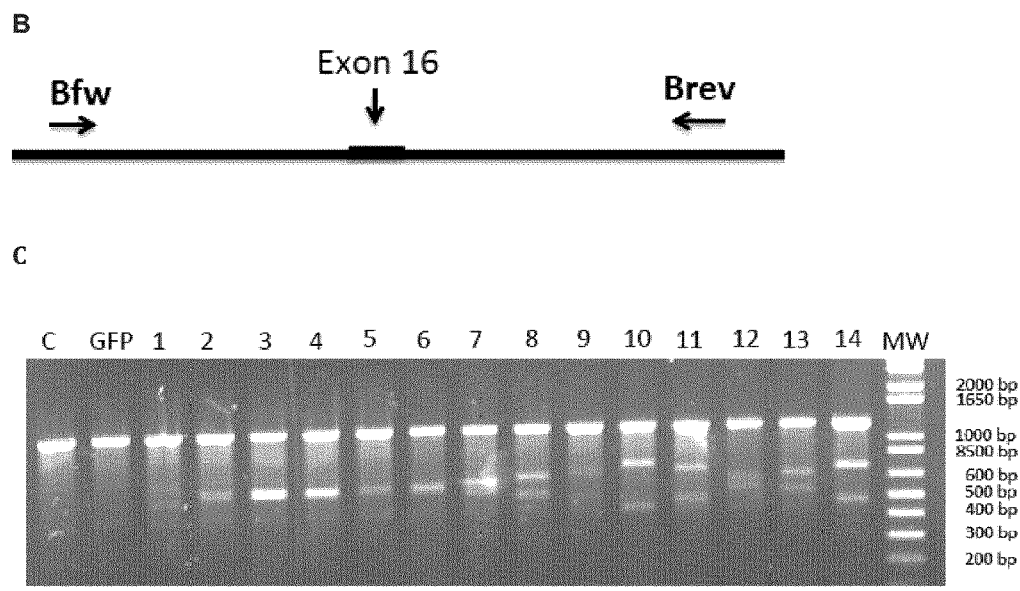
FIG. 6 shows that gRNAs of the present invention efficiently target the human APP gene in HEK 293T cells. (A) Schematic representation of the pX330™ plasmid encoding the humanized Cas9 enzyme (hSpCas9) and gRNAs transfected in HEK 293T cells to induce mutations in the endogenous APP gene.

As shown in FIG. 6C, incubation of amplified APP fragments with the Surveyor™ enzyme resulted in the presence of an additional band on the agarose gel for all gRNAs tested. Some gRNAs were however more efficient than others in cutting the target sequence. These results indicate that transfection of human cells with the various pX330™ plasmids can efficiently target and induce double strand breaks in the APP gene. These breaks were spontaneously repaired by Non Homologous End Joining (NHEJ) resulting in micro-insertions or micro-deletions (INDELs) in the APP gene.

The gRNA#8 (FIG. 5B, Tables 3 and 4, SEQ ID NO: 15) was selected for further investigation but other gRNAs were shown to be effective and may be used in accordance with the present invention.

EXAMPLE 3

Figure 7A:
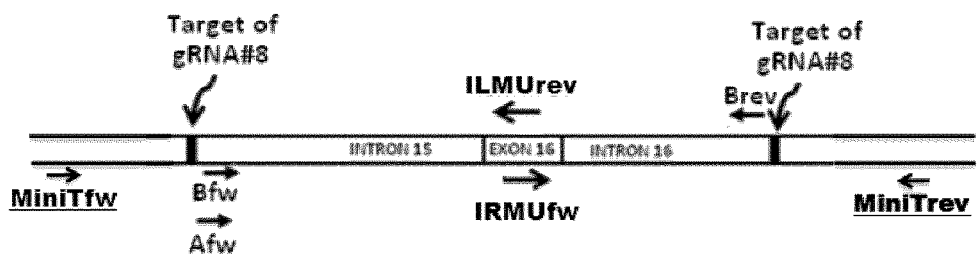
FIG. 7 shows the pMiniT-Patch plasmid construct encoding a donor DNA used to modify the APP gene by homologous recombination. (A) Schematic representation of the pMiniT-Patch plasmid. (B) Nucleic acid sequence of the donor plasmid MiniT-Patch (SEQ ID NO: 45). The donor DNA patch is (SEQ ID NO: 46), located between the two gRNA#8 sequences. The nucleotide sequence of exon 16 is shown in italics. Primer sequences (MiniTfw (SEQ ID NO: 51); Bfw (SEQ ID NO: 43); IRMUfw (SEQ ID NO: 49); ILMUrev (SEQ ID NO: 50); MiniT rev (SEQ ID NO: 52)) and gRNA#8 target sequence+PAM (SEQ ID NO: 16) are also identified. Mutated nucleotides in Exon 16 are in lowercase. Two of these mutations change the alanine at position 673 to a threonine, which has been previously shown to reduce the production of toxic Aβ peptides and to protect against Alzheimer's disease. Other nucleotides have been changed (i.e., mutations introduced) but without changing the resulting amino acid (i.e., silent mutation). These changes have been made to prevent recognition of the corrected APP gene by the gRNA and thus, recuting of the modified APP gene.

Endogenous APP Gene and pMini-Patch Plasmid are Efficiently Targeted by the CRISPR System in Human Cells The next step toward modifying the APP gene to reduce toxic Aβ production is to make a donor DNA that can be used to modify the gene by homologous recombination (FIG. 7). The donor DNA (called pMiniT-Patch) prepared contained about 500 nucleotides of the APP gene (homology sequences) on each side of the sequence targeted by the gRNA#8 (see FIGS. 7A and B). This donor DNA also contained a mutation in the codon encoding amino acid 673 of the APP gene, which replaced the alanine (A) by a threonine (T). The donor DNA also contained modifications in some of the nucleotides of exon 16 to prevent the APP gene from being cut again by gRNA#8/Cas9 after its modification by Homologous Directed Repair (HDR, see FIGS. 4B and 7B). One nucleotide of intron 16 of the APP gene was also modified to a G in pMiniT-Patch to modify the APP gene sequence to ACTAGT, which can be cut by the restriction enzyme Spe1 (FIG. 7B). This is to permit a rapid detection of the corrected APP gene. Finally, the pMiniT-Patch also contained at each end of the homology sequence used for repair of the APP gene, the sequence targeted by the gRNA#8. This is to permit linearization of the pMiniT-Patch plasmid and to separate the correcting oligonucleotide from the backbone of the plasmid (see Example 1 for more details about plasmid constructions). The pMiniT-patch plasmid allows replacing whole Exon 16 in the APP gene, together with portions of intron 15 and intron 16.

Human cells (HEK 293T) were next transfected with the pMiniT-Patch plasmid described above and with various amounts of the pX330™ plasmid (from 5 µg to 1 µg) containing or not the gRNA#8 and containing or not the nucleic acid sequence encoding a Cas9 nuclease. Genomic DNA was extracted from the cells 72 hours post-transfection.

The APP gene was amplified with primers Afw and Arev (see positions of primers in FIGS. 8B and C and Table 3) resulting in a 1245 bp amplicon. Next, a Surveyor™ enzyme test on the PCR product obtained by amplification of the APP gene was performed. As expected, transfection of cells with the pMiniT-Patch plasmid alone did not result in the presence of any additional amplification product and thus is unable, alone (i.e., without the presence of Cas9 and gRNA) to introduce a mutation in the APP gene (FIG. 9B, lane 1). However, digestion of the PCR product obtained on DNA extracted from cells transfected with decreasing amounts (from 5 µg to 1 µg) of pX330™ (coding for gRNA#8 and Cas9) with the Surveyor™ enzyme resulted in the presence of 2 additional bands (602 bp and 643 bp) (FIG. 9B). These results demonstrate that the gRNA#8 can produce either micro-insertions or micro-deletions (INDELs) or Homologous Directed Repair (HDR) in the APP gene (Lanes 2-5 of FIG. 9). The presence of additional bands reflects the ability of gRNA#8 and Cas9 encoded by the pX330™ plasmid to target and cut the endogenous APP gene. The cuts are later repaired by Non Homologous End Joining (NHEJ) and are detected by the Surveyor™ enzyme.

Co-transfection of various ratios of pMiniT-Patch and pX330™ plasmids (4:1 µg, 2.5:2.5 µg and 1:4 µg of pMiniT-Patch: pX330™) also resulted in the presence of additional bands due to the cut of the APP gene by the gRNA#8 and the Cas9, repaired either by NHEJ or by Homologous Directed Repair (HDR) with the pMiniT-Patch (FIG. 9B, lanes 6-8).

The DNA of the human cells transfected or not with pMiniT-Patch and pX330™ (coding for gRNA#8 and Cas9) was also amplified with primers MiniTfw and Brev or with MiniTrev and Bfw (see position and sequence of these primers in FIG. 7), which specifically amplify the donor plasmid but not the genomic DNA. The amplicons (respectively 1339 bp and 1317 bp) were incubated with the Surveyor™ enzyme. This generated in each case 2 fragments (respectively 150 pb+1189pb and 125 pb+1192pb) (FIG. 10). These results demonstrate that the donor plasmid (pMiniT-Patch) was cut by the gRNA#8/Cas9 combination. These cuts were produced because of the presence of the target sequence of the gRNA#8 on both sides of the patch inserted in the pMiniT-Patch donor plasmid. These two gRNA target sequences were inserted in the donor plasmid to permit its linearization by the combined action of the gRNA#8 and Cas9 nuclease. This linear fragment is expected to favor homologous recombination with genomic DNA following a cut in the targeted APP DNA by the CRISPR system (i.e., gRNA#8 and Cas9 nuclease).

EXAMPLE 4

Figure 8A:
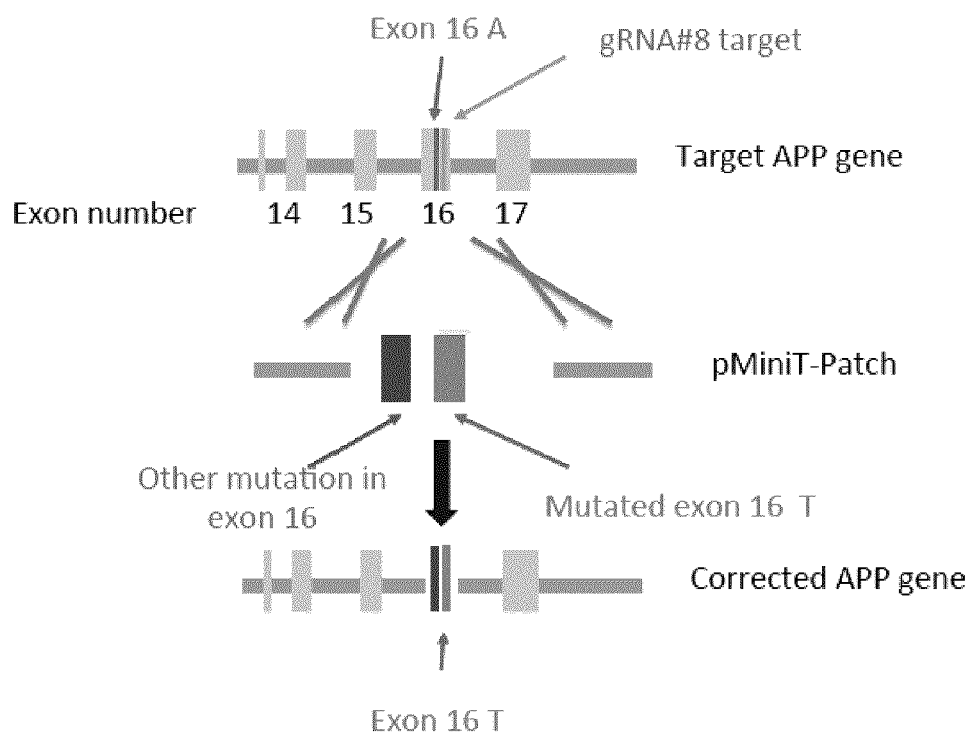
FIG. 8 shows how the APP gene is corrected by the pMini-Patch plasmid using Homologous Directed Repair (HDR). (A) Schematic representation of the correction of the APP gene by Homologous Directed Repair. (B) Schematic representation of the primers used to amplify the mutated APP gene. (C) Partial sequence (SEQ ID NO: 47) of the mutated (corrected) APP gene comprising a A673T substitution. The nucleic acid sequence includes a partial sequence of intron 15, followed by the complete sequence of exon 16 (nucleotides 278148-278248 in italic, SEQ ID NO: 48, corrected Exon 16) and a partial sequence of intron 16. Various primer positions are shown. The mutated oligonucleotides are in bold. A new SpeI site was introduced at position 278275-278280. The sequences of forward primers Cfw (SEQ ID NO: 38), Bfw (SEQ ID NO: 43) and IRMUfw (SEQ ID NO: 49) are underlined. The sequences of primers Afw (SEQ ID NO: 39), Brev (SEQ ID NO: 40), Arev (SEQ ID NO: 41) and Crev (SEQ ID NO: 42) are highlighted and bold.
Figure 8B:
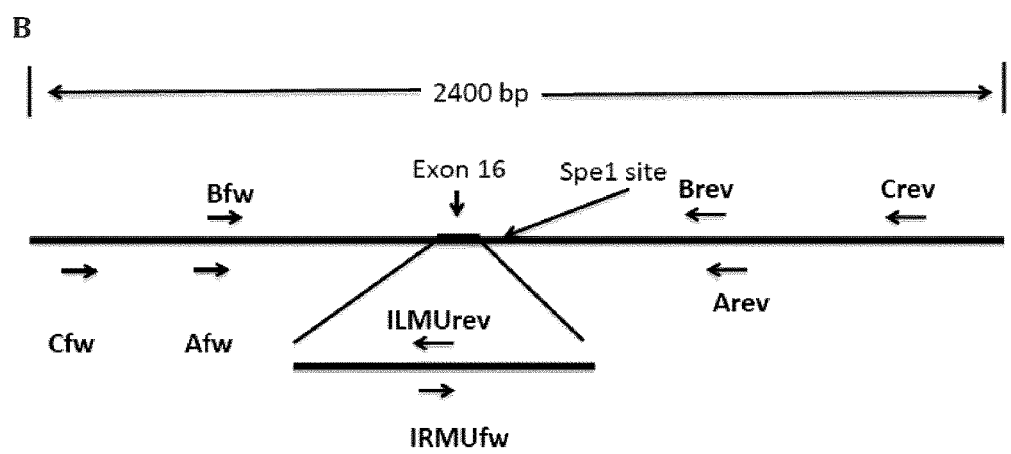

The pMiniT-Patch Plasmid/gRNA/Cas9 Combination Efficiently Introduce a Protective Mutation in the Endogenous APP Gene of Human Cells The presence of mutations in the APP gene introduced by the pMiniT-Patch plasmid/gRNA#8/Cas9 combination was confirmed by amplifying DNA of human cells transfected or not with pMiniT-Patch and pX330™ (coding for gRNA#8 and Cas9) with 3 different sets of primers: 1) IRMUfw and Arev, 2) Cfw and ILMUrev and 3) IRMUfw and Crev (see position and sequence of these primers in FIG. 8B and Table 3). The ILMUrev and the IRMUfw can only hybridize with the mutated sequence of APP exon 16 present in the donor plasmid (i.e., pMiniT-Patch) and in the mutated genomic DNA but not with the wild type APP gene. On the contrary, the Arev, Cfw and Crev primers only hybridize with APP gene sequences, which are not present in the pMiniT-Patch plasmid. Thus, DNA amplification with these pairs can only be obtained if the APP gene has been modified by Homology Directed Repair with the donor DNA.

Figure 12:
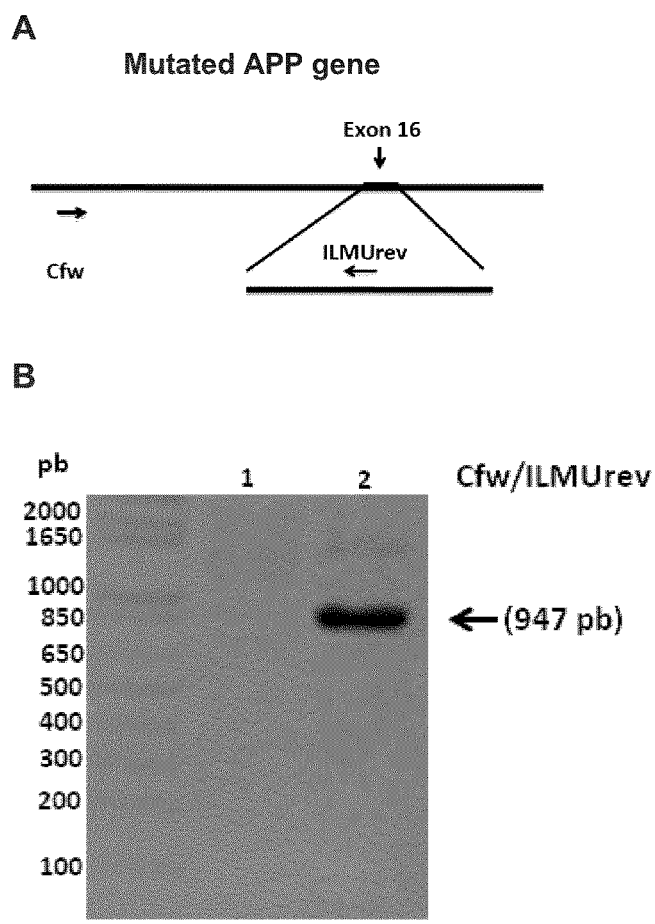
FIG. 12 shows the PCR amplification with primers Cfw (SEQ ID NO: 38) and ILMUrev (SEQ ID NO: 50) of the mutated APP gene in human cells. The mutation was introduced by Homologous Recombination between the patch sequence (including the A673T APP sequence) and the endogenous APP gene following cell transfection with the pMiniT-Patch and pX330™ plasmids (encoding gRNA#8 and Cas9 nuclease) as described in Example 3. A. Schematic representation of the primer positions on the targeted mutated APP gene. The Cfw primer targets a sequence, which is present in the endogenous APP gene but not in the repair pMiniT-Patch plasmid. The ILMUrev primer hybridizes with a sequence, which is present only when the APP gene has been repaired by homologous recombination and the patch sequence introduced in the APP gene. The sequence targeted by the ILMUrev sequence includes a portion in the patch/repair sequence (from the MiniT-Patch plasmid) and a sequence in the APP gene, which is present only if the gene has been repaired by HR. (B) RedSafe™ agarose gel showing PCR-amplified product (947 bp). Lane 1: negative control: cells in a 6 well plate transfected only with 5 μg of the pMiniT-patch plasmid. Lane 2: 293T cells in a 6 well plate transfected with 4 μg of pX330™ (coding for gRNA#8 and Cas9) and with 1 μg of pMiniT-Patch.
Figure 13:
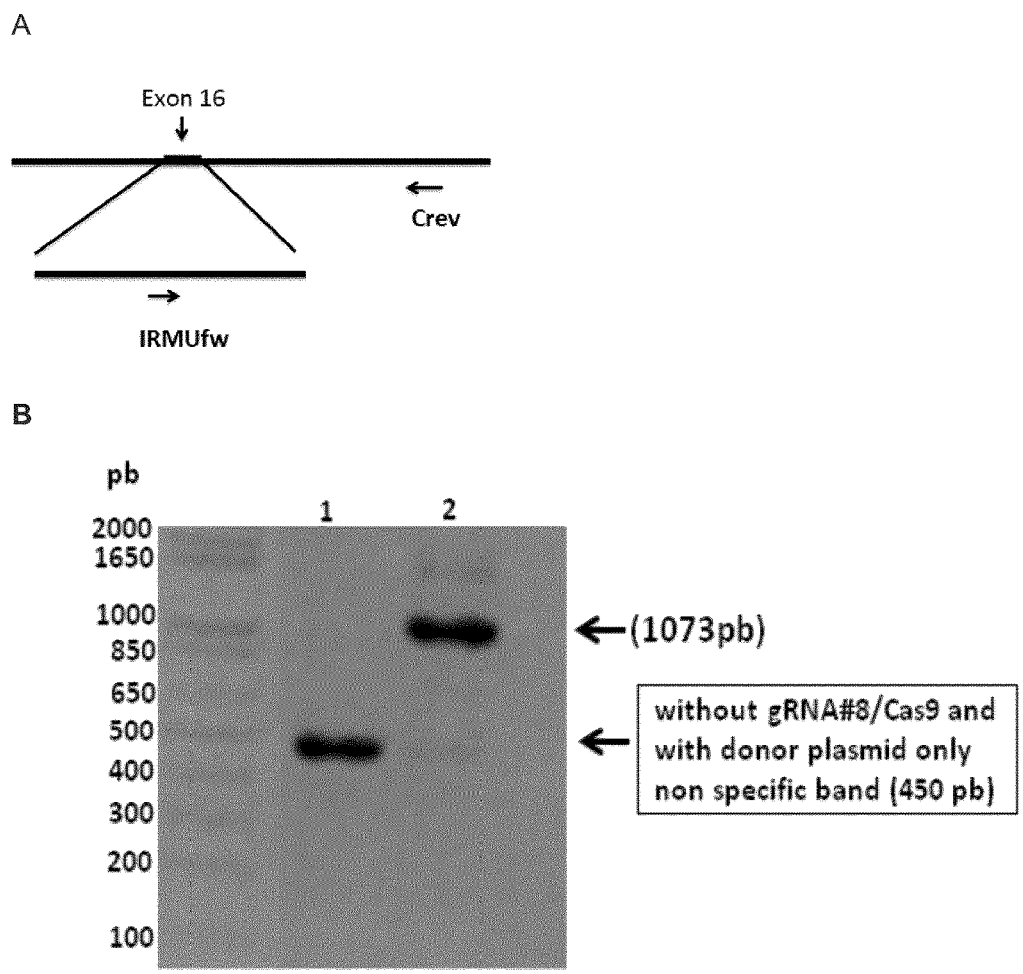
FIG. 13 shows the PCR amplification with primers IRMUfw and Crev of the mutated APP gene in human cells. The mutation was introduced by Homologous Recombination between the pMiniT-Patch plasmid and the endogenous APP gene following cell transfection with the pMiniT-Patch and pX330™ plasmids (encoding gRNA#8 and Cas9 nuclease) as described in Example 3. (A) Schematic representation of the primer positions on the targeted mutated APP gene. Primer Crev (SEQ ID NO: 42) targets a sequence, which is present only in the endogenous APP gene but not in the pMiniT-Patch repair plasmid. The IRMUfw primer (SEQ ID NO: 49) hybridizes with a sequence in the repair plasmid and with a sequence in the APP gene only if the gene has been repaired by homologous recombination. (B) RedSafe™ agarose gel showing PCR amplified product (1073 bp). Lane 1: negative control: cells in a 6 well plate transfected only with 5 μg of the pMiniT-patch plasmid shows a non-specific PCR fragment (~450 pb). Lane 2: 293T cells transfected with 4 μg of pX330™ (coding for gRNA#8 and Cas9) and with 1 μg of pMiniT-Patch.

Amplification with all 3 pairs of primers on DNA collected 72 hours post-transfection resulted in the presence of amplicons of expected sizes of 608 bp (primers IRMUfw and Arev-FIG. 11), 947 bp (primers Cfw and ILMUrev FIG. 12) and 1073 bp (IRMUfw and Crev FIG. 13) suggesting that the protective A673T mutation was efficiently introduced in the APP gene. These amplicons were cloned in the pMiniT plasmid and sequenced. The sequencing results are presented in FIGS. 14, 15 and 16.

The mutated sequences amplified with the IRMUfw and Arev primer pair and the IRMUfw and Crev primer pair contained the additional Spe1 site introduced with the pMiniT-Patch plasmid at position 161 and 85 of the amplicon respectively. These sequences confirmed the presence of the mutations (A673T and Spe1 site) in the APP gene. Since the pMiniT-Patch donor plasmid contained the codons for all the wild type amino acids of exon 16 of APP (with the exception of the A673T mutation), the homologous recombination thus also permits to correct any mutation present in the APP gene and responsible for a familial form of Alzheimer's disease.

The results of these 3 amplification and sequencing experiments demonstrated that the APP gene can be efficiently modified by Homology Directed Repair using the Patch/CRISPR system of the present invention. The sequencing experiments clearly confirm that the APP gene was appropriately corrected in the cell genome.

EXAMPLE 5

An ssODN Encoding a Portion of the APP Gene and a PCR Amplicon from the pMiniT-Patch Plasmid Efficiently Introduce a Protective Mutation in the Endogenous APP Gene of Human Cells The APP gene may also be corrected by transfecting the gRNA#8 and the Cas9 with a donor sequence, which is smaller than the pMiniT-Patch. Two different donor DNAs were used: 1) a single stranded oligodeoxynucleotide (ssODN, 199 nucleotides in length, FIG. 17A, SEQ! ID NO: 59) synthesized by IDT (Integrated DNA Technologies inc.) and 2) an amplicon obtained by amplifying a 1179 bp sequence of pMiniT-Patch with primers Bfw and Brev (SEQ ID NO: 60). The 293T cells were transfected with the pX330™ (gRNA#8 and hSpCas9) and with the ssDNA or the amplicon. The presence of mutations in the APP gene induced by both types of donor was confirmed by amplifying the genomic DNA with primers Cfw and ILMUrev (FIG. 17B, lane 2 for the amplicon and lanes 3 and 4 for the ssODN). The presence of the corrections in the APP gene was confirmed in both cases by cloning and sequencing of the PCR product as described in Example 4.

EXAMPLE 6

Modification of the Endogenous APP Polynucleotide Gene Using a FLAG Donor Sequence or FLAG-STOP Donor Sequence The APP gene may also be modified by introducing a FLAG sequence into exon 16. This was achieved by modifying the pMiniT-Patch to introduce only the FLAG in exon 16 (pMiniT-Patch-FLAG, FIG. 18) or a FLAG followed by a stop codon (pMiniT-Patch-FLAG-Stop, FIG. 19). The 293T cells were transfected with plasmids pX330™ and the pMiniT-Patch-Flag or the pMiniT-Patch-Flag-Stop. The cell DNA was amplified 72 hours post-transfection with primers Cfw and ILMUrev. The presence of a PCR product confirmed that the APP gene had been modified by homologous recombination (FIG. 17B lanes 5 and 6 respectively). The presence of the recombination was confirmed by cloning and sequencing the PCR products.

293T cells were transfected with various plasmids: well #1: 400 ng of px330 (gRNA#8 and the Cas9 gene) and 400 ng of pMiniT-Patch-FLAG, well #2: 400 ng of px330 (gRNA#8 and the Cas9 gene) and 400 ng of pMiniT-Patch-FLAG-STOP, well #3: only 400 ng of px330 (gRNA#8 and the Cas9 gene) (no donor DNA) and well #4: only 400 ng of the donor DNA (pMiniT-Patch-FLAG) but no px330 (gRNA#8 and the Cas9 gene). The genomic DNA was extracted 72 hours post-transfection and the APP gene was amplified with Cfw and Crev. The PCR product of 1993 bp was digested with Spe1 and migrated on a 2% agarose gel stained with Redsafe™. Two additional bands (1002 and 991 bp) were detected in lanes 1 and 2 (FIG. 20) confirming that the APP gene had been mutated by HDR resulting in the insertion of the new Spe1 site, which was not present when the donor DNA (pMiniT-Patch-FLAG or pMiniT-Patch-FLAG-STOP) or the gRNA#8 and the Cas9 gene were absent.

The PCR amplification of amplicons of expected sizes and the sequencing results demonstrated that the APP gene has been modified by Homology Directed Repair with the pMiniT-Patch, pMiniT-Patch-FLAG and pMiniT-Patch-FLAG-STOP. All the sequencing results clearly confirm that the APP gene was corrected in the cell's genome.

EXAMPLE 7

The β-Secretase-Dependent C99 Fragment is not Produced by Cells Harboring the A673T Mutation in Both APP Alleles 293T cells were nucleofected with plasmid pX458™ (pSpCas9(BB)-2A-GFP), (gift from Feng Zhang, purchased from Addgene plasmid #48138, see FIG. 24), coding for the gRNA#8 and the Cas9-2A-eGFP, and with the plasmid pMiniT-Patch described above. The pX458™ plasmid was prepared and tested as described in Example 1 for the px330 plasmid. The fluorescent green cells were separated by FACS and individual cells were deposited in each well of a 96 wells plate. The cell clones were expanded. The DNA and the proteins were extracted from individual clones. Part of intron 15 to intron 16 of the APP gene was amplified by PCR using primers Cfw and Brev (see sequence in attachment). The amplicons were first digested with EcoR1 enzyme, which cuts only wild type APP gene, and with the Spe1 enzyme, which cuts only the mutated APP gene. Clones that were cut by both enzymes are clones in which only one of the two APP alleles was mutated. Only clones, which amplicons were not cut by EcoR1 but cut by Spe1, were kept for further investigation because this cutting pattern occurs only when both APP alleles are mutated. The amplicon of such a clone was cloned in the pMiniT plasmid and sequenced. The sequence confirmed the presence of the A673T and of the Spe1 mutation in that clone (see FIG. 25). The cells of this mutated clone and a normal cell population were transfected with a plasmid coding for the β-Secretase enzyme. This plasmid was obtained by amplifying a human brain cDNA library and the sequence is identical to the BACE1 beta-site APP-cleaving enzyme 1 (ref NM_0121104.4). The transfected cells were also grown with or without the presence of a γ-Secretase inhibitor (L-685,458

Tocris Bioscience #2627). Control cells (no inhibitor) were not transfected with the β-secretase plasmid and not incubated with the γ-Secretase inhibitor. The proteins were extracted from the cells 48 hours after the transfection. A western blot was made using a mAb (Sigma #A8717) against the C terminal of the APP protein.

Figure 26:
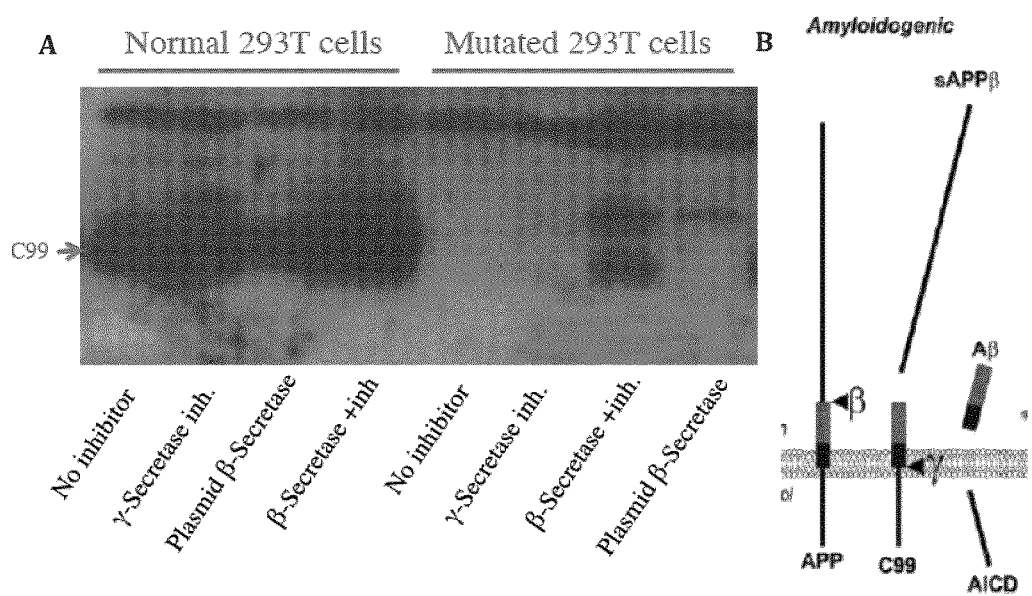
FIG. 26 shows that the APP protein of cells (in which both alleles have been modified to incorporate the A673T protective mutation by the combination of CRISPR and homologous recombination) is less frequently cut by the β-Secretase enzyme than the wild type APP protein. (A) Normal 293T cells and a clone of 293T cells having both APP alleles containing the A673T mutation were used for the experiment. The C99 fragment was abundantly present in all conditions in the normal cells (lanes 1 to 4 of the figure). However, the C99 fragment was not detected in the mutated cells with (lane 6) or without (lane 5) the γ-Secretase inhibitor. Even in the presence of the β-Secretase plasmid, the C99 fragment was not detected (lane 8). However the C99 fragment was detected in the mutated cells in presence of both the β-Secretase plasmid and of the γ-Secretase inhibitor, which permitted an accumulation of the C99 fragment (lane 7). (B) Schematic representation of the processing pathway of APP by the beta and gamma secretases.

In normal cells, the C99 fragment was detected and increased when the γ-Secretase inhibitor prevented its degradation (FIG. 26, lanes 1 and 2). When the β-Secretase plasmid was transfected in normal cells to increase the cutting of the mutated APP protein by this enzyme, the C99 fragment was also detected (FIG. 26, lane 3). This C99 fragment was however detected more abundantly when the normal cells transfected with the β-Secretase plasmid were incubated with the γ-Secretase inhibitor to permit the accumulation of the fragment (FIG. 26, lane 4). In the cells that contained the A673T mutation, the C99 fragment was not detected, even when the cells were incubated with the γ-Secretase inhibitor (FIG. 26, lanes 5 and 6). This indicated that the C99 fragment resulting form the β-Secretase cutting was rare and not detected even when the γ-Secretase inhibitor prevented its degradation. When the β-Secretase plasmid was transfected in these mutated cells to increase the cutting of the mutated APP protein by this enzyme, the C99 fragment was not detected (FIG. 26, lane 8). This C99 fragment was however detected when the mutated cells transfected with the β-Secretase plasmid were incubated with γ-Secretase inhibitor to permit the accumulation of the fragment (FIG. 26, lane 7). This experiment demonstrated that the APP protein, containing the A673T mutation following by homologous recombination induced the cutting of the APP gene by the CRISPR system, is less frequently cut by the β-Secretase enzyme than the wild type APP protein.

The scope of the claims should not be limited by the preferred embodiments set forth in the examples, but should be given the broadest interpretation consistent with the description as a whole.

REFERENCES

1. Ferri C P, et al. (2005) Global prevalence of dementia: a Delphi consensus study. *Lancet* 366(9503):2112-2117.
2. Plassman B L, et al. (2007) Prevalence of dementia in the United States: the aging, demographics, and memory study. *Neuroepidemiology* 29(1-2):125-132.
3. Qiu C, Kivipelto M, & von Strauss E (2009) Epidemiology of Alzheimer's disease: occurrence, determinants, and strategies toward intervention. *Dialogues in clinical neuroscience* 11(2):111-128.
4. Masters C L, et al. (1985) Neuronal origin of a cerebral amyloid: neurofibrillary tangles of Alzheimer's disease contain the same protein as the amyloid of plaque cores and blood vessels. *EMBO J* 4(11):2757-2763.
5. Zhang Y W, Thompson R, Zhang H, & Xu H (2011) APP processing in Alzheimer's disease. *Molecular brain* 4:3.
6. Hussain I, et al. (1999) Identification of a novel aspartic protease (Asp 2) as beta-secretase. *Mol Cell Neurosci* 14(6):419-427.
7. Sinha S, et al. (1999) Purification and cloning of amyloid precursor protein beta-secretase from human brain. *Nature* 402(6761):537-540.
8. Schmitt H P (2006) Protein ubiquitination, degradation and the proteasome in neuro-degenerative disorders: no clear evidence for a significant pathogenetic role of proteasome failure in Alzheimer disease and related disorders. *Med Hypotheses* 67(2):311-317.
9. St George-Hyslop P H (2000) Molecular genetics of Alzheimer's disease. *Biological psychiatry* 47(3):183-199.
10. Jonsson T, et al. (2012) A mutation in APP protects against Alzheimer's disease and age-related cognitive decline. *Nature* 488(7409):96-99.
11. Kero M, et al. (2013) Amyloid precursor protein (APP) A673T mutation in the elderly Finnish population. *Neurobiology of aging* 34 (5): 1518 e1511-1513.
12. Mullan M, et al. (1992) A pathogenic mutation for probable Alzheimer's disease in the APP gene at the N-terminus of beta-amyloid. *Nat Genet* 1(5):345-347.
13. Moro M L, et al. (2012) APP mutations in the Abeta coding region are associated with abundant cerebral deposition of Abeta38. *Acta Neuropathol* 124(6):809-821.
14. Janssen J C, et al. (2003) Early onset familial Alzheimer's disease: Mutation frequency in 31 families. *Neurology* 60(2):235-239.
15. Wakutani Y, et al. (2004) Novel amyloid precursor protein gene missense mutation (D678N) in probable familial Alzheimer's disease. *J Neurol Neurosurg Psychiatry* 75(7):1039-1042.
16. Lan M Y, Liu J S, Wu Y S, Peng C H, & Chang Y Y (2014) A novel APP mutation (D678H) in a Taiwanese patient exhibiting dementia and cerebral microvasculopathy. *Journal of clinical neuroscience: official journal of the Neurosurgical Society of Australasia* 21 (3): 513-515.
17. Brouwers N, Sleegers K, & Van Broeckhoven C (2008) Molecular genetics of Alzheimer's disease: an update. *Ann Med* 40(8):562-583.
18. Hendriks L, et al. (1992) Presenile dementia and cerebral haemorrhage linked to a mutation at codon 692 of the beta-amyloid precursor protein gene. *Nat Genet* 1(3):218-221.
19. Levy E, et al. (1990) Mutation of the Alzheimer's disease amyloid gene in hereditary cerebral hemorrhage, Dutch type. *Science* 248(4959): 1124-1126.
20. Kamino K, et al. (1992) Linkage and mutational analysis of familial Alzheimer disease kindreds for the APP gene region. *Am J Hum Genet* 51(5):998-1014.
21. Tomiyama T, et al. (2008) A new amyloid beta variant favoring oligomerization in Alzheimer's-type dementia. *Ann Neurol* 63(3):377-387.
22. Grabowski T J, Cho H S, Vonsattel J P, Rebeck G W, & Greenberg S M (2001) Novel amyloid precursor protein mutation in an Iowa family with dementia and severe cerebral amyloid angiopathy. *Ann Neurol* 49(6):697-705.
23. Obici L, et al. (2005) A novel AbetaPP mutation exclusively associated with cerebral amyloid angiopathy. *Ann Neurol* 58(4):639-644.
24. Carter D A, et al. (1992) More missense in amyloid gene. *Nat Genet* 2(4):255-256.
25. Rossi G, et al. (2004) A family with Alzheimer disease and strokes associated with A713T mutation of the APP gene. *Neurology* 63(5):910-912.
26. Jones C T, et al. (1992) Mutation in codon 713 of the beta amyloid precursor protein gene presenting with schizophrenia. *Nat Genet* 1(4):306-309.
27. Pasalar P, et al. (2002) An Iranian family with Alzheimer's disease caused by a novel APP mutation (Thr714Ala). *Neurology* 58(10): 1574-1575.
28. Kumar-Singh S, et al. (2000) Nonfibrillar diffuse amyloid deposition due to a gamma(42)-secretase site mutation points to an essential role for N-truncated A beta(42) in Alzheimer's disease. *Hum Mol Genet* 9(18):2589-2598.
29. Ancolio K, et al. (1999) Unusual phenotypic alteration of beta amyloid precursor protein (betaAPP) maturation by a new Val-715->Met betaAPP-770 mutation responsible for probable early-onset Alzheimer's disease. *Proc Natl Acad Sci USA* 96(7):4119-4124.
30. Eckman C B, et al. (1997) A new pathogenic mutation in the APP gene (I716V) increases the relative proportion of A beta 42(43). *Hum Mol Genet* 6(12):2087-2089.
31. Guardia-Laguarta C, et al. (2010) Clinical, neuropathologic, and biochemical profile of the amyloid precursor protein 1716F mutation. *J Neuropathol Exp Neuro* 69(1): 53-59.
32. Goate A, et al. (1991) Segregation of a missense mutation in the amyloid precursor protein gene with familial Alzheimer's disease. *Nature* 349(6311):704-706.
33. Murrell J R, Hake A M, Quaid K A, Farlow M R, & Ghetti B (2000) Early-onset Alzheimer disease caused by a new mutation (V717L) in the amyloid precursor protein gene. *Arch Neurol* 57(6):885-887.
34. Murrell J, Farlow M, Ghetti B, & Benson M D (1991) A mutation in the amyloid precursor protein associated with hereditary Alzheimer's disease. *Science* 254(5028): 97-99.
35. Chartier-Harlin M C, et al. (1991) Early-onset Alzheimer's disease caused by mutations at codon 717 of the beta-amyloid precursor protein gene. *Nature* 353(6347): 844-846.
36. Kwok J B, et al. (2000) Novel Leu723Pro amyloid precursor protein mutation increases amyloid beta42(43) peptide levels and induces apoptosis. *Ann Neurol* 47(2): 249-253.
37. Theuns J, et al. (2006) Alzheimer dementia caused by a novel mutation located in the APP C-terminal intracytosolic fragment. *Hum Mutat* 27(9):888-896.
38. Guerreiro R J, et al. (2010) Genetic screening of Alzheimer's disease genes in Iberian and African samples yields novel mutations in presenilins and APP. *Neurobiology of aging* 31(5):725-731.
39. Gaj T, Gersbach C A, & Barbas C F, 3rd (2013) ZFN, TALEN, and CRISPR/Cas-based methods for genome engineering. *Trends Biotechnol* 31(7): 397-405.
40. Arnould S, et al. (2011) The I-CreI meganuclease and its engineered derivatives: applications from cell modification to gene therapy. *Protein engineering, design & selection: PEDS* 24(1-2):27-31.
41. Menke D B (2013) Engineering subtle targeted mutations into the mouse genome. *Genesis* 51(9):605-618.
42. Mali P, et al. (2013) RNA-guided human genome engineering via Cas9. *Science* 339(6121):823-826.
43. Jinek M, et al. (2012) A programmable dual-RNA-guided DNA endonuclease in adaptive bacterial immunity. *Science* 337(6096):816-821.
44. Ran F A, et al. (2013) Double nicking by RNA-guided CRISPR Cas9 for enhanced genome editing specificity. *Cell* 154(6):1380-1389.
45. Tsai S Q, et al. (2014) Dimeric CRISPR RNA-guided FokI nucleases for highly specific genome editing. *Nat Biotechnol*.
46. Hou Z, et al. (2013) Efficient genome engineering in human pluripotent stem cells using Cas9 from *Neisseria meningitidis*. *Proc Natl Acad Sci USA* 110(39):15644-15649.
47. Deltcheva E, et al. (2011) CRISPR RNA maturation by trans-encoded small RNA and host factor RNase III. *Nature* 471(7340):602-607.
48. Sapranauskas R, et al. (2011) The *Streptococcus thermophilus* CRISPR/Cas system provides immunity in *Escherichia coli*. *Nucleic Acids Res* 39(21):9275-9282.
49. Zender L, Kuhnel F, Kock R, Manns M, & Kubicka S (2002) VP22-mediated intercellular transport of p53 in hepatoma cells in vitro and in vivo. *Cancer Gene Ther* 9(6):489-496.
50. Noguchi H, Kaneto H, Weir G C, & Bonner-Weir S (2003) PDX-1 protein containing its own antennapedia-like protein transduction domain can transduce pancreatic duct and islet cells. *Diabetes* 52(7):1732-1737.
51. Trehin R, Krauss U, Beck-Sickinger A G, Merkle H P, & Nielsen H M (2004) Cellular uptake but low permeation of human calcitonin-derived cell penetrating peptides and Tat(47-57) through well-differentiated epithelial models. *Pharm Res* 21(7):1248-1256.
52. Kakimoto S, et al. (2009) The conjugation of diphtheria toxin T domain to poly(ethylenimine) based vectors for enhanced endosomal escape during gene transfection. *Biomaterials* 30(3):402-408.
53. Kakudo T, et al. (2004) Transferrin-modified liposomes equipped with a pH-sensitive fusogenic peptide: an artificial viral-like delivery system. *Biochemistry* 43(19): 5618-5628.
54. Fominaya J, Uherek C, & Wels W (1998) A chimeric fusion protein containing transforming growth factor-alpha mediates gene transfer via binding to the EGF receptor. *Gene Ther* 5(4):521-530.
55. El-Sayed A, Futaki S, & Harashima H (2009) Delivery of macromolecules using arginine-rich cell-penetrating peptides: ways to overcome endosomal entrapment. *The AAPS journal* 11(1): β-22.
56. Kichler A, Leborgne C, Marz J, Danos O, & Bechinger B (2003) Histidine-rich amphipathic peptide antibiotics promote efficient delivery of DNA into mammalian cells. *Proc Natl Acad Sci USA* 100(4):1564-1568.
57. Salomone F, et al. (2012) A novel chimeric cell-penetrating peptide with membrane-disruptive properties for efficient endosomal escape. *J Control Release* 163(3): 293-303.
58. Kwon E J, Bergen J M, & Pun S H (2008) Application of an HIV gp41-derived peptide for enhanced intracellular trafficking of synthetic gene and siRNA delivery vehicles. *Bioconjug Chem* 19(4):920-927.
59. Midoux P, Kichler A, Boutin V, Maurizot J C, & Monsigny M (1998) Membrane permeabilization and efficient gene transfer by a peptide containing several histidines. *Bioconjug Chem* 9(2):260-267.
60. Lorieau J L, Louis J M, & Bax A (2010) The complete influenza hemagglutinin fusion domain adopts a tight helical hairpin arrangement at the lipid:water interface. *Proc Natl Acad Sci USA* 107(25):11341-11346.
61. Lundberg P, El-Andaloussi S, Sutlu T, Johansson H, & Langel U (2007) Delivery of short interfering RNA using endosomolytic cell-penetrating peptides. *FASEB J* 21(11): 2664-2671.
62. Pearson W R & Lipman D J (1988) Improved tools for biological sequence comparison. *Proc Natl Acad Sci USA* 85(8):2444-2448.
63. Altschul S F, Gish W, Miller W, Myers E W, & Lipman D J (1990) Basic local alignment search tool. *J Mol Biol* 215(3):403-410.
64. Ausubel (2010) *Current Protocols in Molecular Biology* (Green Publishing Associates, Inc., and John Wiley & Sons, Inc.,).
65. Ran F A, Cong L, Yan W X, Scott D A, Gootenberg J S, Kriz A J, Zetsche B, Shalem O, Wu X, Makarova K S, Koonin E V, Sharp P A, Zhang F *Nature*. 2015 Apr. 1. doi: 10.1038/nature14299

The invention claimed is:

1. A method of decreasing Amyloid Precursor Protein (APP) processing into Aβ peptide by a cell comprising providing said cell with:
 (i) at least one guide RNA (gRNA) comprising:
  (a) a gRNA guide sequence comprising a seed region of at least 10 consecutive nucleotides of a target sequence in an endogenous APP gene polynucleotide sequence present in said cell;
  (b) a Cas9 recognition sequence,
  wherein the target sequence of the gRNA guide sequence is contiguous to a protospacer adjacent motif (PAM) in the endogenous APP gene polynucleotide sequence and wherein said PAM is recognized by a ribonucleoprotein complex comprising a Cas9 nuclease or nickase; and
  wherein the target sequence is located within a region defined by (I) nucleotide 278133 to nucleotide 278155, (II) 278158 to 278223, or (III) nucleotide 278291 to nucleotide 278312, of the region of the APP polynucleotide gene sequence defined by nucleotides 277141 to nucleotide 279540 set forth in FIG. 5 (SEQ ID NO: 35), or in a corresponding location in the endogenous APP polynucleotide gene sequence present in said cell, or wherein the target sequence is located within the antisense sequence of a region defined by (IV) nucleotide 278049 to nucleotide 278070 or (V) nucleotide 278209 to nucleotide 278287, of the region of the APP polynucleotide gene sequence defined by nucleotides 277141 to nucleotide 279540 set forth in FIG. 5

(SEQ ID NO: 35), or in a corresponding location in the endogenous APP polynucleotide gene sequence present in said cell;

(ii) a Cas9 nuclease or nickase or a nucleic acid encoding a Cas9 nuclease or nickase; and (iii) a donor nucleic acid comprising an APP polynucleotide gene sequence or fragment thereof, which comprises at least one modification with respect to the endogenous APP polynucleotide gene sequence present in said cell, wherein said donor nucleic acid is integrated in said APP gene polynucleotide sequence of said cell and wherein said modification decreases the amount of Aβ produced by said cell.

2. The method of claim 1, wherein the target sequence of said gRNA comprises the following nucleic acid sequence:

```
                                    (SEQ ID NO: 5)
(i)    5'-TATGATGTAATACAGGTTC-3';

(SEQ ID NO: 7)
(ii)   5'-ATGATGTAATACAGGTTCT-3';

(SEQ ID NO: 11)
(iii)  5'-TTGACAAATATCAAGACGG-3';

(SEQ ID NO: 13)
(iv)   5'-GAGATCTCTGAAGTGAAGA-3';

(SEQ ID NO: 15)
(v)    5'-CAGAATTCCGACATGACTC-3';

(SEQ ID NO: 19)
(vi)   5'-CCAAATGACCTATTAACTC-3';

(SEQ ID NO: 21)
(vii)  5'-CTACCCAAAACTTCTTTCT-3';
```

```
                                    (SEQ ID NO: 25)
(viii) 5'-TTCATATCCTGAGTCATGT-3';
or
                                    (SEQ ID NO: 27)
(ix)   5'-GACAAACAGTAGTGGAAAG-3'.
```

3. The method of claim 2, wherein said method comprises providing the cell with a gRNA targeting the nucleic acid sequence 5'-CAGAATTCCGACATGACTC-3' (SEQ ID NO: 15).

4. The method of claim 1, wherein the gRNA comprises the following nucleic acid sequence:

```
                                    (SEQ ID NO: 117)
(i)    5' UAUGAUGUAAUACAGGUUC 3';

(SEQ ID NO: 118)
(ii)   5' AUGAUGUAAUACAGGUUCU 3';

(SEQ ID NO: 120)
(iii)  5' UUGACAAAUAUCAAGACGG 3';

(SEQ ID NO: 121)
(iv)   5' GAGAUCUCUGAAGUGAAGA 3';

(SEQ ID NO: 122)
(v)    5' CAGAAUUCCGACAUGACUCA 3';

(SEQ ID NO: 124)
(vi)   5' CCAAAUGACCUAUUAACUC 3';

(SEQ ID NO: 125)
(vii)  5' CUACCCAAAACUUCUUUCU 3';

(SEQ ID NO: 127)
(viii) 5' UUCAUAUCCUGAGUCAUGU 3';
or
                                    (SEQ ID NO: 128)
(ix)   5' GACAAACAGUAGUGGAAAG 3'.
```

* * * * *

SEQUENCE LISTING

<160> NUMBER OF SEQ ID NOS: 135

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1
atttatgagt aaaactaat                                                19

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 2
atttatgagt aaaactaatt gg                                            22

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
tttaattatg atgtaatac                                                19

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
tttaattatg atgtaataca gg                                            22

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
tatgatgtaa tacaggttc                                                19

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
tatgatgtaa tacaggttct gg                                            22

<210> SEQ ID NO 7
<211> LENGTH: 19
<212> TYPE: DNA
<213> ORGANISM: Artificial sequence

```
<220> FEATURE:
<223> OTHER INFORMATION: Synthetic oligonucleotide

<400> SEQUENCE: 7
atgatgtaat acaggttct                                              19

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
atgatgtaat acaggttctg gg                                          22

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
gggttgacaa atatcaaga                                              19

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 10
gggttgacaa atatcaagac gg                                          22

<210> SEQ ID NO 11
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 11
ttgacaaata tcaagacgg                                              19

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
ttgacaaata tcaagacgga gg                                          22

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
gagatctctg aagtgaaga                                              19
```

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
gagatctctg aagtgaagat gg                                            22

<210> SEQ ID NO 15
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 15
cagaattccg acatgactc                                                19

<210> SEQ ID NO 16
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 16
cagaattccg acatgactca gg                                            22

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 17
gaagttcatc atcaaaaat                                                19

<210> SEQ ID NO 18
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 18
gaagttcatc atcaaaaatt gg                                            22

<210> SEQ ID NO 19
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 19
ccaaatgacc tattaactc                                                19

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
ccaaatgacc tattaactct gg                                        22

<210> SEQ ID NO 21
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 21
ctacccaaaa cttctttct                                            19

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
ctacccaaaa cttctttcta gg                                        22

<210> SEQ ID NO 23
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 23
catcataatt aaagtatgc                                            19

<210> SEQ ID NO 24
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 24
catcataatt aaagtatgca gg                                        22

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
ttcatatcct gagtcatgt                                            19

<210> SEQ ID NO 26
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 26
ttcatatcct gagtcatgtc gg                                        22

<210> SEQ ID NO 27

```
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 27
gacaaacagt agtggaaag                                                     19

<210> SEQ ID NO 28
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 28
gacaaacagt agtggaaaga gg                                                 22

<210> SEQ ID NO 29
<211> LENGTH: 102
<212> TYPE: PRT
<213> ORGANISM: Homosapiens

<400> SEQUENCE: 29

Lys Met Asp Ala Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val Ile Ala Thr Val Ile
        35                  40                  45

Val Ile Thr Leu Val Met Leu Lys Lys Lys Gln Tyr Thr Ser Ile His
    50                  55                  60

His Gly Val Val Glu Val Asp Ala Ala Val Thr Pro Glu Glu Arg His
65                  70                  75                  80

Leu Ser Lys Met Gln Gln Asn Gly Tyr Glu Asn Pro Thr Tyr Lys Phe
                85                  90                  95

Phe Glu Gln Met Gln Asn
            100

<210> SEQ ID NO 30
<211> LENGTH: 770
<212> TYPE: PRT
<213> ORGANISM: Homosapiens

<400> SEQUENCE: 30

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110
```

```
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
        130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
        275                 280                 285
Glu Val Cys Ser Glu Gln Ala Glu Thr Gly Pro Cys Arg Ala Met Ile
290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
```

Gln Val Met Thr His Leu Arg Val Ile Tyr Glu Arg Met Asn Gln Ser
            530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
            675                 680                 685

Val Phe Phe Ala Glu Asp Val Gly Ser Asn Lys Gly Ala Ile Ile Gly
            690                 695                 700

Leu Met Val Gly Gly Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
    770

<210> SEQ ID NO 31
<211> LENGTH: 101
<212> TYPE: DNA
<213> ORGANISM: homosapiens

<400> SEQUENCE: 31
gttctgggtt gacaaatatc aagacggagg agatctctga agtgaagatg gatgcagaat    60
tccgacatga ctcaggatat gaagttcatc atcaaaaatt g                        101

<210> SEQ ID NO 32
<211> LENGTH: 33
<212> TYPE: PRT
<213> ORGANISM: homosapiens

<400> SEQUENCE: 32

Ser Gly Leu Thr Asn Ile Lys Thr Glu Glu Ile Ser Glu Val Lys Met
1               5                   10                  15

Asp Ala Glu Phe Arg His Asp Ser Gly Tyr Glu Val His Gln Lys
            20                  25                  30

Leu

<210> SEQ ID NO 33
<211> LENGTH: 101

<212> TYPE: DNA
<213> ORGANISM: homosapiens

<400> SEQUENCE: 33

```
gttctgggtt gacaaatatc aagacggagg agatctctga agtgaagatg gatacggagt    60
ttaggcacga ttcaggatat gaagttcatc atcaaaaatt g                       101
```

<210> SEQ ID NO 34
<211> LENGTH: 33
<212> TYPE: PRT
<213> ORGANISM: Artificial sequence
<220> FEATURE:
<223> OTHER INFORMATION: Synthetic peptide

<400> SEQUENCE: 34

```
Ser Gly Leu Thr Asn Ile Lys Thr Glu Glu Ile Ser Glu Val Lys Met
 1               5                  10                  15

Asp Thr Glu Phe Arg His Asp Ser Gly Tyr Glu Val His His Gln Lys
                20                  25                  30

Leu
```

<210> SEQ ID NO 35
<211> LENGTH: 2400
<212> TYPE: DNA
<213> ORGANISM: homosapiens

<400> SEQUENCE: 35

```
aagttacagg gaagctgatt ctggcttcat gtaaaaaaag gacagtttgg gcaggcaaat    60
ctatcaaaaa atggagggaa attgatacat tcctctatgt tcaaacagga actgacaatc   120
tgcccctggg tgggaacacg gtagagaaga tgacttcaaa agcccttttc atcctaaaat   180
tctgatgttt gataattaaa tgttatagca tggacactga catttacatt tttttacttat   240
gttttggtt tttaaatgac tctgcatttt gttttaagct tcaaattatt atttgaataa    300
tgaaattcat cagaacaatt agtgttaaga atcatatagc aatttataga aaaggaagag   360
ttcgtaggtt ataaattctg ttagttgcta agaagcattt ttaaaattat gtactatagc   420
tctttattca gcagacgaac caattacaat ctgtgtaact agaacacttg actaaaatta   480
tataatttttt acaacgcttc actgcataga tacatgaaca taatttatttt gtaattggaa   540
caaagcccca agtagcagt tttgttctac caggtaatta atgctcattt ttaaagcctt    600
ttattattat ttctgaagta atgagtgcac atggaaaaag acacataata ggctaaacaa   660
taagcccgta agccaagcca acatattcca ggaacaaatc cttgccaacc tctcaaccag   720
gatttaactt ctgcttttcc cccatttttca aaaattatag catgtattta aaggcagcag   780
aagccttact ttcaggtttc ccttacccctt tcatttcttt ttgttcaaaa taggtagtaa    840
ttgaagtttt aaatataggg tatcattttt ctttaagagt catttatcaa tttttcttcta    900
acttcaggcc tagaaagaag ttttgggtag gctttgtctt acagtgttat tatttatgag   960
taaaactaat tggttgtcct gcatacttta attatgatgt aatacaggtt ctgggttgac   1020
aaatatcaag acggaggaga tctctgaagt gaagatggat gcagaattcc gacatgactc   1080
aggatatgaa gttcatcatc aaaaattggt acgtaaaata atttacctct ttccactact   1140
gtttgtcttg ccaaatgacc tattaactct ggttcatcct gtgctagaaa tcaaattaag   1200
gaaaagataa aaatacaatg cttgcctata ggattaccat gaaaacatga agaaaataaa    1260
taggctaggc tgagcgcagt ggctcaagcc tgtaatccca gcactttggg aggccaaggc    1320
```

```
gggtggatca cgaggtcaga aattcgagac cagcctggcc aatatggtga aaccccatct    1380
ctactaaaaa tacaaaaaag attagctggg tgtggtggca acacctgta gtcccagctg    1440 ctggggaggc tgacgcagga gacttgcttg aacccaggag gtggaggttg cagtgagctg    1500
agatcgtgcc taggcgacag agcgagactc catcccaaaa aaaaaaaga aaagaaagag    1560 gctgtatgta tagttctttc agactacaag gcagcaaagt tcgtgcatga ctcgggactt    1620
aaagtggaat taatttcaat atagcagcca ctttgacttc cactgtgttt tctgggaaaa    1680
taggtttaca ataggtttat ttgaaggatc aaacacatgc atacactgct tggtttttaca   1740 gaacactta tgtggcttaa attcacatcc ggaactgtct tcctttaccc attcatttct    1800
cccccagctc tttcttttca ttccctcccc tacctcccat gatttaactt ctcttgcaag    1860
agtaagatca tggagtgagc aggaccccat gatgttcccg atagtgttat tcatcaaaag    1920
gtttgtgcaa agaagacagc agcttccttt tcagatgaaa tcacttttcc cccctaatgt    1980
tagaattgga gtaaatcaaa aagccacatc tcctttgtgg tcagctctag tagttatata    2040
aaatccttta ccaaaagctt agaaatggag ataaatcaaa tcgtggatta tgttagggtt    2100
ccatcttatc agtaggtgca gtaagagggt taaattaatg aagacgacaa ttttatcaca    2160
ttcagtggtg gacagaaaaa tggtaagaaa atttccatag caataatact taaagttatc    2220
tcaggcactt cttttgtttt gttttgtgtg tgtgtgtgtg tgagtgttac ttttttccaa    2280
gcagaaaatg tcttttcaat attcataaag ttgataaatc ctagtattaa tctctaaaag    2340
aaacacctcc aaattattat ttatgcctta cttgactcca ataattgta gcaaataaaa     2400
```

<210> SEQ ID NO 36
<211> LENGTH: 1007
<212> TYPE: DNA
<213> ORGANISM: homosapiens
<400> SEQUENCE: 36

```
aagttacagg gaagctgatt ctggcttcat gtaaaaaaag gacagtttgg gcaggcaaat      60
ctatcaaaaa atggagggaa attgatacat tcctctatgt tcaaacagga actgacaatc     120
tgcccctggg tgggaacacg gtagagaaga tgacttcaaa agccctttc atcctaaaat      180 tctgatgttt gataattaaa tgttatagca tggacactga catttacatt ttttacttat     240 gttttttggtt tttaaatgac tctgcatttt gttttaagct tcaaattatt atttgaataa    300
tgaaattcat cagaacaatt agtgttaaga atcatatagc aatttataga aaaggaagag    360
ttcgtaggtt ataaattctg ttagttgcta agaagcattt ttaaaattat gtactatagc    420
tctttattca gcagacgaac caattacaat ctgtgtaact agaacacttg actaaaatta    480 tataatttt acaacgcttc actgcataga tacatgaaca taatttattt gtaattggaa    540
caaagcccca aagtagcagt tttgttctac caggtaatta atgctcattt ttaaagcctt    600
ttattattat ttctgaagta atgagtgcac atggaaaaag acacataata ggctaaacaa    660
taagcccgta agccaagcca acatattcca ggaacaaatc cttgccaacc tctcaaccag    720
gatttaactt ctgctttttcc cccattttca aaaattatag catgtattta aaggcagcag    780
aagccttact ttcaggtttc ccttacccctt tcatttcttt ttgttcaaaa taggtagtaa    840
ttgaagtttt aaatataggg tatcatttt ctttaagagt catttatcaa ttttcttcta    900
acttcaggcc tagaaagaag ttttgggtag gctttgtctt acagtgttat tatttatgag    960
taaaactaat tggttgtcct gcatacttta attatgatgt aatacag                  1007
```

<210> SEQ ID NO 37
<211> LENGTH: 1292
<212> TYPE: DNA
<213> ORGANISM: homosapiens

<400> SEQUENCE: 37

```
gtacgtaaaa taatttacct ctttccacta ctgtttgtct tgccaaatga cctattaact      60
ctggttcatc ctgtgctaga aatcaaatta aggaaaagat aaaaatacaa tgcttgccta     120
taggattacc atgaaaacat gaagaaaata aataggctag gctgagcgca gtggctcaag     180
cctgtaatcc cagcactttg ggaggccaag gcggtggat cacgaggtca gaaattcgag      240
accagcctgg ccaatatggt gaaacccat ctctactaaa aatacaaaaa agattagctg      300
ggtgtggtgg caaacacctg tagtcccagc tgctgggag gctgacgcag gagacttgct      360
tgaacccagg aggtggaggt tgcagtgagc tgagatcgtg cctaggcgac agagcgagac     420
tccatcccaa aaaaaaaaa gaaagaaag aggctgtatg tatagttctt tcagactaca       480
aggcagcaaa gttcgtgcat gactcgggac ttaaagtgga attaatttca atatagcagc     540
cactttgact tccactgtgt tttctgggaa ataggttta caataggttt atttgaagga      600
tcaaacacat gcatacactg cttggtttta cagaacactt tatgtggctt aaattcacat     660
ccggaactgt cttcctttac ccattcattt ctcccccagc tctttctttt cattccctcc     720
cctacctccc atgatttaac ttctcttgca agagtaagat catggagtga gcaggacccc     780
atgatgttcc cgatagtgtt attcatcaaa aggtttgtgc aaagaagaca gcagcttcct     840
tttcagatga aatcacttt ccccctaat gttagaattg gagtaaatca aaagccaca        900
tctcctttgt ggtcagctct agtagttata taaaatcctt taccaaaagc ttagaaatgg     960
agataaatca aatcgtggat tatgttaggg ttccatctta tcagtaggtg cagtaagagg    1020
gttaaattaa tgaagacgac aattttatca cattcagtgg tggacagaaa aatggtaaga    1080
aaatttccat agcaataata cttaaagtta tctcaggcac ttcttttgtt ttgttttgtg    1140
tgtgtgtgtg tgtgagtgtt actttttcc aagcagaaaa tgtctttca atattcataa     1200
agttgataaa tcctagtatt aatctctaaa agaaacacct ccaaattatt atttatgcct    1260
tacttgactc caaataattg tagcaaataa aa                                  1292
```

<210> SEQ ID NO 38
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 38

```
tgggaacacg gtagagaaga tgacttcaaa                                       30
```

<210> SEQ ID NO 39
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 39

```
gctctttatt cagcagacg                                                   19
```

<210> SEQ ID NO 40
<211> LENGTH: 22
<212> TYPE: DNA

```
<213> ORGANISM: Artificial sequence
<220> FEATURE:
<223> OTHER INFORMATION: Synthetic oligonucleotide

<400> SEQUENCE: 40
cacgaacttt gctgccttgt ag                                              22

<210> SEQ ID NO 41
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 41
gtggaagtca aagtggctgc tat                                             23

<210> SEQ ID NO 42
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 42
cctcttactg cacctactga taag                                            24

<210> SEQ ID NO 43
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 43
ttcagcagac gaaccaatta ca                                              22

<210> SEQ ID NO 44
<211> LENGTH: 113
<212> TYPE: DNA
<213> ORGANISM: Artificial sequence
<220> FEATURE:
<223> OTHER INFORMATION: Synthetic polynucleotide

<400> SEQUENCE: 44
aaaggacgaa caccgggtct tcgagaagac ctgttttaga gctagaaata gcaagttaaa     60
ataaggctag tccgttatca acttgaaaaa gtggcaccga gtcggtgctt ttt           113

<210> SEQ ID NO 45
<211> LENGTH: 3750
<212> TYPE: DNA
<213> ORGANISM: Artificial sequence
<220> FEATURE:
<223> OTHER INFORMATION: Synthetic polynucleotide
<220> FEATURE:
<221> NAME/KEY: n
<222> LOCATION: (1500)..(1500)
<223> OTHER INFORMATION: n= A, C, G or T
<220> FEATURE:
<221> NAME/KEY: misc_feature
<222> LOCATION: (1500)..(1500)
<220> FEATURE:
<221> NAME/KEY: misc_feature
<222> LOCATION: (1543)..(1543)

<400> SEQUENCE: 45
ccggttcaga caggataaag aggaaagaat gttagacaac acccgcttac gcatagctat     60
```

```
tcagaaatca ggccgtttaa gcgatgattc acgagaattg ctggcccgct gcggcataaa      120
aattaattta cacactcagc gctgatgaat cccctaatga ttttggtaaa aatcattaag      180
ttaaggtgga cacacatctt gtcatatgat taaatggttt cgcgaaaaat caataatcag      240
acaacaagat gtgcgaactc gatattttac acgactctct ttaccaattc tgccccgaat      300
tacacttaaa acgactcaac agcttaacgt tggcttgcca cgcattactt gactgtaaaa      360
ctctcactct taccgaactt ggccgtaacc tgccaaccaa agcgagaaca aaacataaca      420
tcaaacgaat cgaccgattg ttaggtaatc gtcacctcca caaagagcga ctcgctgtat      480
cgctcgaggg atccgaattc aggaggtaaa aaccatgata tagcagaatt ccgacatgac      540
tcaggttcag cagacgaacc aattacaatc tgtgtaacta gaacacttga ctaaaattat      600
ataattttta caacgcttca ctgcatagat acatgaacat aatttatttg taattggaac      660
aaagccccaa agtagcagtt ttgttctacc aggtaattaa tgctcatttt taaagccttt      720
tattattatt tctgaagtaa tgagtgcaca tggaaaaaga cacataatag gctaaacaat      780
aagcccgtaa gccaagccaa catattccag gaacaaatcc ttgccaacct ctcaaccagg      840
atttaacttc tgcttttccc ccatttttcaa aaattatagc atgtatttaa aggcagcaga      900
agccttactt tcaggtttcc cttacccttt catttctttt tgttcaaaat aggtagtaat      960
tgaagtttta aatatagggt atcattttc tttaagagtc atttatcaat tttcttctaa      1020
cttcaggcct agaaagaagt tttgggtagg cttttgtctta cagtgttatt atttatgagt      1080
aaaactaatt ggttgtcctg catactttaa ttatgatgta atacaggttc tgggttgaca      1140
aatatcaaga cggaggagat ctctgaagtg aagatggata cggagtttag gcacgattca      1200
ggatatgaag ttcatcatca aaaattggta cgtaaaataa tttacctctt tccactagtg      1260
tttgtcttgc caaatgacct attaactctg gttcatcctg tgctagaaat caaattaagg      1320
aaaagataaa aatacaatgc ttgcctatag gattaccatg aaaacatgaa gaaaataaat      1380
aggctaggct gagcgcagtg gctcaagcct gtaatcccag cactttggga ggccaaggcg      1440
ggtggatcac gaggtcagaa attcgagacc agcctggcca atatggtgaa accccatctn      1500
tactaaaaat acaaaaaaga ttagctgggt gtggtggcaa acncctgtag tcccagctgc      1560
tggggaggct gacgcaggag acttgcttga acccaggagg tggaggttgc agtgagctga      1620
gatcgtgcct aggcgacaga gcgagactcc atcccaaaaa aaaaaaaaga aaagaaagag      1680
gctgtatgta tagttctttc agactacaag gcagcaaagt tcgtgcagaa ttccgacatg      1740
actcaggact gataataatg acgtcagaat tctcgagtcg gggaaatgtg cgcggaaccc      1800
ctatttgttt attttctaa atacattcaa atatgtatcc gctcatgaga caataaccct      1860
gataaatgct tcaataatat tgaaaaagga gagtatgag tattcaacat ttccgtgtcg      1920
cccttattcc cttttttgcg gcattttgcc ttcctgtttt tgctcaccca gaaacgctgg      1980
tgaaagtaaa agatgctgaa gatcagttgg gtgcacgagt gggttacatc gaactggatc      2040
tcaacagcgg taagatcctt gagagttttc gccccgaaga acgttttcca atgatgagca      2100
cttttaaagt tctgctatgt ggcgcggtat tatcccgtat tgacgccggg caagagcaac      2160
tcggtcgccg catacactat tctcagaatg acttggttga gtactcacca gtcacagaaa      2220
agcatcttac ggatggcatg acagtaagag aattatgcag tgctgccata accatgagtg      2280
ataacactgc ggccaactta cttctgacaa cgatcgagg accgaaggag ctaaccgctt      2340
ttttgcacaa catgggggat catgtaactc gccttgatcg ttgggaaccg gagctgaatg      2400
```

```
aagccatacc aaacgacgag cgtgacacca cgatgcctgt agcaatggca acaacgttgc    2460
gcaaactatt aactggcgaa ctacttactc tagcttcccg gcaacaatta atagactgga    2520
tggaggcgga taaagttgca ggaccacttc tgcgctcggc ccttccggct ggctggttta    2580
ttgctgataa atctggagcc ggtgagcgtg gtctcgcgg tatcattgca gcactggggc     2640
cagatggtaa gccctcccgt atcgtagtta tctacacgac ggggagtcag gcaactatgg    2700
atgaacgaaa tagacagatc gctgagatag gtgcctcact gattaagcat tggtaactgt    2760
cagaccaagt ttactcatat atactttaga ttgatttaaa acttcatttt taatttaaaa    2820
ggatctaggt gaagatcctt tttgataatc tcatgaccaa atcccttaa cgtgagtttt     2880 cgttccactg agcgtcagac cccgtagaaa agatcaaagg atcttcttga tccttttt     2940 ttctgcgcgt aatctgctgc ttgcaaacaa aaaaaccacc gctaccagcg gtggtttgtt    3000
tgccggatca agagctacca actctttttc cgaaggtaac tggcttcagc agagcgcaga    3060
taccaaatac tgttcttcta gtgtagccgt agttaggcca ccacttcaag aactctgtag    3120
caccgcctac atacctcgct ctgctaatcc tgttaccagt ggctgctgcc agtggcgata    3180
agtcgtgtct taccgggttg gactcaagac gatagttacc ggataaggcg cagcggtcgg    3240
gctgaacggg gggttcgtgc acacagccca gcttggagcg aacgacctac accgaactga    3300
gatacctaca gcgtgagcta tgagaaagcg ccacgcttcc gaagggaga aaggcggaca     3360 ggtatccggt aagcggcagg gtcggaacag gagagcgcac gagggagctt ccaggggaa     3420 acgcctggta tctttatagt cctgtcgggt ttcgccacct ctgacttgag cgtcgatttt    3480
tgtgatgctc gtcaggggg cggagcctat ggaaaaacgc cagcaatgcg ccttttttac     3540
ggttcctggc cttttgctgg ccttttgctc acatgttctt tcctgcgtta tccctgatt     3600 ctgtggataa ccgtattacc gcctttgagt gagctgatac cgctcgccgc agccgaacga    3660
ccgagcgcag cgagtcagtg agcgaggaag cggaagagcg cccaatacgc aaaccgcctc    3720
tccccgcgcg ttggccgatt cattaatgca                                    3750
```

<210> SEQ ID NO 46
<211> LENGTH: 1229
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (981)..(981)
<223> OTHER INFORMATION: n= A, C, G or T
<220> FEATURE:
<221> NAME/KEY: misc_feature
<222> LOCATION: (1024)..(1024)
<223> OTHER INFORMATION: n= A, C, G or T

<400> SEQUENCE: 46

```
atagcagaat tccgacatga ctcaggttca gcagacgaac caattacaat ctgtgtaact      60
agaacacttg actaaaatta tataattttt acaacgcttc actgcataga tacatgaaca    120
taatttattt gtaattggaa caaagcccca agtagcagt tttgttctac caggtaatta     180
atgctcattt ttaaagcctt ttattattat ttctgaagta atgagtgcac atggaaaaag    240
acacataata ggctaaacaa taagcccgta agccaagcca acatattcca ggaacaaatc    300
cttgccaacc tctcaaccag gatttaactt ctgcttttcc cccatttca aaaattatag     360 catgtattta aaggcagcag aagccttact ttcaggtttc ccttacccct tcatttcttt    420
ttgttcaaaa taggtagtaa ttgaagtttt aaatataggg tatcattttt ctttaagagt    480
```

```
catttatcaa ttttcttcta acttcaggcc tagaaagaag ttttgggtag gctttgtctt      540
acagtgttat tatttatgag taaaactaat tggttgtcct gcatacttta attatgatgt      600
aatacaggtt ctgggttgac aaatatcaag acggaggaga tctctgaagt gaagatggat      660
acggagttta ggcacgattc aggatatgaa gttcatcatc aaaaattggt acgtaaaata      720
atttacctct ttccactagt gtttgtcttg ccaaatgacc tattaactct ggttcatcct      780
gtgctagaaa tcaaattaag gaaaagataa aaatacaatg cttgcctata ggattaccat      840
gaaaacatga agaaaataaa taggctaggc tgagcgcagt ggctcaagcc tgtaatccca      900
gcactttggg aggccaaggc gggtggatca cgaggtcaga aattcgagac cagcctggcc      960
aatatggtga accccatct ntactaaaaa tacaaaaaag attagctggg tgtggtggca     1020
aacnnctgta gtcccagctg ctggggaggc tgacgcagga gacttgcttg aacccaggag     1080
gtggaggttg cagtgagctg agatcgtgcc taggcgacag agcgagactc catcccaaaa     1140 aaaaaaaag aaaagaaaga ggctgtatgt atagttcttt cagactacaa ggcagcaaag     1200
ttcgtgcaga attccgacat gactcagga                                      1229

<210> SEQ ID NO 47
<211> LENGTH: 2400
<212> TYPE: DNA
<213> ORGANISM: Artificial sequence
<220> FEATURE:
<223> OTHER INFORMATION: Synthetic polynucleotide

<400> SEQUENCE: 47
aagttacagg gaagctgatt ctggcttcat gtaaaaaaag gacagtttgg gcaggcaaat       60
ctatcaaaaa atggagggaa attgatacat tcctctatgt tcaaacagga actgacaatc      120
tgcccctggg tgggaacacg gtagagaaga tgacttcaaa agccctttc atcctaaaat       180 tctgatgttt gataattaaa tgttatagca tggacactga catttacatt ttttacttat      240 gttttggtt tttaaatgac tctgcatttt gttttaagct tcaaattatt atttgaataa      300
tgaaattcat cagaacaatt agtgttaaga atcatatagc aatttataga aaggaagag      360 ttcgtaggtt ataaattctg ttagttgcta agaagcattt ttaaaattat gtactatagc      420
tctttattca gcagacgaac caattacaat ctgtgtaact agaacacttg actaaaatta      480 tataatttt acaacgcttc actgcataga tacatgaaca taatttatttt gtaattggaa      540 caaagcccca agtagcagt tttgttctac caggtaatta atgctcattt ttaaagcctt      600
ttattattat ttctgaagta atgagtgcac atggaaaaag acacataata ggctaaacaa      660
taagcccgta agccaagcca acatattcca ggaacaaatc cttgccaacc tctcaaccag      720
gatttaactt ctgcttttcc cccatttca aaaattatag catgtattta aaggcagcag      780
aagccttact ttcaggtttc ccttacccctt tcatttcttt ttgttcaaaa taggtagtaa      840
ttgaagtttt aaatataggg tatcattttt ctttaagagt catttatcaa ttttcttcta      900
acttcaggcc tagaaagaag ttttgggtag gctttgtctt acagtgttat tatttatgag      960
taaaactaat tggttgtcct gcatacttta attatgatgt aatacaggtt ctgggttgac     1020
aaatatcaag acggaggaga tctctgaagt gaagatggat acggagttta ggcacgattc     1080
aggatatgaa gttcatcatc aaaaattggt acgtaaaata atttacctct ttccactagt     1140
gtttgtcttg ccaaatgacc tattaactct ggttcatcct gtgctagaaa tcaaattaag     1200
gaaaagataa aaatacaatg cttgcctata ggattaccat gaaaacatga agaaaataaa     1260
```

```
taggctaggc tgagcgcagt ggctcaagcc tgtaatccca gcactttggg aggccaaggc    1320
gggtggatca cgaggtcaga aattcgagac cagcctggcc aatatggtga accccatct    1380 ctactaaaaa tacaaaaaag attagctggg tgtggtggca acacctgta gtcccagctg    1440 ctggggaggc tgacgcagga gacttgcttg aacccaggag gtggaggttg cagtgagctg    1500
agatcgtgcc taggcgacag agcgagactc catcccaaaa aaaaaaaga aagaaagag    1560 gctgtatgta tagttctttc agactacaag gcagcaaagt tcgtgcatga ctcgggactt    1620
aaagtggaat taatttcaat atagcagcca ctttgacttc cactgtgttt tctgggaaaa    1680
taggtttaca ataggtttat ttgaaggatc aaacacatgc atacactgct tggttttaca    1740
gaacacttta tgtggcttaa attcacatcc ggaactgtct tcctttaccc attcatttct    1800
cccccagctc tttcttttca ttccctcccc tacctcccat gatttaactt ctcttgcaag    1860
agtaagatca tggagtgagc aggaccccat gatgttcccg atagtgttat tcatcaaaag    1920
gtttgtgcaa agaagacagc agcttccttt tcagatgaaa tcacttttcc cccctaatgt    1980
tagaattgga gtaaatcaaa aagccacatc tcctttgtgg tcagctctag tagttatata    2040
aaatccttta ccaaaagctt agaaatggag ataaatcaaa tcgtggatta tgttagggtt    2100
ccatcttatc agtaggtgca gtaagagggt taaattaatg aagacgacaa ttttatcaca    2160
ttcagtggtg gacagaaaaa tggtaagaaa atttccatag caataatact taaagttatc    2220
tcaggcactt cttttgtttt gttttgtgtg tgtgtgtgtg tgagtgttac ttttttccaa    2280
gcagaaaatg tcttttcaat attcataaag ttgataaatc ctagtattaa tctctaaaag    2340
aaacacctcc aaattattat ttatgcctta cttgactcca ataattgta gcaaataaaa    2400

<210> SEQ ID NO 48
<211> LENGTH: 100
<212> TYPE: DNA
<213> ORGANISM: Artificial sequence
<220> FEATURE:
<223> OTHER INFORMATION: Synthetic polynucleotide

<400> SEQUENCE: 48 ttctggggttg acaaatatca agacggagga gatctctgaa gtgaagatgg atacggagtt    60
taggcacgat tcaggatatg aagttcatca tcaaaaattg                          100

<210> SEQ ID NO 49
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 49
tggatacgga gtttaggcac gattc                                          25

<210> SEQ ID NO 50
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 50
cctgaatcgt gcctaaactc cgt                                            23

<210> SEQ ID NO 51
<211> LENGTH: 22
```

<212> TYPE: DNA
<213> ORGANISM: Artificial sequence
<220> FEATURE:
<223> OTHER INFORMATION: Synthetic oligonucleotide

<400> SEQUENCE: 51
acctgccaac caaagcgaga ac                                            22

<210> SEQ ID NO 52
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 52
tcagggttat tgtctcatga gcg                                           23

<210> SEQ ID NO 53
<211> LENGTH: 609
<212> TYPE: DNA
<213> ORGANISM: Artificial sequence
<220> FEATURE:
<223> OTHER INFORMATION: Synthetic polynucleotide

<400> SEQUENCE: 53
tggatacgga gtttaggcac gattcaggat atgaagttca tcatcaaaaa ttggtacgta     60
aaataattta cctctttcca ctagtgtttg tcttgccaaa tgacctatta actctggttc    120
atcctgtgct agaaatcaaa ttaaggaaaa gataaaaata caatgcttgc ctataggatt    180
accatgaaaa catgaagaaa ataaataggc taggctgagc gcagtggctc aagcctgtaa    240
tcccagcact ttgggaggcc aaggcgggtg gatcacgagg tcagaaattc gagaccagcc    300
tggccaatat ggtgaaaccc catctctact aaaaatacaa aaaagattag ctgggtgtgg    360
tggcaaacac ctgtagtccc agctgctggg gaggctgacg caggagactt gcttgaaccc    420
aggaggtgga ggttgcagtg agctgagatc gtgcctaggc gacagagcga gactccatcc    480
caaaaaaaaa aaagaaaaag aaagaggctg tatgtatagt tctttcagac tacaaggcag    540
caaagttcgt gcatgactcg ggacttaaag tggaattaat ttcaatatag cagccacttt    600
gacttccac                                                          609

<210> SEQ ID NO 54
<211> LENGTH: 609
<212> TYPE: DNA
<213> ORGANISM: Homosapiens

<400> SEQUENCE: 54
tggatgcaga attccgacat gactcaggat atgaagttca tcatcaaaaa ttggtacgta     60
aaataattta cctctttcca ctactgtttg tcttgccaaa tgacctatta actctggttc    120
atcctgtgct agaaatcaaa ttaaggaaaa gataaaaata caatgcttgc ctataggatt    180
accatgaaaa catgaagaaa ataaataggc taggctgagc gcagtggctc aagcctgtaa    240
tcccagcact ttgggaggcc aaggcgggtg gatcacgagg tcagaaattc gagaccagcc    300
tggccaatat ggtgaaaccc catctctact aaaaatacaa aaaagattag ctgggtgtgg    360
tggcaaacac ctgtagtccc agctgctggg gaggctgacg caggagactt gcttgaaccc    420
aggaggtgga ggttgcagtg agctgagatc gtgcctaggc gacagagcga gactccatcc    480
caaaaaaaaa aaagaaaaag aaagaggctg tatgtatagt tctttcagac tacaaggcag    540

```
caaagttcgt gcatgactcg ggacttaaag tggaattaat ttcaatatag cagccacttt      600
gacttccac                                                              609

<210> SEQ ID NO 55
<211> LENGTH: 947
<212> TYPE: DNA
<213> ORGANISM: Homosapiens

<400> SEQUENCE: 55
cacggtagag aagatgactt caaaagccct tttcatccta aaattctgat gtttgataat       60
taaatgttat agcatggaca ctgacattta cattttttac ttatgttttt ggttttaaa      120 tgactctgca ttttgtttta agcttcaaat tattatttga ataatgaaat tcatcagaac     180
aattagtgtt aagaatcata tagcaattta tagaaaagga agagttcgta ggttataaat     240
tctgttagtt gctaagaagc attttaaaa ttatgtacta tagctcttta ttcagcagac      300
gaaccaatta caatctgtgt aactagaaca cttgactaaa attatataat ttttacaacg    360
cttcactgca tagatacatg aacataattt atttgtaatt ggaacaaagc cccaaagtag    420
cagttttgtt ctaccaggta attaatgctc attttaaag ccttttatta ttatttctga     480
agtaatgagt gcacatggaa aaagacacat aataggctaa acaataagcc cgtaagccaa    540
gccaacatat tccaggaaca aatccttgcc aacctctcaa ccaggattta acttctgctt    600
ttcccccatt tcaaaaatt atagcatgta tttaaaggca gcagaagcct tactttcagg     660
tttcccttac cctttcattt cttttgttc aaaataggta gtaattgaag ttttaaatat    720
agggtatcat ttttctttaa gagtcattta tcaattttct tctaacttca ggcctagaaa    780
gaagttttgg gtaggctttg tcttacagtg ttattattta tgagtaaaac taattggttg    840
tcctgcatac tttaattatg atgtaataca ggttctgggt tgacaaatat caagacggag    900
gagatctctg aagtgaagat ggatgcagaa ttccgacatg actcagg                  947

<210> SEQ ID NO 56
<211> LENGTH: 947
<212> TYPE: DNA
<213> ORGANISM: Artificial sequence
<220> FEATURE:
<223> OTHER INFORMATION: Synthetic polynucleotide

<400> SEQUENCE: 56
cacggtagag aagatgactt caaaagccct tttcatccta aaattctgat gtttgataat       60
taaatgttat agcatggaca ctgacattta cattttttac ttatgttttt ggttttaaa      120 tgactctgca ttttgtttta agcttcaaat tattatttga ataatgaaat tcatcagaac     180
aattagtgtt aagaatcata tagcaattta tagaaaagga agagttcgta ggttataaat     240
tctgttagtt gctaagaagc attttaaaa ttatgtacta tagctcttta ttcagcagac      300
gaaccaatta caatctgtgt aactagaaca cttgactaaa attatataat ttttacaacg    360
cttcactgca tagatacatg aacataattt atttgtaatt ggaacaaagc cccaaagtag    420
cagttttgtt ctaccaggta attaatgctc attttaaag ccttttatta ttatttctga     480
agtaatgagt gcacatggaa aaagacacat aataggctaa acaataagcc cgtaagccaa    540
gccaacatat tccaggaaca aatccttgcc aacctctcaa ccaggattta acttctgctt    600
ttcccccatt tcaaaaatt atagcatgta tttaaaggca gcagaagcct tactttcagg     660
tttcccttac cctttcattt cttttgttc aaaataggta gtaattgaag ttttaaatat    720
agggtatcat ttttctttaa gagtcattta tcaattttct tctaacttca ggcctagaaa    780
```

```
gaagttttgg gtaggctttg tcttacagtg ttattattta tgagtaaaac taattggttg    840
tcctgcatac tttaattatg atgtaataca ggttctgggt tgacaaatat caagacggag    900
gagatctctg aagtgaagat ggatacggag tttaggcacg attcagg                  947
```

<210> SEQ ID NO 57
<211> LENGTH: 1073
<212> TYPE: DNA
<213> ORGANISM: Homosapiens

<400> SEQUENCE: 57

```
tggatgcaga attccgacat gactcaggat atgaagttca tcatcaaaaa ttggtacgta     60
aaataattta cctctttcca ctactgtttg tcttgccaaa tgacctatta actctggttc    120
atcctgtgct agaaatcaaa ttaaggaaaa gataaaaata caatgcttgc ctataggatt    180
accatgaaaa catgaagaaa ataaataggc taggctgagc gcagtggctc aagcctgtaa    240
tcccagcact tgggaggcc aaggcgggtg atcacgagg tcagaaattc gagaccagcc     300
tggccaatat ggtgaaaccc catctctact aaaaatacaa aaagattag ctgggtgtgg    360 tggcaaacac ctgtagtccc agctgctggg gaggctgacg caggagactt gcttgaaccc    420
aggaggtgga ggttgcagtg agctgagatc gtgcctaggc gacagagcga gactccatcc    480
caaaaaaaaa aagaaaaga agaggctgt atgtatagtt ctttcagact acaaggcagc     540
aaagttcgtg catgactcgg gacttaaagt ggaattaatt tcaatatagc agccactttg    600
acttccactg tgttttctgg gaaaataggt ttacaatagg tttatttgaa ggatcaaaca    660
catgcataca ctgcttggtt ttacagaaca ctttatgtgg cttaaattca catccggaac    720
tgtcttcctt tacccattca tttctccccc agctctttct tttcattccc tcccctacct    780
cccatgattt aacttctctt gcaagagtaa gatcatggag tgagcaggac cccatgatgt    840
tcccgatagt gttattcatc aaaaggtttg tgcaaagaag acagcagctt ccttttcaga    900
tgaaatcact tttccccct aatgttagaa ttggagtaaa tcaaaagcc acatctcctt     960 tgtggtcagc tctagtagtt atataaaatc ctttaccaaa agcttagaaa tggagataaa   1020
tcaaatcgtg gattatgtta gggttccatc ttatcagtag gtgcagtaag agg          1073
```

<210> SEQ ID NO 58
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 58

```
tggatacgga gttaggcac gattcaggat atgaagttca tcatcaaaaa ttggtacgta     60
aaataattta cctctttcca ctactgtttg tcttgccaaa tgacctatta actctggttc    120
atcctgtgct agaaatcaaa ttaaggaaaa gataaaaata caatgcttgc ctataggatt    180
accatgaaaa catgaagaaa ataaataggc taggctgagc gcagtggctc aagcctgtaa    240
tcccagcact tgggaggcc aaggcgggtg atcacgagg tcagaaattc gagaccagcc     300
tggccaatat ggtgaaaccc catctctact aaaaatacaa aaagattag ctgggtgtgg    360 tggcaaacac ctgtagtccc agctgctggg gaggctgacg caggagactt gcttgaaccc    420
aggaggtgga ggttgcagtg agctgagatc gtgcctaggc gacagagcga gactccatcc    480
caaaaaaaaa aagaaaaga agaggctgt atgtatagtt ctttcagact acaaggcagc     540
```

```
aaagttcgtg catgactcgg gacttaaagt ggaattaatt tcaatatagc agccactttg    600
acttccactg tgttttctgg gaaataggt  ttacaatagg tttatttgaa ggatcaaaca    660
catgcataca ctgcttggtt ttacagaaca ctttatgtgg cttaaattca catccggaac    720
tgtcttcctt tacccattca tttctccccc agctctttct tttcattccc tcccctacct    780
cccatgattt aacttctctt gcaagagtaa gatcatggag tgagcaggac cccatgatgt    840
tcccgatagt gttattcatc aaaaggtttg tgcaaagaag acagcagctt ccttttcaga    900
tgaaatcact tttcccccct aatgttagaa ttggagtaaa tcaaaaagcc acatctcctt    960
tgtggtcagc tctagtagtt atataaaatc ctttaccaaa agcttagaaa tggagataaa   1020
tcaaatcgtg gattatgtta gggttccatc ttatcagtag gtgcagtaag agg           1073

<210> SEQ ID NO 59
<211> LENGTH: 199
<212> TYPE: DNA
<213> ORGANISM: Artificial sequence
<220> FEATURE:
<223> OTHER INFORMATION: Synthetic polynucleotide

<400> SEQUENCE: 59
aattggttgt cctgcatact ttaattatga tgtaatacag gttctgggtt gacaaatatc     60
aagacggagg agatctctga agtgaagatg gatacggagt ttaggcacga ttcaggatat    120
gaagttcatc atcaaaaatt ggtacgtaaa ataatttacc tctttccact agtgtttgtc    180
ttgccaaatg acctattaa                                                 199

<210> SEQ ID NO 60
<211> LENGTH: 1179
<212> TYPE: DNA
<213> ORGANISM: Artificial sequence
<220> FEATURE:
<223> OTHER INFORMATION: Synthetic polynucleotide

<400> SEQUENCE: 60
ttcagcagac gaaccaatta caatctgtgt aactagaaca cttgactaaa attatataat     60
ttttacaacg cttcactgca tagatacatg aacataattt atttgtaatt ggaacaaagc    120
cccaaagtag cagttttgtt ctaccaggta attaatgctc attttttaaag cctttttatta   180 ttatttctga gtaatgagt  gcacatggaa aaagacacat aataggctaa acaataagcc    240
cgtaagccaa gccaacatat tccaggaaca aatccttgcc aacctctcaa ccaggattta    300
acttctgctt tccccccatt ttcaaaaatt atagcatgta tttaaaggca gcagaagcct    360
tactttcagg tttcccttac cctttcattt cttttttgttc aaaataggta gtaattgaag    420
ttttaaatat agggtatcat ttttctttaa gagtcattta tcaattttct tctaacttca    480
ggcctagaaa gaagttttgg gtaggctttg tcttacagtg ttattattta tgagtaaaac    540
taattggttg tcctgcatac tttaattatg atgtaataca ggttctgggt tgacaaatat    600
caagacggag agatctctg  aagtgaagat ggatacggag tttaggcacg attcaggata    660
tgaagttcat catcaaaaat tggtacgtaa ataatttac  ctctttccac tagtgtttgt    720
cttgccaaat gacctattaa ctctggttca tcctgtgcta gaaatcaaat taaggaaaag    780
ataaaaatac aatgcttgcc tataggatta ccatgaaaac atgaagaaaa taaataggct    840
aggctgagcg cagtggctca agcctgtaat cccagcactt tgggaggcca aggcgggtgg    900
atcacgaggt cagaaattcg agaccagcct ggccaatatg gtgaaacccc atctctacta    960
aaaatacaaa aaagattagc tgggtgtggt ggcaaacacc tgtagtccca gctgctgggg   1020
```

```
aggctgacgc aggagacttg cttgaaccca ggaggtggag gttgcagtga gctgagatcg    1080
tgcctaggcg acagagcgag actccatccc aaaaaaaaaa aagaaaagaa agaggctgta    1140
tgtatagttc tttcagacta caaggcagca aagttcgtg                           1179
```

<210> SEQ ID NO 61
<211> LENGTH: 1523
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: n= A, C, G or T
<220> FEATURE:
<221> NAME/KEY: misc_feature
<222> LOCATION: (11)..(11)
<223> OTHER INFORMATION: n= A, C, G or T
<220> FEATURE:
<221> NAME/KEY: misc_feature
<222> LOCATION: (13)..(21)
<223> OTHER INFORMATION: n= A, C, G or T
<220> FEATURE:
<221> NAME/KEY: misc_feature
<222> LOCATION: (23)..(23)
<223> OTHER INFORMATION: n= A, C, G or T
<220> FEATURE:
<221> NAME/KEY: misc_feature
<222> LOCATION: (23)..(23)
<223> OTHER INFORMATION: n= A, C, G or T
<220> FEATURE:
<221> NAME/KEY: misc_feature
<222> LOCATION: (26)..(26)
<223> OTHER INFORMATION: n= A, C, G or T
<220> FEATURE:
<221> NAME/KEY: misc_feature
<222> LOCATION: (888)..(888)
<223> OTHER INFORMATION: n= A, C, G or T
<220> FEATURE:
<221> NAME/KEY: misc_feature
<222> LOCATION: (957)..(957)
<223> OTHER INFORMATION: n= A, C, G or T
<220> FEATURE:
<221> NAME/KEY: misc_feature
<222> LOCATION: (1171)..(1171)
<223> OTHER INFORMATION: n= A, C, G or T
<220> FEATURE:
<221> NAME/KEY: misc_feature
<222> LOCATION: (1305)..(1305)
<223> OTHER INFORMATION: n= A, C, G or T
<220> FEATURE:
<221> NAME/KEY: misc_feature
<222> LOCATION: (1492)..(1492)
<223> OTHER INFORMATION: n= A, C, G or T
<220> FEATURE:
<221> NAME/KEY: misc_feature
<222> LOCATION: (1492)..(1492)
<223> OTHER INFORMATION: n= A, C, G or T
<220> FEATURE:
<221> NAME/KEY: misc_feature
<222> LOCATION: (1499)..(1499)
<223> OTHER INFORMATION: n= A, C, G or T
<220> FEATURE:
<221> NAME/KEY: misc_feature
<222> LOCATION: (1500)..(1500)
<223> OTHER INFORMATION: n= A, C, G or T
<220> FEATURE:
<221> NAME/KEY: misc_feature
<222> LOCATION: (1502)..(1502)
<223> OTHER INFORMATION: n= A, C, G or T
<220> FEATURE:
<221> NAME/KEY: misc_feature
<222> LOCATION: (1504)..(1505)
<223> OTHER INFORMATION: n= A, C, G or T
<220> FEATURE:

<221> NAME/KEY: misc_feature
<222> LOCATION: (1504)..(1505)
<223> OTHER INFORMATION: n= A, C, G or T
<220> FEATURE:
<221> NAME/KEY: misc_feature
<222> LOCATION: (1507)..(1510)
<223> OTHER INFORMATION: n= A, C, G or T
<220> FEATURE:
<221> NAME/KEY: misc_feature
<222> LOCATION: (1512)..(1512)
<223> OTHER INFORMATION: n= A, C, G or T
<220> FEATURE:
<221> NAME/KEY: misc_feature
<222> LOCATION: (1519)..(1520)
<223> OTHER INFORMATION: n= A, C, G or T

<400> SEQUENCE: 61

```
cncttgggca ngnnnnnnnn ncnctntcac gaatcgaccg attgttaggt aatcgtcacc    60
tccacaaaga gcgactcgct gtatcgctcg agggatccga attcaggagg taaaaaccat   120
gatatagcag aattccgaca tgactcaggt tcagcagacg aaccaattac aatctgtgta   180
actagaacac ttgactaaaa ttatataatt tttacaacgc ttcactgcat agatacatga   240
acataattta tttgtaattg gaacaaagcc ccaaagtagc agttttgttc taccaggtaa   300
ttaatgctca tttttaaagc cttttattat tatttctgaa gtaatgagtg cacatggaaa   360
aagacacata ataggctaaa caataagccc gtaagccaag ccaacatatt ccaggaacaa   420
atccttgcca acctctcaac caggatttaa cttctgcttt tccccatttt tcaaaaatta   480
tagcatgtat ttaaaggcag cagaagcctt actttcaggt ttccttaccc tttcatttct   540
tttgttcaaa taggtagtaa ttgaagttta aatatagggt atcattttct ttaagagtca   600
tttatcaatt ttcttctaac ttcaggccta gaaagaagtt ttgggtaggc tttgtcttac   660
agtgttatta tttatgagta aaactaattg gttgtcctgc atactttaat tatgatgtaa   720
tacaggttct gggttgacaa atatcaagac ggaggagatc tctgaagtga agatggatac   780
ggagtttagg cacgattcag gatatgaagt tcatcatcaa aaattggact acaaagacca   840
tgacggtgat tataaagatc atgacatcga ctacaaggat gacgatgnca agtgataagt   900
acgtaaaata atttacctct ttccactagt gtttgtcttg ccaaatgacc tattaantct   960
ggttcatcct gtgctagaaa tcaaattaag gaaaagataa aaatacaatg cttgcctata  1020
ggattaccat gaaaacatga agaaaataaa taggctaggc tgagcgcagt ggctcaagcc  1080
tgtaatccca gcactttggg aggccaaggc gggtggatca cgaggtcaga aattcgagac  1140
cagcctggcc aatatggtga aaccccatct ntactaaaaa tacaaaaaag attagctggg  1200
tgtggtggca aacacctgta gtcccagctg ctggggaggc tgacgcagga gacttgcttg  1260
aacccaggag gtggaggttg cagtgagctg agatcgtgcc taggngacag agcgagactc  1320
catcccaaaa aaaaaaaaag aaaagaaaga ggctgtatgt atagttcttt cagactacaa  1380
ggcagcaaag ttcgtgcaga attccgacat gactcaggac tgataataat gacgtcagaa  1440
ttctcgagtc ggggaaatgt gcgcggaacc cctatttgtt tatttctaa ancatcaann  1500
gnanntnnnn tncccctcnn atg                                          1523
```

<210> SEQ ID NO 62
<211> LENGTH: 66
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (62)..(62)
<223> OTHER INFORMATION: n= A, C, G or T

<400> SEQUENCE: 62
gactacaaag accatgacgg tgattataaa gatcatgaca tcgactacaa ggatgacgat      60 gncaag                                                                 66

<210> SEQ ID NO 63
<211> LENGTH: 22
<212> TYPE: PRT
<213> ORGANISM: Artificial sequence
<220> FEATURE:
<223> OTHER INFORMATION: Synthetic peptide

<400> SEQUENCE: 63

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 64
<211> LENGTH: 1517
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: n= A, C, G or T
<220> FEATURE:
<221> NAME/KEY: misc_feature
<222> LOCATION: (11)..(11)
<223> OTHER INFORMATION: n= A, C, G or T
<220> FEATURE:
<221> NAME/KEY: misc_feature
<222> LOCATION: (13)..(21)
<223> OTHER INFORMATION: n= A, C, G or T
<220> FEATURE:
<221> NAME/KEY: misc_feature
<222> LOCATION: (23)..(23)
<223> OTHER INFORMATION: n= A, C, G or T
<220> FEATURE:
<221> NAME/KEY: misc_feature
<222> LOCATION: (26)..(26)
<223> OTHER INFORMATION: n= A, C, G or T
<220> FEATURE:
<221> NAME/KEY: misc_feature
<222> LOCATION: (888)..(888)
<223> OTHER INFORMATION: n= A, C, G or T
<220> FEATURE:
<221> NAME/KEY: misc_feature
<222> LOCATION: (951)..(951)
<223> OTHER INFORMATION: n= A, C, G or T
<220> FEATURE:
<221> NAME/KEY: misc_feature
<222> LOCATION: (1165)..(1165)
<223> OTHER INFORMATION: n= A, C, G or T
<220> FEATURE:
<221> NAME/KEY: misc_feature
<222> LOCATION: (1299)..(1299)
<223> OTHER INFORMATION: n= A, C, G or T
<220> FEATURE:
<221> NAME/KEY: misc_feature
<222> LOCATION: (1486)..(1486)
<223> OTHER INFORMATION: n= A, C, G or T
<220> FEATURE:
<221> NAME/KEY: misc_feature
<222> LOCATION: (1493)..(1493)
<223> OTHER INFORMATION: n= A, C, G or T
<220> FEATURE:
<221> NAME/KEY: misc_feature
<222> LOCATION: (1494)..(1494)

<223> OTHER INFORMATION: n= A, C, G or T
<220> FEATURE:
<221> NAME/KEY: misc_feature
<222> LOCATION: (1496)..(1496)
<223> OTHER INFORMATION: n= A, C, G or T
<220> FEATURE:
<221> NAME/KEY: misc_feature
<222> LOCATION: (1498)..(1499)
<223> OTHER INFORMATION: n= A, C, G or T
<220> FEATURE:
<221> NAME/KEY: misc_feature
<222> LOCATION: (1501)..(1504)
<223> OTHER INFORMATION: n= A, C, G or T
<220> FEATURE:
<221> NAME/KEY: misc_feature
<222> LOCATION: (1506)..(1506)
<223> OTHER INFORMATION: n= A, C, G or T
<220> FEATURE:
<221> NAME/KEY: misc_feature
<222> LOCATION: (1513)..(1514)
<223> OTHER INFORMATION: n= A, C, G or T

<400> SEQUENCE: 64

```
cncttgggca ngnnnnnnnn ncnctntcac gaatcgaccg attgttaggt aatcgtcacc      60
tccacaaaga gcgactcgct gtatcgctcg agggatccga attcaggagg taaaaaccat     120
gatatagcag aattccgaca tgactcaggt tcagcagacg aaccaattac aatctgtgta     180
actagaacac ttgactaaaa ttatataatt tttacaacgc ttcactgcat agatacatga     240
acataatttta tttgtaattg gaacaaagcc ccaaagtagc agttttgttc taccaggtaa     300
ttaatgctca tttttaaagc cttttattat tatttctgaa gtaatgagtg cacatggaaa     360
aagacacata ataggctaaa caataagccc gtaagccaag ccaacatatt ccaggaacaa     420
atccttgcca acctctcaac caggatttaa cttctgcttt tccccatttt tcaaaaatta     480
tagcatgtat ttaaaggcag cagaagcctt actttcaggt ttccttaccc tttcatttct     540
tttgttcaaa taggtagtaa ttgaagttta aatatagggt atcattttct ttaagagtca     600
tttatcaatt ttcttctaac ttcaggccta gaaagaagtt ttgggtaggc tttgtcttac     660
agtgttatta tttatgagta aaactaattg gttgtcctgc atactttaat tatgatgtaa     720
tacaggttct gggttgacaa atatcaagac ggaggagatc tctgaagtga agatggatac     780
ggagtttagg cacgattcag gatatgaagt tcatcatcaa aaattggact acaaagacca     840
tgacggtgat tataaagatc atgacatcga ctacaaggat gacgatgnca aggtacgtaa     900
aataatttac ctcttttccac tagtgttttgt cttgccaaat gacctattaa ntctggttca     960
tcctgtgcta gaaatcaaat taaggaaaag ataaaaatac aatgcttgcc tataggatta    1020
ccatgaaaac atgaagaaaa taaataggct aggctgagcg cagtggctca gcctgtaat    1080
cccagcactt tgggaggcca aggcgggtgg atcacgaggt cagaaattcg agaccagcct    1140
ggccaatatg gtgaaacccc atctntacta aaaatacaaa aaagattagc tgggtgtggt    1200
ggcaaacacc tgtagtccca gctgctgggg aggctgacgc aggagacttg cttgaaccca    1260
ggaggtggag gttgcagtga gctgagatcg tgcctaggng acagagcgag actccatccc    1320
aaaaaaaaaa aaagaaaaga aagaggctgt atgtatagtt ctttcagact acaaggcagc    1380
aaagttcgtg cagaattccg acatgactca ggactgataa taatgacgtc agaattctcg    1440
agtcggggaa atgtgcgcgg aacccctatt tgtttatttt ctaaancatc aanngnannt    1500
nnnntncccc tcnnatg                                                  1517
```

<210> SEQ ID NO 65
<211> LENGTH: 1180

<212> TYPE: DNA
<213> ORGANISM: Artificial sequence
<220> FEATURE:
<223> OTHER INFORMATION: Synthetic polynucleotide

<400> SEQUENCE: 65

| | | | | | |
|---|---|---|---|---|---|
| ttcagcagac | gaaccaatta | caatctgtgt | aactagaaca | cttgactaaa | attatataat | 60 |
| ttttacaacg | cttcactgca | tagatacatg | aacataattt | atttgtaatt | ggaacaaagc | 120 |
| cccaaagtag | cagttttgtt | ctaccaggta | attaatgctc | attttttaaag | ccttttatta | 180 |
| ttatttctga | agtaatgagt | gcacatggaa | aaagacacat | aataggctaa | acaataagcc | 240 |
| cgtaagccaa | gccaacatat | tccaggaaca | aatccttgcc | aacctctcaa | ccaggattta | 300 |
| acttctgctt | ttcccccatt | ttcaaaaatt | atagcatgta | tttaaaggca | gcagaagcct | 360 |
| tactttcagg | tttcccttac | cctttcattt | cttttttgttc | aaaataggta | gtaattgaag | 420 |
| ttttaaatat | agggtatcat | ttttctttaa | gagtcattta | tcaattttct | tctaacttca | 480 |
| ggcttagaaa | gaagttttgg | gtaggctttg | tcttacagtg | ttattattta | tgagtaaaac | 540 |
| taattggttg | tcctgcatac | tttaattatg | atgtaataca | ggttctgggt | tgacaaatat | 600 |
| caagacggag | gagatctctg | aagtgaagat | ggatgcagaa | ttccgacatg | actcaggata | 660 |
| tgaagttcat | catcaaaaat | tggtacgtaa | aataatttac | ctcttttccac | tactgtttgt | 720 |
| cttgccaaat | gacctattaa | ctctggttca | tcctgtgcta | gaaatcaaat | taaggaaaag | 780 |
| ataaaaatac | aatgcttgcc | tataggatta | ccatgaaaac | atgaagaaaa | taaataggct | 840 |
| aggctgagcg | cagtggctca | agcctgtaat | cccagcactt | tgggaggcca | aggcgggtgg | 900 |
| atcacgaggt | cagaaattcg | agaccagcct | ggccaatatg | gtgaaacccc | atctctacta | 960 |
| aaaatacaaa | aaagattagc | tgggtgtggt | ggcaaacacc | tgtagtccca | gctgctgggg | 1020 |
| aggctgacgc | aggagacttg | cttgaaccca | ggaggtggag | gttgcagtga | gctgagatcg | 1080 |
| tgcctaggcg | acagagcgag | actccatccc | aaaaaaaaaa | aaagaaaaga | aagaggctgt | 1140 |
| atgtatagtt | ctttcagact | acaaggcagc | aaagttcgtg | | | 1180 |

<210> SEQ ID NO 66
<211> LENGTH: 441
<212> TYPE: DNA
<213> ORGANISM: Artificial sequence
<220> FEATURE:
<223> OTHER INFORMATION: Synthetic polynucleotide

<400> SEQUENCE: 66

| | | | | | |
|---|---|---|---|---|---|
| atcaattttc | ttctaacttc | aggcctagaa | agaagttttg | ggtaggcttt | gtcttacagt | 60 |
| gttattattt | atgagtaaaa | ctaattggtt | gtcctgcata | ctttaattat | gatgtaatac | 120 |
| aggttctggg | ttgacaaata | tcaagacgga | ggagatctct | gaagtgaaga | tggatacgga | 180 |
| gtttaggcac | gattcaggat | atgaagttca | tcatcaaaaa | ttggtacgta | aaataattta | 240 |
| cctctttcca | ctagtgtttg | tcttgccaaa | tgacctatta | actctggttc | atcctgtgct | 300 |
| agaaatcaaa | ttaaggaaaa | gataaaaata | caatgcttgc | ctataggatt | accatgaaaa | 360 |
| catgaagaaa | ataaataggc | taggctgagc | gcagtggctc | aagcctgtaa | tcccagcact | 420 |
| ttgggaggcc | aaggcgggtg | g | | | | 441 |

<210> SEQ ID NO 67
<211> LENGTH: 1224
<212> TYPE: DNA
<213> ORGANISM: Artificial sequence
<220> FEATURE:

<223> OTHER INFORMATION: Synthetic polynucleotide

<400> SEQUENCE: 67

```
cagaattccg acatgactca ggttcagcag acgaaccaat tacaatctgt gtaactagaa      60
cacttgacta aaattatata attttttacaa cgcttcactg catagataca tgaacataat    120
ttatttgtaa ttggaacaaa gccccaaagt agcagttttg ttctaccagg taattaatgc    180
tcattttaa agccttttat tattatttct gaagtaatga gtgcacatgg aaaaagacac     240
ataataggct aaacaataag cccgtaagcc aagccaacat attccaggaa caaatccttg     300
ccaacctctc aaccaggatt taacttctgc ttttccccca ttttcaaaaa ttatagcatg     360
tatttaaagg cagcagaagc cttactttca ggtttcccctt acccttttcat ttcttttttgt  420
tcaaaatagg tagtaattga agttttaaat atagggtatc attttttcttt aagagtcatt    480
tatcaatttt cttctaactt caggcctaga aagaagtttt gggtaggctt tgtcttacag     540
tgttattatt tatgagtaaa actaattggt tgtcctgcat actttaatta tgatgtaata    600
caggttctgg gttgacaaat atcaagacgg aggagatctc tgaagtgaag atggatacgg    660
agtttaggca cgattcagga tatgaagttc atcatcaaaa attggtacgt aaaataattt   720
acctcttttcc actagtgttt gtcttgccaa atgacctatt aactctggtt catcctgtgc    780
tagaaatcaa attaaggaaa agataaaaat acaatgcttg cctataggat taccatgaaa    840
acatgaagaa aataaatagg ctaggctgag cgcagtggct caagcctgta atcccagcac    900
tttgggaggc caaggcgggt ggatcacgag gtcagaaatt cgagaccagc ctggccaata    960
tggtgaaacc ccatctctac taaaaataca aaaaagatta gctgggtgtg gtggcaaaca   1020
cctgtagtcc cagctgctgg ggaggctgac gcaggagact tgcttgaacc caggaggtgg   1080
aggttgcagt gagctgagat cgtgcctagg cgacagagcg agactccatc ccaaaaaaaa   1140
aaaagaaaa gaaagaggct gtatgtatag ttctttcaga ctacaaggca gcaaagttcg   1200
tgcagaattc cgacatgact cagg                                          1224
```

<210> SEQ ID NO 68
<211> LENGTH: 101
<212> TYPE: DNA
<213> ORGANISM: Artificial sequence
<220> FEATURE:
<223> OTHER INFORMATION: Synthetic polynucleotide

<400> SEQUENCE: 68

```
gttctgggtt gacaaatatc aagacggagg agatctctga agtgaagatg gatacggagt      60
ttaggcacga ttcaggatat gaagttcatc atcaaaaatt g                        101
```

<210> SEQ ID NO 69
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 69

```
atcaattttc ttctaacttc agg                                             23
```

<210> SEQ ID NO 70
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 70
ccacccgcct tggcctccca aag                                          23

<210> SEQ ID NO 71
<211> LENGTH: 507
<212> TYPE: DNA
<213> ORGANISM: Artificial sequence
<220> FEATURE:
<223> OTHER INFORMATION: Synthetic polynucleotide

<400> SEQUENCE: 71
atcaattttc ttctaacttc aggcctagaa agaagttttg ggtaggcttt gtcttacagt      60
gttattattt atgagtaaaa ctaattggtt gtcctgcata ctttaattat gatgtaatac     120
aggttctggg ttgacaaata tcaagacgga ggagatctct gaagtgaaga tggatacgga     180
gtttaggcac gattcaggat atgaagttca tcatcaaaaa ttggactaca aagaccatga     240
cggtgattat aaagatcatg acatcgacta caaggatgac gatgacaagg tacgtaaaat     300
aatttacctc tttccactag tgtttgtctt gccaaatgac ctattaactc tggttcatcc     360
tgtgctagaa atcaaattaa ggaaaagata aaaatacaat gcttgcctat aggattacca     420
tgaaaacatg aagaaaataa ataggctagg ctgagcgcag tggctcaagc ctgtaatccc     480
agcactttgg gaggccaagg cgggtgg                                        507

<210> SEQ ID NO 72
<211> LENGTH: 513
<212> TYPE: DNA
<213> ORGANISM: Artificial sequence
<220> FEATURE:
<223> OTHER INFORMATION: Synthetic polynucleotide

<400> SEQUENCE: 72
atcaattttc ttctaacttc aggcctagaa agaagttttg ggtaggcttt gtcttacagt      60
gttattattt atgagtaaaa ctaattggtt gtcctgcata ctttaattat gatgtaatac     120
aggttctggg ttgacaaata tcaagacgga ggagatctct gaagtgaaga tggatacgga     180
gtttaggcac gattcaggat atgaagttca tcatcaaaaa ttggactaca aagaccatga     240
cggtgattat aaagatcatg acatcgacta caaggatgac gatgacaagt gataagtacg     300
taaaataatt tacctctttc cactagtgtt tgtcttgcca aatgacctat taactctggt     360
tcatcctgtg ctagaaatca aattaaggaa aagataaaaa tacaatgctt gcctatagga     420
ttaccatgaa aacatgaaga aaataaatag gctaggctga gcgcagtggc tcaagcctgt     480
aatcccagca ctttgggagg ccaaggcggg tgg                                 513

<210> SEQ ID NO 73
<211> LENGTH: 1500
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: n= A, C, G or T
<220> FEATURE:
<221> NAME/KEY: misc_feature
<222> LOCATION: (16)..(18)
<223> OTHER INFORMATION: n= A, C, G or T
<220> FEATURE:
<221> NAME/KEY: misc_feature
<222> LOCATION: (20)..(21)

<223> OTHER INFORMATION: n= A, C, G or T
<220> FEATURE:
<221> NAME/KEY: misc_feature
<222> LOCATION: (873)..(873)
<223> OTHER INFORMATION: n= A, C, G or T
<220> FEATURE:
<221> NAME/KEY: misc_feature
<222> LOCATION: (1491)..(1491)
<223> OTHER INFORMATION: n= A, C, G or T
<220> FEATURE:
<221> NAME/KEY: misc_feature
<222> LOCATION: (1498)..(1498)
<223> OTHER INFORMATION: n= A, C, G or T

<400> SEQUENCE: 73

```
gggtnggccc cgaacnnncn ntaataacga tcgaccgatt gttaggtaat cgtcacctcc      60
acaaagagcg actcgctgta tcgctcgagg gatccgaatt caggaggtaa aaaccatgat     120
atagcagaat tccgacatga ctcaggttca gcagacgaac caattacaat ctgtgtaact     180
agaacacttg actaaaatta tataattttt acaacgcttc actgcataga tacatgaaca     240
taatttattt gtaattggaa caaagccccca agtagcagt tttgttctac caggtaatta     300
atgctcattt ttaaagcctt ttattattat ttctgaagta atgagtgcac atggaaaaag     360
acacataata ggctaaacaa taagcccgta agccaagcca acatattcca ggaacaaatc     420
cttgccaacc tctcaaccag gatttaactt ctgcttttcc cccatttca aaaattatag      480
catgtattta aaggcagcag aagccttact ttcaggtttc ccttacccctt tcatttcttt    540
tgttcaaaat aggtagtaat tgaagttta aatatagggt atcattttct ttaagagtca     600
tttatcaatt ttcttctaac ttcaggccta gaaagaagtt tgggtaggc tttgtcttac     660
agtgttatta tttatgagta aaactaattg gttgtcctgc atactttaat tatgatgtaa     720
tacaggttct gggttgacaa atatcaagac ggaggagatc tctgaagtga agatggatac     780
ggagtttagg cacgattcag gatatgaagt tcatcatcaa aaattggact acaaagacca     840
tgactgtgat tataaagatc atgacatcga ctncaaggat gacgatgaca agtgataagt     900
acgtaaaata atttacctct ttccactagt gtttgtcttg ccaaatgacc tattaactct     960
ggttcatcct gtgctagaaa tcaaattaag gaaaagataa aaatacaatg cttgcctata    1020
ggattaccat gaaaacatga agaaaataaa taggctaggc tgagcgcagt ggctcaagcc    1080
tgtaatccca gcactttggg aggccaaggc gggtggatca cgaggtcaga aattcgagac    1140
cagcctggcc aatatggtga aaccccatct ctactaaaaa tacaaaaaag attagctggg    1200
tgtggtggca acacctgta gtcccagctg ctggggaggc tgacgcagga gacttgcttg    1260
aacccaggag gtggaggttg cagtgagctg agatcgtgcc taggcgacag agcgagactc    1320
catcccaaaa aaaaaaaaag aaaagaaaga ggctgtatgt atagttcttt cagactacaa    1380
ggcagcaaag ttcgtgcaga attccgacat gactcaggac tgataataat gacgtcagaa    1440
ttctcgagtc ggggaaatgt gcgcggaacc cctatttgtt tatttctaaa ncatcaaggg    1500
```

<210> SEQ ID NO 74
<211> LENGTH: 1520
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: n= A, C, G or T
<220> FEATURE:
<221> NAME/KEY: misc_feature

```
<222> LOCATION: (16)..(18)
<223> OTHER INFORMATION: n= A, C, G or T
<220> FEATURE:
<221> NAME/KEY: misc_feature
<222> LOCATION: (20)..(21)
<223> OTHER INFORMATION: n= A, C, G or T
<220> FEATURE:
<221> NAME/KEY: misc_feature
<222> LOCATION: (873)..(873)
<223> OTHER INFORMATION: n= A, C, G or T
<220> FEATURE:
<221> NAME/KEY: misc_feature
<222> LOCATION: (1490)..(1490)
<223> OTHER INFORMATION: n= A, C, G or T
<220> FEATURE:
<221> NAME/KEY: misc_feature
<222> LOCATION: (1497)..(1497)
<223> OTHER INFORMATION: n= A, C, G or T
<220> FEATURE:
<221> NAME/KEY: misc_feature
<222> LOCATION: (1505)..(1505)
<223> OTHER INFORMATION: n= A, C, G or T
<220> FEATURE:
<221> NAME/KEY: misc_feature
<222> LOCATION: (1507)..(1509)
<223> OTHER INFORMATION: n= A, C, G or T
<220> FEATURE:
<221> NAME/KEY: misc_feature
<222> LOCATION: (1511)..(1519)
<223> OTHER INFORMATION: n= A, C, G or T

<400> SEQUENCE: 74
gggtnggccc cgaacnnncn ntaataacga tcgaccgatt gttaggtaat cgtcacctcc      60
acaaagagcg actcgctgta tcgctcgagg gatccgaatt caggaggtaa aaaccatgat    120
atagcagaat tccgacatga ctcaggttca gcagacgaac caattacaat ctgtgtaact    180
agaacacttg actaaaatta tataattttt acaacgcttc actgcataga tacatgaaca    240
taatttattt gtaattggaa caaagcccca agtagcagt tttgttctac caggtaatta    300
atgctcattt ttaaagcctt ttattattat ttctgaagta atgagtgcac atggaaaaag    360
acacataata ggctaaacaa taagcccgta agccaagcca acatattcca ggaacaaatc    420
cttgccaacc tctcaaccag gatttaactt ctgcttttcc cccatttca aaaattatag     480 catgtattta aaggcagcag aagccttact ttcaggtttc ccttaccctt tcatttcttt    540
tgttcaaaat aggtagtaat tgaagtttta aatatagggt atcattttct ttaagagtca    600
tttatcaatt ttcttctaac ttcaggccta gaaagaagtt ttgggtaggc tttgtcttac    660
agtgttatta tttatgagta aaactaattg gttgtcctgc atactttaat tatgatgtaa    720
tacaggttct gggttgacaa atatcaagac ggaggagatc tctgaagtga agatggatac    780
ggagtttagg cacgattcag gatatgaagt tcatcatcaa aaattggact acaaagacca    840
tgactgtgat tataaagatc atgacatcga ctncaaggat gacgatgaca agtgataagt    900
acgtaaaata atttacctct ttccactagt gtttgtcttg ccaaatgacc tattaactct    960
ggttcatcct gtgctagaaa tcaaattaag gaaaagataa aaatacaatg cttgcctata    1020
ggattaccat gaaaacatga agaaaataaa taggctaggc tgagcgcagt ggctcaagcc    1080
tgtaatccca gcactttggg aggccaaggc gggtggatca cgaggtcaga aattcgagac    1140
cagcctggcc aatatggtga accccatct ctactaaaaa tacaaaaaag attagctggg    1200
tgtggtggca acacctgta gtcccagctg ctggggaggc tgacgcagga gacttgcttg    1260
aacccaggag gtggaggttg cagtgagctg agatcgtgcc taggcgacag agcgagactc    1320
catcccaaaa aaaaaaaaag aaaagaaaga ggctgtatgt aagttctttc agactacaag    1380
```

```
gcagcaaagt tcgtgcagaa ttccgacatg actcaggact gataataatg acgtcagaat    1440
tctcgagtcg gggaaatgtg cgcggaaccc ctatttgttt atttctaaan catcaanggg    1500
ttaanannna nnnnnnnnng                                                 1520

<210> SEQ ID NO 75
<211> LENGTH: 8506
<212> TYPE: DNA
<213> ORGANISM: Artificial sequence
<220> FEATURE:
<223> OTHER INFORMATION: Synthetic  polynucleotide

<400> SEQUENCE: 75
gagggcctat ttcccatgat tccttcatat ttgcatatac gatacaaggc tgttagagag      60
ataattggaa ttaatttgac tgtaaacaca agatattag tacaaaatac gtgacgtaga     120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg ggtcttcgag aagacctgtt ttagagctag aaatagcaag ttaaaataag    300
gctagtccgt tatcaacttg aaaaagtggc accgagtcgg tgcttttttg ttttagagct    360
agaaatagca agttaaaata aggctagtcc gttttagcg cgtgcgccaa ttctgcagac    420
aaatggctct agaggtaccc gttacataac ttacggtaaa tggcccgcct ggctgaccgc    480
ccaacgaccc ccgcccattg acgtcaatag taacgccaat agggactttc cattgacgtc    540
aatgggtgga gtatttacgg taaactgccc acttggcagt acatcaagtg tatcatatgc    600
caagtacgcc ccctattgac gtcaatgacg gtaaatggcc cgcctggcat tgtgcccagt    660
acatgacctt atgggacttt cctacttggc agtacatcta cgtattagtc atcgctatta    720
ccatggtcga ggtgagcccc acgttctgct tcactctccc catctccccc cctccccac     780 ccccaatttt gtatttattt attttttaat tattttgtgc agcgatgggg gcggggggg     840 gggggggcg cgcgccaggc ggggcggggc ggggcgaggg gcgggcggg gcgaggcgga     900 gaggtgcggc ggcagccaat cagagcggcg cgctccgaaa gtttccttt atggcgaggc     960 ggcggcggcg gcgccctat aaaaagcgaa gcgcgcggcg gcgggagtc gctgcgacgc    1020 tgccttcgcc ccgtgccccg ctccgccgcc gcctcgcgcc gcccgccccg gctctgactg    1080
accgcgttac tcccacaggt gagcgggcgg gacggcccct tctcctccggg ctgtaattag    1140 ctgagcaaga ggtaagggtt taagggatgg ttggttggtg gggtattaat gtttaattac    1200
ctggagcacc tgcctgaaat cactttttt caggttggac cggtgccacc atggactata    1260
aggaccacga cggagactac aaggatcatg atattgatta caaagacgat gacgataaga    1320 tggcccaaa gaagaagcgg aaggtcggta tccacggagt cccagcagcc gacaagaagt    1380
acagcatcgg cctggacatc ggcaccaact ctgtgggctg ggccgtgatc accgacgagt    1440
acaaggtgcc cagcaagaaa ttcaaggtgc tgggcaacac cgaccggcac agcatcaaga    1500
agaacctgat cggagccctg ctgttcgaca gcggcgaaac agccgaggcc acccggctga    1560
agagaaccgc cagaagaaga taccaccagac ggaagaaccg gatctgctat ctgcaagaga    1620
tcttcagcaa cgagatggcc aaggtggacg acagcttctt ccacagactg gaagagtcct    1680
tcctggtgga agaggataag aagcacgagc ggcaccccat cttcggcaac atcgtggacg    1740
aggtggccta ccacgagaag taccccacca tctaccacct gagaaagaaa ctggtggaca    1800
gcaccgacaa ggccgacctg cggctgatct atctggccct ggcccacatg atcaagttcc    1860
ggggccactt cctgatcgag ggcgacctga accccgacaa cagcgacgtg gacaagctgt    1920
```

```
tcatccagct ggtgcagacc tacaaccagc tgttcgagga aaaccccatc aacgccagcg   1980
gcgtggacgc caaggccatc ctgtctgcca gactgagcaa gagcagacgg ctggaaaatc   2040
tgatcgccca gctgcccggc gagaagaaga atggcctgtt cggaaacctg attgccctga   2100
gcctgggcct gaccccaac ttcaagagca acttcgacct ggccgaggat gccaaactgc    2160
agctgagcaa ggacacctac gacgacgacc tggacaacct gctggcccag atcggcgacc   2220
agtacgccga cctgtttctg gccgccaaga acctgtccga cgccatcctg ctgagcgaca   2280
tcctgagagt gaacaccgag atcaccaagg ccccctgag cgcctctatg atcaagagat    2340
acgacgagca ccaccaggac ctgaccctgc tgaaagctct cgtgcggcag cagctgcctg   2400
agaagtacaa agagattttc ttcgaccaga gcaagaacgg ctacgccggc tacattgacg   2460
gcggagccag ccaggaagag ttctacaagt tcatcaagcc catcctggaa agatgggacg   2520
gcaccgagga actgctcgtg aagctgaaca gagaggacct gctgcggaag cagcggacct   2580
tcgacaacgg cagcatcccc caccagatcc acctgggaga gctgcacgcc attctgcggc   2640
ggcaggaaga tttttaccca ttcctgaagg acaaccggga aaagatcgag aagatcctga   2700
ccttccgcat ccctactac gtgggccctc tggccagggg aaacagcaga ttcgcctgga    2760
tgaccagaaa gagcgaggaa accatcaccc cctggaactt cgaggaagtg gtggacaagg   2820
gcgcttccgc ccagagcttc atcgagcgga tgaccaactt cgataagaac ctgcccaacg   2880
agaaggtgct gcccaagcac agcctgctgt acgagtactt caccgtgtat aacgagctga   2940
ccaaagtgaa atacgtgacc gagggaatga aaagcccgc cttcctgagc ggcgagcaga   3000
aaaaggccat cgtggacctg ctgttcaaga ccaaccggaa agtgaccgtg aagcagctga   3060
aagaggacta cttcaagaaa atcgagtgct tcgactccgt ggaaatctcc ggcgtggaag   3120
atcggttcaa cgcctccctg ggcacatacc acgatctgct gaaaattatc aaggacaagg   3180
acttcctgga caatgaggaa aacgaggaca ttctggaaga tatcgtgctg accctgacac   3240
tgtttgagga cagagagatg atcgaggaac ggctgaaaac ctatgcccac ctgttcgacg   3300
acaaagtgat gaagcagctg aagcggcgga tataccggg ctggggcagg ctgagccgga    3360
agctgatcaa cggcatccgg gacaagcagt ccggcaagac aatcctggat ttcctgaagt   3420
ccgacggctt cgccaacaga aacttcatgc agctgatcca cgacgacagc ctgacctta    3480 aagaggacat ccagaaagcc caggtgtccg gccagggcga tagcctgcac gagcacattg   3540
ccaatctggc cggcagcccc gccattaaga agggcatcct gcagacagtg aaggtggtgg   3600
acgagctcgt gaaagtgatg ggccggcaca gcccgagaa catcgtgatc gaaatggcca   3660
gagagaacca gaccacccag aagggacaga agaacagccg cgagagaatg aagcggatcg   3720
aagagggcat caaagagctg ggcagccaga tcctgaaaga acaccccgtg gaaaacaccc   3780
agctgcagaa cgagaagctg tacctgtact acctgcagaa tgggcgggat atgtacgtgg   3840
accaggaact ggacatcaac cggctgtccg actacgatgt ggaccatatc gtgcctcaga   3900
gctttctgaa ggacgactcc atcgacaaca aggtgctgac cagaagcgac aagaaccggg   3960
gcaagagcga caacgtgccc tccgaagagg tcgtgaagaa gatgaagaac tactggcggc   4020
agctgctgaa cgccaagctg attacccaga gaaagttcga caatctgacc aaggccgaga   4080
gaggcggcct gagcgaactg gataaggccg gcttcatcaa gagacagctg gtggaaaccc   4140
ggcagatcac aaagcacgtg gcacagatcc tggactcccg gatgaacact aagtacgacg   4200
agaatgacaa gctgatccgg gaagtgaaag tgatcaccct gaagtccaag ctggtgtccg   4260
```

```
atttccggaa ggatttccag ttttacaaag tgcgcgagat caacaactac caccacgccc    4320
acgacgccta cctgaacgcc gtcgtgggaa ccgccctgat caaaaagtac cctaagctgg    4380
aaagcgagtt cgtgtacggc gactacaagg tgtacgacgt gcggaagatg atcgccaaga    4440
gcgagcagga atcggcaag gctaccgcca agtacttctt ctacagcaac atcatgaact     4500
ttttcaagac cgagattacc ctggccaacg gcgagatccg gaagcggcct ctgatcgaga    4560
caaacggcga aaccggggag atcgtgtggg ataagggccg ggattttgcc accgtgcgga    4620
aagtgctgag catgccccaa gtgaatatcg tgaaaaagac cgaggtgcag acaggcggct    4680
tcagcaaaga gtctatcctg cccaagagga acagcgataa gctgatcgcc agaaagaagg    4740
actgggaccc taagaagtac ggcggcttcg acagccccac cgtggcctat tctgtgctgg    4800
tggtggccaa agtggaaaag gcaagtccaa agaaactgaa gagtgtgaaa gagctgctgg    4860
ggatcaccat catggaaaga agcagcttcg agaagaatcc catcgacttt ctggaagcca    4920
agggctacaa agaagtgaaa aaggacctga tcatcaagct gcctaagtac tccctgttcg    4980
agctggaaaa cggccggaag agaatgctgg cctctgccgg cgaactgcag aagggaaacg    5040
aactggccct gcctccaaa tatgtgaact tcctgtacct ggccagccac tatgagaagc     5100
tgaagggctc ccccgaggat aatgagcaga acagctgtt tgtggaacag cacaagcact     5160
acctggacga gatcatcgag cagatcagcg agttctccaa gagagtgatc ctggccgacg    5220
ctaatctgga caaagtgctg tccgcctaca acaagcaccg ggataagccc atcagagagc    5280
aggccgagaa tatcatccac ctgtttaccc tgaccaatct gggagcccct gccgccttca    5340
agtactttga caccaccatc gaccggaaga ggtacaccag caccaaagag gtgctggacg    5400
ccaccctgat ccaccagagc atcaccggcc tgtacgagac acggatcgac ctgtctcagc    5460
tgggaggcga caaaaggccg gcggccacga aaaaggccgg ccaggcaaaa agaaaaagt     5520
aagaattcct agagctcgct gatcagcctc gactgtgcct tctagttgcc agccatctgt    5580
tgtttgcccc tccccgtgc cttccttgac cctggaaggt gccactccca ctgtcctttc     5640
ctaataaaat gaggaaattg catcgcattg tctgagtagg tgtcattcta ttctgggggg    5700
tgggggtgggg caggacagca agggggagga ttgggaagag aatagcaggc atgctgggga   5760
gcggccgcag gaaccctag tgatggagtt ggccactccc tctctgcgcg ctcgctcgct    5820
cactgaggcc gggcgaccaa aggtcgcccg acgcccgggc tttgcccggg cggcctcagt    5880
gagcgagcga gcgcgcagct gcctgcaggg gcgcctgatg cggtattttc tccttacgca    5940
tctgtgcggt atttcacacc gcatacgtca aagcaaccat agtacgcgcc ctgtagcggc    6000
gcattaagcg cggcgggtgt ggtggttacg cgcagcgtga ccgctacact tgccagcgcc    6060
ctagcgcccg ctcctttcgc tttcttccct cctttctcg ccacgttcgc cggctttccc     6120
cgtcaagctc taaatcgggg gctcccttta gggttccgat ttagtgcttt acggcacctc    6180
gaccccaaaa aacttgattt gggtgatggt tcacgtagtg gccatcgcc ctgatagacg     6240
gttttcgcc ctttgacgtt ggagtccacg ttctttaata gtggactctt gttccaaact     6300
ggaacaacac tcaaccctat ctcgggctat tcttttgatt tataagggat tttgccgatt    6360
tcggcctatt ggttaaaaaa tgagctgatt taacaaaaat ttaacgcgaa ttttaacaaa    6420
atattaacgt ttacaatttt atggtgcact ctcagtacaa tctgctctga tgccgcatag    6480
ttaagccagc cccgacaccc gccaacaccc gctgacgcgc cctgacgggc ttgtctgctc    6540
ccggcatccg cttacagaca agctgtgacc gtctccggga gctgcatgtg tcagaggttt    6600
tcaccgtcat caccgaaacg cgcgagacga aagggcctcg tgatacgcct atttttatag    6660
```

```
gttaatgtca tgataataat ggtttcttag acgtcaggtg gcacttttcg gggaaatgtg    6720
cgcggaaccc ctatttgttt attttttctaa atacattcaa atatgtatcc gctcatgaga    6780
caataaccct gataaatgct tcaataatat tgaaaaagga agagtatgag tattcaacat    6840
ttccgtgtcg ccccttattcc cttttttgcg gcattttgcc ttcctgtttt tgctcaccca    6900
gaaacgctgg tgaaagtaaa agatgctgaa gatcagttgg gtgcacgagt gggttacatc    6960
gaactggatc tcaacagcgg taagatcctt gagagttttc gccccgaaga acgttttcca    7020
atgatgagca cttttaaagt tctgctatgt ggcgcggtat tatcccgtat tgacgccggg    7080
caagagcaac tcggtcgccg catacactat tctcagaatg acttggttga gtactcacca    7140
gtcacagaaa agcatcttac ggatggcatg acagtaagag aattatgcag tgctgccata    7200
accatgagtg ataacactgc ggccaactta cttctgacaa cgatcggagg accgaaggag    7260
ctaaccgctt ttttgcacaa catgggggat catgtaactc gccttgatcg ttgggaaccg    7320
gagctgaatg aagccatacc aaacgacgag cgtgacacca cgatgcctgt agcaatggca    7380
acaacgttgc gcaaactatt aactggcgaa ctacttactc tagcttcccg gcaacaatta    7440
atagactgga tggaggcgga taaagttgca ggaccacttc tgcgctcggc ccttccggct    7500
ggctggttta ttgctgataa atctggagcc ggtgagcgtg gaagccgcgg tatcattgca    7560
gcactggggc cagatggtaa gccctcccgt atcgtagtta tctacacgac ggggagtcag    7620
gcaactatgg atgaacgaaa tagacagatc gctgagatag gtgcctcact gattaagcat    7680
tggtaactgt cagaccaagt ttactcatat atactttaga ttgatttaaa acttcatttt    7740
taatttaaaa ggatctaggt gaagatcctt tttgataatc tcatgaccaa aatcccttaa    7800
cgtgagtttt cgttccactg agcgtcagac cccgtagaaa agatcaaagg atcttcttga    7860 gatcctttt ttctgcgcgt aatctgctgc ttgcaaacaa aaaaaccacc gctaccagcg    7920
gtggtttgtt tgccggatca agagctacca actctttttc cgaaggtaac tggcttcagc    7980
agagcgcaga taccaaatac tgtccttcta gtgtagccgt agttaggcca ccacttcaag    8040
aactctgtag caccgcctac atacctcgct ctgctaatcc tgttaccagt ggctgctgcc    8100
agtggcgata agtcgtgtct taccgggttg gactcaagac gatagttacc ggataaggcg    8160
cagcggtcgg gctgaacggg gggttcgtgc acacagccca gcttggagcg aacgacctac    8220
accgaactga gatacctaca gcgtgagcta tgagaaagcg ccacgcttcc cgaagggaga    8280
aaggcggaca ggtatccggt aagcggcagg gtcggaacag gagagcgcac gagggagctt    8340
ccagggggaa acgcctggta tctttatagt cctgtcgggt ttcgccacct ctgacttgag    8400
cgtcgatttt tgtgatgctc gtcagggggg cggagcctat ggaaaaacgc cagcaacgcg    8460
gcctttttac ggttcctggc cttttgctgg ccttttgctc acatgt             8506
```

<210> SEQ ID NO 76
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 76
gtcttcgaga agac                                                       14

<210> SEQ ID NO 77
<211> LENGTH: 69
<212> TYPE: DNA

<213> ORGANISM: Artificial sequence
<220> FEATURE:
<223> OTHER INFORMATION: Synthetic polynucleotide

<400> SEQUENCE: 77

| | |
|---|---|
| atggactata aggaccacga cggagactac aaggatcatg atattgatta caaagacgat | 60 |
| gacgataag | 69 |

<210> SEQ ID NO 78
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 78

| | |
|---|---|
| ccaaagaaga agcggaaggt c | 21 |

<210> SEQ ID NO 79
<211> LENGTH: 4176
<212> TYPE: DNA
<213> ORGANISM: Artificial sequence
<220> FEATURE:
<223> OTHER INFORMATION: Synthetic polynucleotide

<400> SEQUENCE: 79

| | |
|---|---|
| ggtatccacg gagtcccagc agccgacaag aagtacagca tcggcctgga catcggcacc | 60 |
| aactctgtgg gctgggccgt gatcaccgac gagtacaagg tgcccagcaa gaaattcaag | 120 |
| gtgctgggca acaccgaccg gcacagcatc aagaagaacc tgatcggagc cctgctgttc | 180 |
| gacagcggcg aaacagccga ggccacccgg ctgaagagaa ccgccagaag aagatacacc | 240 |
| agacggaaga ccggatctg ctatctgcaa gagatcttca gcaacgagat ggccaaggtg | 300 |
| gacgacagct tcttccacag actggaagag tccttcctgg tggaagagga taagaagcac | 360 |
| gagcggcacc ccatcttcgg caacatcgtg gacgaggtgg cctaccacga agtaccccc | 420 |
| accatctacc acctgagaaa gaaactggtg gacagcaccg acaaggccga cctgcggctg | 480 |
| atctatctgg ccctggccca catgatcaag ttccggggcc acttcctgat cgagggcgac | 540 |
| ctgaaccccg acaacagcga cgtggacaag ctgttcatcc agctggtgca gacctacaac | 600 |
| cagctgttcg aggaaaaccc catcaacgcc agcggcgtgg acgccaaggc catcctgtct | 660 |
| gccagactga gcaagagcag acggctggaa atctgatcg cccagctgcc cggcgagaag | 720 |
| aagaatggcc tgttcggaaa cctgattgcc ctgagcctgg gcctgacccc caacttcaag | 780 |
| agcaacttcg acctggccga ggatgccaaa ctgcagctga gcaaggacac ctacgacgac | 840 |
| gacctggaca acctgctggc ccagatcggc gaccagtacg ccgacctgtt tctggccgcc | 900 |
| aagaacctgt ccgacgccat cctgctgagc gacatcctga gagtgaacac cgagatcacc | 960 |
| aaggcccccc tgagcgcctc tatgatcaag agatacgacg agcaccacca ggacctgacc | 1020 |
| ctgctgaaag ctctcgtgcg gcagcagctg cctgagaagt acaaagagat tttcttcgac | 1080 |
| cagagcaaga acggctacgc cggctacatt gacggcggag ccagccagga agttctac | 1140 |
| aagttcatca gcccatcct ggaaaagatg gacggcaccg aggaactgct cgtgaagctg | 1200 |
| aacagagagg acctgctgcg gaagcagcgg accttcgaca acggcagcat cccccaccag | 1260 |
| atccacctgg gagagctgca cgccattctg cggcggcagg aagatttta cccattcctg | 1320 |
| aaggacaacc gggaaaagat cgagaagatc ctgaccttcc gcatccccta ctacgtgggc | 1380 |
| cctctggcca ggggaaacag cagattcgcc tggatgacca gaaagagcga ggaaaccatc | 1440 |

```
accccctgga acttcgagga agtggtggac aagggcgctt ccgcccagag cttcatcgag   1500
cggatgacca acttcgataa gaacctgccc aacgagaagg tgctgcccaa gcacagcctg   1560
ctgtacgagt acttcaccgt gtataacgag ctgaccaaag tgaaatacgt gaccgaggga   1620
atgagaaagc ccgccttcct gagcggcgag cagaaaaagg ccatcgtgga cctgctgttc   1680
aagaccaacc ggaaagtgac cgtgaagcag ctgaaagagg actacttcaa gaaaatcgag   1740
tgcttcgact ccgtggaaat ctccggcgtg gaagatcggt tcaacgcctc cctgggcaca   1800
taccacgatc tgctgaaaat tatcaaggac aaggacttcc tggacaatga ggaaaacgag   1860
gacattctgg aagatatcgt gctgaccctg acactgtttg aggacagaga gatgatcgag   1920
gaacggctga aaacctatgc ccacctgttc gacgacaaag tgatgaagca gctgaagcgg   1980
cggagataca ccggctgggg caggctgagc cggaagctga tcaacggcat ccgggacaag   2040
cagtccggca agacaatcct ggatttcctg aagtccgacg gcttcgccaa cagaaacttc   2100
atgcagctga tccacgacga cagcctgacc tttaaagagg acatccagaa agcccaggtg   2160
tccggccagg gcgatagcct gcacgagcac attgccaatc tggccggcag ccccgccatt   2220
aagaagggca tcctgcagac agtgaaggtg gtggacgagc tcgtgaaagt gatgggccgg   2280
cacaagcccg agaacatcgt gatcgaaatg gccagagaga accagaccac ccagaaggga   2340
cagaagaaca gccgcgagag aatgaagcgg atcgagaggg gcatcaaaga gctgggcagc   2400
cagatcctga aagaacaccc cgtggaaaac acccagctgc agaacgagaa gctgtacctg   2460
tactacctgc agaatgggcg ggatatgtac gtggaccagg aactggacat caaccggctg   2520
tccgactacg atgtggacca tatcgtgcct cagagctttc tgaaggacga ctccatcgac   2580
aacaaggtgc tgaccagaag cgacaagaac cggggcaaga gcgacaacgt gcccctccgaa   2640 gaggtcgtga agaagatgaa gaactactgg cggcagctgc tgaacgccaa gctgattacc   2700
cagagaaagt tcgacaatct gaccaaggcc gagagaggcg gcctgagcga actggataag   2760
gccggcttca tcaagagaca gctggtggaa acccggcaga tcacaaagca cgtggcacag   2820
atcctggact cccggatgaa cactaagtac gacgagaatg acaagctgat ccggaagtg    2880 aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aacttttca agaccgagat taccctggcc   3180
aacggcgaga tccggaagcg gcctctgatc gagacaaacg gcgaaaccgg ggagatcgtg   3240
tgggataagg gccgggattt tgccaccgtg cggaaagtgc tgagcatgcc ccaagtgaat   3300
atcgtgaaaa agaccgaggt gcagacaggc ggcttcagca agagtctat cctgcccaag   3360 aggaacagcg ataagctgat cgccagaaag aaggactggg accctaagaa gtacggcggc   3420
ttcgacagcc ccaccgtggc ctattctgtg ctggtggtgg ccaaagtgga aagggcaag   3480 tccaagaaac tgaagagtgt gaaagagctg ctgggatca ccatcatgga agaagcagc   3540 ttcgagaaga atcccatcga ctttctggaa gccaagggct acaaagaagt gaaaaaggac   3600
ctgatcatca agctgcctaa gtactccctg ttcgagctgg aaaacggccg gaagagaatg   3660
ctggcctctg ccggcgaact gcagaaggga acgaactgg ccctgccctc caaatatgtg   3720
aacttcctgt acctggccag ccactatgag aagctgaagg gctcccccga ggataatgag   3780
```

-continued

```
cagaaacagc tgtttgtgga acagcacaag cactacctgg acgagatcat cgagcagatc   3840
agcgagttct ccaagagagt gatcctggcc gacgctaatc tggacaaagt gctgtccgcc   3900
tacaacaagc accgggataa gcccatcaga gagcaggccg agaatatcat ccacctgttt   3960
accctgacca atctgggagc ccctgccgcc ttcaagtact ttgacaccac catcgaccgg   4020
aagaggtaca ccagcaccaa agaggtgctg gacgccaccc tgatccacca gagcatcacc   4080
ggcctgtacg agacacggat cgacctgtct cagctgggag gcgacaaaag gccggcggcc   4140
acgaaaaagg ccggccaggc aaaaaagaaa aagtaa                             4176
```

```
<210> SEQ ID NO 80
<211> LENGTH: 1422
<212> TYPE: PRT
<213> ORGANISM: Artificial sequence
<220> FEATURE:
<223> OTHER INFORMATION: Synthetic polypeptide

<400> SEQUENCE: 80

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val Gly
            20                  25                  30

Ile His Gly Val Pro Ala Ala Asp Lys Lys Tyr Ser Ile Gly Leu Asp
        35                  40                  45

Ile Gly Thr Asn Ser Val Gly Trp Ala Val Ile Thr Asp Glu Tyr Lys
    50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
    130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
    210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
```

```
              290                 295                 300
Ser Lys Asp Thr Tyr Asp Asp Leu Asp Asn Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
                340                 345                 350

Ala Pro Leu Ser Ala Ser Met Ile Lys Arg Tyr Asp Glu His His Gln
                355                 360                 365

Asp Leu Thr Leu Leu Lys Ala Leu Val Arg Gln Gln Leu Pro Glu Lys
                370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
                420                 425                 430

Arg Glu Asp Leu Leu Arg Lys Gln Arg Thr Phe Asp Asn Gly Ser Ile
                435                 440                 445

Pro His Gln Ile His Leu Gly Glu Leu His Ala Ile Leu Arg Arg Gln
                450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
                500                 505                 510

Pro Trp Asn Phe Glu Glu Val Val Asp Lys Gly Ala Ser Ala Gln Ser
                515                 520                 525

Phe Ile Glu Arg Met Thr Asn Phe Asp Lys Asn Leu Pro Asn Glu Lys
                530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
                580                 585                 590

Thr Asn Arg Lys Val Thr Val Lys Gln Leu Lys Glu Asp Tyr Phe Lys
                595                 600                 605

Lys Ile Glu Cys Phe Asp Ser Val Glu Ile Ser Gly Val Glu Asp Arg
610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
                660                 665                 670

Arg Leu Lys Thr Tyr Ala His Leu Phe Asp Asp Lys Val Met Lys Gln
                675                 680                 685

Leu Lys Arg Arg Arg Tyr Thr Gly Trp Gly Arg Leu Ser Arg Lys Leu
                690                 695                 700

Ile Asn Gly Ile Arg Asp Lys Gln Ser Gly Lys Thr Ile Leu Asp Phe
705                 710                 715                 720
```

-continued

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
                755                 760                 765

Pro Ala Ile Lys Lys Gly Ile Leu Gln Thr Val Lys Val Val Asp Glu
770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
                820                 825                 830

Ile Leu Lys Glu His Pro Val Glu Asn Thr Gln Leu Gln Asn Glu Lys
                835                 840                 845

Leu Tyr Leu Tyr Tyr Leu Gln Asn Gly Arg Asp Met Tyr Val Asp Gln
850                 855                 860

Glu Leu Asp Ile Asn Arg Leu Ser Asp Tyr Asp Val Asp His Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
                900                 905                 910

Val Val Lys Lys Met Lys Asn Tyr Trp Arg Gln Leu Leu Asn Ala Lys
                915                 920                 925

Leu Ile Thr Gln Arg Lys Phe Asp Asn Leu Thr Lys Ala Glu Arg Gly
930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
                980                 985                 990

Val Ile Thr Leu Lys Ser Lys Leu Val Ser Asp Phe Arg Lys Asp Phe
                995                 1000                1005

Gln Phe Tyr Lys Val Arg Glu Ile Asn Asn Tyr His His Ala His
    1010                1015                1020

Asp Ala Tyr Leu Asn Ala Val Val Gly Thr Ala Leu Ile Lys Lys
    1025                1030                1035

Tyr Pro Lys Leu Glu Ser Glu Phe Val Tyr Gly Asp Tyr Lys Val
    1040                1045                1050

Tyr Asp Val Arg Lys Met Ile Ala Lys Ser Glu Gln Glu Ile Gly
    1055                1060                1065

Lys Ala Thr Ala Lys Tyr Phe Phe Tyr Ser Asn Ile Met Asn Phe
    1070                1075                1080

Phe Lys Thr Glu Ile Thr Leu Ala Asn Gly Glu Ile Arg Lys Arg
    1085                1090                1095

Pro Leu Ile Glu Thr Asn Gly Glu Thr Gly Glu Ile Val Trp Asp
    1100                1105                1110

Lys Gly Arg Asp Phe Ala Thr Val Arg Lys Val Leu Ser Met Pro
    1115                1120                1125

| | | | | | | | | | |
|---|---|---|---|---|---|---|---|---|---|
| Gln | Val | Asn | Ile | Val | Lys | Lys | Thr | Glu | Val | Gln | Thr | Gly | Gly | Phe |
| 1130 | | | | 1135 | | | | 1140 | |

Gln Val Asn Ile Val Lys Lys Thr Glu Val Gln Thr Gly Gly Phe
     1130                1135               1140

Ser Lys Glu Ser Ile Leu Pro Lys Arg Asn Ser Asp Lys Leu Ile
     1145                1150               1155

Ala Arg Lys Lys Asp Trp Asp Pro Lys Lys Tyr Gly Gly Phe Asp
     1160                1165               1170

Ser Pro Thr Val Ala Tyr Ser Val Leu Val Ala Lys Val Glu
     1175                1180               1185

Lys Gly Lys Ser Lys Lys Leu Lys Ser Val Lys Glu Leu Leu Gly
     1190                1195               1200

Ile Thr Ile Met Glu Arg Ser Ser Phe Glu Lys Asn Pro Ile Asp
     1205                1210               1215

Phe Leu Glu Ala Lys Gly Tyr Lys Glu Val Lys Lys Asp Leu Ile
     1220                1225               1230

Ile Lys Leu Pro Lys Tyr Ser Leu Phe Glu Leu Glu Asn Gly Arg
     1235                1240               1245

Lys Arg Met Leu Ala Ser Ala Gly Glu Leu Gln Lys Gly Asn Glu
     1250                1255               1260

Leu Ala Leu Pro Ser Lys Tyr Val Asn Phe Leu Tyr Leu Ala Ser
     1265                1270               1275

His Tyr Glu Lys Leu Lys Gly Ser Pro Glu Asp Asn Glu Gln Lys
     1280                1285               1290

Gln Leu Phe Val Glu Gln His Lys His Tyr Leu Asp Glu Ile Ile
     1295                1300               1305

Glu Gln Ile Ser Glu Phe Ser Lys Arg Val Ile Leu Ala Asp Ala
     1310                1315               1320

Asn Leu Asp Lys Val Leu Ser Ala Tyr Asn Lys His Arg Asp Lys
     1325                1330               1335

Pro Ile Arg Glu Gln Ala Glu Asn Ile Ile His Leu Phe Thr Leu
     1340                1345               1350

Thr Asn Leu Gly Ala Pro Ala Ala Phe Lys Tyr Phe Asp Thr Thr
     1355                1360               1365

Ile Asp Arg Lys Arg Tyr Thr Ser Thr Lys Glu Val Leu Asp Ala
     1370                1375               1380

Thr Leu Ile His Gln Ser Ile Thr Gly Leu Tyr Glu Thr Arg Ile
     1385                1390               1395

Asp Leu Ser Gln Leu Gly Gly Asp Lys Arg Pro Ala Ala Thr Lys
     1400                1405               1410

Lys Ala Gly Gln Ala Lys Lys Lys Lys
     1415                1420

<210> SEQ ID NO 81
<211> LENGTH: 9289
<212> TYPE: DNA
<213> ORGANISM: Artificial sequence
<220> FEATURE:
<223> OTHER INFORMATION: Synthetic polynucleotide

<400> SEQUENCE: 81
gagggcctat ttcccatgat tccttcatat ttgcatatac gatacaaggc tgttagagag    60
ataattggaa ttaatttgac tgtaaacaca agatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg ggtcttcgag aagacctgtt ttagagctag aaatagcaag ttaaaataag   300

```
gctagtccgt tatcaacttg aaaaagtggc accgagtcgg tgcttttttg ttttagagct      360
agaaatagca agttaaaata aggctagtcc gttttagcg cgtgcgccaa ttctgcagac       420
aaatggctct agaggtaccc gttacataac ttacggtaaa tggcccgcct ggctgaccgc      480
ccaacgaccc ccgcccattg acgtcaatag taacgccaat agggactttc cattgacgtc      540
aatgggtgga gtatttacgg taaactgccc acttggcagt acatcaagtg tatcatatgc      600
caagtacgcc ccctattgac gtcaatgacg gtaaatggcc cgcctggcat tgtgcccagt      660
acatgacctt atgggacttt cctacttggc agtacatcta cgtattagtc atcgctatta      720
ccatggtcga ggtgagcccc acgttctgct tcactctccc catctccccc cctccccac       780 ccccaatttt gtatttattt attttttaat tattttgtgc agcgatgggg gcggggggggg     840 ggggggggcg cgcgccaggc ggggcggggc ggggcgaggg gcgggcggg gcgaggcgga       900 gaggtgcggc ggcagccaat cagagcggcg cgctccgaaa gtttcctttt atggcgaggc      960
ggcggcggcg gcggcccctat aaaaagcgaa gcgcgcggcg ggcgggagtc gctgcgacgc    1020
tgccttcgcc ccgtgccccg ctccgccgcc gcctcgcgcc gcccgccccg gctctgactg     1080
accgcgttac tcccacaggt gagcgggcgg gacggccctt ctcctccggg ctgtaattag     1140
ctgagcaaga ggtaagggtt taagggatgg ttggttggtg gggtattaat gtttaattac     1200
ctggagcacc tgcctgaaat cacttttttt caggttggac cggtgccacc atggactata    1260
aggaccacga cggagactac aaggatcatg atattgatta caaagacgat gacgataaga    1320
tggccccaaa gaagaagcgg aaggtcggta tccacggagt cccagcagcc gacaagaagt    1380
acagcatcgg cctggacatc ggcaccaact ctgtgggctg ggccgtgatc accgacgagt    1440
acaaggtgcc cagcaagaaa ttcaaggtgc tgggcaacac cgaccggcac agcatcaaga    1500
agaacctgat cggagccctg ctgttcgaca gcggcgaaac agccgaggcc accggctga     1560 agagaaccgc cagaagaaga tacaccgacg gaagaaccg atctgctat ctgcaagaga      1620 tcttcagcaa cgagatggcc aaggtggacg acagcttctt ccacagactg gaagagtcct    1680
tcctggtgga agaggataag aagcacgagc ggcaccccat cttcggcaac atcgtggacg    1740
aggtggccta ccacgagaag tacccacca tctaccacct gagaaagaaa ctggtggaca     1800
gcaccgacaa ggccgacctg cggctgatct atctggccct ggcccacatg atcaagttcc    1860
ggggccactt cctgatcgag ggcgacctga accccgacaa cagcgacgtg gacaagctgt    1920
tcatccagct ggtgcagacc tacaaccagc tgttcgagga aaaccccatc aacgccagcg    1980
gcgtggacgc caaggccatc ctgtctgcca gactgagcaa gagcagacgg ctggaaaatc    2040
tgatcgccca gctgcccggc gagaagaaga tggcctgtt cggaaacctg attgccctga    2100
gcctgggcct gaccccaac ttcaagagca acttcgacct ggccgaggat gccaaactgc     2160
agctgagcaa ggacacctac gacgacgacc tggacaacct gctggcccag atcggcgacc    2220
agtacgccga cctgtttctg gccgccaaga acctgtccga cgccatcctg ctgagcgaca    2280
tcctgagagt gaacaccgag atcaccaagg ccccctgag cgcctctatg atcaagagat    2340
acgacgagca ccaccaggac ctgacctgc tgaaagctct cgtgcggcag cagctgcctg     2400
agaagtacaa agagattttc ttcgaccaga gcaagaacgg ctacgccggc tacattgacg    2460
gcggagccag ccaggaagag ttctacaagt tcatcaagcc catcctggaa aagatggacg    2520
gcaccgagga actgctcgtg aagctgaaca gagaggacct gctgcggaag cagcggacct    2580
tcgacaacgg cagcatcccc caccagatcc acctgggaga gctgcacgcc attctgcggc    2640
```

```
ggcaggaaga ttttttaccca ttcctgaagg acaaccggga aaagatcgag aagatcctga   2700
ccttccgcat cccctactac gtgggccctc tggccagggg aaacagcaga ttcgcctgga   2760
tgaccagaaa gagcgaggaa accatcaccc cctggaactt cgaggaagtg gtggacaagg   2820
gcgcttccgc ccagagcttc atcgagcgga tgaccaactt cgataagaac ctgcccaacg   2880
agaaggtgct gcccaagcac agcctgctgt acgagtactt caccgtgtat aacgagctga   2940
ccaaagtgaa atacgtgacc gagggaatga gaaagcccgc cttcctgagc ggcgagcaga   3000
aaaaggccat cgtggacctg ctgttcaaga ccaaccggaa agtgaccgtg aagcagctga   3060
aagaggacta cttcaagaaa atcgagtgct tcgactccgt ggaaatctcc ggcgtggaag   3120
atcggttcaa cgcctccctg ggcacatacc acgatctgct gaaaattatc aaggacaagg   3180
acttcctgga caatgaggaa aacgaggaca ttctggaaga tatcgtgctg accctgacac   3240
tgtttgagga cagagagatg atcgaggaac ggctgaaaac ctatgcccac ctgttcgacg   3300
acaaagtgat gaagcagctg aagcggcgga tataccggct ggggcagg ctgagccgga   3360 agctgatcaa cggcatccgg acaagcagt ccggcaagac aatcctggat ttcctgaagt   3420
ccgacggctt cgccaacaga aacttcatgc agctgatcca cgacgacagc ctgacctttta   3480 aagaggacat ccagaaagcc caggtgtccg gccagggcga tagcctgcac gagcacattg   3540
ccaatctggc cggcagcccc gccattaaga agggcatcct gcagacagtg aaggtggtgg   3600
acgagctcgt gaaagtgatg ggccggcaca gcccgagaa catcgtgatc gaaatggcca   3660
gagagaacca gaccacccag aagggacaga gaacagccg cgagagaatg aagcggatcg   3720
aagagggcat caaagagctg ggcagccaga tcctgaaaga acaccccgtg aaaacacccc   3780
agctgcagaa cgagaagctg tacctgtact acctgcagaa tgggcgggat atgtacgtgg   3840
accaggaact ggacatcaac cggctgtccg actacgatgt ggaccatatc gtgcctcaga   3900
gctttctgaa ggacgactcc atcgacaaca aggtgctgac cagaagcgac aagaaccggg   3960
gcaagagcga caacgtgccc tccgaagagg tcgtgaagaa gatgaagaac tactggcggc   4020
agctgctgaa cgccaagctg attacccaga gaaagttcga caatctgacc aaggccgaga   4080
gaggcggcct gagcgaactg gataaggccg gcttcatcaa gagacagctg gtggaaaccc   4140
ggcagatcac aaagcacgtg gcacagatcc tggactcccg gatgaacact aagtacgacg   4200
agaatgacaa gctgatccgg gaagtgaaag tgatcaccct gaagtccaag ctggtgtccg   4260
atttccggaa ggatttccag ttttacaaag tgcgcgagat caacaactac caccacgccc   4320
acgacgccta cctgaacgcc gtcgtgggaa ccgccctgat caaaaagtac cctaagctgg   4380
aaagcgagtt cgtgtacggc gactacaagg tgtacgacgt gcggaagatg atcgccaaga   4440
gcgagcagga aatcggcaag gctaccgcca agtacttctt ctacagcaac atcatgaact   4500
ttttcaagac cgagattacc ctggccaacg gcgagatccg gaagcggcct ctgatcgaga   4560
caaacggcga aaccggggag atcgtgtggg ataaggcg ggattttgcc accgtgcgga   4620
aagtgctgag catgccccaa gtgaatatcg tgaaaaagac cgaggtgcag acaggcggct   4680
tcagcaaaga gtctatcctg cccaagagga acagcgataa gctgatcgcc agaaagaagg   4740
actgggaccc taagaagtac ggcggcttcg acagccccac cgtggcctat tctgtgctgg   4800
tggtggccaa agtggaaaag gcaagtcca agaaactgaa gagtgtgaaa gagctgctgg   4860
ggatcaccat catggaaaga agcagcttcg agaagaatcc catcgacttt ctggaagcca   4920
agggctacaa agaagtgaaa aaggacctga tcatcaagct gcctaagtac tccctgttcg   4980
agctggaaaa cggccggaag agaatgctgg cctctgccgg cgaactgcag aagggaaacg   5040
```

```
aactggccct gccctccaaa tatgtgaact tcctgtacct ggccagccac tatgagaagc   5100
tgaagggctc ccccgaggat aatgagcaga acagctgtt tgtggaacag cacaagcact   5160
acctggacga gatcatcgag cagatcagcg agttctccaa gagagtgatc ctggccgacg   5220
ctaatctgga caaagtgctg tccgcctaca caagcaccg gataagccc atcagagagc   5280 aggccgagaa tatcatccac ctgtttaccc tgaccaatct gggagcccct gccgccttca   5340
agtactttga caccaccatc gaccggaaga ggtacaccag caccaaagag gtgctggacg   5400
ccaccctgat ccaccagagc atcaccggcc tgtacgagac acggatcgac ctgtctcagc   5460
tgggaggcga caaaaggccg gcggccacga aaaaggccgg ccaggcaaaa aagaaaaagg   5520
aattcggcag tggagagggc agaggaagtc tgctaacatg cggtgacgtc gaggagaatc   5580
ctggcccagt gagcaagggc gaggagctgt tcaccgggt ggtgcccatc ctggtcgagc   5640
tggacggcga cgtaaacggc cacaagttca gcgtgtccgg cgagggcgag ggcgatgcca   5700
cctacggcaa gctgaccctg aagttcatct gcaccaccgg caagctgccc gtgccctggc   5760
ccaccctcgt gaccaccctg acctacggcg tgcagtgctt cagccgctac cccgaccaca   5820
tgaagcagca cgacttcttc aagtccgcca tgcccgaagg ctacgtccag gagcgcacca   5880
tcttcttcaa ggacgacggc aactacaaga cccgcgccga ggtgaagttc gagggcgaca   5940
ccctggtgaa ccgcatcgag ctgaagggca tcgacttcaa ggaggacggc aacatcctgg   6000
ggcacaagct ggagtacaac tacaacagcc acaacgtcta tatcatggcc gacaagcaga   6060
agaacggcat caaggtgaac ttcaagatcc gccacaacat cgaggacggc agcgtgcagc   6120
tcgccgacca ctaccagcag aacacccca tcggcgacgg ccccgtgctg ctgcccgaca   6180
accactacct gagcacccag tccgccctga gcaaagaccc caacgagaag cgcgatcaca   6240
tggtcctgct ggagttcgtg accgccgccg ggatcactct cggcatggac gagctgtaca   6300
aggaattcta actagagctc gctgatcagc ctcgactgtg ccttctagtt gccagccatc   6360
tgttgtttgc ccctcccccg tgccttcctt gaccctggaa ggtgccactc ccactgtcct   6420
ttcctaataa aatgaggaaa ttgcatcgca ttgtctgagt aggtgtcatt ctattctggg   6480
gggtggggtg gggcaggaca gcaaggggga ggattgggaa gagaatagca ggcatgctgg   6540
ggagcggccg caggaacccc tagtgatgga gttggccact ccctctctgc gcgctcgctc   6600
gctcactgag gccgggcgac caaggtcgc ccgacgcccg gctttgccc gggcggcctc   6660 agtgagcgag cgagcgcgca gctgcctgca ggggcgcctg atgcggtatt ttctccttac   6720
gcatctgtgc ggtatttcac accgcatacg tcaaagcaac catagtacgc gccctgtagc   6780
ggcgcattaa gcgcggcggg tgtggtggtt acgcgcagcg tgaccgctac acttgccagc   6840
gccctagcgc ccgctccttt cgctttcttc ccttcctttc tcgccacgtt cgccggcttt   6900
ccccgtcaag ctctaaatcg ggggctccct ttagggttcc gatttagtgc tttacggcac   6960
ctcgacccca aaaaacttga tttgggtgat ggttcacgta gtgggccatc gccctgatag   7020 acggttttc gccctttgac gttggagtcc acgttcttta atagtggact cttgttccaa   7080
actggaacaa cactcaaccc tatctcgggc tattcttttg atttataagg gattttgccg   7140
atttcggcct attggttaaa aaatgagctg atttaacaaa aatttaacgc gaattttaac   7200
aaaatattaa cgtttacaat tttatggtgc actctcagta caatctgctc tgatgccgca   7260
tagttaagcc agccccgaca cccgccaaca cccgctgacg cgccctgacg gcttgtctg   7320 ctcccggcat ccgcttacag acaagctgtg accgtctccg ggagctgcat gtgtcagagg   7380
```

```
ttttcaccgt catcaccgaa acgcgcgaga cgaaagggcc tcgtgatacg cctattttta    7440
taggttaatg tcatgataat aatggtttct tagacgtcag gtggcacttt tcggggaaat    7500
gtgcgcggaa cccctatttg tttattttc taaatacatt caaatatgta tccgctcatg    7560
agacaataac cctgataaat gcttcaataa tattgaaaaa ggaagagtat gagtattcaa    7620
catttccgtg tcgcccttat tcccttttt gcggcatttt gccttcctgt ttttgctcac    7680
ccagaaacgc tggtgaaagt aaaagatgct gaagatcagt tgggtgcacg agtgggttac    7740
atcgaactgg atctcaacag cggtaagatc cttgagagtt ttcgccccga agaacgtttt    7800
ccaatgatga gcactttaa agttctgcta tgtggcgcgg tattatcccg tattgacgcc    7860
gggcaagagc aactcggtcg ccgcatacac tattctcaga atgacttggt tgagtactca    7920
ccagtcacag aaaagcatct tacgatggc atgacagtaa agaattatg cagtgctgcc    7980
ataaccatga gtgataacac tgcggccaac ttacttctga caacgatcgg aggaccgaag    8040
gagctaaccg cttttttgca acatgggg gatcatgtaa ctcgccttga tcgttgggaa    8100
ccggagctga atgaagccat accaaacgac gagcgtgaca ccacgatgcc tgtagcaatg    8160
gcaacaacgt tgcgcaaact attaactggc gaactactta ctctagcttc ccggcaacaa    8220
ttaatagact ggatggaggc ggataaagtt gcaggaccac ttctgcgctc ggcccttccg    8280
gctggctggt ttattgctga taaatctgga gccggtgagc gtggaagccg cggtatcatt    8340
gcagcactgg ggccagatgg taagccctcc cgtatcgtag ttatctacac gacggggagt    8400
caggcaacta tggatgaacg aaatagacag atcgctgaga taggtgcctc actgattaag    8460
cattggtaac tgtcagacca gtttactca tatatacttt agattgattt aaaacttcat    8520
ttttaattta aaaggatcta ggtgaagatc ctttttgata atctcatgac caaaatccct    8580
taacgtgagt tttcgttcca ctgagcgtca gaccccgtag aaaagatcaa aggatcttct    8640
tgagatcctt ttttctgcg cgtaatctgc tgcttgcaaa caaaaaaacc accgctacca    8700
gcggtggttt gtttgccgga tcaagagcta ccaactcttt ttccgaaggt aactggcttc    8760
agcagagcgc agataccaaa tactgtcctt ctagtgtagc cgtagttagg ccaccacttc    8820
aagaactctg tagcaccgcc tacatacctc gctctgctaa tcctgttacc agtggctgct    8880
gccagtggcg ataagtcgtg tcttaccggg ttggactcaa gacgatagtt accggataag    8940
gcgcagcggt cgggctgaac ggggggttcg tgcacacagc ccagcttgga gcgaacgacc    9000
tacaccgaac tgagatacct acagcgtgag ctatgagaaa gcgccacgct tcccgaaggg    9060
agaaaggcgg acaggtatcc ggtaagcggc agggtcggaa caggagagcg cacgagggag    9120
cttccagggg gaaacgcctg gtatctttat agtcctgtcg ggtttcgcca cctctgactt    9180
gagcgtcgat ttttgtgatg ctcgtcaggg gggcggagcc tatggaaaaa cgccagcaac    9240
gcggcctttt tacggttcct ggccttttgc tggccttttg ctcacatgt                9289

<210> SEQ ID NO 82
<211> LENGTH: 360
<212> TYPE: DNA
<213> ORGANISM: Homosapiens

<400> SEQUENCE: 82
taggctttgt cttacagtgt tattatttat gagtaaaact aattggttgt cctgcatact      60
ttaattatga tgtaatacag gttctgggtt gacaaatatc aagacggagg agatctctga     120
agtgaagatg gatgcagaat tccgacatga ctcaggatat gaagttcatc atcaaaaatt     180
ggtacgtaaa ataatttacc tctttccact actgtttgtc ttgccaaatg acctattaac     240
```

```
tctggttcat cctgtgctag aaatcaaatt aaggaaaaga taaaaataca atgcttgcct      300
ataggattac catgaaaaca tgaagaaaat aaataggcta ggctgagcgc agtggctcaa      360
```

<210> SEQ ID NO 83
<211> LENGTH: 360
<212> TYPE: DNA
<213> ORGANISM: Homosapiens

<400> SEQUENCE: 83

```
taggctttgt cttacagtgt tattatttat gagtaaaact aattggttgt cctgcatact       60
ttaattatga tgtaatacag gttctgggtt gacaaatatc aagacggagg agatctctga      120
agtgaagatg gatacggagt ttaggcacga ttcaggatat gaagttcatc atcaaaaatt      180
ggtacgtaaa ataatttacc tctttccact agtgtttgtc ttgccaaatg acctattaac      240
tctggttcat cctgtgctag aaatcaaatt aaggaaaaga taaaaataca atgcttgcct      300
ataggattac catgaaaaca tgaagaaaat aaataggcta ggctgagcgc agtggctcaa      360
```

<210> SEQ ID NO 84
<211> LENGTH: 7
<212> TYPE: PRT
<213> ORGANISM: Artificial sequence
<220> FEATURE:
<223> OTHER INFORMATION: Synthetic peptide

<400> SEQUENCE: 84

Pro Lys Lys Lys Arg Lys Val
1               5

<210> SEQ ID NO 85
<211> LENGTH: 16
<212> TYPE: PRT
<213> ORGANISM: Artificial sequence
<220> FEATURE:
<223> OTHER INFORMATION: Synthetic peptide

<400> SEQUENCE: 85

Lys Arg Pro Ala Ala Thr Lys Lys Ala Gly Gln Ala Lys Lys Lys Lys
1               5                   10                  15

<210> SEQ ID NO 86
<211> LENGTH: 11
<212> TYPE: PRT
<213> ORGANISM: Artificial sequence
<220> FEATURE:
<223> OTHER INFORMATION: Synthetic peptide

<400> SEQUENCE: 86

Ser Pro Lys Lys Lys Arg Lys Val Glu Ala Ser
1               5                   10

<210> SEQ ID NO 87
<211> LENGTH: 6
<212> TYPE: PRT
<213> ORGANISM: Artificial sequence
<220> FEATURE:
<223> OTHER INFORMATION: Synthetic peptide

<400> SEQUENCE: 87

Lys Lys Lys Arg Lys Val
1               5

<210> SEQ ID NO 88

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 88

Ser Pro Lys Lys Lys Arg Lys Val Glu Ala Ser Pro Lys Lys Lys Arg
1               5                   10                  15

Lys Val

<210> SEQ ID NO 89
<211> LENGTH: 5
<212> TYPE: PRT
<213> ORGANISM: Artificial sequence
<220> FEATURE:
<223> OTHER INFORMATION: Synthetic peptide

<400> SEQUENCE: 89

Lys Lys Lys Arg Lys
1               5

<210> SEQ ID NO 90
<211> LENGTH: 11
<212> TYPE: PRT
<213> ORGANISM: Artificial sequence
<220> FEATURE:
<223> OTHER INFORMATION: Synthetic peptide

<400> SEQUENCE: 90

Tyr Gly Arg Lys Lys Arg Arg Gln Arg Arg
1               5                   10

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Arg Arg Gln Arg Arg Thr Ser Lys Leu Met Lys Arg
1               5                   10

<210> SEQ ID NO 92
<211> LENGTH: 27
<212> TYPE: PRT
<213> ORGANISM: Artificial sequence
<220> FEATURE:
<223> OTHER INFORMATION: Synthetic peptide

<400> SEQUENCE: 92

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 93
<211> LENGTH: 33
<212> TYPE: PRT
<213> ORGANISM: Artificial sequence
<220> FEATURE:
<223> OTHER INFORMATION: Synthetic peptide

<400> SEQUENCE: 93

Lys Ala Leu Ala Trp Glu Ala Lys Leu Ala Lys Ala Leu Ala Lys Ala
```

```
                1               5                  10                 15
Leu Ala Lys His Leu Ala Lys Ala Leu Ala Lys Ala Leu Lys Cys Glu
                20                 25                 30
Ala

<210> SEQ ID NO 94
<211> LENGTH: 16
<212> TYPE: PRT
<213> ORGANISM: Artificial sequence
<220> FEATURE:
<223> OTHER INFORMATION: Synthetic peptide

<400> SEQUENCE: 94

Arg Gln Ile Lys Ile Trp Phe Gln Asn Arg Arg Met Lys Trp Lys Lys
1               5                   10                  15

<210> SEQ ID NO 95
<211> LENGTH: 8
<212> TYPE: PRT
<213> ORGANISM: Artificial sequence
<220> FEATURE:
<223> OTHER INFORMATION: Synthetic peptide

<400> SEQUENCE: 95

Lys Lys Arg Arg Gln Arg Arg Arg
1               5

<210> SEQ ID NO 96
<211> LENGTH: 9
<212> TYPE: PRT
<213> ORGANISM: Artificial sequence
<220> FEATURE:
<223> OTHER INFORMATION: Synthetic peptide

<400> SEQUENCE: 96

Arg Lys Lys Arg Arg Gln Arg Arg Arg
1               5

<210> SEQ ID NO 97
<211> LENGTH: 14
<212> TYPE: PRT
<213> ORGANISM: Artificial sequence
<220> FEATURE:
<223> OTHER INFORMATION: Synthetic peptide

<400> SEQUENCE: 97

Ser Gly Tyr Gly Arg Lys Lys Arg Arg Gln Arg Arg Arg Cys
1               5                   10

<210> SEQ ID NO 98
<211> LENGTH: 21
<212> TYPE: PRT
<213> ORGANISM: Artificial sequence
<220> FEATURE:
<223> OTHER INFORMATION: Synthetic peptide

<400> SEQUENCE: 98

Lys Glu Thr Trp Trp Glu Thr Trp Trp Thr Glu Trp Ser Gln Pro Lys
1               5                   10                  15

Lys Lys Arg Lys Val
                20

<210> SEQ ID NO 99
<211> LENGTH: 189
<212> TYPE: PRT
```

```
<213> ORGANISM: Artificial sequence
<220> FEATURE:
<223> OTHER INFORMATION: Synthetic peptide

<400> SEQUENCE: 99
```

Val Gly Ser Ser Leu Ser Cys Ile Asn Leu Asp Trp Asp Val Ile Arg
1               5                   10                  15

Asp Lys Thr Lys Thr Lys Ile Glu Ser Leu Lys Glu His Gly Pro Ile
            20                  25                  30

Lys Asn Lys Met Ser Glu Ser Pro Asn Lys Thr Val Ser Glu Glu Lys
        35                  40                  45

Ala Lys Gln Tyr Leu Glu Glu Phe His Gln Thr Ala Leu Glu His Pro
    50                  55                  60

Glu Leu Ser Glu Leu Lys Thr Val Thr Gly Thr Asn Pro Val Phe Ala
65                  70                  75                  80

Gly Ala Asn Tyr Ala Ala Trp Ala Val Asn Val Ala Gln Val Ile Asp
                85                  90                  95

Ser Glu Thr Ala Asp Asn Leu Glu Lys Thr Thr Ala Ala Leu Ser Ile
            100                 105                 110

Leu Pro Gly Ile Gly Ser Val Met Gly Ile Ala Asp Gly Ala Val His
        115                 120                 125

His Asn Thr Glu Glu Ile Val Ala Gln Ser Ile Ala Leu Ser Ser Leu
    130                 135                 140

Met Val Ala Gln Ala Ile Pro Leu Val Gly Glu Leu Val Asp Ile Gly
145                 150                 155                 160

Phe Ala Ala Tyr Asn Phe Val Glu Ser Ile Ile Asn Leu Phe Gln Val
                165                 170                 175

Val His Asn Ser Tyr Asn Arg Pro Ala Tyr Ser Pro Gly
            180                 185

```
<210> SEQ ID NO 100
<211> LENGTH: 30
<212> TYPE: PRT
<213> ORGANISM: Artificial sequence
<220> FEATURE:
<223> OTHER INFORMATION: Synthetic peptide

<400> SEQUENCE: 100
```

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

```
<210> SEQ ID NO 101
<211> LENGTH: 115
<212> TYPE: PRT
<213> ORGANISM: Artificial sequence
<220> FEATURE:
<223> OTHER INFORMATION: Synthetic peptide

<400> SEQUENCE: 101
```

Val Leu Ala Gly Asn Pro Ala Lys His Asp Leu Asp Ile Lys Pro Thr
1               5                   10                  15

Val Ile Ser His Arg Leu His Phe Pro Glu Gly Gly Ser Leu Ala Ala
            20                  25                  30

Leu Thr Ala His Gln Ala Cys His Leu Pro Leu Glu Thr Phe Thr Arg
            35                  40                  45

His Arg Gln Pro Arg Gly Trp Glu Gln Leu Glu Gln Cys Gly Tyr Pro
        50                  55                  60

Val Gln Arg Leu Val Ala Leu Tyr Leu Ala Ala Arg Leu Ser Trp Asn
65                  70                  75                  80

Gln Val Asp Gln Val Ile Arg Asn Ala Leu Ala Ser Pro Gly Ser Gly
                85                  90                  95

Gly Asp Leu Gly Glu Ala Ile Arg Glu Gln Pro Glu Gln Ala Arg Leu
            100                 105                 110

Ala Leu Thr
        115

<210> SEQ ID NO 102
<211> LENGTH: 24
<212> TYPE: PRT
<213> ORGANISM: Artificial sequence
<220> FEATURE:
<223> OTHER INFORMATION: Synthetic peptide

<400> SEQUENCE: 102

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 103
<211> LENGTH: 26
<212> TYPE: PRT
<213> ORGANISM: Artificial sequence
<220> FEATURE:
<223> OTHER INFORMATION: Synthetic peptide

<400> SEQUENCE: 103

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 104
<211> LENGTH: 18
<212> TYPE: PRT
<213> ORGANISM: Artificial sequence
<220> FEATURE:
<223> OTHER INFORMATION: Synthetic peptide

<400> SEQUENCE: 104

Lys Trp Lys Leu Phe Lys Lys Ile Gly Ala Val Leu Lys Val Leu Thr
1               5                   10                  15

Thr Gly

<210> SEQ ID NO 105
<211> LENGTH: 24
<212> TYPE: PRT
<213> ORGANISM: Artificial sequence
<220> FEATURE:
<223> OTHER INFORMATION: Synthetic peptide

<400> SEQUENCE: 105

Leu Leu Gly Arg Arg Gly Trp Glu Val Leu Lys Tyr Trp Trp Asn Leu
1               5                   10                  15

Leu Gln Tyr Trp Ser Gln Glu Leu
            20

<210> SEQ ID NO 106
<211> LENGTH: 23

```
<212> TYPE: PRT
<213> ORGANISM: Artificial sequence
<220> FEATURE:
<223> OTHER INFORMATION: Synthetic peptide

<400> SEQUENCE: 106

Gly Leu Phe His Ala Ile Ala His Phe Ile His Gly Gly Trp His Gly
1               5                   10                  15

Leu Ile His Gly Trp Tyr Gly
            20

<210> SEQ ID NO 107
<211> LENGTH: 23
<212> TYPE: PRT
<213> ORGANISM: Artificial sequence
<220> FEATURE:
<223> OTHER INFORMATION: Synthetic peptide

<400> SEQUENCE: 107

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 108
<211> LENGTH: 23
<212> TYPE: PRT
<213> ORGANISM: Artificial sequence
<220> FEATURE:
<223> OTHER INFORMATION: Synthetic peptide

<400> SEQUENCE: 108

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 109
<211> LENGTH: 189
<212> TYPE: PRT
<213> ORGANISM: Artificial sequence
<220> FEATURE:
<223> OTHER INFORMATION: Synthetic peptide

<400> SEQUENCE: 109

Val Gly Ser Ser Leu Ser Cys Ile Asn Leu Asp Trp Asp Val Ile Arg
1               5                   10                  15

Asp Lys Thr Lys Thr Lys Ile Glu Ser Leu Lys Glu His Gly Pro Ile
            20                  25                  30

Lys Asn Lys Met Ser Glu Ser Pro Asn Lys Thr Val Ser Glu Glu Lys
        35                  40                  45

Ala Lys Gln Tyr Leu Glu Glu Phe His Gln Thr Ala Leu Glu His Pro
    50                  55                  60

Glu Leu Ser Glu Leu Lys Thr Val Thr Gly Thr Asn Pro Val Phe Ala
65                  70                  75                  80

Gly Ala Asn Tyr Ala Ala Trp Ala Val Asn Val Ala Gln Val Ile Asp
                85                  90                  95

Ser Glu Thr Ala Asp Asn Leu Glu Lys Thr Thr Ala Ala Leu Ser Ile
            100                 105                 110

Leu Pro Gly Ile Gly Ser Val Met Gly Ile Ala Asp Gly Ala Val His
        115                 120                 125
```

-continued

His Asn Thr Glu Glu Ile Val Ala Gln Ser Ile Ala Leu Ser Ser Leu
            130                 135                 140

Met Val Ala Gln Ala Ile Pro Leu Val Gly Glu Leu Val Asp Ile Gly
145                 150                 155                 160

Phe Ala Ala Tyr Asn Phe Val Glu Ser Ile Ile Asn Leu Phe Gln Val
                165                 170                 175

Val His Asn Ser Tyr Asn Arg Pro Ala Tyr Ser Pro Gly
            180                 185

<210> SEQ ID NO 110
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(24)
<223> OTHER INFORMATION: n=A, C, G or T

<400> SEQUENCE: 110
caccgnnnnn nnnnnnnnnn nnnn                                          24

<210> SEQ ID NO 111
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(20)
<223> OTHER INFORMATION: n= A, C, G or T

<400> SEQUENCE: 111
cnnnnnnnnn nnnnnnnnnn caaa                                          24

<210> SEQ ID NO 112
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 112
atagcagaat tccgacatga ctcaggttca gcagacgaac caattaca              48

<210> SEQ ID NO 113
<211> LENGTH: 44
<212> TYPE: DNA
<213> ORGANISM: Artificial sequence
<220> FEATURE:
<223> OTHER INFORMATION: Syntheticoligonucleotide

<400> SEQUENCE: 113
cctgagtcat gtcggaattc tgcacgaact tgctgccttt gtag                    44

<210> SEQ ID NO 114
<211> LENGTH: 1391
<212> TYPE: PRT
<213> ORGANISM: Artificial sequence
<220> FEATURE:
<223> OTHER INFORMATION: Synthetic peptide

<400> SEQUENCE: 114

Gly Ile His Gly Val Pro Ala Ala Asp Lys Lys Tyr Ser Ile Gly Leu

-continued

```
1               5                   10                  15
Asp Ile Gly Thr Asn Ser Val Gly Trp Ala Ile Thr Asp Glu Tyr
                20                  25                  30
Lys Val Pro Ser Lys Lys Phe Lys Val Leu Gly Asn Thr Asp Arg His
        35                  40                  45
Ser Ile Lys Lys Asn Leu Ile Gly Ala Leu Leu Phe Asp Ser Gly Glu
        50                  55                  60
Thr Ala Glu Ala Thr Arg Leu Lys Arg Thr Ala Arg Arg Arg Tyr Thr
65                  70                  75                  80
Arg Arg Lys Asn Arg Ile Cys Tyr Leu Gln Glu Ile Phe Ser Asn Glu
                85                  90                  95
Met Ala Lys Val Asp Asp Ser Phe Phe His Arg Leu Glu Glu Ser Phe
                100                 105                 110
Leu Val Glu Glu Asp Lys Lys His Glu Arg His Pro Ile Phe Gly Asn
                115                 120                 125
Ile Val Asp Glu Val Ala Tyr His Glu Lys Tyr Pro Thr Ile Tyr His
                130                 135                 140
Leu Arg Lys Lys Leu Val Asp Ser Thr Asp Lys Ala Asp Leu Arg Leu
145                 150                 155                 160
Ile Tyr Leu Ala Leu Ala His Met Ile Lys Phe Arg Gly His Phe Leu
                165                 170                 175
Ile Glu Gly Asp Leu Asn Pro Asp Asn Ser Asp Val Asp Lys Leu Phe
                180                 185                 190
Ile Gln Leu Val Gln Thr Tyr Asn Gln Leu Phe Glu Glu Asn Pro Ile
                195                 200                 205
Asn Ala Ser Gly Val Asp Ala Lys Ala Ile Leu Ser Ala Arg Leu Ser
                210                 215                 220
Lys Ser Arg Arg Leu Glu Asn Leu Ile Ala Gln Leu Pro Gly Glu Lys
225                 230                 235                 240
Lys Asn Gly Leu Phe Gly Asn Leu Ile Ala Leu Ser Leu Gly Leu Thr
                245                 250                 255
Pro Asn Phe Lys Ser Asn Phe Asp Leu Ala Glu Asp Ala Lys Leu Gln
                260                 265                 270
Leu Ser Lys Asp Thr Tyr Asp Asp Leu Asp Asn Leu Leu Ala Gln
                275                 280                 285
Ile Gly Asp Gln Tyr Ala Asp Leu Phe Leu Ala Ala Lys Asn Leu Ser
                290                 295                 300
Asp Ala Ile Leu Leu Ser Asp Ile Leu Arg Val Asn Thr Glu Ile Thr
305                 310                 315                 320
Lys Ala Pro Leu Ser Ala Ser Met Ile Lys Arg Tyr Asp Glu His His
                325                 330                 335
Gln Asp Leu Thr Leu Leu Lys Ala Leu Val Arg Gln Gln Leu Pro Glu
                340                 345                 350
Lys Tyr Lys Glu Ile Phe Phe Asp Gln Ser Lys Asn Gly Tyr Ala Gly
                355                 360                 365
Tyr Ile Asp Gly Gly Ala Ser Gln Glu Glu Phe Tyr Lys Phe Ile Lys
                370                 375                 380
Pro Ile Leu Glu Lys Met Asp Gly Thr Glu Glu Leu Leu Val Lys Leu
385                 390                 395                 400
Asn Arg Glu Asp Leu Leu Arg Lys Gln Arg Thr Phe Asp Asn Gly Ser
                405                 410                 415
Ile Pro His Gln Ile His Leu Gly Glu Leu His Ala Ile Leu Arg Arg
                420                 425                 430
```

```
Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
        450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
                500                 505                 510

Lys Val Leu Pro Lys His Ser Leu Leu Tyr Glu Tyr Phe Thr Val Tyr
            515                 520                 525

Asn Glu Leu Thr Lys Val Lys Tyr Val Thr Glu Gly Met Arg Lys Pro
            530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
                580                 585                 590

Arg Phe Asn Ala Ser Leu Gly Thr Tyr His Asp Leu Leu Lys Ile Ile
            595                 600                 605

Lys Asp Lys Asp Phe Leu Asp Asn Glu Glu Asn Glu Asp Ile Leu Glu
            610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
                660                 665                 670

Leu Ile Asn Gly Ile Arg Asp Lys Gln Ser Gly Lys Thr Ile Leu Asp
            675                 680                 685

Phe Leu Lys Ser Asp Gly Phe Ala Asn Arg Asn Phe Met Gln Leu Ile
            690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
                740                 745                 750

Glu Leu Val Lys Val Met Gly Arg His Lys Pro Glu Asn Ile Val Ile
            755                 760                 765

Glu Met Ala Arg Glu Asn Gln Thr Thr Gln Lys Gly Gln Lys Asn Ser
            770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
                820                 825                 830

Gln Glu Leu Asp Ile Asn Arg Leu Ser Asp Tyr Asp Val Asp His Ile
            835                 840                 845
```

Val Pro Gln Ser Phe Leu Lys Asp Asp Ser Ile Asp Asn Lys Val Leu
850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
            885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
            915                 920                 925

Val Glu Thr Arg Gln Ile Thr Lys His Val Ala Gln Ile Leu Asp Ser
930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
            965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
            995                 1000                1005

Pro Lys Leu Glu Ser Glu Phe Val Tyr Gly Asp Tyr Lys Val Tyr
    1010            1015            1020

Asp Val Arg Lys Met Ile Ala Lys Ser Glu Gln Glu Ile Gly Lys
    1025            1030            1035

Ala Thr Ala Lys Tyr Phe Phe Tyr Ser Asn Ile Met Asn Phe Phe
    1040            1045            1050

Lys Thr Glu Ile Thr Leu Ala Asn Gly Glu Ile Arg Lys Arg Pro
    1055            1060            1065

Leu Ile Glu Thr Asn Gly Glu Thr Gly Glu Ile Val Trp Asp Lys
    1070            1075            1080

Gly Arg Asp Phe Ala Thr Val Arg Lys Val Leu Ser Met Pro Gln
    1085            1090            1095

Val Asn Ile Val Lys Lys Thr Glu Val Gln Thr Gly Gly Phe Ser
    1100            1105            1110

Lys Glu Ser Ile Leu Pro Lys Arg Asn Ser Asp Lys Leu Ile Ala
    1115            1120            1125

Arg Lys Lys Asp Trp Asp Pro Lys Lys Tyr Gly Gly Phe Asp Ser
    1130            1135            1140

Pro Thr Val Ala Tyr Ser Val Leu Val Val Ala Lys Val Glu Lys
    1145            1150            1155

Gly Lys Ser Lys Lys Leu Lys Ser Val Lys Glu Leu Leu Gly Ile
    1160            1165            1170

Thr Ile Met Glu Arg Ser Ser Phe Glu Lys Asn Pro Ile Asp Phe
    1175            1180            1185

Leu Glu Ala Lys Gly Tyr Lys Glu Val Lys Lys Asp Leu Ile Ile
    1190            1195            1200

Lys Leu Pro Lys Tyr Ser Leu Phe Glu Leu Glu Asn Gly Arg Lys
    1205            1210            1215

Arg Met Leu Ala Ser Ala Gly Glu Leu Gln Lys Gly Asn Glu Leu
    1220            1225            1230

Ala Leu Pro Ser Lys Tyr Val Asn Phe Leu Tyr Leu Ala Ser His
    1235            1240            1245

Tyr Glu Lys Leu Lys Gly Ser Pro Glu Asp Asn Glu Gln Lys Gln

-continued

```
               1250               1255               1260

Leu Phe Val Glu Gln His Lys His Tyr Leu Asp Glu Ile Ile Glu
    1265                1270                1275

Gln Ile Ser Glu Phe Ser Lys Arg Val Ile Leu Ala Asp Ala Asn
    1280                1285                1290

Leu Asp Lys Val Leu Ser Ala Tyr Asn Lys His Arg Asp Lys Pro
    1295                1300                1305

Ile Arg Glu Gln Ala Glu Asn Ile Ile His Leu Phe Thr Leu Thr
    1310                1315                1320

Asn Leu Gly Ala Pro Ala Ala Phe Lys Tyr Phe Asp Thr Thr Ile
    1325                1330                1335

Asp Arg Lys Arg Tyr Thr Ser Thr Lys Glu Val Leu Asp Ala Thr
    1340                1345                1350

Leu Ile His Gln Ser Ile Thr Gly Leu Tyr Glu Thr Arg Ile Asp
    1355                1360                1365

Leu Ser Gln Leu Gly Gly Asp Lys Arg Pro Ala Ala Thr Lys Lys
    1370                1375                1380

Ala Gly Gln Ala Lys Lys Lys Lys
    1385                1390

<210> SEQ ID NO 115
<211> LENGTH: 19
<212> TYPE: RNA
<213> ORGANISM: Artificial Sequence
<220> FEATURE:
<223> OTHER INFORMATION: Synthetetic oligonucleotide

<400> SEQUENCE: 115
auuuaugagu aaaacuaau                                                    19

<210> SEQ ID NO 116
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 116
uuuaauuaug auguaauac                                                    19

<210> SEQ ID NO 117
<211> LENGTH: 19
<212> TYPE: RNA
<213> ORGANISM: Artificial sequence
<220> FEATURE:
<223> OTHER INFORMATION: Synthetitic oligonucleotide

<400> SEQUENCE: 117
uaugauguaa uacagguuc                                                    19

<210> SEQ ID NO 118
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 118
augauguaau acagguucu                                                    19

<210> SEQ ID NO 119
```

```
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 119
ggguugacaa auaucaaga                                                   19

<210> SEQ ID NO 120
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 120
uugacaaaua ucaagacgg                                                   19

<210> SEQ ID NO 121
<211> LENGTH: 19
<212> TYPE: RNA
<213> ORGANISM: Artificial sequence
<220> FEATURE:
<223> OTHER INFORMATION: synthetic oligonucleotide

<400> SEQUENCE: 121
gagaucucug aagugaaga                                                   19

<210> SEQ ID NO 122
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 122
cagaauuccg acaugacuca                                                  20

<210> SEQ ID NO 123
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 123
gaaguucauc aucaaaaau                                                   19

<210> SEQ ID NO 124
<211> LENGTH: 19
<212> TYPE: RNA
<213> ORGANISM: Artificial sequence
<220> FEATURE:
<223> OTHER INFORMATION: Synthetic construct

<400> SEQUENCE: 124
ccaaaugacc uauuaacuc                                                   19

<210> SEQ ID NO 125
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 125
```
cuacccaaaa cuucuuucu                                                19

<210> SEQ ID NO 126
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 126
caucauaauu aaaguaugc                                                19

<210> SEQ ID NO 127
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 127
uucauauccu gagucaugu                                                19

<210> SEQ ID NO 128
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 128
gacaaacagu aguggaaag                                                19

<210> SEQ ID NO 129
<211> LENGTH: 81
<212> TYPE: RNA
<213> ORGANISM: Artificial sequence
<220> FEATURE:
<223> OTHER INFORMATION: Synthetic oligonucleotide

<400> SEQUENCE: 129
guuuuagagc uagaaauagc aaguuaaaau aaggcuaguc cguuaucaac uugaaaaagu    60
ggcaccgagu cggugcuuuu u                                             81

<210> SEQ ID NO 130
<211> LENGTH: 108
<212> TYPE: DNA
<213> ORGANISM: Artificial sequence
<220> FEATURE:
<223> OTHER INFORMATION: Synthetic oligonucleotide

<400> SEQUENCE: 130
agcaagttaa aataaggcta gtccgttatc aacttgaaaa agtggcaccg agtcggtgct    60 ttttgtttt agagctagaa atagcaagtt aaaataaggc tagtccgt                108

<210> SEQ ID NO 131
<211> LENGTH: 108
<212> TYPE: RNA
<213> ORGANISM: Artificial sequence
<220> FEATURE:
<223> OTHER INFORMATION: Synthetic oligonucleotide

<400> SEQUENCE: 131
agcaaguuaa aauaaggcua guccguuauc aacuugaaaa aguggcaccg agucggugcu    60

```
uuuuuguuuu agagcuagaa auagcaaguu aaaauaaggc uaguccgu        108

<210> SEQ ID NO 132
<211> LENGTH: 82
<212> TYPE: DNA
<213> ORGANISM: Artificial sequence
<220> FEATURE:
<223> OTHER INFORMATION: Synthetic oligonucleotide

<400> SEQUENCE: 132
gttttagagc tagaaatagc aagttaaaat aaggctagtc cgttatcaac ttgaaaaagt    60
ggcaccgagt cggtgctttt tt                                             82

<210> SEQ ID NO 133
<211> LENGTH: 82
<212> TYPE: RNA
<213> ORGANISM: Artificial sequence
<220> FEATURE:
<223> OTHER INFORMATION: Synthetic oligonucleotide

<400> SEQUENCE: 133
guuuuagagc uagaaauagc aaguuaaaau aaggcuaguc cguuaucaac uugaaaaagu    60
ggcaccgagu cggugcuuuu uu                                             82

<210> SEQ ID NO 134
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 134
tagcaagtta aaataaggct agtccgttat caacttgaaa aagtggcacc gagtcggtgc    60
tttttt                                                               66

<210> SEQ ID NO 135
<211> LENGTH: 66
<212> TYPE: RNA
<213> ORGANISM: Artificial sequence
<220> FEATURE:
<223> OTHER INFORMATION: Synthetic oligonucleotide

<400> SEQUENCE: 135
uagcaaguua aaauaaggcu aguccguuau caacuugaaa aaguggcacc gagucggugc    60
uuuuuu                                                               66
```